(12) United States Patent
Beier et al.

(10) Patent No.: US 8,981,111 B2
(45) Date of Patent: Mar. 17, 2015

(54) FUNGICIDE HYDROXIMOYL-HETEROCYCLES DERIVATIVES

(75) Inventors: Christian Beier, Saint Genis-Laval (FR); Jürgen Benting, Leichlingen (DE); David Bernier, Lyons (FR); Isabelle Christian, Lyons (FR); Pierre-Yves Coqueron, Lyons (FR); Philippe Desbordes, Lyons (FR); Christophe Dubost, Lyons (FR); Pierre Genix, Lyons (FR); Marie-Claire Grosjean-Cournoyer, Curis Au Mont D'or (FR); Daniela Portz, Vettweiss (DE); Rachel Rama, Lyons (FR); Philippe Rinolfi, Châtillon d'Azergues (FR); Arnd Voerste, Köln (DE); Ulrike Wachendorff-Neumann, Neuwied (DE)

(73) Assignee: Bayer Cropscience AG (DE)

( * ) Notice: Subject to any disclaimer, the term of this patent is extended or adjusted under 35 U.S.C. 154(b) by 656 days.

(21) Appl. No.: 12/989,361

(22) PCT Filed: Apr. 21, 2009

(86) PCT No.: PCT/EP2009/054693
§ 371 (c)(1),
(2), (4) Date: Oct. 22, 2010

(87) PCT Pub. No.: WO2009/130193
PCT Pub. Date: Oct. 29, 2009

(65) Prior Publication Data
US 2011/0034445 A1  Feb. 10, 2011

(30) Foreign Application Priority Data
Apr. 22, 2008  (EP) ..................... 08356062

(51) Int. Cl.
| | | |
|---|---|---|
| C07D 403/00 | (2006.01) |
| C07D 249/08 | (2006.01) |
| C07D 213/74 | (2006.01) |
| C07D 213/75 | (2006.01) |
| C07D 239/42 | (2006.01) |
| C07D 239/74 | (2006.01) |
| C07D 277/40 | (2006.01) |
| C07D 277/42 | (2006.01) |
| C07D 277/46 | (2006.01) |
| C07D 401/04 | (2006.01) |
| C07D 401/12 | (2006.01) |
| C07D 405/12 | (2006.01) |
| C07D 409/04 | (2006.01) |
| C07D 409/12 | (2006.01) |

(52) U.S. Cl.
CPC ............ C07D 213/74 (2013.01); C07D 213/75 (2013.01); C07D 239/42 (2013.01); C07D 239/74 (2013.01); C07D 277/40 (2013.01); C07D 277/42 (2013.01); C07D 277/46 (2013.01); C07D 401/04 (2013.01); C07D 401/12 (2013.01); C07D 405/12 (2013.01); C07D 409/04 (2013.01); C07D 409/12 (2013.01)
USPC ........................................ 548/255; 548/262.2

(58) Field of Classification Search
USPC ............................................... 548/262.2, 255
See application file for complete search history.

(56) References Cited

U.S. PATENT DOCUMENTS

| | | | |
|---|---|---|---|
| 4,843,068 A | 6/1989 | Hamaguchi et al. | ............ 514/63 |
| 5,583,249 A | 12/1996 | Pfifner et al. | .................... 560/35 |
| 5,728,696 A | 3/1998 | Kuhn et al. | ................ 514/235.5 |
| 6,340,697 B1 * | 1/2002 | Kobori et al. | ................. 514/364 |

FOREIGN PATENT DOCUMENTS

| | | |
|---|---|---|
| DE | 4020384 A1 | 1/1992 |
| EP | 0004754 B1 | 10/1979 |
| EP | 1038874 A1 | 9/2000 |
| EP | 1184382 A * | 3/2002 |
| EP | 1184382 A1 * | 3/2002 |
| JP | WO 00/75138 A1 | 12/2000 |
| WO | WO 93/21157 | 10/1993 |
| WO | WO 96/06072 | 2/1996 |

* cited by examiner

*Primary Examiner* — James O Wilson
*Assistant Examiner* — Oluwafemi Masha
(74) *Attorney, Agent, or Firm* — Ostrolenk Faber LLP

(57) ABSTRACT

The present invention relates to hydroximoyl-heterocycle derivatives, their process of preparation, intermediate compounds for their preparation, their use as fungicide active agents, particularly in the form of fungicide compositions, and methods for the control of phytopathogenic fungi, notably of plants, using these compounds or compositions.

19 Claims, No Drawings

FUNGICIDE HYDROXIMOYL-HETEROCYCLES DERIVATIVES

CROSS REFERENCE TO RELATED APPLICATION(S)

The present application is a 35 U.S.C. §371 national phase conversion of PCT/EP2009/054693 filed Apr. 21, 2009, which claims priority of European Application No.08356062.3 filed Apr. 22, 2008. The PCT International Application was published in the English language.

The present invention relates to hydroximoyl-heterocycle derivatives, their process of preparation, their use as fungicide active agents, particularly in the form of fungicide compositions, and methods for the control of phytopathogenic fungi, notably of plants, using these compounds or compositions.

In European patent application n° 1184382, there are disclosed certain heterocyclyloxime derivatives of the following chemical structure:

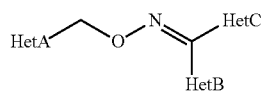

that are excluded from the scope of the present invention.

In European patent application n° 1426371, there are disclosed certain tetrazoyloxime derivatives of the following chemical structure:

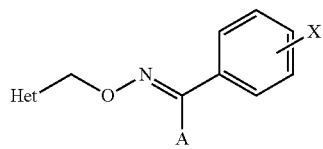

wherein A represents a tetrazolyl group, Het represents either a particular pyridinyl group or a particular thiazolyl group.

Nevertheless, these compounds do not prove to provide a comparable utility than the compounds according to the invention.

It is always of high-interest in agriculture to use novel pesticide compounds in order to avoid or to control the development of resistant strains to the active ingredients. It is also of high-interest to use novel compounds being more active than those already known, with the aim of decreasing the amounts of active compound to be used, whilst at the same time maintaining effectiveness at least equivalent to the already known compounds. We have now found a new family of compounds which possess the above mentioned effects or advantages.

Accordingly, the present invention provides hydroximoyl-heterocycle derivatives of formula (I)

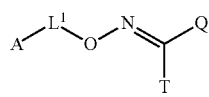

(I)

wherein
T represents a substituted or non-substituted heterocyclyl group that is selected in the list consisting of $T^1$ to $T^{117}$:

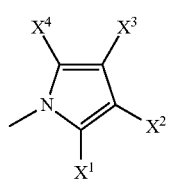 $T^1$

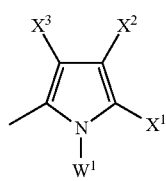 $T^2$

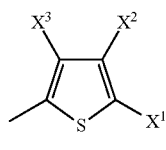 $T^3$

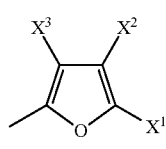 $T^4$

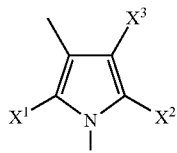 $T^5$

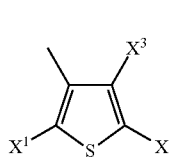 $T^6$

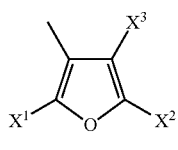 $T^7$

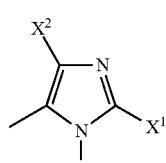 $T^8$

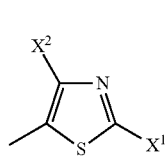 $T^9$

-continued
T10
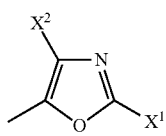
T11
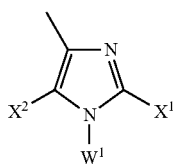
T12
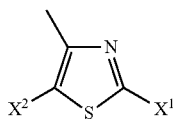
T13
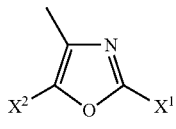
T14
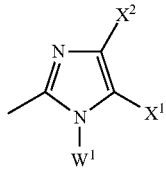
T15
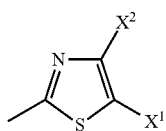
T16
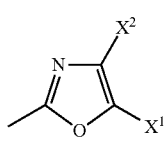
T17
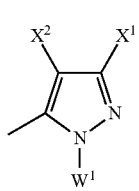
T18
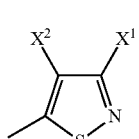
T19
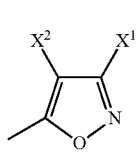
-continued
T20
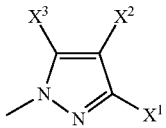
T21
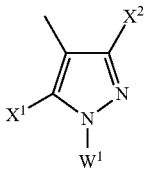
T22
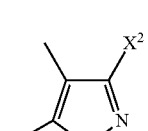
T23
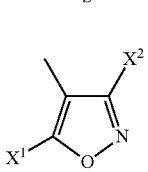
T24
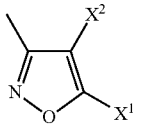
T25
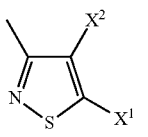
T26
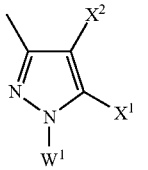
T27
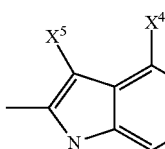
T28
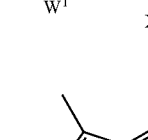
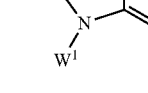

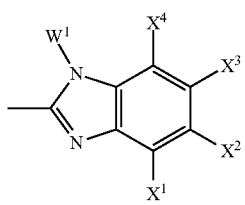 T29
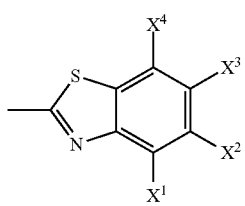 T30
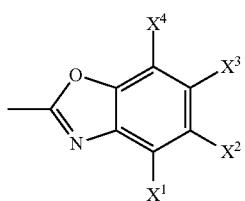 T31
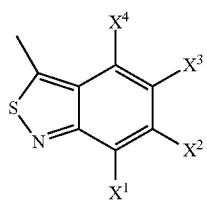 T32
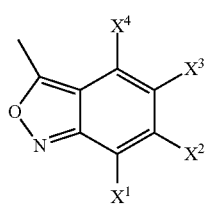 T33
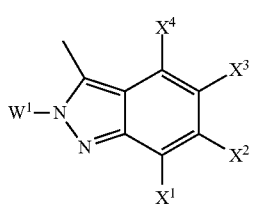 T34
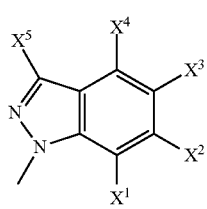 T35
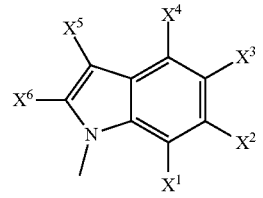 T36
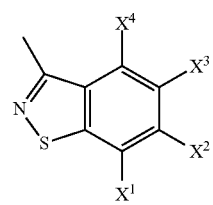 T37
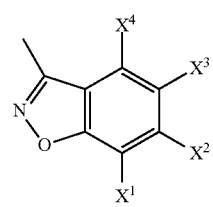 T38
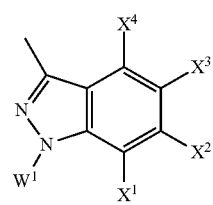 T39
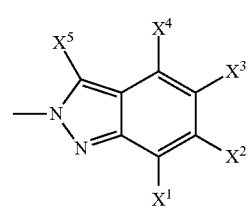 T40
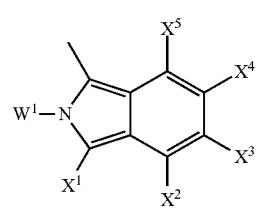 T41
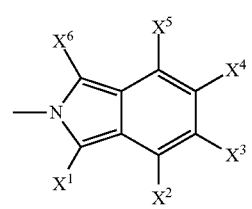 T42

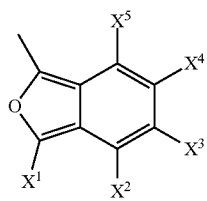
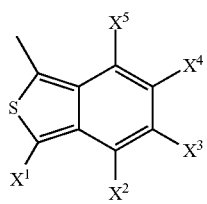
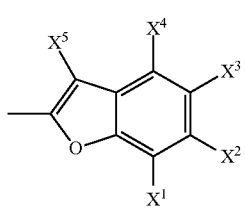
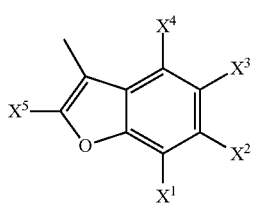
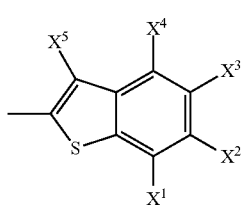
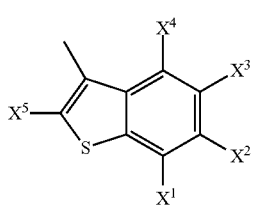
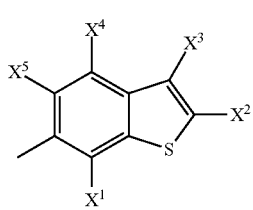
T⁴³
T⁴⁴
T⁴⁵
T⁴⁶
T⁴⁷
T⁴⁸
T⁴⁹
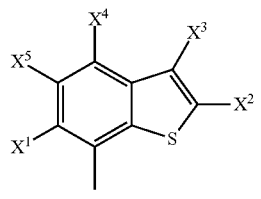
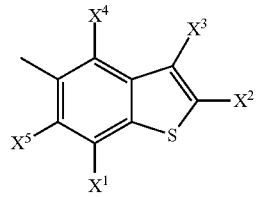
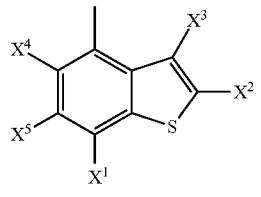
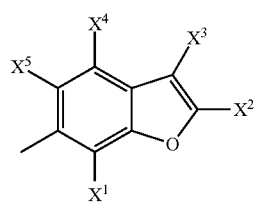
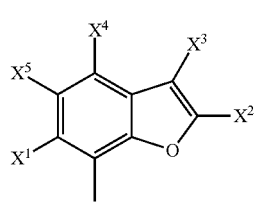
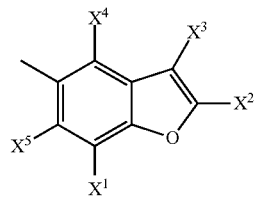
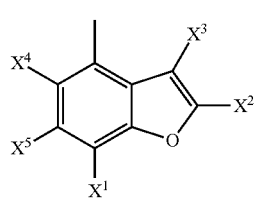
T⁵⁰
T⁵¹
T⁵²
T⁵³
T⁵⁴
T⁵⁵
T⁵⁶

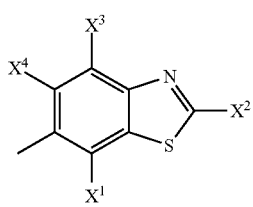
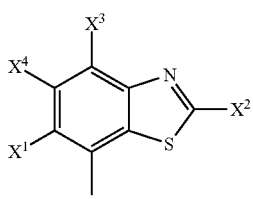
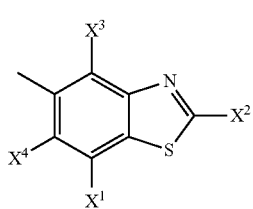
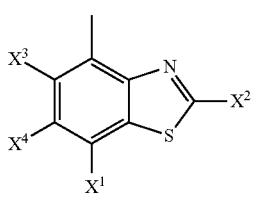
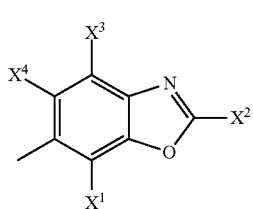
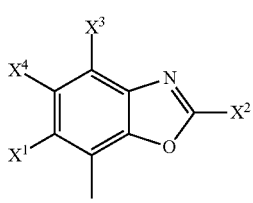
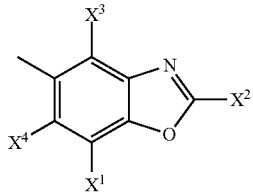
T57
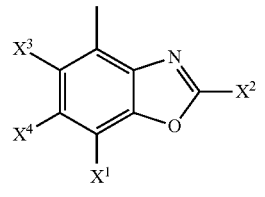
T58
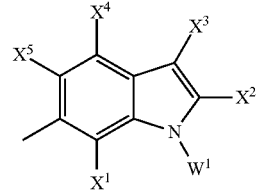
T59
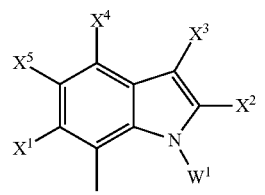
T60
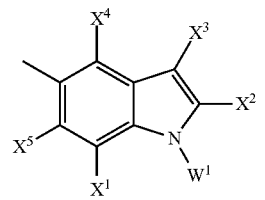
T61
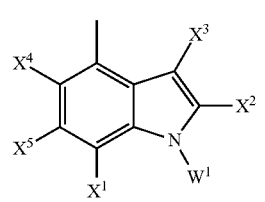
T62
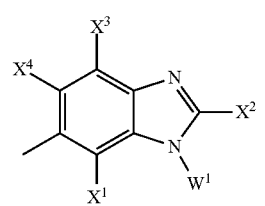
T63
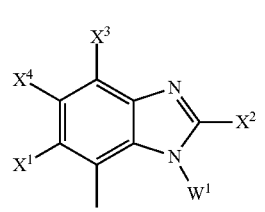
T64
T65
T66
T67
T68
T69
T70

-continued
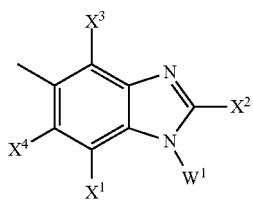
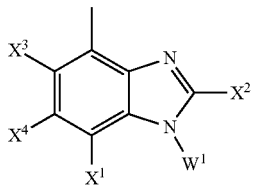
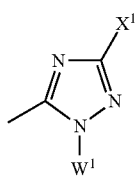
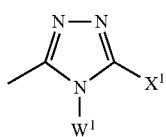
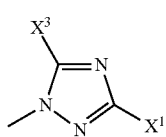
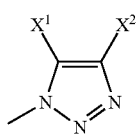
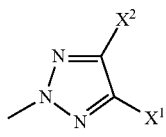
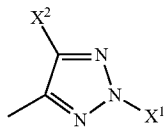
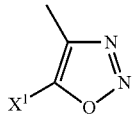
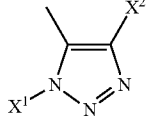
-continued
$T^{71}$ 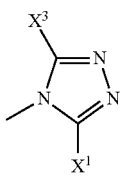
$T^{72}$ 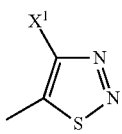
$T^{73}$ 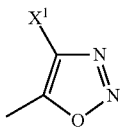
$T^{74}$ 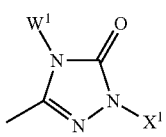
$T^{75}$ 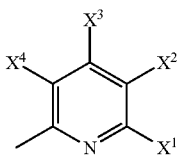
$T^{76}$ 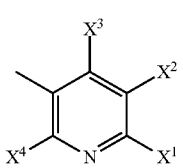
$T^{77}$ 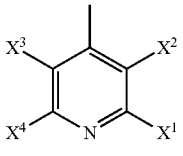
$T^{78}$
$T^{79}$
$T^{80}$ 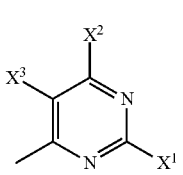
$T^{81}$
$T^{82}$
$T^{83}$
$T^{84}$
$T^{85}$
$T^{86}$
$T^{88}$
$T^{89}$
$T^{90}$

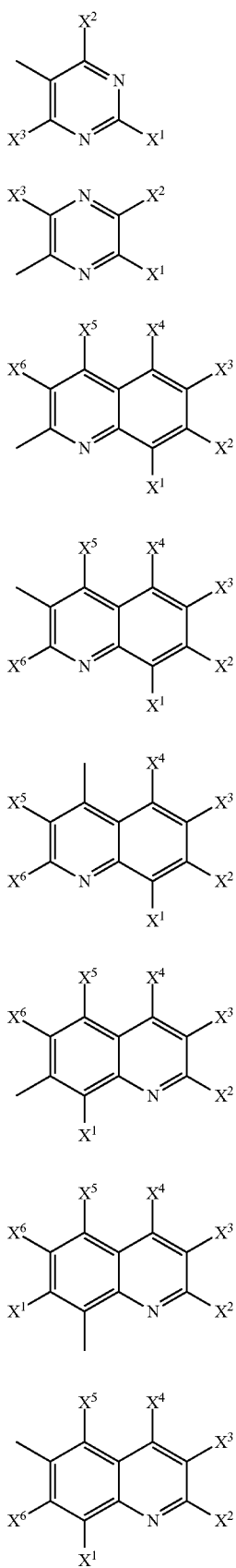
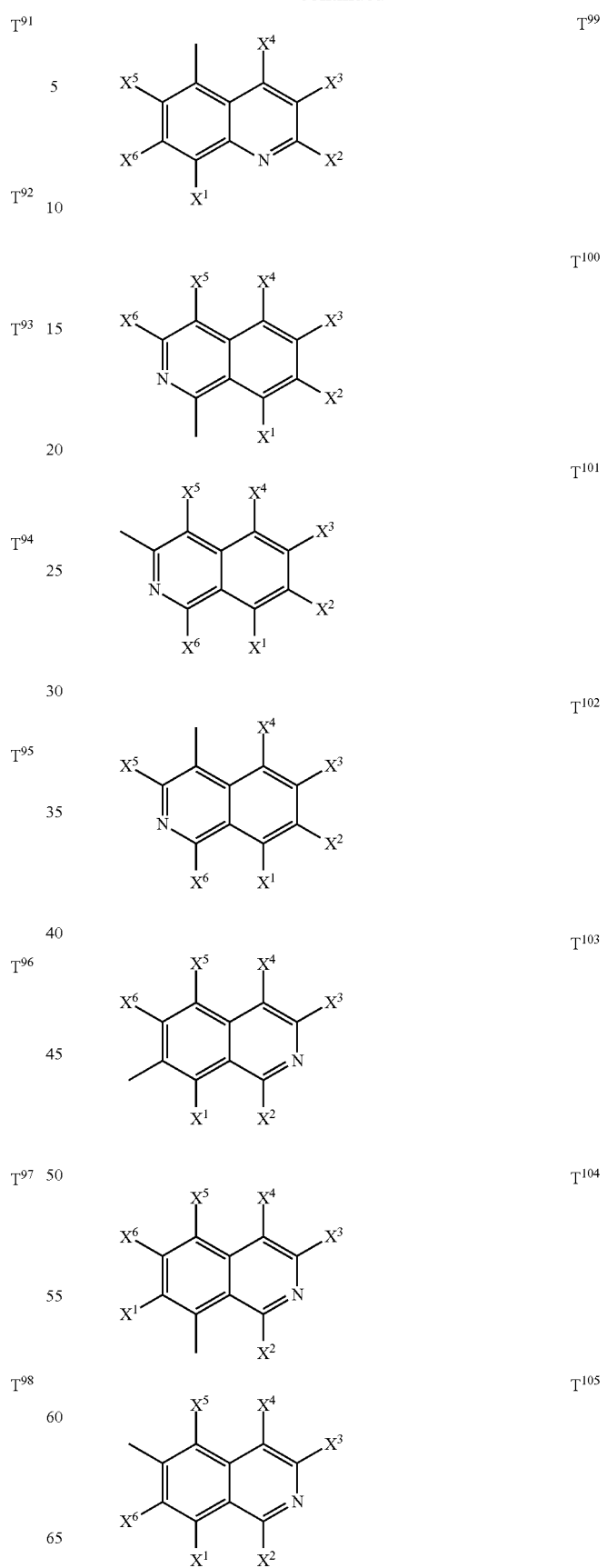

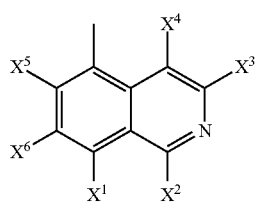
T106

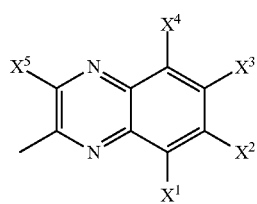
T107

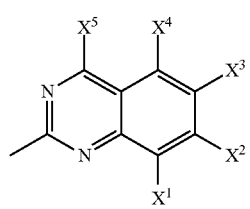
T108

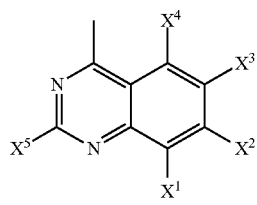
T109

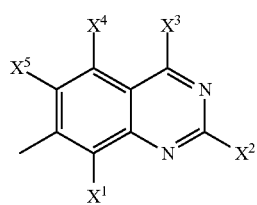
T110

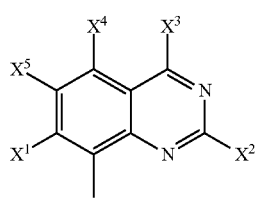
T111

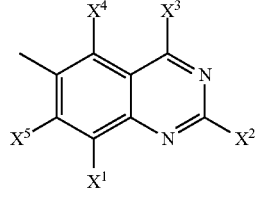
T112

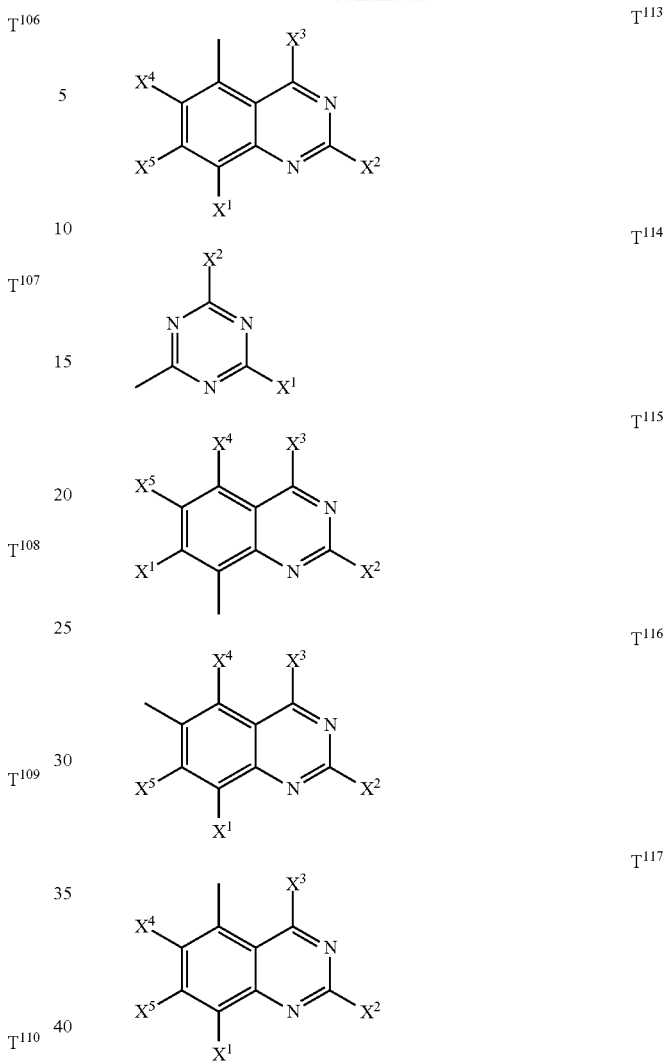

wherein $X^1$ to $X^6$ independently represent a hydrogen atom, a halogen atom, a nitro group, a hydroxy group, a cyano group, an amino group, a sulphenyl group, a formyl group, a substituted or non-substituted carbaldehyde O—($C_1$-$C_8$-alkyl)oxime, a formyloxy group, a formylamino group, a carbamoyl group, a N-hydroxycarbamoyl group, a pentafluoro-$\lambda^6$-sulphenyl group, a formylamino group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$-alkyl-($C_1$-$C_8$-alkylamino)amino group, a substituted or non-substituted (hydroxyimino)-$C_1$-$C_6$-alkyl group, substituted or non-substituted $C_1$-$C_8$-alkyl, substituted or non-substituted tri($C_1$-$C_8$-alkyl)silyl-$C_1$-$C_8$-alkyl, substituted or non-substituted $C_1$-$C_8$-cycloalkyl, substituted or non-substituted tri($C_1$-$C_8$-alkyl)silyl-$C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non- $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-$C_1$-$C_8$-alkylcarbamoylamino, substituted or non-substituted di-$C_1$-$C_8$-halogenoalkylcarbamoylamino having 1 to 5 halogen atoms, substituted or non-substituted N—$C_1$-$C_8$-alkyl-($C_1$-$C_8$-alkylcarbamoyl)amino, substituted or non-substituted N—$C_1$-$C_8$-alkyl-($C_1$-$C_8$-halogenoalkylcarbamoyl)amino having 1 to 5 halogen atoms, substituted or non-substituted N—$C_1$-$C_8$-alkyl-(di-$C_1$-$C_8$-alkylcarbamoyl)amino, substituted or non-substituted N—$C_1$-$C_8$-alkyl-(di-$C_1$-$C_8$-halogenoalkylcarbamoyl)amino having 1 to 5 halogen atoms, substituted or non-substituted $C_1$-$C_8$-alkylaminocarbonyloxy, substituted or non-substituted di-$C_1$-$C_8$-alkylaminocarbonyloxy, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyl, substituted or non-substituted $C_1$-$C_8$-alkoxycarbamothioyl, substituted or non-substituted N—$C_1$-$C_8$-alkyl-$C_1$-$C_8$-alkoxycarbamothioyll, substituted or non-substituted $C_1$-$C_8$-alkylthioylamino, substituted or non-substituted $C_1$-$C_8$-halogenoalkylthioylamino having 1 to 5 halogen atoms, substituted or non-substituted ($C_1$-$C_8$-alkyl-carbamothioyl)-oxy, substituted or non-substituted substituted or non-substituted (di-$C_1$-$C_8$-alkyl-carbamothioyl)-oxy, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_1$-$C_8$-alkylsulphinyl, substituted or non-substituted $C_1$-$C_8$-halogenoalkylsulphinyl having 1 to 5 halogen atoms, substituted or non-substituted $C_1$-$C_8$-alkylsulphonyl, substituted or non-substituted $C_1$-$C_8$-halogenoalkylsulphonyl having 1 to 5 halogen atoms, substituted or non-substituted $C_1$-$C_8$-alkylaminosulfamoyl, substituted or non-substituted di-$C_1$-$C_8$-alkylaminosulfamoyl, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$-alkynyloxyimino)-$C_1$-$C_6$-alkyl, substituted or non-substituted (benzyloxyimino)-$C_1$-$C_6$-alkyl, substituted or non-substituted benzyloxy, substituted or non-substituted benzylsulphenyl, substituted or non-substituted benzylamino, substituted or non-substituted phenoxy, substituted or non-substituted phenylsulphenyl, substituted or non-substituted phenylamino, substituted or non-substituted aryl, substituted or non-substituted aryl-[$C_1$-$C_8$]-alkyl, substituted or non-substituted tri($C_1$-$C_8$-alkyl)silyloxy, substituted or non-substituted $C_1$-$C_8$-alkylsulfenylamino, substituted or non-substituted $C_1$-$C_8$-halogenoalkylsulphinylamino having 1 to 5 halogen atoms, substituted or non-substituted $C_1$-$C_8$-alkylsulphonylamino, substituted or non-substituted $C_1$-$C_8$-halogenoalkylsulphonylamino having 1 to 5 halogen atoms, substituted or non-substituted $C_1$-$C_8$-alkoxysulphonylamino, substituted or non-substituted $C_1$-$C_8$-halogenoxysulphonylamino having 1 to 5 halogen atoms, substituted or non-substituted tri($C_1$-$C_8$-alkyl)silyl, substituted or non-substituted ($C_1$-$C_6$-alkylideneamino)oxy, substituted or non-substituted ($C_1$-$C_6$-alkenylideneamino)oxy, substituted or non-substituted ($C_1$-$C_6$-alkynylideneamino)oxy, substituted or non-substituted (benzylideneamino)oxy;

$W^1$ independently represents a hydrogen atom, a formyl group, a substituted or non-substituted carbaldehyde O—($C_1$-$C_8$-alkyl)oxime, a carbamoyl group, a N-hydroxycarbamoyl group, a formylamino group, substituted or non-substituted $C_1$-$C_8$-alkyl, substituted or non-substituted tri($C_1$-$C_8$-alkyl)silyl-$C_1$-$C_8$-alkyl, substituted or non-substituted $C_1$-$C_8$-cycloalkyl, substituted or non-substituted tri($C_1$-$C_8$-alkyl)silyl-$C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_2$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted C₁-C₈-alkylcarbamothioyl, substituted or non-substituted di-C₁-C₈-alkylcarbamothioyl, substituted or non-substituted N—C₁-C₈-alkyloxycarbamothioyll, substituted or non-substituted C₁-C₈-alkoxycarbamothioyl, substituted or non-substituted N—C₁-C₈-alkyl-C₁-C₈-alkoxycarbamothioyl, substituted or non-substituted C₁-C₈-alkylsulphinyl, substituted or non-substituted C₁-C₈-halogenoalkylsulphinyl having 1 to 5 halogen atoms, substituted or non-substituted C₁-C₈-alkylsulphonyl, substituted or non-substituted C₁-C₈-halogenoalkylsulphonyl having 1 to 5 halogen atoms, substituted or non-substituted C₁-C₈-alkylaminosulfamoyl, substituted or non-substituted di-C₁-C₈-alkylaminosulfamoyl, substituted or non-substituted aryl, substituted or non-substituted aryl-[C₁-C₈]-alkyl;

$L^1$ represents a direct bond or a divalent group selected in the list consisting of —(CR¹R²)ₙ— —(CR¹R²)ₘ—C(=O)—(CR¹R²)ₚ— —(CR¹R²)ₘ—(CR¹=CR²)—(CR¹R²)ₚ— —(CR¹R²)ₘ—C(=O)—O—(CR¹R²)ₚ— —(CR¹R²)ₘ—C≡C—(CR¹R²)ₚ— —(CR¹R²)ₘ—O—C(=O)—(CR¹R²)ₚ— —(CR¹R²)ₘ—O—(CR¹R²)ₚ— —(CR¹R²)ₘ—C(=O)—NH—(CR¹R²)ₚ— —(CR¹R²)ₘ—NH—(CR¹R²)ₚ— —(CR¹R²)ₘ—NH—C(=O)—(CR¹R²)ₚ— wherein n represents 1, 2, 3 or 4;

m and p independently represent 0, 1, 2 or 3;

$R^1$ and $R^2$ independently represent a hydrogen atom, a halogen atom, a cyano group, substituted or non-substituted C₁-C₈-alkyl, substituted or non-substituted C₃-C₈-cycloalkyl, substituted or non-substituted C₁-C₈-halogenoalkyl having 1 to 5 halogen atoms, substituted or non-substituted C₁-C₈-halogenocycloalkyl having 1 to 5 halogen atoms, a C₂-C₈-alkenyl, substituted or non-substituted C₂-C₈-alkynyl, substituted or non-substituted C₁-C₈-alkoxy, substituted or non-substituted C₁-C₈-halogenoalkoxy having 1 to 5 halogen atoms, substituted or non-substituted C₂-C₈-alkenyloxy, substituted or non-substituted C₂-C₈-halogenoalkenyloxy having 1 to 5 halogen atoms, substituted or non-substituted C₃-C₈-alkynyloxy, substituted or non-substituted C₃-C₈-halogenoalkynyloxy having 1 to 5 halogen atoms.

A is selected in the list consisting of $A^1$ to $A^{116}$:

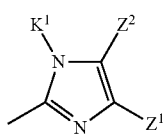
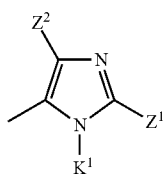
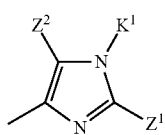
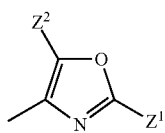
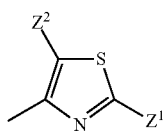
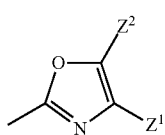
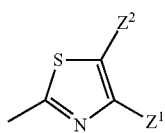
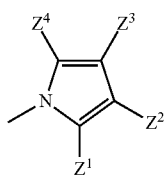
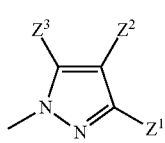
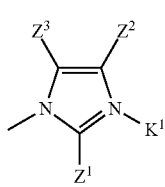
$A^{12}$
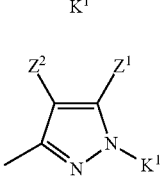
$A^{13}$
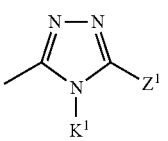
$A^{14}$
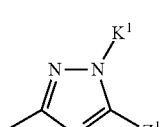
$A^{15}$
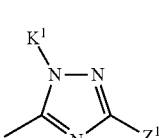
$A^{16}$
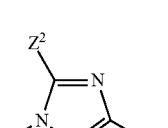
$A^{17}$
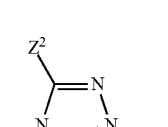
$A^{18}$
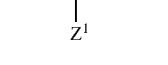
$A^{19}$
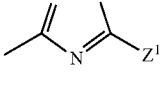
$A^{20}$
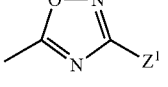
$A^{21}$
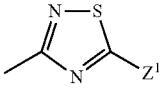
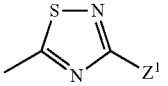
$A^{22}$
$A^{23}$
$A^{24}$
$A^{25}$
$A^{26}$
$A^{27}$
$A^{28}$
$A^{29}$
$A^{30}$
$A^{31}$
$A^{32}$

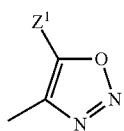
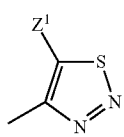
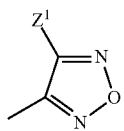
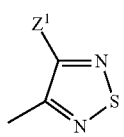
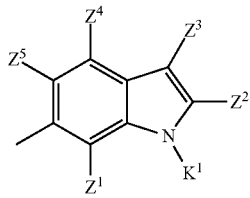
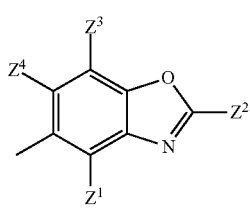
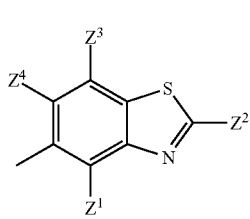
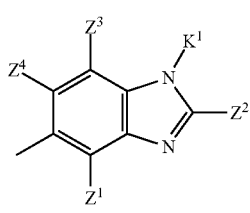
$A^{33}$
$A^{34}$
$A^{35}$
$A^{36}$
$A^{37}$
$A^{38}$
$A^{39}$
$A^{40}$
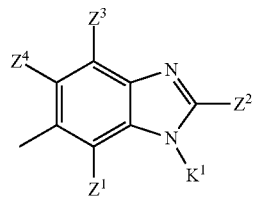
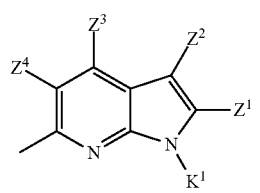
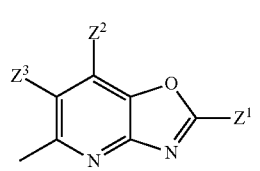
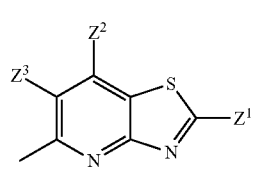
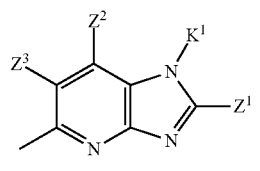
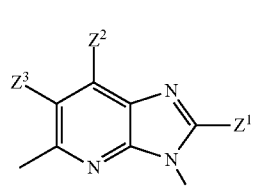
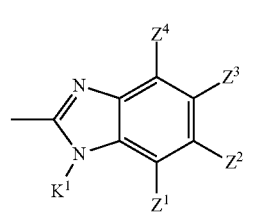
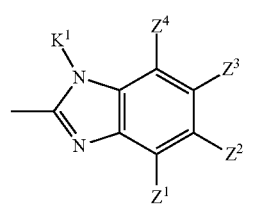
$A^{41}$
$A^{42}$
$A^{43}$
$A^{44}$
$A^{45}$
$A^{46}$
$A^{47}$
$A^{48}$ -continued
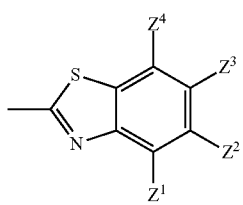 A49
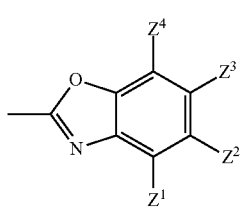 A50
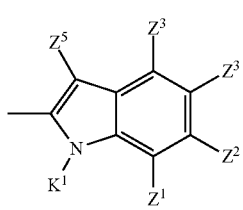 A51
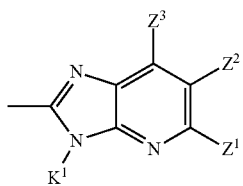 A52
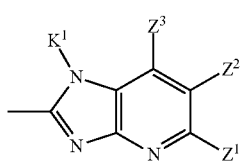 A53
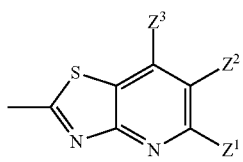 A54
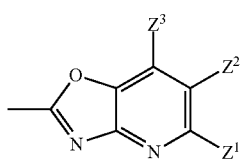 A55
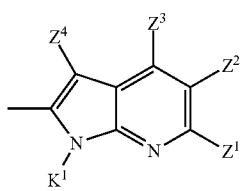 A56
-continued
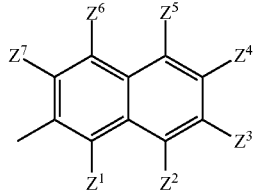 A57
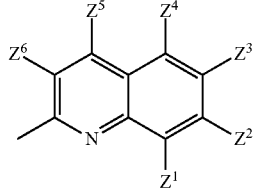 A58
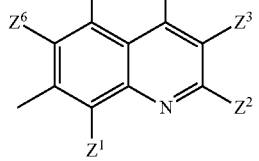 A59
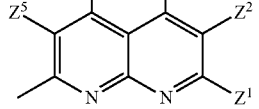 A60
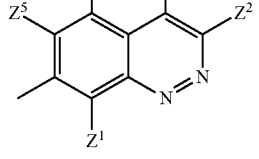 A61
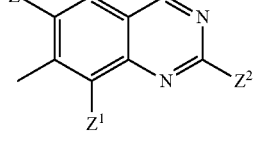 A62
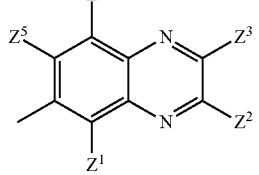 A63
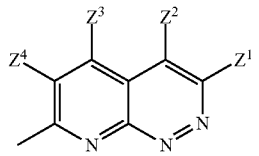 A64

-continued
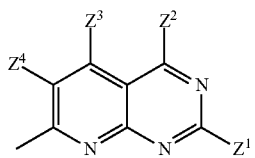
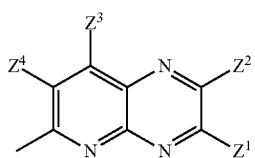
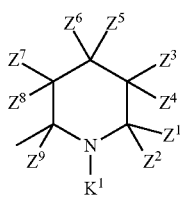
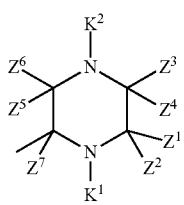
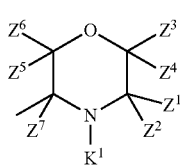
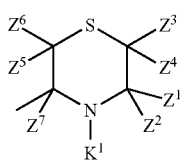
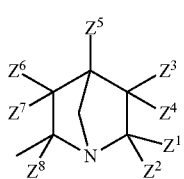
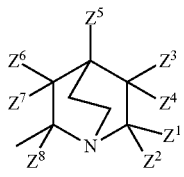
A⁶⁵
A⁶⁶
A⁶⁷
A⁶⁸
A⁶⁹
A⁷⁰
A⁷¹
A⁷²
-continued
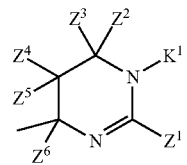
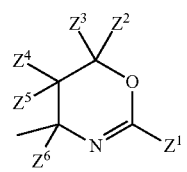
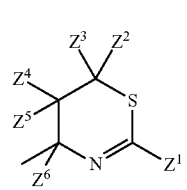
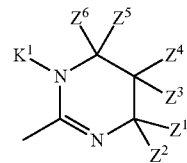
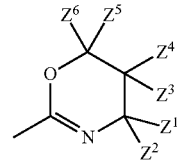
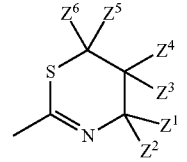
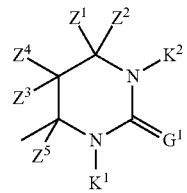
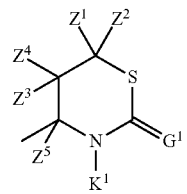
A⁷³
A⁷⁴
A⁷⁵
A⁷⁶
A⁷⁷
A⁷⁸
A⁷⁹
A⁸⁰

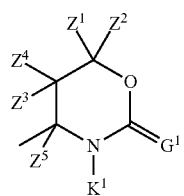 A81
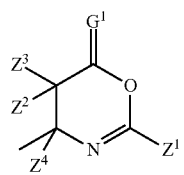 A82
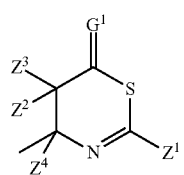 A83
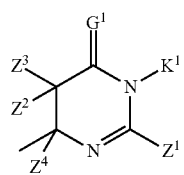 A84
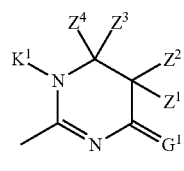 A85
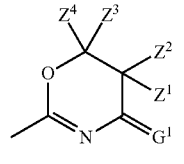 A86
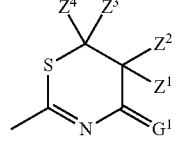 A87
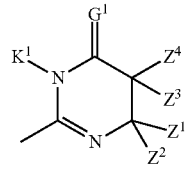 A88
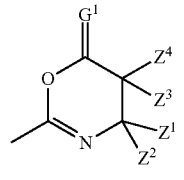 A89
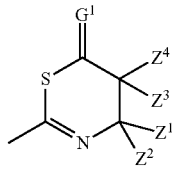 A90
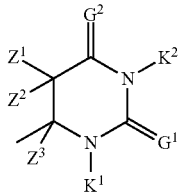 A91
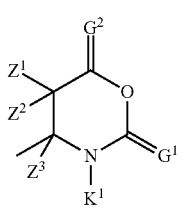 A92
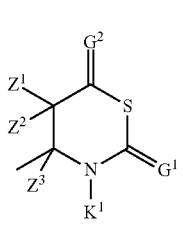 A93
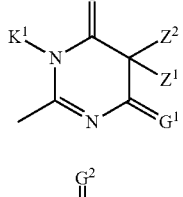 A94
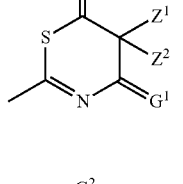 A95
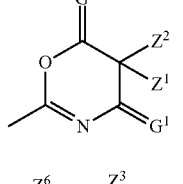 A96
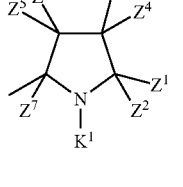 A97

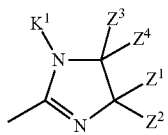 A98
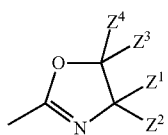 A99
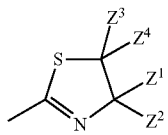 A100
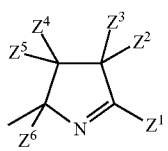 A101
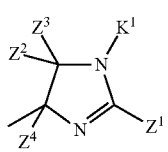 A102
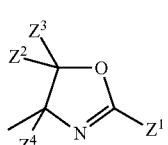 A103
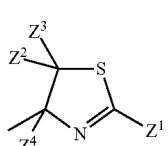 A104
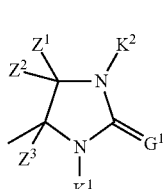 A105
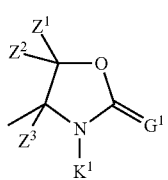 A106
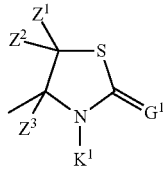 A107
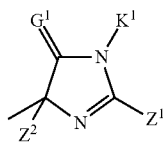 A108
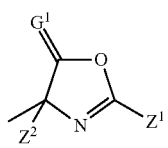 A109
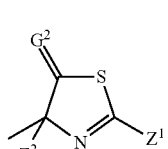 A110
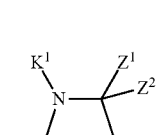 A111
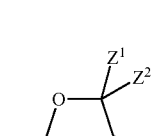 A112
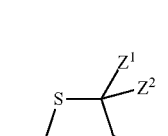 A113
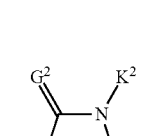 A114
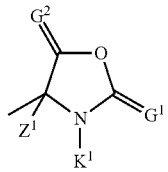 A115

-continued

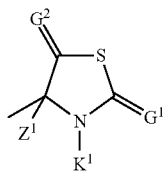

A^116 wherein $Z^1$, $Z^2$, $Z^3$, $Z^4$, $Z^5$, $Z^6$, $Z^7$, $Z^8$ and $Z^9$ independently represent a hydrogen atom, a halogen atom, a nitro group, a hydroxy group, a cyano group, an amino group, a sulphenyl group, a formyl group, a substituted or non-substituted carbaldehyde O—($C_1$-$C_8$-alkyl)oxime, a formyloxy group, a formylamino group, a carbamoyl group, a N-hydroxycarbamoyl group, a pentafluoro-$\lambda^6$-sulphenyl group, a formylamino group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$-alkyl-($C_1$-$C_8$-alkylamino)-amino group, a substituted or non-substituted (hydroxyimino)-$C_1$-$C_6$-alkyl group, substituted or non-substituted $C_1$-$C_8$-alkyl, substituted or non-substituted tri($C_1$-$C_8$-alkyl)silyl-$C_1$-$C_8$-alkyl, substituted or non-substituted $C_3$-$C_8$-cycloalkyl, substituted or non-substituted tri($C_1$-$C_8$-alkyl)silyl-$C_3$-$C_8$-cycloalkyl, substituted or non-substituted $C_1$-$C_8$-halogenoalkyl having 1 to 5 halogen atoms, substituted or non-substituted $C_3$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted ($C_1$-$C_8$-alkoxycarbonyl)amino, substituted or non-substituted ($C_3$-$C_8$-cycloalkoxycarbonyl)amino, substituted or non-substituted $C_1$-$C_8$-halogenoalkoxy having 1 to 5 halogen atoms, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_2$-$C_8$-alkenyloxy, substituted or non-substituted ($C_2$-$C_8$-alkenyloxycarbonyl)amino, substituted or non-substituted $C_2$-$C_8$-halogenoalkenyloxy having 1 to 5 halogen atoms, substituted or non-substituted $C_3$-$C_8$-alkynyloxy, substituted or non-substituted ($C_3$-$C_8$-alkynyloxycarbonyl)amino, substituted or non-substituted $C_3$-$C_8$-halogenoalkynyloxy having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted aryloxycarbonylamino, substituted or non-substituted hetercyclyloxycarbonylamino, substituted or non-substituted arylcarbonylamino, substituted or non-substituted hetercyclylcarbonylamino, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-$C_1$-$C_8$-alkylcarbamoylamino, substituted or non-substituted di-$C_1$-$C_8$-halogenoalkylcarbamoylamino having 1 to 5 halogen atoms, substituted or non-substituted N—$C_1$-$C_8$-alkyl-($C_1$-$C_8$-alkylcarbamoyl)amino, substituted or non-substituted N—$C_1$-$C_8$-alkyl-($C_1$-$C_8$-halogenoalkylcarbamoyl)amino having 1 to 5 halogen atoms, substituted or non-substituted N—$C_1$-$C_8$-alkyl-(di-$C_1$-$C_8$-alkylcarbamoyl)amino, substituted or non-substituted N—$C_1$-$C_8$-alkyl-(di-$C_1$-$C_8$-halogenoalkylcarbamoyl)amino having 1 to 5 halogen atoms, substituted or non-substituted $C_1$-$C_8$-alkylaminocarbonyloxy, substituted or non-substituted di-$C_1$-$C_8$-alkylaminocarbonyloxy, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyl, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylthioylamino, substituted or non-substituted ($C_1$-$C_8$-alkoxythiocarbonyl)amino, substituted or non-substituted $C_1$-$C_8$-halogenoalkylthioylamino having 1 to 5 halogen atoms, substituted or non-substituted ($C_1$-$C_8$-alkyl-carbamothioyl)-oxy, substituted or non-substituted substituted or non-substituted (di-$C_1$-$C_8$-alkyl-carbamothioyl)-oxy, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_1$-$C_8$-alkylsulphinyl, substituted or non-substituted $C_1$-$C_8$-halogenoalkylsulphinyl having 1 to 5 halogen atoms, substituted or non-substituted $C_1$-$C_8$-alkylsulphonyl, substituted or non-substituted $C_1$-$C_8$-halogenoalkylsulphonyl having 1 to 5 halogen atoms, substituted or non-substituted $C_1$-$C_8$-alkylaminosulfamoyl, substituted or non-substituted di-$C_1$-$C_8$-alkylaminosulfamoyl, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$-alkynyloxyimino)-$C_1$-$C_6$-alkyl, substituted or non-substituted (benzyloxyimino)-$C_1$-$C_6$-alkyl, substituted or non-substituted benzyloxy, substituted or non-substituted benzylsulphenyl, substituted or non-substituted benzylamino, substituted or non-substituted phenoxy, substituted or non-substituted phenylsulphenyl, substituted or non-substituted phenylamino, substituted or non-substituted aryl, substituted or non-substituted (arylcarbonyl)amino, substituted or non-substituted (heterocyclylcarbonyl)amino substituted or non-substituted aryl-[$C_1$-$C_8$]-alkyl, substituted or non-substituted tri($C_1$-$C_8$-alkyl)-silyloxy, substituted or non-substituted $C_1$-$C_8$-alkylsulfenylamino, substituted or non-substituted $C_1$-$C_8$-halogenoalkylsulphinylamino having 1 to 5 halogen atoms, substituted or non-substituted $C_1$-$C_8$-alkylsulphonylamino, substituted or non-substituted C₁-C₈-halogenoalkylsulphonylamino having 1 to 5 halogen atoms, substituted or non-substituted C₁-C₈-alkoxysulphonylamino, substituted or non-substituted C₁-C₈-halogenoxysulphonylamino having 1 to 5 halogen atoms, substituted or non-substituted tri(C₁-C₈-alkyl)-silyl, substituted or non-substituted (C₁-C₆-alkylideneamino)oxy, substituted or non-substituted (C₁-C₆-alkenylideneamino)oxy, substituted or non-substituted (C₁-C₆-alkynylideneamino)oxy, substituted or non-substituted (benzylideneamino)oxy;

K¹ and K² independently represent a hydrogen atom, a formyl group, a substituted or non-substituted carbaldehyde O—(C₁-C₈-alkyl)oxime, a carbamoyl group, a N-hydroxycarbamoyl group, a formylamino group, substituted or non-substituted C₁-C₈-alkyl, substituted or non-substituted tri(C₁-C₈-alkyl)silyl-C₁-C₈-alkyl, substituted or non-substituted C₁-C₈-cycloalkyl, substituted or non-substituted tri(C₁-C₈-alkyl)silyl-C₁-C₈-cycloalkyl, substituted or non-substituted C₁-C₈-halogenoalkyl having 1 to 5 halogen atoms, substituted or non-substituted C₁-C₈-halogenocycloalkyl having 1 to 5 halogen atoms, a C₂-C₈-alkenyl, substituted or non-substituted C₂-C₈-alkynyl, substituted or non-substituted C₁-C₈-alkylamino, substituted or non-substituted di-C₁-C₈-alkylamino, substituted or non-substituted C₁-C₈-alkoxy, substituted or non-substituted C₁-C₈-halogenoalkoxy having 1 to 5 halogen atoms, substituted or non-substituted C₂-C₈-alkenyloxy, substituted or non-substituted C₂-C₈-halogenoalkenyloxy having 1 to 5 halogen atoms, substituted or non-substituted C₂-C₈-alkynyloxy, substituted or non-substituted C₃-C₈-halogenoalkynyloxy having 1 to 5 halogen atoms, substituted or non-substituted C₁-C₈-alkylcarbonyl, substituted or non-substituted N—(C₁-C₈-alkoxy)-C₁-C₈-alkanimidoyl, substituted or non-substituted N—(C₁-C₈-alkoxy)-C₁-C₈-halogenoalkanimidoyl having 1 to 5 halogen atoms, substituted or non-substituted C₁-C₈-halogenoalkylcarbonyl having 1 to 5 halogen atoms, substituted or non-substituted C₁-C₈-alkylcarbamoyl, substituted or non-substituted di-C₁-C₈-alkylcarbamoyl, substituted or non-substituted N—C₁-C₈-alkyloxycarbamoyl, substituted or non-substituted C₁-C₈-alkoxycarbamoyl, substituted or non-substituted N—C₁-C₈-alkyl-C₁-C₈-alkoxycarbamoyl, substituted or non-substituted C₁-C₈-alkoxycarbonyl, substituted or non-substituted C₁-C₈-halogenoalkoxycarbonyl having 1 to 5 halogen atoms, substituted or non-substituted C₁-C₈-alkylcarbamothioyl, substituted or non-substituted di-C₁-C₈-alkylcarbamothioyl, substituted or non-substituted N—C₁-C₈-alkyloxycarbamothioyll, substituted or non-substituted C₁-C₈-alkoxycarbamothioyl, substituted or non-substituted N—C₁-C₈-alkyl-C₁-C₈-alkoxycarbamothioyl, substituted or non-substituted C₁-C₈-alkylsulphinyl, substituted or non-substituted C₁-C₈-halogenoalkylsulphinyl having 1 to 5 halogen atoms, substituted or non-substituted C₁-C₈-alkylsulphonyl, substituted or non-substituted C₁-C₈-halogenoalkylsulphonyl having 1 to 5 halogen atoms, substituted or non-substituted C₁-C₈-alkylaminosulfamoyl, substituted or non-substituted di-C₁-C₈-alkylaminosulfamoyl, substituted or non-substituted aryl, substituted or non-substituted aryl-[C₁-C₈]-alkyl;

G¹ and G² are independently selected in the list consisting of oxygen, sulfur, NR³, N—OR⁴ and N—NR⁵R⁶ wherein R³ to R⁶ independently represent a hydrogen atom, a halogen atom, a cyano group, substituted or non-substituted C₁-C₈-alkyl, substituted or non-substituted C₁-C₈-cycloalkyl, substituted or non-substituted C₁-C₈-halogenoalkyl having 1 to 5 halogen atoms, substituted or non-substituted C₁-C₈-halogenocycloalkyl having 1 to 5 halogen atoms, a C₂-C₈-alkenyl, substituted or non-substituted C₂-C₈-alkynyl, substituted or non-substituted C₁-C₈-alkoxy, substituted or non-substituted C₁-C₈-halogenoalkoxy having 1 to 5 halogen atoms, substituted or non-substituted C₂-C₈-alkenyloxy, substituted or non-substituted C₂-C₈-halogenoalkenyloxy having 1 to 5 halogen atoms, substituted or non-substituted C₃-C₈-alkynyloxy, substituted or non-substituted C₃-C₈-halogenoalkynyloxy having 1 to 5 halogen atoms, substituted or non-substituted aryl, substituted or non-substituted aryl-[C₁-C₈]-alkyl;

Q is selected in the list consisting of $Q^1$ to $Q^{112}$:

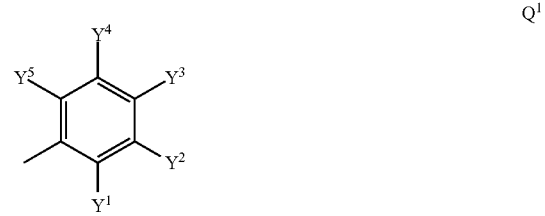

$Q^1$

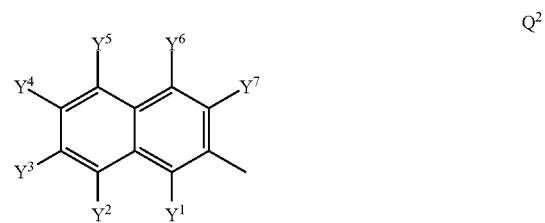

$Q^2$

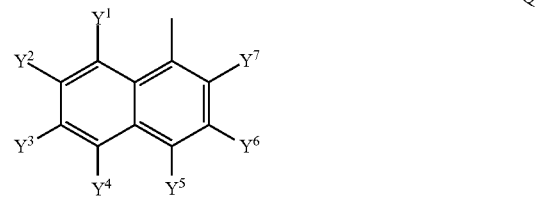

$Q^3$

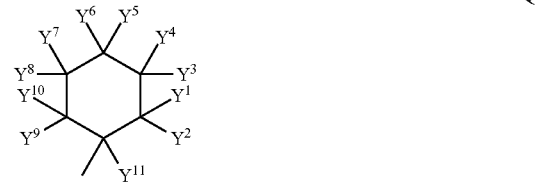

$Q^4$

$Q^5$

$Q^6$

-continued
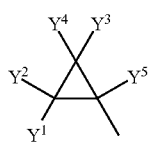 Q⁷
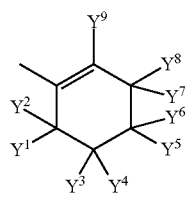 Q⁸
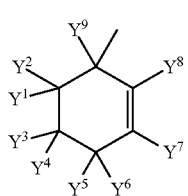 Q⁹
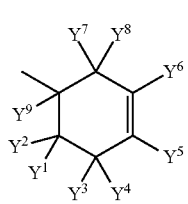 Q¹⁰
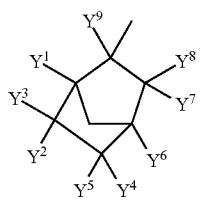 Q¹¹
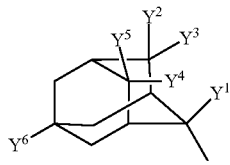 Q¹²
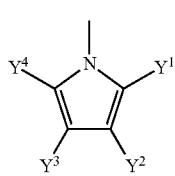 Q¹³
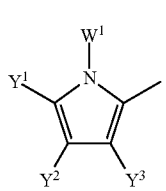 Q¹⁴
-continued
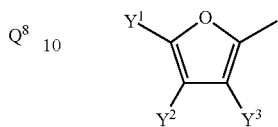 Q¹⁵
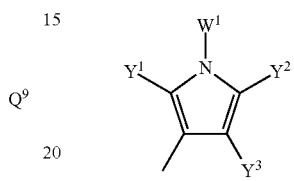 Q¹⁶
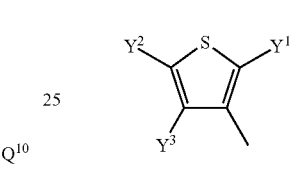 Q¹⁷
 Q¹⁸
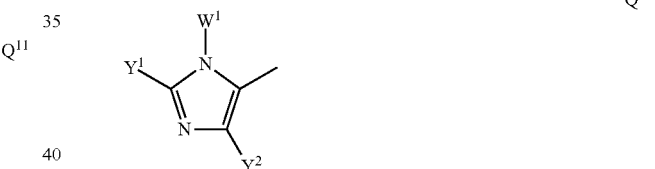 Q¹⁹
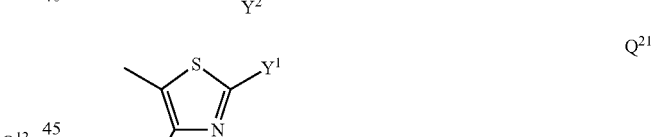 Q²⁰
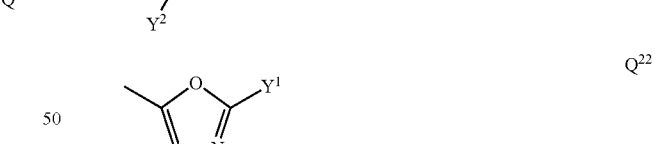 Q²¹
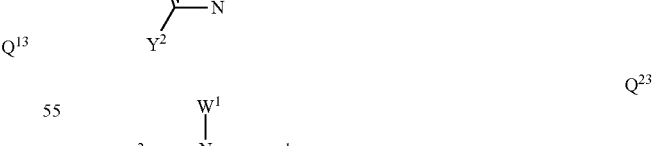 Q²²
 Q²³
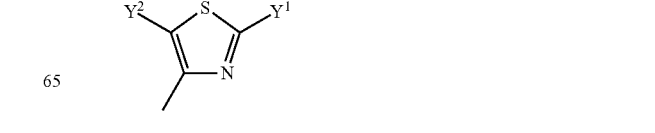 Q²⁴

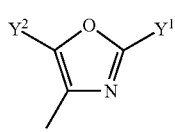 Q25
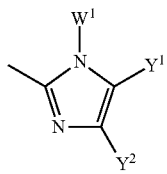 Q26
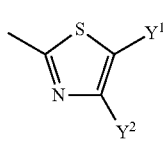 Q27
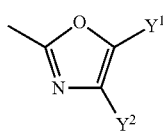 Q28
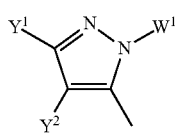 Q29
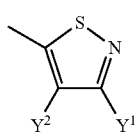 Q30
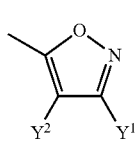 Q31
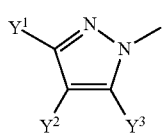 Q32
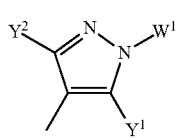 Q33
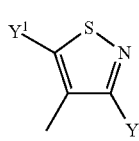 Q34
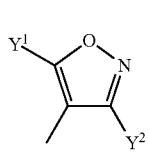 Q35
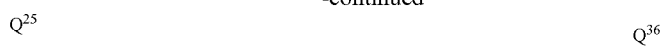 Q36
 Q37
 Q38
 Q39
 Q40
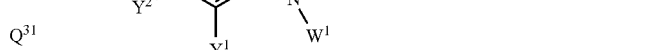 Q41
 Q42
 Q43

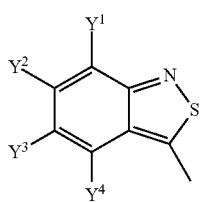
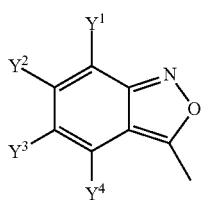
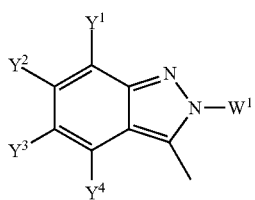
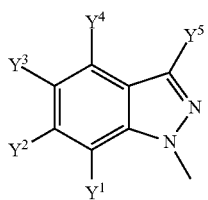
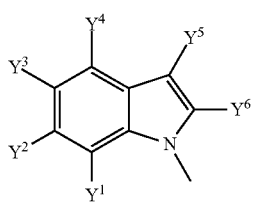
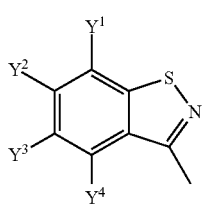
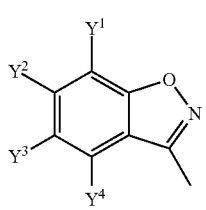
Q44
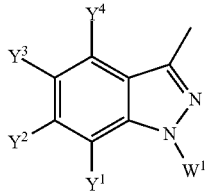
Q45
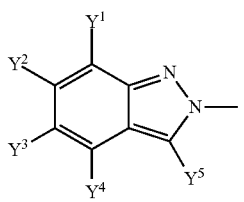
Q46
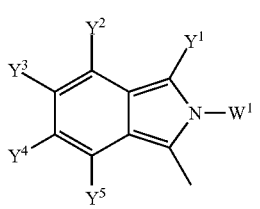
Q47
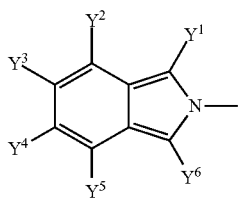
Q48
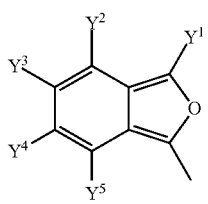
Q49
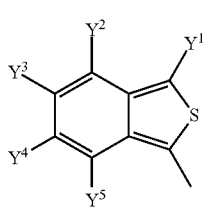
Q50
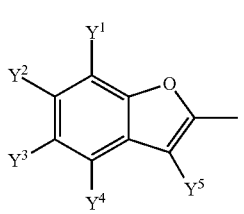
Q51
Q52
Q53
Q54
Q55
Q56
Q57

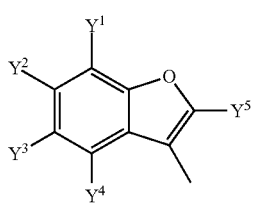
Q58
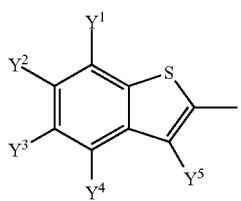
Q59
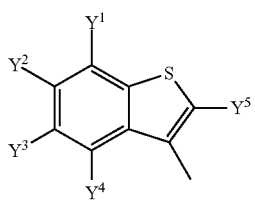
Q60
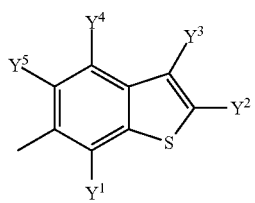
Q61
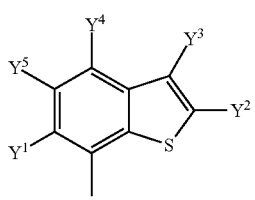
Q62
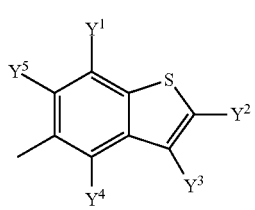
Q63
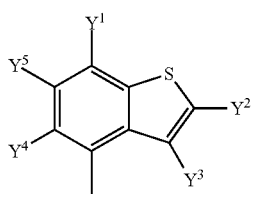
Q64
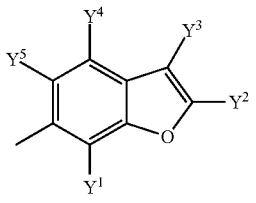
Q65
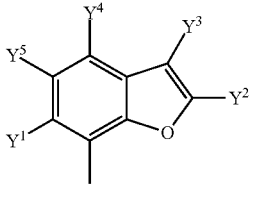
Q66
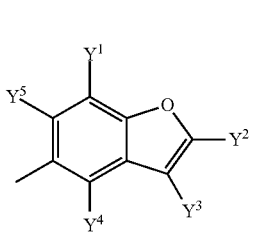
Q67
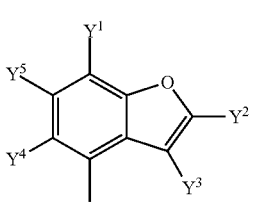
Q68
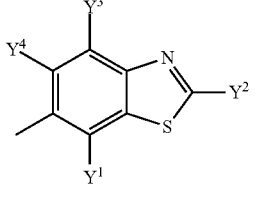
Q69
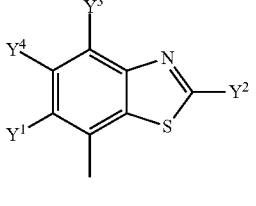
Q70
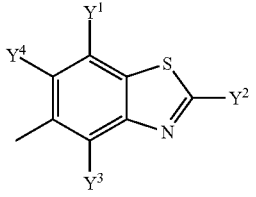
Q71

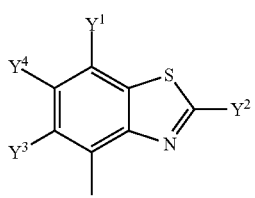
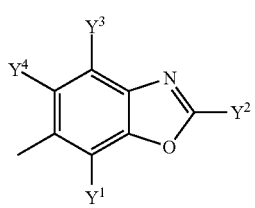
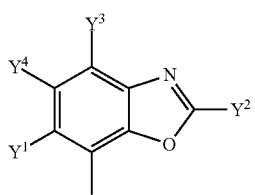
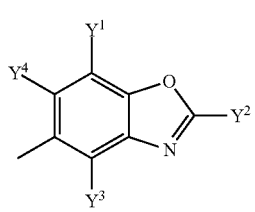
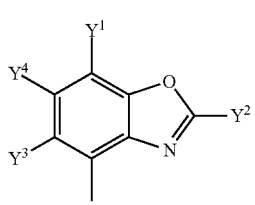
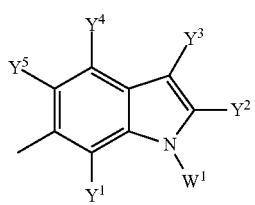
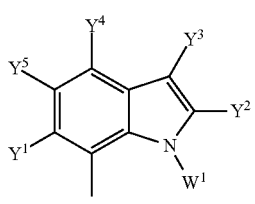
Q72
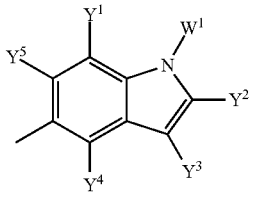
Q73
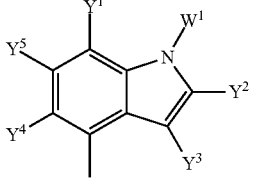
Q74
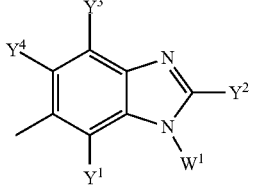
Q75
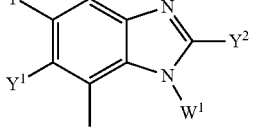
Q76
Q77
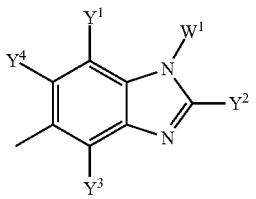
Q78
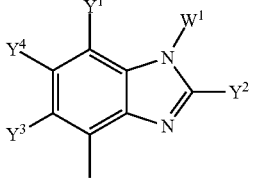
Q79
Q80
Q81
Q82
Q83
Q84
Q85
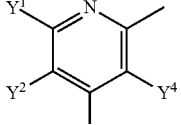
Q86
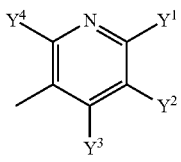

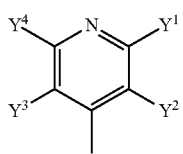
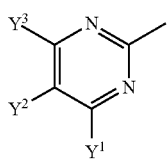
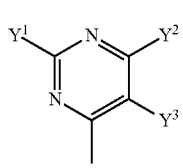
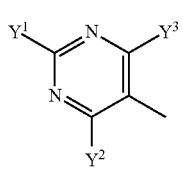
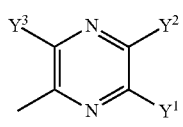
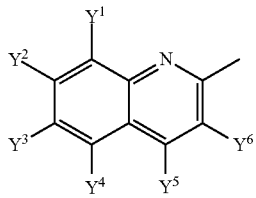
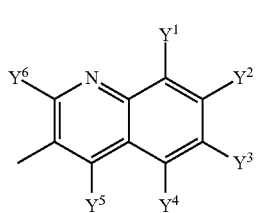
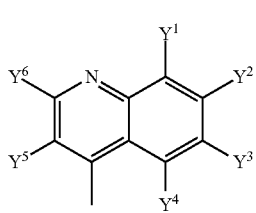
Q87
Q88
Q89
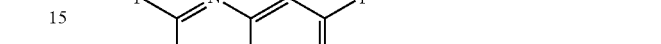
Q90
Q91
Q92
Q93
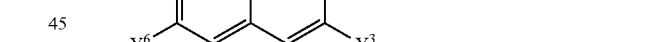
Q94
Q95
Q96
Q97
Q98
Q99
Q100
Q101
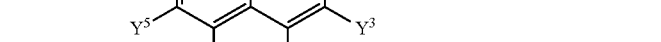

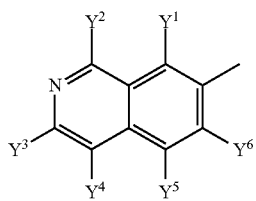
Q¹⁰²

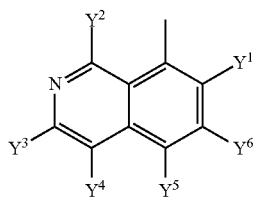
Q¹⁰³

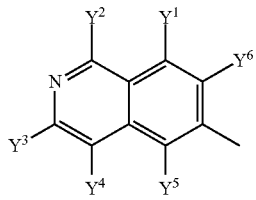
Q¹⁰⁴

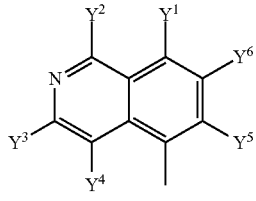
Q¹⁰⁵

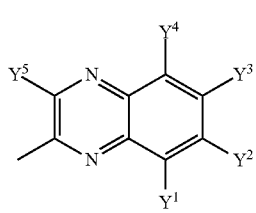
Q¹⁰⁶

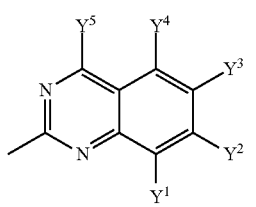
Q¹⁰⁷

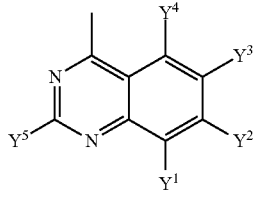
Q¹⁰⁸

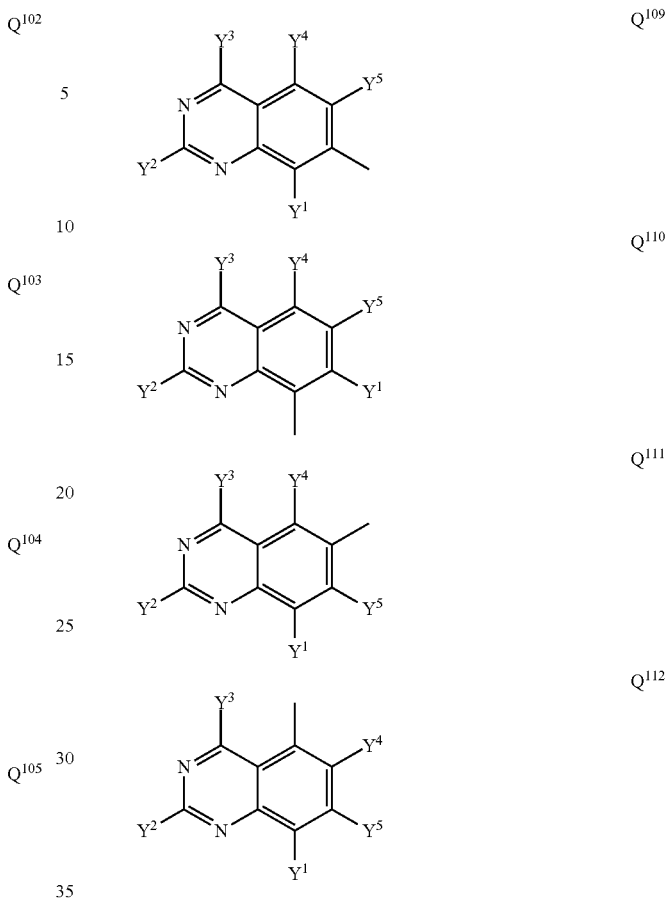

wherein $Y^1$ to $Y^{11}$ independently represent a hydrogen atom, a nitro group, a hydroxy group, a cyano group, an amino group, a sulphenyl group, a formyl group, a substituted or non-substituted carbaldehyde O—($C_1$-$C_8$-alkyl)oxime, a formyloxy group, a formylamino group, a carbamoyl group, a N-hydroxycarbamoyl group, a pentafluoro-$\lambda^6$-sulphenyl group, a formylamino group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$-alkyl-($C_1$-$C_8$-alkylamino)-amino group, a substituted or non-substituted (hydroxyimino)-$C_1$-$C_8$-alkyl group, substituted or non-substituted $C_1$-$C_8$-alkyl, substituted or non-substituted tri($C_1$-$C_8$-alkyl)silyl-$C_1$-$C_8$-alkyl, substituted or non-substituted $C_1$-$C_8$-cycloalkyl, substituted or non-substituted tri($C_1$-$C_8$-alkyl)silyl-$C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-$C_1$-$C_8$-alkylcarbamoylamino, substituted or non-substituted di-$C_1$-$C_8$-halogenoalkylcarbamoylamino having 1 to 5 halogen atoms, substituted or non-substituted N—$C_1$-$C_8$-alkyl-($C_1$-$C_8$-alkylcarbamoyl)amino, substituted or non-substituted N—$C_1$-$C_8$-alkyl-($C_1$-$C_8$-halogenoalkylcarbamoyl)amino having 1 to 5 halogen atoms, substituted or non-substituted N—$C_1$-$C_8$-alkyl-(di-$C_1$-$C_8$-alkylcarbamoyl)amino, substituted or non-substituted N—$C_1$-$C_8$-alkyl-(di-$C_1$-$C_8$-halogenoalkylcarbamoyl)amino having 1 to 5 halogen atoms, substituted or non-substituted $C_1$-$C_8$-alkylaminocarbonyloxy, substituted or non-substituted di-$C_1$-$C_8$-alkylaminocarbonyloxy, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyll, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylthioylamino, substituted or non-substituted $C_1$-$C_8$-halogenoalkylthioylamino having 1 to 5 halogen atoms, substituted or non-substituted ($C_1$-$C_8$-alkyl-carbamothioyl)-oxy, substituted or non-substituted substituted or non-substituted (di-$C_1$-$C_8$-alkyl-carbamothioyl)-oxy, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_1$-$C_8$-alkylsulphinyl, substituted or non-substituted $C_1$-$C_8$-halogenoalkylsulphinyl having 1 to 5 halogen atoms, substituted or non-substituted $C_1$-$C_8$-alkylsulphonyl, substituted or non-substituted $C_1$-$C_8$-halogenoalkylsulphonyl having 1 to 5 halogen atoms, substituted or non-substituted $C_1$-$C_8$-alkylaminosulfamoyl, substituted or non-substituted di-$C_1$-$C_8$-alkylaminosulfamoyl, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$-alkynyloxyimino)-$C_1$-$C_6$-alkyl, substituted or non-substituted (benzyloxyimino)-$C_1$-$C_6$-alkyl, substituted or non-substituted benzyloxy, substituted or non-substituted benzylsulphenyl, substituted or non-substituted benzylamino, substituted or non-substituted phenoxy, substituted or non-substituted phenylsulphenyl, substituted or non-substituted phenylamino, substituted or non-substituted aryl, substituted or non-substituted aryl-[$C_1$-$C_8$]-alkyl, substituted or non-substituted tri($C_1$-$C_8$-alkyl)silyloxy, substituted or non-substituted $C_1$-$C_8$-alkylsulfenylamino, substituted or non-substituted $C_1$-$C_8$-halogenoalkylsulphinylamino having 1 to 5 halogen atoms, substituted or non-substituted $C_1$-$C_8$-alkylsulphonylamino, substituted or non-substituted $C_1$-$C_8$-halogenoalkylsulphonylamino having 1 to 5 halogen atoms, substituted or non-substituted $C_1$-$C_8$-alkoxysulphonylamino, substituted or non-substituted $C_1$-$C_8$-halogenoxysulphonylamino having 1 to 5 halogen atoms, substituted or non-substituted tri($C_1$-$C_8$-alkyl)silyl, substituted or non-substituted ($C_1$-$C_6$-alkylideneamino)oxy, substituted or non-substituted ($C_1$-$C_6$-alkenylideneamino)oxy, substituted or non-substituted ($C_1$-$C_6$-alkynylideneamino)oxy, substituted or non-substituted (benzylideneamino)oxy;

$W^1$ independently represents a group as defined for T;

as well as salts, N-oxides, metallic complexes and metalloidic complexes thereof or (E) and (Z) isomers and mixtures thereof; provided that if T represents $T^8$, $T^{11}$, $T^{12}$, $T^{26}$ or $T^{92}$ then $X^1$ does not represent a hydrogen atom; and if T represents $T^{17}$ then $X^1$ does not represent a hydrogen atom nor a substituted or non-substituted $C_1$-$C_8$-alkyl.

Any of the compounds according to the invention can exist as one or more stereoisomers depending on the number of stereogenic units (as defined by the IUPAC rules) in the compound. The invention thus relates equally to all the stereoisomers, and to the mixtures of all the possible stereoisomers, in all proportions. The stereoisomers can be separated according to the methods which are known per se by the man ordinary skilled in the art.

Notably, the stereostructure of the oxime moiety present in the heterocyclyloxime derivative of formula (I) includes (E) or (Z) isomer, and these stereoisomers form part of the present invention.

According to the invention, the following generic terms are generally used with the following meanings:

halogen means fluorine, chlorine, bromine or iodine;

heteroatom can be nitrogen, oxygen or sulphur;

unless indicated otherwise, a group or a substituent that is substituted according to the invention can be substituted by one or more of the following groups or atoms: a halogen atom, a nitro group, a hydroxy group, a cyano group, an amino group, a sulphenyl group, a pentafluoro-$\lambda^6$-sulphenyl group, a formyl group, a substituted or non-substituted carbaldehyde O—($C_1$-$C_8$-alkyl)oxime, a formyloxy group, a formylamino group, a carbamoyl group, a N-hydroxycarbamoyl group, a formylamino group, a (hydroxyimino)-$C_1$-$C_6$-alkyl group, a $C_1$-$C_8$-alkyl, a tri($C_1$-$C_8$-alkyl)silyl-$C_1$-$C_8$-alkyl, $C_1$-$C_8$-cycloalkyl, tri($C_1$-$C_8$-alkyl)silyl-$C_1$-$C_8$-cycloalkyl, a $C_1$-$C_8$-halogenoalkyl having 1 to 5 halogen atoms, a $C_1$-$C_8$-halogenocycloalkyl having 1 to 5 halogen atoms, a $C_2$-$C_8$-alkenyl, a $C_2$-$C_8$-alkynyl, a $C_2$-$C_8$-alkenyloxy, a $C_2$-$C_8$-alkynyloxy, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulphenyl, a $C_1$-$C_8$-halogenoalkylsulphenyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, substituted or non-substituted $C_1$-$C_8$-alkoxycarbonylamino, substituted or non-substituted $C_1$-$C_8$-halogenoalkoxycarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkylsulphonyl having 1 to 5 halogen atoms, a $C_1$-$C_8$-alkylaminosulfamoyl, a di-$C_1$-$C_8$-alkylaminosulfamoyl, a ($C_1$-$C_6$-alkoxyimino)-$C_1$-$C_6$alkyl, a ($C_1$-$C_6$-alkenyloxyimino)-$C_1$-$C_6$-alkyl, a ($C_1$-$C_6$-alkynyloxyimino)-$C_1$-$C_6$-alkyl, (benzyloxyimino)-$C_1$-$C_6$-alkyl, $C_1$-$C_8$-alkoxyalkyl, $C_1$-$C_8$-halogenoalkoxyalkyl having 1 to 5 halogen atoms, benzyloxy, benzylsulphenyl, benzylamino, phenoxy, phenylsulphenyl, or phenylamino;

the term "aryl" means phenyl or naphthyl;

The term "heterocyclyl" means saturated or unsaturated 4-, 5-, 6- or 7-membered heterocyclyl comprising up to 4 heteroatoms selected in the list consisting of N, O, S.

Preferred compounds of formula (I) according to the invention are those wherein $L^1$ represents a direct bond or a divalent group selected in the list consisting of —$(CR^1R^2)_n$—
—C(=O)—$(CR^1R^2)_p$—$(CR^1R^2)_m$—O— —$(CR^1R^2)_m$—
C(=O)—O——$(CR^1R^2)_m$—NH— —$(CR^1R^2)_m$—C(=O)—NH——$(CR^1R^2)_m$—C(=O)— —$(CR^1R^2)_m$—NH—C(=O)

wherein n represents 1 or 2;

m and p independently represent 0 or 1;

$R^1$ and $R^2$ independently represent a hydrogen atom, a halogen atom, a cyano group, substituted or non-substituted $C_1$-$C_8$-alkyl, substituted or non-substituted $C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms.

More preferred compounds of formula (I) according to the invention are those wherein $L^1$ represents a direct bond or a divalent group selected in the list consisting of —$(CR^1R^2)$—, —C(=O)—$(CR^1R^2)$— and —C(=O)—; wherein $R^1$ and $R^2$ are independently selected in the list consisting of hydrogen, halogen, methyl, ethyl, isopropyl, trifluoromethyl, difluoromethyl, allyl, ethynyl, propargyl, cyclopropyl, methoxy, trifluoromethoxy and cyano.

Other preferred compounds of formula (I) according to the invention are those wherein T is selected in the list consisting of $T^{73}$ to $T^{92}$. Other more preferred compounds of formula (I) according to the invention are those wherein T is selected in the list consisting of $T^{73}$ to $T^{84}$.

Other preferred compounds of formula (I) according to the invention are those wherein $X^1$ to $X^6$ independently represent a hydrogen atom, a halogen atom, a cyano group, an amino group, a sulphenyl group, a pentafluoro-$\lambda^6$-sulphenyl group, substituted or non-substituted $C_1$-$C_8$-alkyl, substituted or non-substituted tri($C_1$-$C_8$-alkyl)silyl-$C_1$-$C_8$-alkyl, substituted or non-substituted $C_1$-$C_8$-cycloalkyl, substituted or non-substituted tri($C_1$-$C_8$-alkyl)silyl-$C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyll, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_1$-$C_8$-alkylsulphonyl, substituted or non-substituted $C_1$-$C_8$-halogenoalkylsulphonyl having 1 to 5 halogen atoms, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$-alkynyloxyimino)-$C_1$-$C_6$-alkyl, substituted or non-substituted (benzyloxyimino)-$C_1$-$C_6$-alkyl, substituted or non-substituted benzyloxy, substituted or non-substituted benzylsulphenyl, substituted or non-substituted phenoxy, substituted or non-substituted phenylsulphenyl, substituted or non-substituted aryl, substituted or non-substituted aryl-[$C_1$-$C_8$]-alkyl, substituted or non-substituted tri($C_1$-$C_8$-alkyl)-silyloxy, substituted or non-substituted tri($C_1$-$C_8$-alkyl)-silyl.

Other more preferred compounds of formula (I) according to the invention are those wherein $X^1$ to $X^6$ independently represent a hydrogen atom, a halogen atom, methyl, isopropyl, isobutyl, tertbutyl, trifluoromethyl, difluoromethyl, allyl, ethynyl, propargyl, cyclopropyl, benzyl, phenethyl, methoxy, trifluoromethoxy, acetyl, trifluoroacetyl and cyano.

Other preferred compounds of formula (I) according to the invention are those wherein $W^1$ represents a hydrogen atom, a halogen atom, a cyano group, substituted or non-substituted $C_1$-$C_8$-alkyl, substituted or non-substituted $C_1$-$C_8$-cycloalkyl, substituted or non-substituted $C_1$-$C_8$-halogenoalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted phenoxy, substituted or non-substituted aryl, substituted or non-substituted aryl-[$C_1$-$C_8$]-alkyl.

Other more preferred compounds of formula (I) according to the invention are those wherein $W^1$ represents a hydrogen atom, a halogen atom, methyl, ethyl, isopropyl, isobutyl, terbutyl, trifluoromethyl, difluoromethyl, allyl, ethynyl, propargyl, cyclopropyl, methoxy, trifluoromethoxy and cyano.

Other preferred compounds of formula (I) according to the invention are those wherein A is selected in the list consisting of $A^1$ to $A^{58}$.

Other more preferred compounds of formula (I) according to the invention are those wherein A is selected in the list consisting of $A^2$, $A^6$, $A^8$, $A^{11}$ to $A^{18}$.

Other preferred compounds of formula (I) according to the invention are those wherein $Z^1$ represents a hydrogen atom, a halogen atom, a hydroxy group, a cyano group, an amino group, a formyloxy group, a formylamino group, a carbamoyl group, a N-hydroxycarbamoyl group, a pentafluoro-$\lambda^6$-sulphenyl group, a formylamino group, substituted or non-substituted $C_1$-$C_8$-alkoxyamino group, substituted or non-substituted N—$C_1$-$C_8$-alkyl-($C_1$-$C_8$-alkoxy)-amino group, a substituted or non-substituted (hydroxyimino)-$C_1$-$C_6$-alkyl group, substituted or non-substituted $C_1$-$C_8$-alkyl, substituted or non-substituted tri($C_1$-$C_8$-alkyl)silyl-$C_1$-$C_8$-alkyl, substituted or non-substituted $C_1$-$C_8$-cycloalkyl, substituted or non-substituted tri($C_1$-$C_8$-alkyl)silyl-$C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-alogenoalkylcarbonylamino having 1 to 5 halogen atoms, substituted or non-substituted ($C_1$-$C_8$-alkoxycarbonyl)amino, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-$C_1$-$C_8$-alkylcarbamoylamino, substituted or non-substituted di-$C_1$-$C_8$-halogenoalkylcarbamoylamino having 1 to 5 halogen atoms, substituted or non-substituted N—$C_1$-$C_8$-alkyl-($C_1$-$C_8$-alkylcarbamoyl)amino, substituted or non-substituted N—$C_1$-$C_8$-alkyl-($C_1$-$C_8$-halogenoalkylcarbamoyl)amino having 1 to 5 halogen atoms, substituted or non-substituted N—$C_1$-$C_8$-alkyl-(di-$C_1$-$C_8$-alkylcarbamoyl)amino, substituted or non-substituted N—$C_1$-$C_8$-alkyl-(di-$C_1$-$C_8$-halogenoalkylcarbamoyl)amino having 1 to 5 halogen atoms, substituted or non-substituted $C_1$-$C_8$-alkylaminocarbonyloxy, substituted or non-substituted di-$C_1$-$C_8$-alkylaminocarbonyloxy, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyl, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylthioylamino, substituted or non-substituted $C_1$-$C_8$-halogenoalkylthioylamino having 1 to 5 halogen atoms, substituted or non-substituted ($C_1$-$C_8$-alkylcarbamothioyl)-oxy, substituted or non-substituted substituted or non-substituted (di-$C_1$-$C_8$-alkyl-carbamothioyl)-oxy, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_1$-$C_8$-alkylaminosulfamoyl, substituted or non-substituted di-$C_1$-$C_8$-alkylaminosulfamoyl, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$-alkynyloxyimino)-$C_1$-$C_6$-alkyl, substituted or non-substituted (benzyloxyimino)-$C_1$-$C_6$-alkyl, substituted or non-substituted benzyloxy, substituted or non-substituted benzylsulphenyl, substituted or non-substituted benzylamino, substituted or non-substituted phenoxy, substituted or non-substituted phenylsulphenyl, substituted or non-substituted phenylamino, substituted or non-substituted aryl, substituted or non-substituted aryl-[$C_1$-$C_8$]-alkyl, substituted or non-substituted tri($C_1$-$C_8$-alkyl)-silyloxy, substituted or non-substituted $C_1$-$C_8$-halogenoalkylsulphinylamino having 1 to 5 halogen atoms, substituted or non-substituted $C_1$-$C_8$-alkylsulphonylamino, substituted or non-substituted $C_1$-$C_8$-halogenoalkylsulphonylamino having 1 to 5 halogen atoms, substituted or non-substituted $C_1$-$C_8$-alkoxysulphonylamino, substituted or non-substituted $C_1$-$C_8$-halogenoxysulphonylamino having 1 to 5 halogen atoms, substituted or non-substituted tri($C_1$-$C_8$-alkyl)-silyl, substituted or non-substituted ($C_1$-$C_6$-alkylideneamino)oxy, substituted or non-substituted ($C_1$-$C_6$-alkenylideneamino)oxy, substituted or non-substituted ($C_1$-$C_6$-alkynylideneamino)oxy, substituted or non-substituted (benzylideneamino)oxy.

Other more preferred compounds of formula (I) according to the invention are those wherein $Z^1$ represents a hydrogen atom, a halogen atom, a cyano group, an amino group, a formyloxy group, a formylamino group, a carbamoyl group, a N-hydroxycarbamoyl group, a formylamino group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted $C_1$-$C_8$-alkyl, substituted or non-substituted tri($C_1$-$C_8$-alkyl)silyl-$C_1$-$C_8$-alkyl, substituted or non-substituted $C_1$-$C_8$-cycloalkyl, substituted or non-substituted $C_1$-$C_8$-halogenoalkyl having 1 to 5 halogen atoms, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulphenyl, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted $C_1$-$C_8$- alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkylcarbonylamino, substituted or non-substituted ($C_1$-$C_8$-alkoxycarbonyl)amino, substituted or non-substituted $C_1$-$C_8$-halogenoalkylcarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-$C_1$-$C_8$-alkylcarbamoylamino, substituted or non-substituted di-$C_1$-$C_8$-halogenoalkylcarbamoylamino having 1 to 5 halogen atoms, substituted or non-substituted N—$C_1$-$C_8$-alkyl-($C_1$-$C_8$-alkylcarbamoyl)amino, substituted or non-substituted N—$C_1$-$C_8$-alkyl-($C_1$-$C_8$-halogenoalkylcarbamoyl)amino having 1 to 5 halogen atoms, substituted or non-substituted N—$C_1$-$C_8$-alkyl-(di-$C_1$-$C_8$-alkylcarbamoyl)amino, substituted or non-substituted N—$C_1$-$C_8$-alkyl-(di-$C_1$-$C_8$-halogenoalkylcarbamoyl)amino having 1 to 5 halogen atoms, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyl, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylthioylamino, substituted or non-substituted $C_1$-$C_8$-halogenoalkylthioylamino having 1 to 5 halogen atoms, substituted or non-substituted benzylamino, substituted or non-substituted phenoxy, substituted or non-substituted phenylamino, substituted or non-substituted aryl, substituted or non-substituted aryl-[$C_1$-$C_8$]-alkyl, substituted or non-substituted $C_1$-$C_8$-halogenoalkylsulphinylamino having 1 to 5 halogen atoms, substituted or non-substituted $C_1$-$C_8$-alkylsulphonylamino, substituted or non-substituted $C_1$-$C_8$-halogenoalkylsulphonylamino having 1 to 5 halogen atoms.

Other preferred compounds of formula (I) according to the invention are those wherein $Z^2$ to $Z^9$ independently represent a hydrogen atom, a halogen atom, a cyano group, substituted or non-substituted $C_1$-$C_8$-alkyl, substituted or non-substituted $C_1$-$C_8$-cycloalkyl, substituted or non-substituted $C_1$-$C_8$-halogenoalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted phenoxy, substituted or non-substituted aryl, substituted or non-substituted aryl-[$C_1$-$C_8$]-alkyl.

Other more preferred compounds of formula (I) according to the invention are those wherein $Z^2$ to $Z^9$ are independently selected in the list consisting of hydrogen, halogen, methyl, ethyl, isopropyl, isobutyl, terbutyl, trifluoromethyl, difluoromethyl, allyl, ethynyl, propargyl, cyclopropyl, methoxy, trifluoromethoxy, acetyl, and cyano.

Other preferred compounds of formula (I) according to the invention are those wherein $K^1$ and $K^2$ are independently selected in the list consisting of hydrogen, methyl, ethyl, isopropyl, isobutyl, terbutyl, allyl, propargyl, cyclopropyl, acetyl, trifluoroacetyl and mesyl.

Other preferred compounds of formula (I) according to the invention are those wherein Q is selected in the list consisting of $Q^1$, $Q^{15}$, $Q^{16}$, $Q^{18}$, $Q^{19}$, $Q^{21}$, $Q^{24}$, $Q^{27}$, $Q^{85}$, $Q^{86}$, $Q^{87}$, $Q^{88}$, $Q^{89}$, $Q^{90}$, $Q^{91}$.

Other preferred compounds of formula (I) according to the invention are those wherein $Y^1$ to $Y^{11}$ independently represent a hydrogen atom, a halogen atom, a cyano group, an amino group, a sulphenyl group, a pentafluoro-$\lambda^6$-sulphenyl group, substituted or non-substituted $C_1$-$C_8$-alkyl, substituted or non-substituted tri($C_1$-$C_8$-alkyl)silyl-$C_1$-$C_8$-alkyl, substituted or non-substituted $C_1$-$C_8$-cycloalkyl, substituted or non-substituted tri($C_1$-$C_8$-alkyl)silyl-$C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyll, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_1$-$C_8$-alkylsulphonyl, substituted or non-substituted $C_1$-$C_8$-halogenoalkylsulphonyl having 1 to 5 halogen atoms, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$-alkynyloxyimino)-$C_1$-$C_6$-alkyl, substituted or non-substituted (benzyloxyimino)-$C_1$-$C_6$-alkyl, substituted or non-substituted benzyloxy, substituted or non-substituted benzylsulphenyl, substituted or non-substituted phenoxy, substituted or non-substituted phenylsulphenyl, substituted or non-substituted aryl, substituted or non-substituted aryl-[$C_1$-$C_8$]-alkyl, substituted or non-substituted tri($C_1$-$C_8$-alkyl)-silyloxy, substituted or non-substituted tri($C_1$-$C_8$-alkyl)-silyl.

Other more preferred compounds of formula (I) according to the invention are those wherein $Y^1$ to $Y^{11}$ independently represent a hydrogen atom, a halogen atom, methyl, isopropyl, isobutyl, tertbutyl, trifluoromethyl, difluoromethyl, allyl, ethynyl, propargyl, cyclopropyl, methoxy, trifluoromethoxy and cyano.

The above mentioned preferences with regard to the substituents of the compounds of formula (I) according to the invention can be combined in various manners. These combinations of preferred features thus provide sub-classes of compounds according to the invention. Examples of such sub-classes of preferred compounds according to the invention can combine:

preferred features of A with preferred features of one or more of $L^1$, T and Q;

preferred features of $L^1$ with preferred features of one or more of A, T and Q;

preferred features T with preferred features of one or more of A, $L^1$ and Q;

preferred features of Q with preferred features of one or more of A, $L^1$ and T.

In these combinations of preferred features of the substituents of the compounds according to the invention, the said preferred features can also be selected among the more preferred features of each of A, $L^1$, T and Q; so as to form most preferred subclasses of compounds according to the invention.

The preferred features of the other substituents of the compounds according to the invention can also be part of such sub-classes of preferred compounds according to the invention, notably the groups of substituents $X^1$ to $X^6$, n, m, $R^1$, $R^2$, $Z^1$ to $Z^9$, $K^1$, $K^2$, $G^1$, $G^2$, $Y^1$ to $Y^{11}$ and $W^1$.

The present invention also relates to a process for the preparation of compounds of formula (I), Thus, according to a further aspect of the present invention, there is a provided a process P1 for the preparation of compounds of formula (I), as herein-defined, as illustrated by the following reaction schemes.

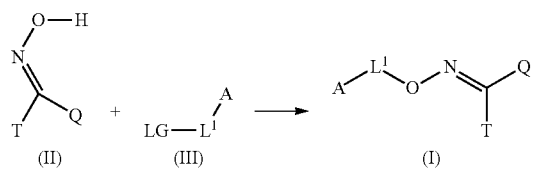

wherein T, A, Q and $L^1$ are as herein-defined and LG represents a leaving group. Suitable leaving groups can be selected in the list consisting of a halogen atom or other customary nucleofugal groups such as triflate, mesylate, or tosylate.

For the compounds of formula (Ia) according to the invention when $Z^1$, $Z^2$, $Z^3$, $Z^4$, $Z^5$, $Z^6$, $Z^7$, $Z^8$ or $Z^9$ represents a hydroxyl group, a sulphenyl group, an amino group, substituted or non-substituted $C_1$-$C_8$-alkylamino, substituted or non-substituted $C_1$-$C_8$-halogenoalkylamino having 1 to 5 halogen atoms, a formylamino group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$-alkyl-($C_1$-$C_8$-alkylamino)-amino group, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkoxycarbonylamino, substituted or non-substituted $C_1$-$C_8$-halogenoalkoxycarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-$C_1$-$C_8$-alkylcarbamoylamino, substituted or non-substituted $C_1$-$C_8$-alkylthioylamino, substituted or non-substituted $C_1$-$C_8$-halogenoalkylthioylamino having 1 to 5 halogen atoms, substituted or non-substituted ($C_1$-$C_8$-alkyl-carbamothioyl)-amino, substituted or non-substituted (di-$C_1$-$C_8$-alkyl-carbamothioyl)-amino, process P1 according to the invention can be completed by a further step comprising the additional modification of this group, notably by a reaction of alkylation, acylation, alkoxycarbonylation, alkylaminocarbonylation and alkylaminothiocarbonylation, to yield to a compound of formula (Ib), according to known methods. In such a case there is provided a process P2 according to the invention and such a process P2 can be illustrated by the following reaction schemes:

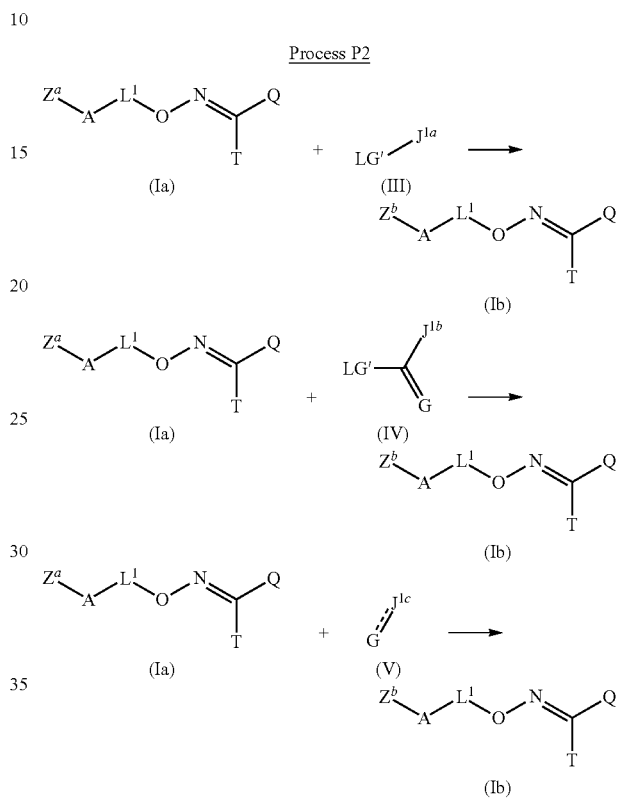

wherein

T, A, Q and $L^1$ are as herein-defined, LG' represents a leaving group, $J^{1a}$ optionally represents substituted or non-substituted $C_1$-$C_8$-alkyl, substituted or non-substituted $C_1$-$C_8$-halogenoalkyl having 1 to 5 halogen atoms, $J^{1b}$ optionally represents a hydrogen atom, substituted or non-substituted $C_1$-$C_8$-alkyl, substituted or non-substituted $C_1$-$C_8$-halogenoalkyl having 1 to 5 halogen atoms, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, $J^{1c}$ optionally represents substituted or non-substituted $C_1$-$C_8$-alkylamino;

$Z^a$ represents a hydroxyl group, a sulphenyl group, an amino group, substituted or non-substituted $C_1$-$C_8$-alkylamino, substituted or non-substituted $C_1$-$C_8$-halogenoalkylamino having 1 to 5 halogen atoms, a formylamino group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$-alkyl-($C_1$-$C_8$-alkylamino)-amino group, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkoxycarbonylamino, substituted or non-substituted $C_1$-$C_8$-halogenoalkoxycarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-$C_1$-$C_8$-alkylcarbamoylamino, substituted or non-substituted $C_1$-$C_8$-alkylthioylamino, substituted or non-substituted $C_1$-$C_8$-halogenoalkylthioylamino having 1 to 5 halogen atoms, substituted or non-substituted ($C_1$-$C_8$-alkyl-carbamothioyl)-amino, substituted or non-substituted (di-$C_1$-$C_8$-alkyl-carbamothioyl)-amino, G represents an oxygen atom or a sulphur atom;

$Z^b$ represents a formyloxy group, a formylamino group, a formylamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$-alkyl-($C_1$-$C_8$-alkylamino)-amino group, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkoxycarbonylamino, substituted or non-substituted $C_1$-$C_8$-halogenoalkoxycarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-$C_1$-$C_8$-alkylcarbamoylamino, substituted or non-substituted di-$C_1$-$C_8$-halogenoalkylcarbamoylamino having 1 to 5 halogen atoms, substituted or non-substituted N—$C_1$-$C_8$-alkyl-($C_1$-$C_8$-alkylcarbamoyl)amino, substituted or non-substituted N—$C_1$-$C_8$-alkyl-($C_1$-$C_8$-halogenoalkylcarbamoyl)amino having 1 to 5 halogen atoms, substituted or non-substituted N—$C_1$-$C_8$-alkyl-(di-$C_1$-$C_8$-alkylcarbamoyl)amino, substituted or non-substituted N—$C_1$-$C_8$-alkyl-(di-$C_1$-$C_8$-halogenoalkylcarbamoyl) amino having 1 to 5 halogen atoms, substituted or non-substituted $C_1$-$C_8$-alkylaminocarbonyloxy, substituted or non-substituted di-$C_1$-$C_8$-alkylaminocarbonyloxy, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyll, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted ($C_1$-$C_8$-alkyl-carbamothioyl)-amino, substituted or non-substituted substituted or non-substituted (di-$C_1$-$C_8$-alkyl-carbamothioyl)-amino, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted benzyloxy, substituted or non-substituted benzylsulphenyl, substituted or non-substituted benzylamino, substituted or non-substituted tri($C_1$-$C_8$-alkyl)-silyloxy.

Suitable leaving groups can be selected in the list consisting of a halogen atom or other customary nucleofugal groups such as alcoolate, hydroxide or cyanide.

For the compounds of formula (Ic) according to the invention when $Z^1$, $Z^2$, $Z^3$, $Z^4$, $Z^5$, $Z^6$, $Z^7$, $Z^8$ or $Z^9$ represent a substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyl, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylthioylamino, substituted or non-substituted $C_1$-$C_8$-halogenoalkylthioylamino having 1 to 5 halogen atoms, substituted or non-substituted ($C_1$-$C_8$-alkyl-carbamothioyl)-oxy, substituted or non-substituted substituted or non-substituted (di-$C_1$-$C_8$-alkyl-carbamothioyl)-oxy, substituted or non-substituted ($C_1$-$C_8$-alkyl-carbamothioyl)-amino, substituted or non-substituted substituted or non-substituted (di-$C_1$-$C_8$-alkyl-carbamothioyl)-amino, process P1 according to the invention can be completed by a further step comprising the additional modification of this group, notably by a reaction of thiocarbonylation in the presence of a thiocarbonylating agent such as 2,4-bis(4-methoxyphenyl)-1,3,2,4-dithiadiphosphetane 2,4-disulfide, phosphorus pentasulfide, sulphur to yield to a compound of formula (Id), according to known methods. In such a case there is provided a process P3 according to the invention and such a process P3 can be illustrated by the following reaction schemes:

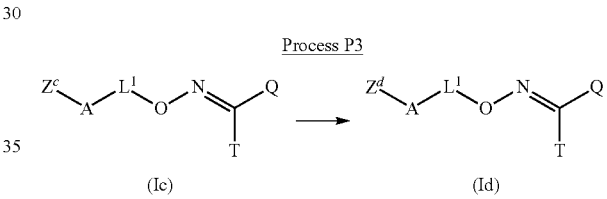

Process P3

(Ic) → (Id)

wherein

T, A, Q and $L^1$ are as herein-defined, $Z^c$ represents a substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted ($C_1$-$C_8$-alkyl-carbamoyl)-oxy, substituted or non-substituted substituted or non-substituted (di-$C_1$-$C_8$-alkyl-carbamoyl)-oxy, substituted or non-substituted ($C_1$-$C_8$-alkyl-carbamoyl)-amino, substituted or non-substituted substituted or non-substituted (di-$C_1$-$C_8$-alkyl-carbamoyl)-amino, And $Z^d$ represents a substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyl, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylthioylamino, substituted or non-substituted $C_1$-$C_8$-halogenoalkylthioylamino having 1 to 5 halogen atoms, substituted or non-substituted ($C_1$-$C_8$-alkyl-carbamothioyl)-oxy, substituted or non-substituted substituted or non-substituted (di-$C_1$-$C_8$-alkyl-carbamothioyl)-oxy, substituted or non-substituted ($C_1$-$C_8$-alkyl-carbamothioyl)-amino, substituted or non-substituted substituted or non-substituted (di-$C_1$-$C_8$-alkyl-carbamothioyl)-amino.

For the compounds of formula (Ie) according to the invention when $Z^1$, $Z^2$, $Z^3$, $Z^4$, $Z^5$, $Z^6$, $Z^7$, $Z^8$ or $Z^9$ represent a hydroxy group, a cyano group, an amino group, a sulphenyl group, a formyloxy group, a formylamino group, a carbamoyl group, a N-hydroxycarbamoyl group, a formylamino group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$-alkyl-($C_1$-$C_8$-alkylamino)-amino group, substituted or non-substituted $C_1$-$C_8$-alkyl, substituted or non-substituted tri($C_1$-$C_8$-alkyl)silyl-$C_1$-$C_8$-alkyl, substituted or non-substituted $C_1$-$C_8$-cycloalkyl, substituted or non-substituted tri($C_1$-$C_8$-alkyl)silyl-$C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkoxycarbonylamino, substituted or non-substituted $C_1$-$C_8$-halogenoalkoxycarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-$C_1$-$C_8$-alkylcarbamoylamino, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted benzyloxy, substituted or non-substituted benzylsulphenyl, substituted or non-substituted benzylamino, substituted or non-substituted phenoxy, substituted or non-substituted phenylsulphenyl, substituted or non-substituted phenylamino, substituted or non-substituted aryl, substituted or non-substituted aryl-[$C_1$-$C_8$]-alkyl, process P1 according to the invention can be completed by a further step comprising the additional modification of this group, notably by a reaction of nucleophilic substitution to yield to a compound of formula (If), according to known methods, optionally in the presence of carbon monoxide or a carbon monoxide generating agent such as $Mo(CO)_6$ or $W(CO)_6$, optionally in the presence of a catalyst notably a transition metal catalyst, such as palladium salts or complexes for example palladium (II) chloride, palladium (II) acetate, tetrakis-(triphenylphosphine)palladium(0), bis-(triphenylphosphine)palladium dichloride (II), tris(dibenzylideneacetone)dipalladium(0), bis(dibenzylideneacetone)palladium(0), or 1,1'-bis(diphenylphosphino)ferrocene-palladium (II) chloride. As an alternative the palladium complex is directly generated in the reaction mixture by separately adding to the reaction mixture a palladium salt and a complex ligand such as a phosphine, for example triethylphosphine, tri-tert-butylphosphine, tricyclohexylphosphine, 2-(dicyclohexylphosphine)biphenyl, 2-(di-tert-butylphosphin)biphenyl, 2-(dicyclohexylphosphine)-2'-(N,N-dimethylamino)-biphenyl, triphenylphosphine, tris-(o-tolyl)phosphine, sodium 3-(diphenylphosphino) benzolsulfonate, tris-2-(methoxyphenyl)phosphine, 2,2'-bis-(diphenylphosphine)-1,1'-binaphthyl, 1,4-bis-(diphenylphosphine)butane, 1,2-bis-(diphenylphosphine) ethane, 1,4-bis-(dicyclohexylphosphine)butane, 1,2-bis-(dicyclohexylphosphine)ethane, 2-(dicyclohexylphosphine)-2'-(N,N-dimethylamino)-biphenyl, bis(diphenylphosphino) ferrocene, tris-(2,4-tert-butylphenyl)-phosphite, (R)-(−)-1-[(S)-2-(diphenylphosphino)ferrocenyl]ethyldi-tert-butylphosphine, (S)-(+)-1-[(R)-2-(diphenylphosphino) ferrocenyl]ethyldicyclohexylphosphine, (R)-(−)-1-[(S)-2-(diphenylphosphino)ferrocenyl] ethyldicyclohexylphosphine, (S)-(+)-1-[(R)-2-(diphenylphosphino)ferrocenyl]ethyldi-t-butylphosphine, optionally in the presence of a base such as an inorganic or an organic base; preferably an alkaline earth metal or alkali metal hydride, hydroxide, amide, alcoholate, acetate, carbonate or hydrogen carbonate, such as sodium hydride, sodium amide, lithium diisopropylamide, sodium methanolate, sodium ethanolate, potassium tert-butanolate, sodium acetate, potassium acetate, calcium acetate, sodium hydroxide, potassium hydroxide, sodium carbonate, potassium carbonate, potassium bicarbonate, sodium bicarbonate, cesium carbonate or ammonium carbonate; and also tertiary amine, such as trimethylamine, triethylamine (TEA), tributylamine, N,N-dimethylaniline, N,N-dimethyl-benzylamine, N,N-diisopropyl-ethylamine (DIPEA), pyridine, N-methylpiperidine, N-methylmorpholine, N,N-dimethylaminopyridine, diazabicyclooctane (DABCO), diazabicyclononene (DBN) or diazabicycloundecene (DBU), to yield a compound of formula (I). In such a case there is provided a process P4 according to the invention and such a process P4 can be illustrated by the following reaction scheme:

Process P4

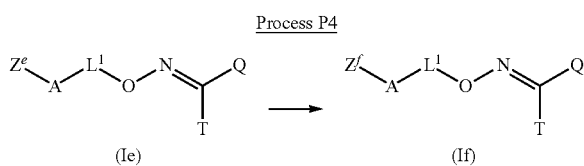

(Ie) (If)

wherein

T, A, Q and $L^1$ are as herein-defined as herein-defined, $Z^e$ represents a halogen atom, and $Z^f$ represents a hydroxy group, a cyano group, an amino group, a sulphenyl group, a formyloxy group, a formylamino group, a carbamoyl group, a N-hydroxycarbamoyl group, a formylamino group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$-alkyl-($C_1$-$C_8$-alkylamino)-amino group, substituted or non-substituted $C_1$-$C_8$-alkyl, substituted or non-substituted tri($C_1$-$C_8$-alkyl)silyl-$C_1$-$C_8$-alkyl, substituted or non-substituted $C_1$-$C_8$-cycloalkyl, substituted or non-substituted tri($C_1$-$C_8$-alkyl)silyl-$C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkoxycarbonylamino, substituted or non-substituted $C_1$-$C_8$-halogenoalkoxycarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-$C_1$-$C_8$-alkylcarbamoylamino, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted benzyloxy, substituted or non-substituted benzylsulphenyl, substituted or non-substituted benzylamino, substituted or non-substituted phenoxy, substituted or non-substituted phenylsulphenyl, substituted or non-substituted phenylamino, substituted or non-substituted aryl, substituted or non-substituted aryl-[$C_1$-$C_8$]-alkyl.

If $Z^1$, $Z^2$, $Z^3$, $Z^4$, $Z^5$, $Z^6$, $Z^7$, $Z^8$ or $Z^9$ represent a protected amino group, carrying out process P2 would previously require a deprotection step in order to yield the amino group. Amino-protecting groups and related methods of cleavage thereof are known and can be found in T. W. Greene and P. G. M. Wuts, *Protective Group in Organic Chemistry*, $3^{rd}$ ed., John Wiley & Sons.

According to the invention, processes P1 and P2 may be performed if appropriate in the presence of a solvent and if appropriate in the presence of a base.

According to the invention, processes P1 and P2 may be performed if appropriate in the presence of a catalyst. Suitable catalyst may be chosen as being 4-dimethyl-aminopyridine, 1-hydroxy-benzotriazole or dimethylformamide.

In case LG' represents a hydroxy group, the process P2 according to the present invention may be performed in the presence of condensing agent. Suitable condensing agent may be chosen as being acid halide former, such as phosgene, phosphorus tri-bro-mide, phosphorus trichloride, phosphorus pentachloride, phosphorus trichloride oxide or thionyl chloride; anhydride former, such as ethyl chloroformate, methyl chloroformate, isopropyl chloroformate, isobutyl chloroformate or methanesulfonyl chloride; carbodiimides, such as N,N'-dicyclohexylcarbodiimide (DCC) or other customary condensing agents, such as phosphorus pentoxide, polyphosphoric acid, N,N'-carbonyl-diimidazole, 2-ethoxy-N-ethoxycarbonyl-1,2-dihydroquinoline (EEDQ), triphenylphosphine/tetrachloromethane, 4-(4,6-dimethoxy[1.3.5]triazin-2-yl)-4-methylmorpholinium chloride hydrate or bromotripyrrolidino-phosphonium-hexafluorophosphate.

Suitable solvents for carrying out processes P1 to P4 according to the invention are customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichlorethane or trichlorethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or iso-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide, or sulphones, such as sulpholane.

Suitable bases for carrying out processes P1 and P2 according to the invention are inorganic and organic bases which are customary for such reactions. Preference is given to using alkaline earth metal, alkali metal hydride, alkali metal hydroxides or alkali metal alkoxides, such as sodium hydroxide, sodium hydride, calcium hydroxide, potassium hydroxide, potassium tert-butoxide or other ammonium hydroxide, alkali metal carbonates, such as sodium carbonate, potassium carbonate, potassium bicarbonate, sodium bicarbonate, cesium carbonate, alkali metal or alkaline earth metal acetates, such as sodium acetate, potassium acetate, calcium acetate, and also tertiary amines, such as trimethylamine, triethylamine, diisopropylethylamine, tributylamine, N,N-dimethylaniline, pyridine, N-methylpiperidine, N,N-dimethylaminopyridine, 1,4-diazabicyclo[2.2.2]octane (DABCO), 1,5-diazabicyclo[4.3.0]non-5-ene (DBN) or 1,8-diaza-bicyclo[5.4.0]undec-7-ene (DBU).

When carrying out processes P1 and P4 according to the invention, the reaction temperature can independently be varied within a relatively wide range. Generally, process P1 according to the invention is carried out at temperatures between −80° C. and 160° C.

Processes P1 to P4 according to the invention are generally independently carried out under atmospheric pressure. However, it is also possible to operate under elevated or reduced pressure.

Work-up is carried out by customary methods. Generally, the reaction mixture is treated with water and the organic phase is separated off and, after drying, concentrated under reduced pressure. If appropriate, the remaining residue can be freed by customary methods, such as chromatography or recrystallization, from any impurities that may still be present.

Compounds according to the invention can be prepared according to the above described processes. It will nevertheless be understood that, on the basis of his general knowledge and of available publications, the skilled worker will be able to adapt these processes according to the specifics of each of the compounds according to the invention that is desired to be synthesised.

When T represents a compound of formula $T^2$ to $T^{19}$, $T^{21}$ to $T^{34}$, $T^{37}$ to $T^{39}$, $T^{41}$, $T^{43}$ to $T^{74}$, $T^{78}$ to $T^{80}$, $T^{82}$ to $T^{117}$ as described previously, the compounds of formula (II), useful as a starting material, can be prepared, for example, by reacting hydroxylamine with the corresponding ketones that can be prepared, for example, according to the method described by R. Raap (*Can. J. Chem.* 1971, 49, 2139) or Regel (*Justus Liebigs Annalen der Chemie.* 1977, 1, 145) by addition of an heterocyclic species, in presence of a base, to esters of formula

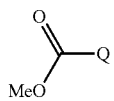

or

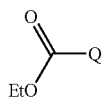

or any of their suitable synthetic equivalents like, for example:

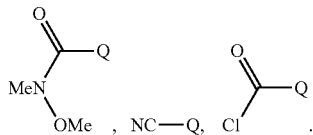

When T represents a compound of formula $T^1$, $T^{20}$, $T^{35}$, $T^{36}$, $T^{40}$, $T^{42}$, $T^{75}$ to $T^{77}$, $T^{81}$ as described previously, the compounds of general formula (II) useful as a starting material, can be prepared, for example, from oximes of formula

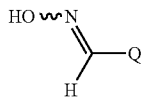

according to the method described by J. Plenkiewicz et al. (*Bull. Soc. Chim. Belg.* 1987, 96, 675) or by De la Hoz (*Journal of Chemical Research, Synopses.* 1987, 7, 240).

In a further aspect, the present invention relates to compounds of formula (II) useful as to intermediate compounds or materials for the process of preparation according to the invention. The present invention thus provides compounds of formula (II) wherein T and Q are as herein-defined:

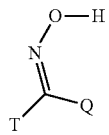

(II)

In a further aspect, the present invention also relates to a fungicide composition comprising an effective and non-phytotoxic amount of an active compound of formula (I).

The expression "effective and non-phytotoxic amount" means an amount of composition according to the invention which is sufficient to control or destroy the fungi present or liable to appear on the crops and which does not entail any appreciable symptom of phytotoxicity for the said crops. Such an amount can vary within a wide range depending on the fungus to be controlled, the type of crop, the climatic conditions and the compounds included in the fungicide composition according to the invention. This amount can be determined by systematic field trials, which are within the capabilities of a person skilled in the art.

Thus, according to the invention, there is provided a fungicide composition comprising, as an active ingredient, an effective amount of a compound of formula (I) as herein defined and an agriculturally acceptable support, carrier or filler.

According to the invention, the term "support" denotes a natural or synthetic organic or inorganic compound with which the active compound of formula (I) is combined or associated to make it easier to apply, notably to the parts of the plant. This support is thus generally inert and should be agriculturally acceptable. The support can be a solid or a liquid. Examples of suitable supports include clays, natural or synthetic silicates, silica, resins, waxes, solid fertilisers, water, alcohols, in particular butanol organic solvents, mineral and plant oils and derivatives thereof. Mixtures of such supports can also be used.

The composition according to the invention can also comprise additional components. In particular, the composition can further comprise a surfactant. The surfactant can be an emulsifier, a dispersing agent or a wetting agent of ionic or non-ionic type or a mixture of such surfactants. Mention can be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols and derivatives of the above compounds containing sulphate, sulphonate and phosphate functions. The presence of at least one surfactant is generally essential if the active compound and/or the inert support are water-insoluble and if the vector agent for the application is water. Preferably, surfactant content can be comprised from 5% to 40% by weight of the composition.

Optionally, additional components can also be included, e.g. protective colloids, adhesives, thickeners, thixotropic agents, penetration agents, stabilisers, sequestering agents. More generally, the active compounds can be combined with any solid or liquid additive, which complies with the usual formulation techniques.

In general, the composition according to the invention can contain from 0.05 to 99% by weight of active compound, preferably 10 to 70% by weight.

Compositions according to the invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry to treatment, water soluble granules or tablets, water soluble powder for seed treatment and wettable powder. These compositions include not only compositions which are ready to be applied to the plant or seed to be treated by means of a suitable device, such as a spraying or dusting device, but also concentrated commercial compositions which must be diluted before application to the crop.

The compounds according to the invention can also be mixed with one or more insecticide, fungicide, bactericide, attractant, acaricide or pheromone active substance or other compounds with biological activity. The mixtures thus obtained have a broadened spectrum of activity. The mixtures with other fungicide compounds are particularly advantageous. The composition according to the invention comprising a mixture of a compound of formula (I) with a bactericide compound can also be particularly advantageous According to another object of the present invention, there is provided a method for controlling the phytopathogenic fungi of plants, crops or seeds, characterized in that an agronomically effective and substantially non-phytotoxic quantity of a pesticide composition according to the invention is applied as seed treatment, foliar application, stem application, drench or drip application (chemigation) to the seed, the plant or to the fruit of the plant or to soil or to inert substrate (e.g. inorganic substrates like sand, rockwool, glasswool; expanded minerals like perlite, vermiculite, zeolite or expanded clay), Pumice, Pyroclastic materials or stuff, synthetic organic substrates (e.g. polyurethane) organic substrates (e.g. peat, composts, tree waste products like coir, wood fibre or chips, tree bark) or to a liquid substrate (e.g. floating hydroponic systems, Nutrient Film Technique, Aeroponics) wherein the plant is growing or wherein it is desired to grow.

The expression "are applied to the plants to be treated" is understood to mean, for the purposes of the present invention, that the pesticide composition which is the subject of the invention can be applied by means of various methods of treatment such as:

spraying onto the aerial parts of the said plants a liquid comprising one of the said compositions, dusting, the incorporation into the soil of granules or powders, spraying, around the said plants and in the case of trees injection or daubing, coating or film-coating the seeds of the said plants with the aid of a plant-protection mixture comprising one of the said compositions.

The method according to the invention can either be a curing, preventing or eradicating method. In this method, a composition used can be prepared beforehand by mixing the two or more compounds according to the invention.

According to an alternative of such a method, it is also possible to apply simultaneously, successively or separately compounds (A) and (B) so as to have the conjugated (A)/(B) effects, of distinct compositions each containing one of the two or three active ingredients (A) or (B).

The dose of active compound usually applied in the method of treatment according to the invention is generally and advantageously for foliar treatments: from 0.1 to 10,000 g/ha, preferably from 10 to 1,000 g/ha, more preferably from 50 to 300 g/ha; in case of drench or drip application, the dose can even be reduced, especially while using inert substrates like rockwool or perlite;

for seed treatment: from 2 to 200 g per 100 kilogram of seed, preferably from 3 to 150 g per 100 kilogram of seed;

for soil treatment: from 0.1 to 10,000 g/ha, preferably from 1 to 5,000 g/ha.

The doses herein indicated are given as illustrative Examples of method according to the invention. A person skilled in the art will know how to adapt the application doses, notably according to the nature of the plant or crop to be treated.

Under specific conditions, for example according to the nature of the phytopathogenic fungus to be treated or controlled, a lower dose can offer adequate protection. Certain climatic conditions, resistance or other factors like the nature of the phytopathogenic fungi or the degree of infestation, for example, of the plants with these fungi, can require higher doses of combined active ingredients. The optimum dose usually depends on several factors, for example on the type of phytopathogenic fungus to be treated, on the type or level of development of the infested plant, on the density of vegetation or alternatively on the method of application.

Without it being limiting, the crop treated with the pesticide composition or combination according to the invention is, for example, grapevine, but this could be cereals, vegetables, lucerne, soybean, market garden crops, turf, wood, tree or horticultural plants.

The method of treatment according to the invention can also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the over-ground parts of the plant such as trunks, stems or stalks, leaves, flowers and fruit of the concerned plant.

Among the plants that can be protected by the method according to the invention, mention can to be made of cotton; flax; vine; fruit or vegetable crops such as *Rosaceae* sp. (for instance pip fruit such as apples and pears, but also stone fruit such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantins), *Rubiaceae* sp., *Theaceae* sp., *Sterculiceae* sp., *Rutaceae* sp. (for instance lemons oranges and grapefruit); *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); major crops such as *Graminae* sp. (for instance maize, lawn or cereals such as wheat, rice, barley and triticale), *Asteraceae* sp. (for instance sunflower), *Cruciferae* sp. (for instance colza), *Fabacae* sp. (for instance peanuts), *Papilionaceae* sp. (for instance soybean), *Solanaceae* sp. (for instance potatoes), *Chenopodiaceae* sp. (for instance beetroots); horticultural and forest crops; as well as genetically modified homologues of these crops.

The method of treatment according to the invention can be used in the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, co suppression technology or RNA interference—RNAi—technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted phytopathogenic fungi and/or microorganisms and/or viruses. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozon exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species (WO 1992/005251, WO 1995/009910, WO 1998/27806, WO 2005/002324, WO 2006/021972 and U.S. Pat. No. 6,229, 072). However, genetic determinants for male sterility can also be located in the nuclear genome. Male sterile plants can also be obtained by plant biotechnology methods such as genetic engineering. A particularly useful means of obtaining male-sterile plants is described in WO 1989/10396 in which, for example, a ribonuclease such as barnase is selectively expressed in the tapetum cells in the stamens. Fertility can then be restored by expression in the tapetum cells of a ribonuclease inhibitor such as barstar (e.g. WO 1991/002069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., Science (1983), 221, 370-371), the CP4 gene of the bacterium *Agrobacterium* sp. (Barry et al., Curr. Topics Plant Physiol. (1992), 7, 139-145), the genes encoding a Petunia EPSPS (Shah et al., Science (1986), 233, 478-481), a Tomato EPSPS (Gasser et al., J. Biol. Chem. (1988),263, 4280-4289), or an Eleusine EPSPS (WO 2001/66704). It can also be a mutated EPSPS as described in for example EP-A 0837944, WO 2000/066746, WO 2000/066747 or WO 2002/026995. Glyphosate-tolerant plants can also be obtained by expressing a gene that encodes a glyphosate oxido-reductase enzyme as described in U.S. Pat. Nos. 5,776,760 and 5,463,175. Glyphosate-tolerant plants can also be obtained by expressing a gene that encodes a glyphosate acetyl transferase enzyme as described in for example WO 2002/036782, WO 2003/092360, WO 2005/012515 and WO 2007/024782. Glyphosate-tolerant plants can also be obtained by selecting plants containing naturally-occurring mutations of the above-mentioned genes, as described in for example WO 2001/024615 or WO 2003/013226.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is an enzyme encoding a phosphinothricin acetyltransferase (such as the bar or pat protein from *Streptomyces* species). Plants expressing an exogenous phosphinothricin acetyltransferase are for example described in U.S. Pat. Nos. 5,561,236; 5,648,477; 5,646,024; 5,273,894; 5,637,489; 5,276,268; 5,739,082; 5,908,810 and 7,112,665.

Further herbicide-tolerant plants are also plants that are made tolerant to the herbicides inhibiting the enzyme hydroxyphenylpyruvatedioxygenase (HPPD).

Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated HPPD enzyme as described in WO 1996/038567, WO 1999/024585 and WO 1999/024586. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 1999/034008 and WO 2002/36787. Tolerance of plants to HPPD inhibitors can also be improved by transforming plants with a gene encoding an enzyme prephenate dehydrogenase in addition to a gene encoding an HPPD-tolerant enzyme, as described in WO 2004/024928.

Still further herbicide resistant plants are plants that are made tolerant to acetolactate synthase (ALS) inhibitors. Known ALS-inhibitors include, for example, sulfonylurea, imidazolinone, triazolopyrimidines, pyrimidinyloxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright, Weed Science (2002), 50, 700-712, but also, in U.S. Pat. Nos. 5,605,011, 5,378,824, 5,141,870, and 5,013,659. The production of sulfonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 1996/033270. Other imidazolinone-tolerant plants are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerant plants are also described in for example WO 2007/024782.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084,082, for rice in WO 1997/41218, for sugar beet in U.S. Pat. No. 5,773,702 and WO 1999/057965, for lettuce in U.S. Pat. No. 5,198,599, or for sunflower in WO 2001/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic to transformation, or by selection of plants containing a mutation imparting such insect resistance. An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al., Microbiology and Molecular Biology Reviews (1998), 62, 807-813, updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1F, Cry2Ab, Cry3Aa, or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al., Nat. Biotechnol. (2001), 19, 668-72; Schnepf et al., Applied Environm. Microbiol. (2006), 71, 1765-1774); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON98034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604;

5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or
6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 1994/21795); or
7) a hybrid insecticidal protein comprising parts from different secreted proteins from *Bacillus thuringiensis* or *Bacillus cereus*, such as a hybrid of the proteins in 1) above or a hybrid of the proteins in 2) above; or
8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102.

Of course, an insect-resistant transgenic plant, as used herein, also includes any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected when using different proteins directed at different target insect species, or to delay insect resistance development to the plants by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:
 a. plants which contain a transgene capable of reducing the expression and/or the activity of poly(ADP-ribose)polymerase (PARP) gene in the plant cells or plants as described in WO 2000/004173 or WO2006/045633 or PCT/EP07/004142.
 b. plants which contain a stress tolerance enhancing transgene capable of reducing the expression and/or the activity of the PARG encoding genes of the plants or plants cells, as described e.g. in WO 2004/090140.
 c. plants which contain a stress tolerance enhancing transgene coding for a plant-functional enzyme of the nicotinamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphoribosyltransferase as described e.g. in WO2006/032469 or WO 2006/133827 or PCT/EP07/002433.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications. Said transgenic plants synthesizing a modified starch are disclosed, for example, in EP 0571427, WO 1995/004826, EP 0719338, WO 1996/15248, WO 1996/19581, WO 1996/27674, WO 1997/11188, WO 1997/26362, WO 1997/32985, WO 1997/42328, WO 1997/44472, WO 1997/45545, WO 1998/27212, WO 1998/40503, W099/58688, WO 1999/58690, WO 1999/58654, WO 2000/008184, WO 2000/008185, WO 2000/008175, WO 2000/28052, WO 2000/77229, WO 2001/12782, WO 2001/12826, WO 2002/101059, WO 2003/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 2000/22140, WO 2006/063862, WO 2006/072603, WO 2002/034923, EP 06090134.5, EP 06090228.5, EP 06090227.7, EP 07090007.1, EP 07090009.7, WO 2001/14569, WO 2002/79410, WO 2003/33540, WO 2004/078983, WO 2001/19975, WO 1995/26407, WO 1996/34968, WO 1998/20145, WO 1999/12950, WO 1999/66050, WO 1999/53072, U.S. Pat. No. 6,734,341, WO 2000/11192, WO 1998/22604, WO 1998/32326, WO 2001/98509, WO 2001/98509, WO 2005/002359, U.S. Pat. No. 5,824,790, U.S. Pat. No. 6,013,861, WO 1994/004693, WO 1994/009144, WO 1994/11520, WO 1995/35026, WO 1997/20936.

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, as disclosed in EP 0663956, WO 1996/001904, WO 1996/021023, WO 1998/039460, and WO 1999/024593, plants producing alpha 1,4 glucans as disclosed in WO 1995/031553, US 2002/031826, U.S. Pat. No. 6,284,479, U.S. Pat. No. 5,712,107, WO 1997/047806, WO 1997/047807, WO 1997/047808 and WO 2000/014249, plants producing alpha-1,6 branched alpha-1,4-glucans, as disclosed in WO 2000/73422, plants producing alternan, as disclosed in WO 2000/047727, EP 06077301.7, U.S. Pat. No. 5,908,975 and EP 0728213, 3) transgenic plants which produce hyaluronan, as for example disclosed in WO 2006/032538, WO 2007/039314, WO 2007/039315, WO 2007/039316, JP 2006/304779, and WO 2005/012529.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:
 a) Plants, such as cotton plants, containing an altered form of cellulose synthase genes as described in WO 1998/000549 b) Plants, such as cotton plants, containing an altered form of rsw2 or rsw3 homologous nucleic acids as described in WO2004/053219
c) Plants, such as cotton plants, with increased expression of sucrose phosphate synthase as described in WO 2001/017333
d) Plants, such as cotton plants, with increased expression of sucrose synthase as described in WO02/45485
e) Plants, such as cotton plants, wherein the timing of the plasmodesmatal gating at the basis of the fiber cell is altered, e.g. through downregulation of fiberselective β 1,3-glucanase as described in WO2005/017157
f) Plants, such as cotton plants, having fibers with altered reactivity, e.g. through the expression of N-acteylglucosaminetransferase gene including nodC and chitinsynthase genes as described in WO2006/136351

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants contain a mutation imparting such altered oil characteristics and include:
   a) Plants, such as oilseed rape plants, producing oil having a high oleic acid content as described e.g. in U.S. Pat. Nos. 5,969,169, 5,840,946 or 6,323,392 or 6,063,947
   b) Plants such as oilseed rape plants, producing oil having a low linolenic acid content as described in U.S. Pat. Nos. 6,270,828, 6,169,190 or 5,965,755
   c) Plant such as oilseed rape plants, producing oil having a low level of saturated fatty acids as described e.g. in U.S. Pat. No. 5,434,283

Particularly useful transgenic plants which may be treated according to the invention are plants which comprise one or more genes which encode one or more toxins, such as the following which are sold under the trade names YIELD GARD® (for example maize, cotton, soya beans), KnockOut® (for example maize), BiteGard® (for example maize), Bt-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or combination of transformation events, that are listed for example in the databases from various national or regional regulatory agencies (see for example http://gmoinfo.jrc.it/gmp_browse.aspx and http://www.agbios.com/dbase.php).

The composition according to the invention can also be used against fungal diseases liable to grow on or inside timber. The term "timber" means all types of species of wood and all types of working of this wood intended for construction, for example solid wood, high-density wood, laminated wood and plywood. The method for treating timber according to the invention mainly consists in contacting one or more compounds according to the invention or a composition according to the invention; this includes for example direct application, spraying, dipping, injection or any other suitable means.

Among the diseases of plants or crops that can be controlled by the method according to the to invention, mention can be made of:

Powdery mildew diseases such as:
*Blumeria* diseases, caused for example by *Blumeria graminis;*
*Podosphaera* diseases, caused for example by *Podosphaera leucotricha;*
*Sphaerotheca* diseases, caused for example by *Sphaerotheca fuliginea;*
*Uncinula* diseases, caused for example by *Uncinula necator;*

Rust diseases such as:
*Gymnosporangium* diseases, caused for example by *Gymnosporangium sabinae;*
*Hemileia* diseases, caused for example by *Hemileia vastatrix;*
*Phakopsora* diseases, caused for example by *Phakopsora pachyrhizi* or *Phakopsora meibomiae;*
*Puccinia* diseases, caused for example by *Puccinia recondite;*
*Uromyces* diseases, caused for example by *Uromyces appendiculatus;*

Oomycete diseases such as:
*Bremia* diseases, caused for example by *Bremia lactucee;*
*Peronospora* diseases, caused for example by *Peronospora pisi* or *P. brassicae;*
*Phytophthora* diseases, caused for example by *Phytophthora infestans;*
*Plasmopara* diseases, caused for example by *Plasmopara viticola;*
*Pseudoperonospora* diseases, caused for example by *Pseudoperonospora humuli* or *Pseudoperonospora cubensis;*
*Pythium* diseases, caused for example by *Pythium ultimum;*

Leafspot, leaf blotch and leaf blight diseases such as:
*Alternaria* diseases, caused for example by *Alternaria solani;*
*Cercospora* diseases, caused for example by *Cercospora beticola;*
*Cladiosporum* diseases, caused for example by *Cladiosporium cucumerinum;*
*Cochliobolus* diseases, caused for example by *Cochliobolus sativus;*
*Colletotrichum* diseases, caused for example by *Colletotrichum lindemuthanium;*
*Cycloconium* diseases, caused for example by *Cycloconium oleaginum;*
*Diaporthe* diseases, caused for example by *Diaporthe citri;*
*Elsinoe* diseases, caused for example by *Elsinoe fawcettii;*
*Gloeosporium* diseases, caused for example by *Gloeosporium laeticolor;*
*Glomerella* diseases, caused for example by *Glomerella cingulata;*
*Guignardia* diseases, caused for example by *Guignardia bidwelli;*
*Leptosphaeria* diseases, caused for example by *Leptosphaeria maculans; Leptosphaeria nodorum;*
*Magnaporthe* diseases, caused for example by *Magnaporthe grisea;*
*Mycosphaerella* diseases, caused for example by *Mycosphaerella graminicola; Mycosphaerella arachidicola; Mycosphaerella fijiensis;*

Phaeosphaeria diseases, caused for example by *Phaeosphaeria nodorum;*
Pyrenophora diseases, caused for example by *Pyrenophora teres;*
Ramularia diseases, caused for example by *Ramularia collo-cygni;*
Rhynchosporium diseases, caused for example by *Rhynchosporium secalis;*
Septoria diseases, caused for example by *Septoria apii* or *Septoria lycopercisi;*
Typhula diseases, caused for example by *Typhula incarnate;*
Venturia diseases, caused for example by *Venturia inaequalis;*
Root and stem diseases such as:
Corticium diseases, caused for example by *Corticium graminearum;*
Fusarium diseases, caused for example by *Fusarium oxysporum;*
Gaeumannomyces diseases, caused for example by *Gaeumannomyces graminis;*
Rhizoctonia diseases, caused for example by *Rhizoctonia solani;*
Tapesia diseases, caused for example by *Tapesia acuformis;*
Thielaviopsis diseases, caused for example by *Thielaviopsis basicola;*
Ear and panicle diseases such as:
Alternaria diseases, caused for example by *Alternaria* spp.;
Aspergillus diseases, caused for example by *Aspergillus flavus;*
Cladosporium diseases, caused for example by *Cladosporium* spp.;
Claviceps diseases, caused for example by *Claviceps purpurea;*
Fusarium diseases, caused for example by *Fusarium culmorum;*
Gibberella diseases, caused for example by *Gibberella zeae;*
Monographella diseases, caused for example by *Monographella nivalis;*
Smut and bunt diseases such as:
Sphacelotheca diseases, caused for example by *Sphacelotheca reiliana;*
Tilletia diseases, caused for example by *Tilletia caries;*
Urocystis diseases, caused for example by *Urocystis occulta;*
Ustilago diseases, caused for example by *Ustilago nuda;*
Fruit rot and mould diseases such as:
Aspergillus diseases, caused for example by *Aspergillus flavus;*
Botrytis diseases, caused for example by *Botrytis cinerea;*
Penicillium diseases, caused for example by *Penicillium expansum;*
Sclerotinia diseases, caused for example by *Sclerotinia sclerotiorum;*
Verticilium diseases, caused for example by *Verticilium alboatrum;*
Seed and soilborne decay, mould, wilt, rot and damping-off diseases:
Alternaria diseases, caused for example by *Alternaria brassicicola*
Aphanomyces diseases, caused for example by *Aphanomyces euteiches*
Ascochyta diseases, caused for example by *Ascochyta lentis*
Aspergillus diseases, caused for example by *Aspergillus flavus*
Cladosporium diseases, caused for example by *Cladosporium herbarum*
Cochliobolus diseases, caused for example by *Cochliobolus sativus*
(Conidiaform: Drechslera, Bipolaris Syn: *Helminthosporium*);
Colletotrichum diseases, caused for example by *Colletotrichum coccodes;*
Fusarium diseases, caused for example by *Fusarium culmorum;*
Gibberella diseases, caused for example by *Gibberella zeae;*
Macrophomina diseases, caused for example by *Macrophomina phaseolina*
Monographella diseases, caused for example by *Monographella nivalis;*
Penicillium diseases, caused for example by *Penicillium expansum*
Phoma diseases, caused for example by *Phoma lingam*
Phomopsis diseases, caused for example by *Phomopsis sojae;*
Phytophthora diseases, caused for example by *Phytophthora cactorum;*
Pyrenophora diseases, caused for example by *Pyrenophora graminea*
Pyricularia diseases, caused for example by *Pyricularia oryzae;*
Pythium diseases, caused for example by *Pythium ultimum;*
Rhizoctonia diseases, caused for example by *Rhizoctonia solani;*
Rhizopus diseases, caused for example by *Rhizopus oryzae*
Sclerotium diseases, caused for example by *Sclerotium rolfsii;*
Septoria diseases, caused for example by *Septoria nodorum;*
Typhula diseases, caused for example by *Typhula incarnata;*
Verticillium diseases, caused for example by *Verticillium dahliae;*
Canker, broom and dieback diseases such as:
Nectria diseases, caused for example by *Nectria galligena;*
Blight diseases such as:
Monilinia diseases, caused for example by *Monilinia laxa;*
Leaf blister or leaf curl diseases such as:
Taphrina diseases, caused for example by *Taphrina deformans;*
Decline diseases of wooden plants such as:
Esca diseases, caused for example by *Phaemoniella clamydospora;*
Eutypa dyeback, caused for example by *Eutypa lata;*
Dutch elm disease, caused for example by *Ceratocystsc ulmi;*

Diseases of flowers and Seeds such as:

*Botrytis* diseases, caused for example by *Botrytis cinerea;*

Diseases of tubers such as:

*Rhizoctonia* diseases, caused for example by *Rhizoctonia solani*

*Helminthosporium* diseases, caused for example by *Helminthosporium solani.*

The compounds according to the invention can also be used for the preparation of composition useful to curatively or preventively treat human or animal fungal diseases such as, for example, mycoses, dermatoses, trichophyton diseases and candidiases or diseases caused by *Aspergillus* spp., for example *Aspergillus fumigatus*.

The various aspects of the invention will now be illustrated with reference to the following table 1 of compound examples and the following preparation or efficacy examples.

The following table 1 illustrates in a non limiting manner examples of compounds according to the invention.

(I)

In table 1 we use the following abbreviations for specified claimed elements "A" and "T" of the generic structure (I) of the invention:

In all cases, when any of $X^2$, $X^3$, $X^4$ is empty in Table 1, it is not an element of the generic structures of the specific structure-element $T^i$.

TABLE 1

| Ex. | A | Z¹ | Z² | Z³ | Z⁴ | Q | T | X¹ | X² | X³ | X⁴ | W¹ | log p | MS_Measured |
|---|---|---|---|---|---|---|---|---|---|---|---|---|---|---|
| 1 | A2 | H | | | | phenyl | T82 | CH$_3$ | | | | | 2.36[a] | 438 |
| 2 | A2 | 1,3-dioxo-1,3-dihydro-2H-isoindol-2-yl | H | H | H | phenyl | T14 | H | H | | | CH$_3$ | 1.8[b] | |
| 3 | A8 | amino | H | H | H | phenyl | T14 | H | | | | CH$_3$ | 1.42[c] | 309 |
| 4 | A2 | amino | H | H | H | phenyl | T73 | H | | | | CH$_3$ | 1[b] | 309[m3] |
| 5 | A2 | 1,3-dioxo-1,3-dihydro-2H-isoindol-2-yl | H | H | H | 3-methylphenyl | T73 | H | | | | CH$_3$ | 3.04[b] | 453[m3] |
| 6 | A2 | amino | H | H | H | 2-methylphenyl | T73 | H | | | | CH$_3$ | 0.96[b] | 323[m3] |
| 7 | A2 | amino | H | H | H | 4-methylphenyl | T73 | H | | | | CH$_3$ | 1.26[b] | 323[m3] |
| 8 | A2 | amino | H | H | H | 3-methylphenyl | T73 | H | | | | CH$_3$ | 1.27[b] | 323[m3] |
| 9 | A2 | 1,3-dioxo-1,3-dihydro-2H-isoindol-2-yl | H | H | H | 2-methylphenyl | T73 | H | | | | CH$_3$ | 2.78[b] | 453[m3] |
| 10 | A2 | 1,3-dioxo-1,3-dihydro-2H-isoindol-2-yl | H | H | H | 4-methylphenyl | T73 | H | | | | CH$_3$ | 2.92[b] | 453[m3] |
| 11 | A2 | amino | H | H | H | phenyl | T14 | H | H | | | CH$_3$ | 1.89[c]; 0.36[b] | 308 |
| 12 | A2 | (2,2-dimethylpropanoyl)amino | H | H | H | phenyl | T14 | H | H | | | CH$_3$ | 1.77[b] | 393 |
| 13 | A2 | 1,3-dioxo-1,3-dihydro-2H-isoindol-2-yl | H | H | H | phenyl | T73 | H | | | | CH$_3$ | 2.76[b] | 439[m3] |
| 14 | A8 | heptanoylamino | H | H | H | phenyl | T73 | H | H | | | CH$_3$ | 2.39[b] | 421 |
| 15 | A8 | (3-methylbutanoyl)amino | H | H | H | phenyl | T14 | H | H | | | CH$_3$ | 1.76[b] | 393 |
| 16 | A8 | hexanoylamino | H | H | H | phenyl | T14 | H | H | | | CH$_3$ | 2.1[b] | 407 |
| 17 | A2 | (cyclopropylcarbonyl)amino | H | H | H | 4-methylphenyl | T73 | H | | | | CH$_3$ | 2.73[b] | 391[m3] |
| 18 | A2 | hexanoylamino | H | H | H | 4-methylphenyl | T73 | H | | | | CH$_3$ | 3.71[b] | 421[m3] |
| 19 | A2 | (2,2-dimethylpropanoyl)amino | H | H | H | 4-methylphenyl | T73 | H | | | | CH$_3$ | 3.31[b] | 407[m3] |
| 20 | A2 | (cyclopropylcarbonyl)amino | H | H | H | 3-methylphenyl | T73 | H | | | | CH$_3$ | 2.73[b] | 391[m3] |
| 21 | A2 | hexanoylamino | H | H | H | 3-methylphenyl | T73 | H | | | | CH$_3$ | 3.71[b] | 421[m3] |
| 22 | A2 | (2,2-dimethylpropanoyl)amino | H | H | H | 3-methylphenyl | T73 | H | | | | CH$_3$ | 3.31[b] | 407[m3] |
| 23 | A2 | (cyclopropylcarbonyl)amino | H | H | H | 2-methylphenyl | T73 | H | | | | CH$_3$ | 2.48[b] | 391[m3] |
| 24 | A2 | hexanoylamino | H | H | H | 2-methylphenyl | T73 | H | | | | CH$_3$ | 3.46[b] | 421[m3] |
| 25 | A2 | (2,2-dimethylpropanoyl)amino | H | H | H | 2-methylphenyl | T73 | H | | | | CH$_3$ | 3.06[b] | 407[m3] |
| 26 | A2 | (2,2-dimethylpropanoyl)amino | H | H | H | phenyl | T73 | H | | | | CH$_3$ | 2.98[b] | 393[m3] |
| 27 | A2 | (cyclopropylcarbonyl)amino | H | H | H | phenyl | T73 | H | | | | CH$_3$ | 2.41[b] | 377[m3] |
| 28 | A2 | hexanoylamino | H | H | H | phenyl | T73 | H | | | | CH$_3$ | 3.39[b] | 407[m3] |
| 29 | A2 | (phenylacetyl)amino | H | H | H | phenyl | T73 | H | | | | CH$_3$ | 3.06[b] | 427[m3] |

TABLE 1-continued

| Ex. | A | $Z^1$ | $Z^2$ | $Z^3$ | $Z^4$ | Q | T | $X^1$ | $X^2$ | $X^3$ | $X^4$ | $W^1$ | log p | MS_Measured |
|---|---|---|---|---|---|---|---|---|---|---|---|---|---|---|
| 30 | A2 | (phenylacetyl)amino | H | H | H | 2-methylphenyl | T73 | H | | | | $CH_3$ | $3.11^{[b]}$ | $441^{[m3]}$ |
| 31 | A2 | (phenylacetyl)amino | H | H | H | 3-methylphenyl | T73 | H | | | | $CH_3$ | $3.35^{[b]}$ | $441^{[m3]}$ |
| 32 | A2 | (phenylacetyl)amino | H | H | H | phenyl | T14 | H | | | | $CH_3$ | $2^{[b]}$ | 426 |
| 33 | A2 | hexanoylamino | H | H | H | phenyl | T14 | H | | | | $CH_3$ | $2.23^{[b]}$ | 406 |
| 34 | A8 | amino | H | H | H | 4-methylphenyl | T73 | H | | | | $CH_3$ | $1.11^{[b]}$ | $324^{[m3]}$ |
| 35 | A2 | [(pentyloxy)carbonyl]amino | H | H | H | phenyl | T73 | H | H | | | $CH_3$ | $3.96^{[b]}$ | $423^{[m3]}$ |
| 36 | A2 | (3-methylbutanoyl)amino | H | H | H | phenyl | T14 | H | | | | $CH_3$ | $1.89^{[b]}$ | 392 |
| 37 | A2 | [(pentyloxy)carbonyl]amino | H | H | H | phenyl | T14 | H | H | | | $CH_3$ | $2.6^{[b]}$ | 422 |
| 38 | A8 | hexanoylamino | H | H | H | 4-methylphenyl | T73 | H | | | | $CH_3$ | $3.42^{[b]}$ | $422^{[\,]}$ |
| 39 | A2 | (2,2-dimethylpropanoyl)amino | H | H | H | 4-methylphenyl | T73 | H | | | | $CH_3$ | $3.02^{[b]}$ | $408^{[m3]}$ |
| 40 | A2 | (cyclopropylcarbonyl)amino | H | H | H | 4-methylphenyl | T73 | H | | | | $CH_3$ | $2.46^{[b]}$ | $392^{[m3]}$ |
| 41 | A2 | [(pentyloxy)carbonyl]amino | H | H | H | 4-methylphenyl | T73 | H | | | | $CH_3$ | $3.76^{[b]}$ | $438^{[m3]}$ |
| 42 | A2 | (5-methoxy-5-oxopentanoyl)amino | H | H | H | 4-methylphenyl | T73 | H | | | | $CH_3$ | $2.68^{[b]}$ | $451^{[m3]}$ |
| 43 | A2 | (5-methoxy-5-oxopentanoyl)amino | H | H | H | phenyl | T73 | H | | | | $CH_3$ | $2.39^{[b]}$ | $437^{[m3]}$ |
| 44 | A2 | [(pentyloxy)carbonyl]amino | H | H | H | 4-methylphenyl | T73 | H | | | | $CH_3$ | $4.31^{[b]}$ | $437^{[m3]}$ |
| 45 | A2 | [(pentyloxy)carbonyl]amino | H | H | H | 2-methylphenyl | T73 | H | | | | $CH_3$ | $4.06^{[b]}$ | $437^{[m3]}$ |
| 46 | A2 | [(pentyloxy)carbonyl]amino | H | H | H | 3-methylphenyl | T73 | H | | | | $CH_3$ | $2.9^{[b]}$ | $453^{[m3]}$ |
| 47 | A2 | H | $CF_3$ | H | H | phenyl | T73 | H | | | | $CH_3$ | $3.44^{[b]}$ | $396^{[m3]}$ |
| 48 | A2 | hexanoylamino | H | H | chloro | 3-methylphenyl | T73 | H | | | | $CH_3$ | $3.55^{[b]}$ | $421^{[m3]}$ |
| 49 | A2 | [(pentyloxy)carbonyl]amino | H | H | H | 3-methylphenyl | T73 | H | | | | $CH_3$ | | |
| 50 | A2 | H | H | H | H | phenyl | T73 | H | H | | | $CH_3$ | $1.51^{[b]}$ | $294^{[m3]}$ |
| 51 | A2 | (1Z,3Z)-buta-1,3-dien-1,4-diyl | H | H | H | phenyl | T73 | H | H | | | $CH_3$ | $2.51^{[b]}$ | $344^{[m3]}$ |
| 52 | A8 | (ethoxycarbonyl)amino | H | H | H | phenyl | T14 | H | H | | | $CH_3$ | $1.47^{[b]}$ | 381 |
| 53 | A8 | (methoxyacetyl)amino | H | H | H | phenyl | T14 | H | H | | | $CH_3$ | $1.2^{[b]}$ | 381 |
| 54 | A8 | [(benzyloxy)acetyl]amino | H | H | H | phenyl | T14 | H | H | | | $CH_3$ | $2.04^{[b]}$ | 457 |
| 55 | A8 | [(pentyloxy)carbonyl]amino | H | H | H | phenyl | T14 | H | H | | | $CH_3$ | $2.28^{[b]}$ | 423 |
| 56 | A8 | [(2-methoxyethoxy)acetyl]amino | H | H | H | phenyl | T14 | H | H | | | $CH_3$ | $1.34^{[b]}$ | 425 |
| 57 | A2 | [(prop-2-en-1-yloxy)carbonyl]amino | H | H | H | phenyl | T14 | H | H | | | $CH_3$ | $1.62^{[b]}$ | 393 |
| 58 | A8 | butanoylamino | H | H | H | phenyl | T14 | H | H | | | $CH_3$ | $1.68^{[b]}$ | 379 |
| 59 | A8 | pentanoylamino | H | H | H | phenyl | T14 | H | H | | | $CH_3$ | $1.95^{[b]}$ | 393 |
| 60 | A2 | amino | H | H | H | phenyl | T80 | $CH_3$ | H | | | | $1.11^{[b]}$ | $309^{[m1]}$ |
| 61 | A8 | 1,3-dioxo-1,3-dihydro-2H-isoindol-2-yl | H | H | H | phenyl | T80 | $CH_3$ | H | | | | $1.92^{[b]}$ | $439^{[m3]}$ |
| 62 | A2 | acetylamino | H | H | H | phenyl | T14 | H | H | | | $CH_3$ | $1.13^{[b]}$ | 351 |
| 63 | A8 | propanoylamino | H | H | H | phenyl | T14 | H | H | | | $CH_3$ | $1.38^{[b]}$ | 365 |

TABLE 1-continued

| Ex. | A | Z¹ | Z² | Z³ | Z⁴ | Q | T | X¹ | X² | X³ | X⁴ | W¹ | log p | MS_Measured |
|---|---|---|---|---|---|---|---|---|---|---|---|---|---|---|
| 64 | A8 | (3-phenylpropanoyl)amino | H | H | H | phenyl | T14 | H | | | | CH₃ | 2.21[b] | 441 |
| 65 | A2 | hexanoylamino | H | H | H | phenyl | T80 | CH₃ | H | | | | 3.52[b] | 407[m3] |
| 66 | A2 | (2,2-dimethylpropanoyl)amino | H | H | H | phenyl | T80 | CH₃ | H | | | | 3.11[b] | 393[m3] |
| 67 | A2 | (cyclopropylcarbonyl)amino | H | H | H | phenyl | T80 | CH₃ | H | | | | 2.55[b] | 377[m3] |
| 68 | A2 | (phenylacetyl)amino | H | H | H | phenyl | T80 | CH₃ | H | | | | 3.19[b] | 427[m3] |
| 69 | A2 | [(pentyloxy)carbonyl]amino | H | H | H | phenyl | T80 | CH₃ | H | | | | 2.46[b] | 423[m3] |
| 70 | A8 | amino | H | H | H | phenyl | T80 | CH₃ | H | | | | 0.96[b] | 310[m3] |
| 71 | A8 | hexanoylamino | H | H | H | phenyl | T73 | CH₃ | | | | | 3.23[b] | 408[m1] |
| 72 | A2 | (butylsulfonyl)amino | H | H | H | phenyl | T73 | H | | | | CH₃ | 4.21[b] | 429[m3] |
| 73 | A2 | bis(butylsulfonyl)amino | H | H | H | phenyl | T73 | H | | | | CH₃ | 2.73[b] | 549[m3] |
| 74 | A2 | (butylsulfonyl)amino | H | H | H | 4-methylphenyl | T73 | H | | | | CH₃ | 3.04[b] | 443[m3] |
| 75 | A2 | (butylsulfonyl)amino | H | H | H | 3-methylphenyl | T73 | H | | | | CH₃ | 3.04[b] | 443[b] |
| 76 | A2 | (butylsulfonyl)amino | H | H | H | phenyl | T80 | CH₃ | H | | | | 2.86[b] | 429[b] |
| 77 | A2 | (2,2-dimethylpropanoyl)amino | H | H | H | phenyl | T80 | CH₃ | H | | | | 2.77[b] | 394[m1] |
| 78 | A2 | bis(butylsulfonyl)amino | H | H | H | 4-methylphenyl | T73 | H | | | | CH₃ | 4.51[b] | 563[m3] |
| 79 | A2 | bis(butylsulfonyl)amino | H | H | H | 3-methylphenyl | T73 | H | | | | CH₃ | 4.49[b] | 563[m3] |
| 80 | A2 | bis(butylsulfonyl)amino | H | H | H | phenyl | T80 | CH₃ | H | | | | 4.26[b] | 549[m3] |
| 81 | A8 | (phenylacetyl)amino | H | H | H | phenyl | T80 | CH₃ | H | | | | 2.84[b] | 428[m1] |
| 82 | A2 | (3-methylbutanoyl)amino | H | H | H | phenyl | T80 | CH₃ | H | | | | 2.77[b] | 394[m1] |
| 83 | A16 | (2,2-dimethylpropanoyl)amino | H | H | H | phenyl | T80 | CH₃ | | | | | 3.06[b] | 399[m1] |
| 84 | A16 | [(pentyloxy)carbonyl]amino | H | H | H | phenyl | T80 | CH₃ | H | | | | 3.76[b] | 429[m1] |
| 85 | A16 | hexanoylamino | H | H | H | phenyl | T80 | CH₃ | H | | | | 3.44[b] | 413[b] |
| 86 | A8 | (3-methylbutanoyl)amino | H | H | H | phenyl | T80 | CH₃ | H | | | | 3[b] | 399[m3] |
| 87 | A8 | [(pentyloxy)carbonyl]amino | H | H | H | phenyl | T80 | CH₃ | | | | | 3.55[b] | 424[m3] |
| 88 | A2 | [(hexyloxy)carbonyl]amino | H | H | H | phenyl | T73 | H | | | | CH₃ | 4.36[b] | 437[m3] |
| 89 | A2 | (propoxycarbonyl)amino | H | H | H | phenyl | T73 | H | | | | CH₃ | 3.15[b] | 395[m3] |
| 90 | A2 | 1,3-dioxo-1,3-dihydro-2H-isoindol-2-yl | | | | phenyl | T8 | H | H | | | CH₃ | 1.81[b] | 438 |
| 91 | A2 | (butoxycarbonyl)amino | H | H | H | phenyl | T73 | H | | | | CH₃ | 3.53[b] | 409[m3] |
| 92 | A2 | [(4-chlorobutoxy)carbonyl]amino | H | H | H | phenyl | T73 | H | | | | CH₃ | 3.39[b] | 443[m3] |
| 93 | A2 | (ethoxycarbonyl)amino | H | H | H | phenyl | T73 | H | | | | CH₃ | 2.71[b] | 381[m3] |
| 94 | A2 | [(but-3-yn-1-yloxy)carbonyl]amino | H | H | H | phenyl | T73 | H | | | | CH₃ | 2.82[b] | 405[m3] |
| 95 | A8 | amino | H | H | H | phenyl | T8 | H | | | | CH₃ | 0.01[b] | 309 |
| 96 | A16 | (3-methylbutanoyl)amino | H | H | H | phenyl | T73 | H | H | | | CH₃ | 2.88[b] | 399[m3] |
| 97 | A2 | amino | H | H | H | phenyl | T8 | H | H | | | CH₃ | 0.25[b] | 308 |
| 98 | A2 | amino | H | H | H | phenyl | T8 | H | H | | | CH₃ | 0.29[b] | 308 |
| 99 | A8 | (2,2-dimethylpropanoyl)amino | H | H | H | phenyl | T8 | H | H | | | CH₃ | 1.76[b] | 393 |
| 100 | A16 | hexanoylamino | H | H | H | phenyl | T73 | H | | | | CH₃ | 3.25[b] | 413[m3] |
| 101 | A16 | (2,2-dimethylpropanoyl)amino | H | H | H | phenyl | T73 | H | | | | CH₃ | 2.92[b] | 399[m3] |

TABLE 1-continued

| Ex. | A | Z¹ | Z² | Z³ | Z⁴ | Q | T | X¹ | X² | X³ | X⁴ | W¹ | log p | MS_Measured |
|---|---|---|---|---|---|---|---|---|---|---|---|---|---|---|
| 102 | A8 | (2,2-dimethylpropanoyl)amino | H | H | | phenyl | T8 | 2,2-dimethylpropanoyl | H | | | CH₃ | 4.84[b] | 477 |
| 103 | A8 | (3-methylbutanoyl)amino | H | | | phenyl | T8 | 3-methyl-1-[(3-methylbutanoyl)oxy]but-1-en-1-yl | H | | | CH₃ | 4.04[b] | 561 |
| 104 | A16 | bis(cyclopropylcarbonyl)amino | H | H | | phenyl | T8 | H | H | | | CH₃ | 1.75[b] | 445 |
| 105 | A2 | [(pentyloxy)carbonyl]amino | H | H | | phenyl | T8 | (pentyloxy)carbonyl | H | | | CH₃ | 5.05[b] | 537 |
| 106 | A2 | [(heptyloxy)carbonyl]amino | H | H | H | phenyl | T73 | H | H | | | CH₃ | 4.86[b] | 451[m3] |
| 107 | A2 | (3-phenylpropanoyl)amino | H | H | H | phenyl | T73 | H | H | | | CH₃ | 3.33[b] | 441[m3] |
| 108 | A8 | bis(2-methylpropanoyl)amino | H | H | | phenyl | T8 | 2-methylpropanoyl | H | | | CH₃ | 4.75[b] | 519 |
| 109 | A8 | (2-methylpropanoyl)amino | H | H | | phenyl | T8 | 2-methylpropanoyl | H | | | CH₃ | 3.62[b] | 449 |
| 110 | A8 | (2-methylpropanoyl)amino | H | H | | phenyl | T8 | 2-methyl-1-[(2-methylpropanoyl)oxy]prop-1-en-1-yl | H | | | CH₃ | 2.77[b] | 519 |
| 111 | A16 | amino | H | H | | phenyl | T8 | H | H | | | CH₃ | 0.69[b] | 314 |
| 112 | A8 | (3-methylbutanoyl)amino | H | H | | phenyl | T8 | H | H | | | CH₃ | 1.99[b] | 393 |
| 113 | A2 | methyl[(pentyloxy)carbonyl]amino | H | H | H | phenyl | T73 | H | H | | | CH₃ | 4.39[b] | 437[m3] |
| 114 | A8 | hexanoylamino | H | H | | phenyl | T8 | H | H | | | CH₃ | 1.94[b] | 407 |
| 115 | A2 | [(pentyloxy)carbonyl]amino | H | H | H | phenyl | T8 | H | H | | | CH₃ | 2.66[b] | 412 |
| 116 | A8 | hexanoylamino | H | H | H | phenyl | T8 | H | H | | | CH₃ | 2.08[b] | 398 |
| 117 | A16 | (2,2-dimethylpropanoyl)amino | H | H | | phenyl | T8 | H | H | | | CH₃ | 1.84[b] | 398 |
| 118 | A16 | (3-methylbutanoyl)amino | H | H | | phenyl | T8 | H | H | | | CH₃ | 1.84[b] | 398 |
| 119 | A16 | (2-methylpropanoyl)amino | H | H | | phenyl | T8 | H | H | | | CH₃ | 1.63[b] | 384 |
| 120 | A2 | hexanoylamino | H | H | H | phenyl | T8 | H | H | | | CH₃ | 2.11[b] | 406 |
| 121 | A8 | (3-methylbutanoyl)amino | H | H | H | phenyl | T8 | H | H | | | CH₃ | 1.84[b] | 392 |
| 122 | A8 | (3-methylbutanoyl)amino | H | H | H | phenyl | T8 | H | H | | | CH₃ | 1.84[b] | 392 |
| 123 | A2 | (2,2-dimethylpropanoyl)amino | H | H | H | phenyl | T8 | H | H | | | CH₃ | 2.1[b] | 392 |
| 124 | A8 | (2-methylpropanoyl)amino | H | H | | phenyl | T8 | H | H | | | CH₃ | 1.49[b] | 379 |
| 125 | A2 | (2-methylpropanoyl)amino | H | H | H | phenyl | T8 | H | H | | | CH₃ | 1.63[b] | 378 |
| 126 | A2 | (2,2-dimethylpropanoyl)amino | H | H | H | phenyl | T8 | H | H | | | CH₃ | 1.85[b] | 392 |
| 127 | A16 | (phenoxyacetyl)amino | H | H | | phenyl | T8 | H | H | | | CH₃ | 2.01[b] | 448 |
| 128 | A8 | pentanoylamino | H | H | | phenyl | T8 | H | H | | | CH₃ | 1.75[b] | 393 |
| 129 | A8 | butanoylamino | H | H | | phenyl | T8 | H | H | | | CH₃ | 1.5[b] | 379 |
| 130 | A8 | heptanoylamino | H | H | | phenyl | T8 | H | H | | | CH₃ | 2.2[b] | 421 |
| 131 | A8 | decanoylamino | H | H | | phenyl | T8 | H | H | | | CH₃ | 2.98[b] | 463 |
| 132 | A8 | (phenoxyacetyl)amino | H | H | | phenyl | T8 | H | H | | | CH₃ | 1.86[b] | 443 |
| 133 | A16 | amino | H | H | | phenyl | T14 | H | H | | | CH₃ | 0.75[b] | 314 |
| 134 | A2 | [(3-phenylpropanoyl)amino]methyl | H | H | H | phenyl | T73 | H | H | | | CH₃ | 2.56[b] | 455[m3] |
| 135 | A2 | (pentanoylamino)methyl | H | H | | phenyl | T73 | H | H | | | CH₃ | 2.28[b] | 407[m3] |
| 136 | A2 | [(3-methylbutanoyl)amino]methyl | H | H | | phenyl | T73 | H | H | | | CH₃ | 2.23[b] | 407[m3] |

TABLE 1-continued

| Ex. | A | Z¹ | Z² | Z³ | Z⁴ | Q | T | X¹ | X² | X³ | X⁴ | W¹ | log p | MS_Measured |
|---|---|---|---|---|---|---|---|---|---|---|---|---|---|---|
| 137 | A2 | [(2,2-dimethylpropanoyl)amino]methyl | H | H | H | phenyl | T73 | H | | | | CH₃ | 2.28[b] | 407[m3] |
| 138 | A2 | [(phenylacetyl)amino]methyl | H | H | H | phenyl | T73 | H | | | | CH₃ | 2.44[b] | 441[m3] |
| 139 | A2 | {[(pentyloxy)carbonyl]amino}methyl | H | H | H | phenyl | T73 | H | | | | CH₃ | 3.19[b] | 437[m3] |
| 140 | A2 | (hexanoylamino)methyl | H | H | H | phenyl | T73 | H | | | | CH₃ | 2.62[b] | 421[m3] |
| 141 | A2 | {[(butoxycarbonyl)amino]methyl | H | H | H | phenyl | T73 | H | | | | CH₃ | 2.84[b] | 423[m3] |
| 142 | A2 | 1,3-dioxo-1,3-dihydro-2H-isoindol-2-yl | H | H | H | phenyl | T84 | CH₃ | | | | CH₃ | 2.66[b] | 469[m3] |
| 143 | A2 | amino | H | H | H | phenyl | T84 | CH₃ | | | | CH₃ | 1.11[b] | 339[m3] |
| 144 | A2 | 1,3-dioxo-1,3-dihydro-2H-isoindol-2-yl | H | H | H | phenyl | T84 | H | | | | CH₃ | 2.3[b] | 439[m3] |
| 145 | A2 | hexanoylamino | H | H | H | phenyl | T84 | CH₃ | | | | CH₃ | 3.27[b] | 437[m3] |
| 146 | A2 | [(pentyloxy)carbonyl]amino | H | H | H | phenyl | T84 | CH₃ | | | | CH₃ | 3.8[b] | 453[m3] |
| 147 | A2 | (2,2-dimethylpropanoyl)amino | H | H | H | phenyl | T84 | CH₃ | | | | CH₃ | 2.86[b] | 423[m3] |
| 148 | A2 | (3-methylbutanoyl)amino | H | H | H | phenyl | T84 | CH₃ | | | | CH₃ | 2.82[b] | 423[m3] |
| 149 | A2 | (phenylacetyl)amino | H | H | H | phenyl | T84 | CH₃ | | | | CH₃ | 2.94[b] | 457[m3] |
| 150 | A2 | (3-phenylpropanoyl)amino | H | H | H | phenyl | T84 | CH₃ | | | | CH₃ | 3.19[b] | 471[m3] |
| 151 | A2 | (3,3,3-trifluoropropanoyl)amino | H | H | H | phenyl | T84 | CH₃ | | | | CH₃ | 2.66[b] | 449[m3] |
| 152 | A2 | (thiophen-2-ylcarbonyl)amino | H | H | H | phenyl | T84 | CH₃ | | | | CH₃ | 2.82[b] | 449[m3] |
| 153 | A2 | (3-cyclopentylpropanoyl)amino | H | H | H | phenyl | T84 | CH₃ | | | | CH₃ | 3.71[b] | 463[m3] |
| 154 | A8 | (cyclopropylcarbonyl)amino | H | H | H | phenyl | T14 | H | H | | | CH₃ | 1.5[b] | 377 |
| 155 | A8 | (phenylacetyl)amino | H | H | H | phenyl | T14 | H | H | | | CH₃ | 2.01[b] | 427 |
| 156 | A2 | amino | H | H | H | phenyl | T74 | H | | | | CH₃ | 0.88[b] | 309[m3] |
| 157 | A2 | [(pentyloxy)carbonyl]amino | H | H | H | phenyl | T74 | H | | | | CH₃ | 3.29[b] | 423[m3] |
| 158 | A2 | (phenylacetyl)amino | H | H | H | phenyl | T74 | H | | | | CH₃ | 2.56[b] | 427[m3] |
| 159 | A2 | [(2-methylpropoxy)carbonyl]amino | H | H | H | phenyl | T74 | H | | | | CH₃ | 2.88[b] | 409[m3] |
| 160 | A2 | (3,3,3-trifluoropropanoyl)amino | H | H | H | phenyl | T74 | H | | | | CH₃ | 2.28[b] | 419[m3] |
| 161 | A2 | (1,3-dioxo-1,3-dihydro-2H-isoindol-2-yl)methyl | H | H | H | phenyl | T73 | H | | | | CH₃ | 2.9[b] | 453[m3] |
| 162 | A2 | aminomethyl | H | H | H | 3-methylphenyl | T73 | H | | | | CH₃ | 0.99[b] | 323[m3] |
| 163 | A2 | 1,3-dioxo-1,3-dihydro-2H-isoindol-2-yl | H | H | H | 3-methylphenyl | T73 | H | H | | | CH₃ | 4.31[b] | 437[m3] |
| 164 | A2 | amino | H | H | H | phenyl | T80 | H | H | | | CH₃ | 1.08[b] | 323[m3] |
| 165 | A16 | amino | H | | H | phenyl | T14 | CH₃ | H | | | | 1.29[b] | 315[m3] |
| 166 | A8 | (3-oxo-2,4-diphenylbutanoyl)amino | H | H | H | phenyl | T74 | H | | | | CH₃ | 2.59[b] | 545 |
| 167 | A2 | (2,2-dimethylpropanoyl)amino | H | H | H | phenyl | T12 | CH₃ | H | | | | 2.44[b] | 393[m3] |
| 168 | A2 | 1,3-dioxo-1,3-dihydro-2H-isoindol-2-yl | H | H | H | phenyl | T12 | CH₃ | | | | | 3.27[b] | 455 |
| 169 | A2 | amino | H | H | H | phenyl | T12 | CH₃ | | | | | 1.7[b] | 325 |
| 170 | A2 | 1,3-dioxo-1,3-dihydro-2H-isoindol-2-yl | H | H | H | phenyl | T12 | CH₃ | | | | | 3.55[b] | 455 |
| 171 | A2 | (3-methylbutanoyl)amino | H | H | H | phenyl | T12 | CH₃ | | | | | 3.46[b] | 409 |

TABLE 1-continued

| Ex. | A | Z¹ | Z² | Z³ | Z⁴ | Q | T | X¹ | X² | X³ | X⁴ | W¹ | log p | MS_Measured |
|---|---|---|---|---|---|---|---|---|---|---|---|---|---|---|
| 172 | A2 | (2,2-dimethylpropanoyl)amino | H | H | H | phenyl | T12 | CH₃ | H | | | | 3.56[b] | 409 |
| 173 | A2 | (phenylacetyl)amino | H | H | H | phenyl | T12 | CH₃ | | | | | 3.61[b] | 443 |
| 174 | A2 | amino | H | H | H | phenyl | T12 | CH₃ | H | | | | 1.47[b] | 325 |
| 175 | A2 | (phenylacetyl)amino | H | H | H | phenyl | T73 | CF₃ | | | | CH₃ | 4.24[b] | 495[m3] |
| 176 | A2 | (3-phenylpropanoyl)amino | H | H | H | phenyl | T73 | CF₃ | | | | CH₃ | 4.49[b] | 509[m3] |
| 177 | A2 | (3-methylbutanoyl)amino | H | H | H | phenyl | T73 | CF₃ | | | | CH₃ | 4.24[b] | 461[m3] |
| 178 | A2 | (2,2-dimethylpropanoyl)amino | H | H | H | phenyl | T73 | CF₃ | | | | CH₃ | 4.31[b] | 461[m3] |
| 179 | A2 | [(pentyloxy)carbonyl]amino | H | H | H | phenyl | T73 | CF₃ | | | | CH₃ | 5.2[b] | 491[b] |
| 180 | A2 | [(2-methylpropoxy)carbonyl]amino | H | H | H | phenyl | T73 | CF₃ | | | | CH₃ | 4.78[b] | 477[m3] |
| 181 | A2 | hexanoylamino | H | H | H | phenyl | T73 | CF₃ | | | | CH₃ | 1.97[b] | 377[m3] |
| 182 | A2 | hexanoylamino | H | H | H | phenyl | T73 | CF₃ | | | | CH₃ | 4.67[b] | 475[m3] |
| 183 | A2 | 1,3-dioxo-1,3-dihydro-2H-isoindol-2-yl | H | H | H | phenyl | T73 | CF₃ | | | | CH₃ | 3.99[b] | 507[m3] |
| 184 | A2 | (cyclopentylcarbonyl)amino | H | H | H | phenyl | T73 | CF₃ | | | | CH₃ | 4.41[b] | 473[m3] |
| 185 | A2 | {[4-(acetyloxy)butoxy]carbonyl}amino | H | H | H | phenyl | T73 | CF₃ | | | | CH₃ | 4.11[b] | 535[m3] |
| 186 | A2 | {[5-methyl-3-(CF₃)-1H-pyrazol-1-yl]acetyl}amino | H | H | H | phenyl | T73 | CF₃ | | | | CH₃ | 4.31[b] | 567[m3] |
| 187 | A2 | [(pentyloxy)carbonyl]amino | H | H | H | phenyl | T12 | CH₃ | H | | | | 4.51[b] | 439 |
| 188 | A2 | hexanoylamino | H | H | H | phenyl | T12 | CH₃ | H | | | | 3.89[b] | |
| 189 | A2 | hexanoylamino | H | H | H | phenyl | T12 | CH₃ | H | | | | 4.26[b] | 423 |
| 190 | A2 | (3-methylbutanoyl)amino | H | H | H | phenyl | T12 | CH₃ | H | | | | 3.75[b] | 409 |
| 191 | A2 | (phenylacetyl)amino | H | H | H | phenyl | T12 | CH₃ | | | | | 3.87[b] | 443 |
| 192 | A2 | 1,3-dioxo-1,3-dihydro-2H-isoindol-2-yl | H | H | H | phenyl | T12 | CF₃ | H | | | CH₃ | 3.31[b] | 507[m3] |
| 193 | A2 | amino | H | H | H | phenyl | T74 | CF₃ | | | | CH₃ | 1.54[b] | 377[m3] |
| 194 | A2 | 1,3-dioxo-1,3-dihydro-2H-isoindol-2-yl | H | H | H | phenyl | T8 | CH₃ | H | | | CH₃ | 1.84[b] | 452 |
| 195 | A2 | [(pentyloxy)carbonyl]amino | H | H | H | phenyl | T12 | CH₃ | | | | CH₃ | 4.92[b] | 439 |
| 196 | A2 | hexanoylamino | H | H | H | phenyl | T74 | CF₃ | | | | CH₃ | 3.94[b] | 475[m3] |
| 197 | A2 | [(pentyloxy)carbonyl]amino | H | H | H | phenyl | T74 | CF₃ | | | | CH₃ | 4.49[b] | 491[m3] |
| 198 | A2 | (2,2-dimethylpropanoyl)amino | H | H | H | phenyl | T74 | CF₃ | H | | | CH₃ | 3.58[b] | 461[m3] |
| 199 | A2 | (3-methylbutanoyl)amino | H | H | H | phenyl | T74 | CF₃ | | | | CH₃ | 3.6[b] | 495[m3] |
| 200 | A2 | (phenylacetyl)amino | H | H | H | phenyl | T74 | CF₃ | | | | CH₃ | 3.85[b] | 509[m3] |
| 201 | A2 | (3-phenylpropanoyl)amino | H | H | H | phenyl | T74 | CF₃ | | | | CH₃ | 3.69[b] | 473[m3] |
| 202 | A2 | (cyclopentylcarbonyl)amino | H | H | H | phenyl | T74 | CF₃ | | | | CH₃ | 4.06[b] | 477[m3] |
| 203 | A2 | [(2-methylpropoxy)carbonyl]amino | H | H | H | phenyl | T74 | CF₃ | | | | CH₃ | | |
| 204 | A2 | (thiophen-2-ylcarbonyl)amino | H | H | H | phenyl | T74 | CF₃ | | | | CH₃ | 3.48[b] | 487[b] |
| 205 | A2 | [(4-ethoxyphenyl)carbonyl]amino | H | H | H | phenyl | T74 | CF₃ | | | | CH₃ | 3.94[b] | 525[b] |
| 206 | A2 | [3-(methylsulfanyl)propanoyl]amino | H | H | H | phenyl | T74 | CF₃ | | | | CH₃ | 3.15[b] | 479[b] |
| 207 | A2 | pentanoylamino | H | H | H | phenyl | T74 | CF₃ | | | | CH₃ | 3.58[b] | 461[m3] |
| 208 | A2 | 2-oxopiperidin-1-yl | H | H | H | phenyl | T73 | H | | | | CH₃ | 2.18[b] | 391[m3] |
| 209 | A2 | amino | H | H | H | phenyl | T8 | CH₃ | H | | | CH₃ | 0.56[b] | 322 |

TABLE 1-continued

| Ex. | A | $Z^1$ | $Z^2$ | $Z^3$ | $Z^4$ | Q | T | $X^1$ | $X^2$ | $X^3$ | $X^4$ | $W^1$ | log p | MS_Measured |
|---|---|---|---|---|---|---|---|---|---|---|---|---|---|---|
| 210 | A2 | $CF_3$ | H | H | methoxy-carbonyl | cyclohexyl | T85 | H | H | H | H | | 4.75[a] | |
| 211 | A2 | [(pentyloxy)carbonyl]amino | H | H | H | phenyl | T8 | $CH_3$ | H | | | $CH_3$ | 3.13[b] | |
| 212 | A2 | hexanoylamino | H | H | H | phenyl | T8 | $CH_3$ | H | | | $CH_3$ | 2.08[b] | |
| 213 | A2 | 1,3-dioxo-1,3-dihydro-2H-isoindol-2-yl | H | H | H | phenyl | T73 | Br | | | | $CH_3$ | 3.58[b] | |
| 214 | A2 | 1,3-dioxo-1,3-dihydro-2H-isoindol-2-yl | H | H | H | phenyl | T82 | $CH_3$ | | | | | 3.69[b] | |
| 215 | A2 | amino | H | H | H | phenyl | T82 | $CH_3$ | | | | | 1.63[b] | |
| 216 | A2 | hexanoylamino | H | H | H | phenyl | T82 | $CH_3$ | | | | | 4.46[b] | |
| 217 | A2 | [(pentyloxy)carbonyl]amino | H | H | H | phenyl | T82 | $CH_3$ | | | | | 5.11[b] | |
| 218 | A2 | (3-methylbutanoyl)amino | H | H | H | phenyl | T82 | $CH_3$ | | | | | 3.96[b] | |
| 219 | A2 | (phenylacetyl)amino | H | H | H | phenyl | T82 | $CH_3$ | | | | | 4.04[b] | |
| 220 | A2 | (3-phenylpropanoyl)amino | H | H | H | phenyl | T82 | $CH_3$ | | | | | 4.31[b] | |
| 221 | A2 | (3-cyclopentylpropanoyl)amino | H | H | H | phenyl | T82 | $CH_3$ | | | | | 5[b] | |
| 222 | A2 | [(2-methylpropoxy)carbonyl]amino | H | H | H | phenyl | T82 | $CH_3$ | | | | | 4.65[b] | |
| 223 | A2 | (3-cyclohexylpropanoyl)amino | H | H | H | phenyl | T82 | $CH_3$ | | | | | 5.41[b] | |
| 224 | A2 | pentanoylamino | H | H | H | phenyl | T82 | $CH_3$ | | | | | 4.04[b] | |
| 225 | A2 | [difluoro(phenoxy)acetyl]amino | H | H | H | phenyl | T82 | $CH_3$ | | | | | 4.7[b] | |
| 226 | A2 | (thiophen-2-ylcarbonyl)amino | H | H | H | phenyl | T82 | $CH_3$ | | | | | | |
| 227 | A2 | 1,3-dioxo-1,3-dihydro-2H-isoindol-2-yl | H | H | H | 3-fluorophenyl | T14 | H | H | | | $CH_3$ | 2.13[b] | |
| 228 | A2 | bromo | H | H | H | phenyl | T74 | H | | | | $CH_3$ | 2.28[b] | |
| 229 | A2 | cyclopropylethynyl | H | H | H | phenyl | T74 | H | | | | $CH_3$ | 2.56[b] | |
| 230 | A2 | 3-cyclopentylprop-1-yn-1-yl | H | H | H | phenyl | T74 | H | | | | $CH_3$ | 3.76[b] | |
| 231 | A2 | 3-cyclohexylprop-1-yn-1-yl | H | H | H | phenyl | T74 | H | | | | $CH_3$ | 4.14[b] | |
| 232 | A2 | phenylethynyl | H | H | H | phenyl | T74 | H | | | | $CH_3$ | 3.15[b] | |
| 233 | A2 | amino | H | H | H | 3-fluorophenyl | T14 | H | | | | $CH_3$ | 0.54[b] | |
| 234 | A2 | [(2-methoxyphenyl)acetyl]amino | H | H | H | phenyl | T73 | H | H | | | $CH_3$ | 3.17[b] | |
| 235 | A2 | [(3-fluorophenyl)acetyl]amino | H | H | H | phenyl | T73 | H | | | | $CH_3$ | 3.15[b] | |
| 236 | A2 | [(2-fluorophenyl)acetyl]amino | H | H | H | phenyl | T73 | H | | | | $CH_3$ | 3.09[b] | |
| 237 | A2 | (3-methoxyphenyl)amino | H | H | H | phenyl | T73 | H | | | | $CH_3$ | 2.17[b] | |
| 238 | A2 | [3-(3-chlorophenyl)propanoyl]amino | H | H | H | phenyl | T73 | H | | | | $CH_3$ | 3.73[b] | |
| 239 | A2 | {3-[3-($CF_3$)phenyl]propanoyl}amino | H | H | H | phenyl | T73 | H | | | | $CH_3$ | 3.87[b] | |
| 240 | A2 | (2-phenylpropanoyl)amino | H | H | H | phenyl | T73 | H | | | | $CH_3$ | 3.42[b] | |
| 241 | A2 | [(3,5-difluorophenyl)acetyl]amino | H | H | H | phenyl | T73 | H | | | | $CH_3$ | 3.33[b] | |
| 242 | A2 | [(4-chlorophenyl)acetyl]amino | H | H | H | phenyl | T73 | H | | | | $CH_3$ | 3.46[b] | |

TABLE 1-continued

| Ex. | A | Z¹ | Z² | Z³ | Z⁴ | Q | T | X¹ | X² | X³ | X⁴ | W¹ | log p | MS_Measured |
|---|---|---|---|---|---|---|---|---|---|---|---|---|---|---|
| 243 | A2 | [(2-chlorophenyl)acetyl]amino | H | H | H | phenyl | T73 | H | | | | | CH$_3$ | 3.31[b] | |
| 244 | A2 | {[3-(CF$_3$)phenyl]acetyl}amino | H | H | H | phenyl | T73 | H | | | | | CH$_3$ | 3.64[b] | |
| 245 | A2 | {[2-(CF$_3$)phenyl]acetyl}amino | H | H | H | phenyl | T73 | H | | | | | CH$_3$ | 3.51[b] | |
| 246 | A2 | [(4-methoxyphenyl)acetyl]amino | H | H | H | phenyl | T73 | H | | | | | CH$_3$ | 3.02[b] | |
| 247 | A2 | [(3-methoxyphenyl)acetyl]amino | H | H | H | phenyl | T73 | H | | | | | CH$_3$ | 3.06[b] | |
| 248 | A2 | (cyclohexylcarbonyl)amino | H | H | H | phenyl | T73 | H | | | | | CH$_3$ | 3.39[b] | |
| 249 | A2 | (4-phenylbutanoyl)amino | H | H | H | phenyl | T73 | H | | | | | CH$_3$ | 3.6[b] | |
| 250 | A2 | {[(phenylsulfanyl)acetyl]amino | H | H | H | phenyl | T73 | H | | | | | CH$_3$ | 3.33[b] | |
| 251 | A2 | (tetrahydro-2H-pyran-2-ylcarbonyl)amino | H | H | H | phenyl | T73 | H | | | | | CH$_3$ | 3.15[b] | |
| 252 | A2 | [(4-ethylphenyl)carbonyl]amino | H | H | H | phenyl | T73 | H | | | | | CH$_3$ | 3.73[b] | |
| 253 | A2 | [(pentyloxy)carbonyl]amino | H | H | H | phenyl | T8 | H | H | | | | CH$_3$ | 2.39[b] | |
| 254 | A2 | decanoylamino | H | H | H | phenyl | T8 | H | H | | | | CH$_3$ | 3.09[b] | |
| 255 | A2 | (phenoxyacetyl)amino | H | H | H | phenyl | T8 | H | H | | | | CH$_3$ | 2.04[b] | |
| 256 | A2 | butanoylamino | H | H | H | phenyl | T8 | H | H | | | | CH$_3$ | 1.6[b] | |
| 257 | A2 | heptanoylamino | H | H | H | phenyl | T8 | H | H | | | | CH$_3$ | 2.3[b] | |
| 258 | A2 | pentanoylamino | H | H | H | phenyl | T8 | H | H | | | | CH$_3$ | 1.82[b] | |
| 259 | A2 | (2-phenylbutanoyl)amino | H | H | H | phenyl | T8 | H | H | | | | CH$_3$ | 2.3[b] | |
| 260 | A8 | bis(cyclopropylcarbonyl)amino | H | H | H | phenyl | T8 | cyclopropylcarbonyl | H | | | | CH$_3$ | 3.73[b] | |
| 261 | A2 | [(4-propylphenyl)carbonyl]amino | H | H | H | phenyl | T73 | H | H | | | | CH$_3$ | 4.24[b] | |
| 262 | A2 | (3-methylpentanoyl)amino | H | H | H | phenyl | T14 | H | H | | | | CH$_3$ | 2.54[b] | |
| 263 | A2 | (2-methylpentanoyl)amino | H | H | H | phenyl | T14 | H | H | | | | CH$_3$ | 2.54[b] | |
| 264 | A2 | (thiophen-2-ylacetyl)amino | H | H | H | phenyl | T14 | H | H | | | | CH$_3$ | 2.23[b] | |
| 265 | A2 | [(2-methoxyphenyl)acetyl]amino | H | H | H | phenyl | T14 | H | H | | | | CH$_3$ | 2.61[b] | |
| 266 | A2 | [(2-chlorophenyl)acetyl]amino | H | H | H | phenyl | T14 | H | H | | | | CH$_3$ | 2.33[b] | |
| 267 | A2 | [(3-methoxyphenyl)acetyl]amino | H | H | H | phenyl | T14 | H | H | | | | CH$_3$ | 2.37[b] | |
| 268 | A2 | [(2-methoxyphenyl)acetyl]amino | H | H | H | phenyl | T14 | H | H | | | | CH$_3$ | 2.47[b] | |
| 269 | A2 | [(2-fluorophenyl)acetyl]amino | H | H | H | phenyl | T14 | H | H | | | | CH$_3$ | 2.4[b] | |
| 270 | A2 | [(4-methoxyphenyl)acetyl]amino | H | H | H | phenyl | T14 | H | H | | | | CH$_3$ | 4.53[b] | |
| 271 | A2 | (3-methoxypropanoyl)amino | H | H | H | phenyl | T14 | H | H | | | | CH$_3$ | 1.9[b] | |
| 272 | A2 | (methylsulfanyl)propanoyl]amino | H | H | H | phenyl | T14 | H | H | | | | CH$_3$ | 1.81[b] | |
| 273 | A2 | [(4-methoxyphenyl)acetyl]amino | H | H | H | 3-fluorophenyl | T14 | H | H | | | | CH$_3$ | 2.54[b] | |
| 274 | A2 | [(3-methoxyphenyl)acetyl]amino | H | H | H | 3-fluorophenyl | T14 | H | H | | | | CH$_3$ | 2.58[b] | |

TABLE 1-continued

| Ex. | A | $Z^1$ | $Z^2$ | $Z^3$ | $Z^4$ | Q | T | $X^1$ | $X^2$ | $X^3$ | $X^4$ | $W^1$ | log p | MS_Measured |
|---|---|---|---|---|---|---|---|---|---|---|---|---|---|---|
| 275 | A2 | [(2-methoxyphenyl)acetyl]amino | H | H | H | 3-fluorophenyl | T14 | H | H | | | $CH_3$ | 2.66[b] | |
| 276 | A2 | [(2-fluorophenyl)acetyl]amino | H | H | H | 3-fluorophenyl | T14 | H | H | | | $CH_3$ | 2.59[b] | |
| 277 | A2 | (3-methoxypropanoyl)amino | H | H | H | 3-fluorophenyl | T14 | H | H | | | $CH_3$ | 1.69[b] | |
| 278 | A2 | (2-phenylpropanoyl)amino | H | H | H | 3-fluorophenyl | T14 | H | H | | | $CH_3$ | 2.92[b] | |
| 279 | A2 | {[5-methyl-3-($CF_3$)-1H-pyrazol-1-yl]acetyl}amino | H | H | H | phenyl | T14 | H | H | | | $CH_3$ | 2.61[b] | |
| 280 | A2 | (phenoxyacetyl)amino | H | H | H | phenyl | T14 | H | H | | | $CH_3$ | 2.58[b] | |
| 281 | A2 | (3-cyclopentylpropanoyl)amino | H | H | H | phenyl | T14 | H | H | | | $CH_3$ | 3.19[b] | |
| 282 | A2 | cyclohexylpropanoyl)amino | H | H | H | phenyl | T14 | H | H | | | $CH_3$ | 3.67[b] | |
| 283 | A2 | [(phenylsulfanyl)acetyl]amino | H | H | H | phenyl | T14 | H | H | | | $CH_3$ | 2.63[b] | |
| 284 | A2 | (3-cyclopentylpropanoyl)amino | H | H | H | 3-fluorophenyl | T14 | H | H | | | $CH_3$ | 3.44[b] | |
| 285 | A2 | (3-cyclohexylpropanoyl)amino | H | H | H | 3-fluorophenyl | T14 | H | H | | | $CH_3$ | 3.92[b] | |
| 286 | A2 | [(phenylsulfanyl)acetyl]amino | H | H | H | 3-fluorophenyl | T14 | H | H | | | $CH_3$ | 2.82[b] | |
| 287 | A2 | [3-(methylsulfanyl)propanoyl]amino | H | H | H | 3-fluorophenyl | T14 | H | H | | | $CH_3$ | 2.07[b] | |
| 288 | A2 | (3-methylpentanoyl)amino | H | H | H | 3-fluorophenyl | T14 | H | H | | | $CH_3$ | 2.77[b] | |
| 289 | A2 | (2-methylpentanoyl)amino | H | H | H | 3-fluorophenyl | T14 | H | H | | | $CH_3$ | 2.77[b] | |
| 290 | A2 | (thiophen-2-ylacetyl)amino | H | H | H | 3-fluorophenyl | T14 | H | H | | | $CH_3$ | 2.44[b] | |
| 291 | A2 | [(2-chlorophenyl)acetyl]amino | H | H | H | 3-fluorophenyl | T14 | H | H | | | $CH_3$ | 2.8[b] | |
| 292 | A2 | {[5-methyl-3-($CF_3$)-1H-pyrazol-1-yl]acetyl}amino | H | H | H | 3-fluorophenyl | T14 | H | H | | | $CH_3$ | 2.8[b] | |
| 293 | A2 | (phenoxyacetyl)amino | H | H | H | 3-fluorophenyl | T14 | H | H | | | $CH_3$ | 2.63[b] | |
| 294 | A2 | [(4-fluorophenyl)acetyl]amino | H | H | H | phenyl | T73 | H | H | | | $CH_3$ | 3.15[b] | |
| 295 | A2 | [3-(5-chlorothiophen-2-yl)propanoyl]amino | H | H | H | phenyl | T73 | H | | | | $CH_3$ | 3.74[b] | |
| 296 | A2 | [3-(3,5-dichlorophenyl)propanoyl]amino | H | H | H | phenyl | T73 | H | | | | $CH_3$ | 4.29[b] | |
| 297 | A2 | [3-(4-methoxyphenyl)propanoyl]amino | H | H | H | phenyl | T73 | H | | | | $CH_3$ | 3.25[b] | |
| 298 | A2 | [3-(3-methoxyphenyl)propanoyl]amino | H | H | H | phenyl | T73 | H | | | | $CH_3$ | 3.25[b] | |
| 299 | A2 | [3-(2-methoxyphenyl)propanoyl]amino | H | H | H | phenyl | T73 | H | | | | $CH_3$ | 3.44[b] | |
| 300 | A2 | [3-(4-chlorophenyl)propanoyl]amino | H | H | H | phenyl | T73 | H | | | | $CH_3$ | 3.72[b] | |
| 301 | A2 | [3-(2-chlorophenyl)propanoyl]amino | H | H | H | phenyl | T73 | H | | | | $CH_3$ | 3.72[b] | |
| 302 | A2 | {3-[4-($CF_3$)phenyl]propanoyl}amino | H | H | H | phenyl | T73 | H | | | | $CH_3$ | 3.9[b] | |
| 303 | A2 | {3-[2-($CF_3$)phenyl]propanoyl}amino | H | H | H | phenyl | T73 | H | | | | $CH_3$ | 3.87[b] | |

TABLE 1-continued

| Ex. | A | Z¹ | Z² | Z³ | Z⁴ | Q | T | X¹ | X² | X³ | X⁴ | W¹ | log p | MS_Measured |
|---|---|---|---|---|---|---|---|---|---|---|---|---|---|---|
| 304 | A2 | [(2-phenylcyclopropyl)carbonyl]amino | H | H | H | phenyl | T73 | H | | | | CH₃ | 3.61[b] | |
| 305 | A2 | [(but-3-en-1-yloxy)carbonyl]amino | H | H | H | phenyl | T73 | H | | | | CH₃ | 3.21[b] | |
| 306 | A2 | (4-methylpentanoyl)amino | H | H | H | phenyl | T73 | H | | | | CH₃ | 3.37[b] | |
| 307 | A2 | (3-methylpentanoyl)amino | H | H | H | phenyl | T73 | H | | | | CH₃ | 3.31[b] | |
| 308 | A2 | (5-chloropentanoyl)amino | H | H | H | phenyl | T73 | H | | | | CH₃ | 2.98[b] | |
| 309 | A2 | hex-5-ynoylamino | H | H | H | phenyl | T73 | H | | | | CH₃ | 2.7[b] | |
| 310 | A2 | pent-4-enoylamino | H | H | H | phenyl | T73 | H | | | | CH₃ | 2.77[b] | |
| 311 | A2 | (thiophen-2-ylacetyl)amino | H | H | H | phenyl | T73 | H | | | | CH₃ | 2.98[b] | |
| 312 | A2 | (tetrahydro-2H-pyran-4-ylcarbonyl)amino | H | H | H | phenyl | T73 | H | | | | CH₃ | 2.22[b] | |
| 313 | A2 | [(3-chlorophenyl)acetyl]amino | H | H | H | phenyl | T73 | H | | | | CH₃ | 3.5[b] | |
| 314 | A2 | but-3-enoylamino | H | H | H | phenyl | T73 | H | | | | CH₃ | 2.51[b] | |
| 315 | A2 | [(2-methylbutoxy)carbonyl]amino | H | H | H | phenyl | T73 | H | | | | CH₃ | | |
| 316 | A2 | [(2-methylpropoxy)carbonyl]amino | H | H | H | phenyl | T73 | H | | | | CH₃ | 3.52[b] | |
| 317 | A2 | [(3-methylbutoxy)carbonyl]amino | H | H | H | phenyl | T73 | H | | | | CH₃ | 3.9[b] | |
| 318 | A2 | [(pentyloxy)carbonyl]amino | H | H | H | phenyl | T10 | H | CH₃ | | | | 4.34[b] | |
| 319 | A2 | [(pentyloxy)carbonyl]amino | H | H | H | phenyl | T10 | H | CH₃ | | | | 4.54[b] | |
| 320 | A2 | hexanoylamino | H | H | H | phenyl | T10 | H | CH₃ | | | | 3.94[b] | |
| 321 | A16 | [(pentyloxy)carbonyl]amino | H | H | H | phenyl | T10 | H | CH₃ | | | | 4.09[b] | |
| 322 | A16 | [(pentyloxy)carbonyl]amino | H | H | H | phenyl | T10 | H | CH₃ | | | | 3.87[b] | |
| 323 | A2 | hexanoylamino | H | H | H | phenyl | T10 | H | CH₃ | | | | 3.67[b] | |
| 324 | A2 | [(2-methylbutoxy)carbonyl]amino | H | H | H | phenyl | T14 | H | H | | | CH₃ | 2.52[b] | |
| 325 | A2 | [(2-methylpropoxy)carbonyl]amino | H | H | H | phenyl | T14 | H | H | | | CH₃ | 2.21[b] | |
| 326 | A2 | [(3-methylbutoxy)carbonyl]amino | H | H | H | phenyl | T14 | H | H | | | CH₃ | 2.51[b] | |
| 327 | A2 | [(2,2,2-trichloroethoxy)carbonyl]amino | H | H | H | phenyl | T14 | H | H | | | CH₃ | 2.45[b] | |
| 328 | A2 | [(but-3-en-1-yloxy)carbonyl]amino | H | H | H | phenyl | T14 | H | H | | | CH₃ | 2.02[b] | |
| 329 | A2 | (4-methylpentanoyl)amino | H | H | H | phenyl | T14 | H | H | | | CH₃ | 2.15[b] | |
| 330 | A2 | [(prop-2-yn-1-yloxy)carbonyl]amino | H | H | H | phenyl | T14 | H | H | | | CH₃ | 1.66[b] | |
| 331 | A2 | [3-(5-chlorothiophen-2-yl)propanoyl]amino | H | H | H | phenyl | T14 | H | H | | | CH₃ | 2.49[b] | |
| 332 | A2 | [(but-3-yn-1-yloxy)carbonyl]amino | H | H | H | phenyl | T14 | H | H | | | CH₃ | 1.78[b] | |
| 333 | A2 | (2-phenylpropanoyl)amino | H | H | H | phenyl | T14 | H | H | | | CH₃ | 2.21[b] | |
| 334 | A2 | [(butylsulfanyl)carbonyl]amino | H | H | H | phenyl | T14 | H | H | | | CH₃ | 2.58[b] | |
| 335 | A2 | [3-(5-chlorothiophen-2-yl)propanoyl]amino | H | H | H | 3-fluorophenyl | T14 | H | H | | | CH₃ | 2.77[b] | |
| 336 | A2 | [(but-3-yn-1-yloxy)carbonyl]amino | H | H | H | 3-fluorophenyl | T14 | H | H | | | CH₃ | 1.98[b] | |

TABLE 1-continued

| Ex. | A | $Z^1$ | $Z^2$ | $Z^3$ | $Z^4$ | Q | T | $X^1$ | $X^2$ | $X^3$ | $X^4$ | $W^1$ | log p | MS_Measured |
|---|---|---|---|---|---|---|---|---|---|---|---|---|---|---|
| 337 | A2 | [methoxy(phenyl)acetyl]amino | H | H | H | phenyl | T14 | H | H | | | $CH_3$ | $2.15^{[b]}$ | |
| 338 | A2 | (tetrahydro-2H-pyran-2-yl)carbonyl]amino | H | H | H | phenyl | T14 | H | H | | | $CH_3$ | $1.93^{[b]}$ | |
| 339 | A2 | [(2-methoxyethoxy)carbonyl]amino | H | H | H | phenyl | T14 | H | H | | | $CH_3$ | $1.34^{[b]}$ | |
| 340 | A2 | [(tetrahydro-2H-pyran-2-yl)carbonyl]amino | H | H | H | 3-fluorophenyl | T14 | H | H | | | $CH_3$ | $2.17^{[b]}$ | |
| 341 | A2 | [(2-methoxyethoxy)carbonyl]amino | H | H | H | 3-fluorophenyl | T14 | H | H | | | $CH_3$ | $1.66^{[b]}$ | |
| 342 | A2 | [(butylsulfanyl)carbonyl]amino | H | H | H | 3-fluorophenyl | T14 | H | H | | | $CH_3$ | $2.88^{[b]}$ | |
| 343 | A2 | [(2-fluoroethoxy)carbonyl]amino | H | H | H | 3-fluorophenyl | T14 | H | H | | | $CH_3$ | $1.75^{[b]}$ | |
| 344 | A2 | [(2-methylbutoxy)carbonyl]amino | H | H | H | 3-fluorophenyl | T14 | H | H | | | $CH_3$ | $2.82^{[b]}$ | |
| 345 | A2 | [(2-methylpropoxy)carbonyl]amino | H | H | H | 3-fluorophenyl | T14 | H | H | | | $CH_3$ | $2.51^{[b]}$ | |
| 346 | A2 | [(3-methylbutoxy)carbonyl]amino | H | H | H | 3-fluorophenyl | T14 | H | H | | | $CH_3$ | $2.82^{[b]}$ | |
| 347 | A2 | [(2,2,2-trichloroethoxy)carbonyl]amino | H | H | H | 3-fluorophenyl | T14 | H | H | | | $CH_3$ | $2.73^{[b]}$ | |
| 348 | A2 | (4-methylpentanoyl)amino | H | H | H | 3-fluorophenyl | T14 | H | H | | | $CH_3$ | $2.42^{[b]}$ | |
| 349 | A2 | [methoxy(phenyl)acetyl]amino | H | H | H | 3-fluorophenyl | T14 | H | H | | | $CH_3$ | $2.42^{[b]}$ | |
| 350 | A16 | amino | H | H | | phenyl | T10 | H | $CH_3$ | | | | $1.3^{[b]}$ | |
| 351 | A16 | amino | H | H | | phenyl | T10 | H | $CH_3$ | | | | $1.46^{[b]}$ | |
| 352 | A2 | 1,3-dioxo-1,3-dihydro-2H-isoindol-2-yl | H | H | H | phenyl | T10 | H | $CH_3$ | | | | $3.25^{[b]}$ | |
| 353 | A2 | 1,3-dioxo-1,3-dihydro-2H-isoindol-2-yl | H | H | H | phenyl | T10 | H | $CH_3$ | | | | $3.09^{[b]}$ | |
| 354 | A2 | hex-1-yn-1-yl | H | H | H | phenyl | T74 | H | H | H | | $CH_3$ | $3.23^{[b]}$ | |
| 355 | A2 | $CF_3$ | H | H | methoxycarbonyl | phenyl | T85 | H | H | H | | | $3.45^{[a]}$ | |
| 356 | A2 | 1,3-dioxo-1,3-dihydro-2H-isoindol-2-yl | H | H | H | 3-bromo-4-methoxyphenyl | T85 | H | $CF_3$ | H | Cl | | $4.78^{[b]}$ | 646 |
| 357 | A16 | amino | H | | | 3-bromo-4-methoxyphenyl | T85 | H | $CF_3$ | H | Cl | | 2.8 | 522 |
| 358 | A2 | amino | H | H | H | 3-bromo-4-methoxyphenyl | T85 | H | $CF_3$ | H | Cl | | $2.54^{[b]}$ | 516 |
| 359 | A2 | (2,2-dimethylpropanoyl)amino | H | H | H | 3-bromo-4-methoxyphenyl | T85 | H | $CF_3$ | H | Cl | | $5.2^{[b]}$ | 600 |
| 360 | A2 | (cyclopropylcarbonyl)amino | H | H | H | 3-bromo-4-methoxyphenyl | T85 | H | $CF_3$ | H | Cl | | $4.54^{[b]}$ | 584 |
| 361 | A2 | (trifluoroacetyl)amino | H | H | H | 3-bromo-4-methoxyphenyl | T85 | H | $CF_3$ | H | Cl | | $4.97^{[b]}$ | 612 |
| 362 | A2 | [(2-methoxyethoxy)acetyl]amino | H | H | H | 3-bromo-4-methoxyphenyl | T85 | H | $CF_3$ | H | Cl | | $4.51^{[b]}$ | 632 |
| 363 | A2 | [(pentyloxy)carbonyl]amino | H | H | H | 3-bromo-4-methoxyphenyl | T85 | H | $CF_3$ | H | Cl | | $6.13^{[b]}$ | 630 |
| 364 | A2 | (phenylcarbonyl)amino | H | H | H | 3-bromo-4-methoxyphenyl | T85 | H | $CF_3$ | H | Cl | | $5.23^{[b]}$ | 620 |

TABLE 1-continued

| Ex. | A | Z¹ | Z² | Z³ | Z⁴ | Q | T | X¹ | X² | X³ | X⁴ | W¹ | log p | MS_Measured |
|---|---|---|---|---|---|---|---|---|---|---|---|---|---|---|
| 365 | A2 | (phenylacetyl)amino | H | H | H | 3-bromo-4-methoxyphenyl | T85 | H | CF₃ | H | Cl | | 5.08[b] | 634 |
| 366 | A2 | nonanoylamino | H | H | H | 3-bromo-4-methoxyphenyl | T85 | H | CF₃ | H | Cl | | 6.65[b] | 656 |
| 367 | A2 | (2-methylpropanoyl)amino | H | H | H | 3-bromo-4-methoxyphenyl | T85 | H | CF₃ | H | Cl | | 4.73[b] | 586 |
| 368 | A2 | hexanoylamino | H | H | H | 3-bromo-4-methoxyphenyl | T85 | H | CF₃ | H | Cl | | 5.44[b] | 614 |
| 369 | A2 | heptanoylamino | H | H | H | 3-bromo-4-methoxyphenyl | T85 | H | CF₃ | H | Cl | | 5.82[b] | 628 |
| 370 | A2 | (3-methylbutanoyl)amino | H | H | H | 3-bromo-4-methoxyphenyl | T85 | H | CF₃ | H | Cl | | 5.03[b] | 600 |
| 371 | A16 | [(pentyloxy)carbonyl]amino | H | H | H | 3-bromo-4-methoxyphenyl | T85 | H | CF₃ | H | Cl | | 5.59[b] | 636 |
| 372 | A2 | 1,3-dioxo-1,3-dihydro-2H-isoindol-2-yl | H | H | H | phenyl | T92 | CH₃ | H | CH₃ | | | | 3.35[b] | |
| 373 | A2 | amino | H | H | H | phenyl | T92 | CH₃ | H | CH₃ | | | | 1.31[b] | |
| 374 | A2 | (propoxycarbonyl)amino | H | H | H | phenyl | T92 | CH₃ | H | CH₃ | | | | 3.81[b] | |
| 375 | A2 | [(hexyloxy)carbonyl]amino | H | H | H | phenyl | T92 | CH₃ | H | CH₃ | | | | 5.2[b] | |
| 376 | A2 | (butoxycarbonyl)amino | H | H | H | phenyl | T92 | CH₃ | H | CH₃ | | | | 4.29[b] | |
| 377 | A2 | hexanoylamino | H | H | H | phenyl | T92 | CH₃ | H | CH₃ | | | | 4.09[b] | |
| 378 | A2 | [(pentyloxy)carbonyl]amino | H | H | H | phenyl | T92 | CH₃ | H | CH₃ | | | | 4.75[b] | |
| 379 | A2 | pentanoylamino | H | H | H | phenyl | T92 | CH₃ | H | CH₃ | | | | 3.65[b] | |
| 380 | A2 | heptanoylamino | H | H | H | phenyl | T92 | CH₃ | H | CH₃ | | | | 4.54[b] | |
| 381 | A2 | butanoylamino | H | H | H | phenyl | T92 | CH₃ | H | CH₃ | | | | 3.21[b] | |
| 382 | A8 | amino | H | H | H | thiophen-3-yl | T18 | Cl | H | | | | | 1.86[b] | 386 |
| 383 | A16 | amino | H | H | H | thiophen-3-yl | T18 | Cl | H | | | | | 2.51[b] | 391 |
| 384 | A8 | (2,2-dimethylpropanoyl)amino | H | H | H | thiophen-3-yl | T18 | Cl | H | | | | | 4.67[b] | 470 |
| 385 | A2 | 1,3-dioxo-1,3-dihydro-2H-isoindol-2-yl | H | H | H | thiophen-2-yl | T14 | H | H | | | | CH₃ | 1.78[b] | 444 |
| 386 | A8 | amino | H | H | H | thiophen-2-yl | T14 | H | H | | | | CH₃ | 1.13[c] | 315 |
| 387 | A2 | amino | H | H | H | thiophen-2-yl | T14 | H | H | | | | CH₃ | 1.74[c] | 314 |
| 388 | A8 | hexanoylamino | H | H | H | thiophen-2-yl | T14 | H | H | | | | CH₃ | 1.93[b] | 413 |
| 389 | A8 | (3-methylbutanoyl)amino | H | H | H | thiophen-2-yl | T14 | H | H | | | | CH₃ | 1.59[b] | 399 |
| 390 | A8 | (2,2-dimethylpropanoyl)amino | H | H | H | thiophen-2-yl | T14 | H | H | | | | CH₃ | 1.56[b] | 399 |
| 391 | A2 | amino | H | H | H | thiophen-2-yl | T73 | H | H | | | | CH₃ | 0.82[b] | 315[m2] |
| 392 | A2 | (3-phenylpropanoyl)amino | H | H | H | thiophen-2-yl | T73 | H | H | | | | CH₃ | 3.17[b] | 447[m2] |
| 393 | A2 | hexanoylamino | H | H | H | thiophen-2-yl | T73 | H | H | | | | CH₃ | 3.23[b] | 413[m3] |
| 394 | A2 | [(pentyloxy)carbonyl]amino | H | H | H | thiophen-2-yl | T73 | H | H | | | | CH₃ | 3.82[b] | 429[m3] |
| 395 | A2 | (2,2-dimethylpropanoyl)amino | H | H | H | thiophen-2-yl | T73 | H | H | | | | CH₃ | 2.82[b] | 399 |
| 396 | A2 | (3-methylbutanoyl)amino | H | H | H | thiophen-2-yl | T73 | H | H | | | | CH₃ | 2.78[d]; 2.78[b] | 399[m2] |
| 397 | A8 | amino | H | H | | thiophen-2-yl | T73 | H | H | | | | CH₃ | 0.47[b] | 316[m3] |
| 398 | A16 | amino | H | H | H | thiophen-2-yl | T73 | H | H | | | | CH₃ | 0.92[b] | 321[m3] |
| 399 | A16 | hexanoylamino | H | H | H | thiophen-2-yl | T73 | H | H | | | | CH₃ | 3.23[b] | 419[m3] |
| 400 | A16 | [(pentyloxy)carbonyl]amino | H | H | H | thiophen-2-yl | T73 | H | H | | | | CH₃ | 3.53[b] | 435[m3] |

TABLE 1-continued

| Ex. | A | Z¹ | Z² | Z³ | Z⁴ | Q | T | X¹ | X² | X³ | X⁴ | W¹ | log p | MS_Measured |
|---|---|---|---|---|---|---|---|---|---|---|---|---|---|---|
| 401 | A16 | (2,2-dimethylpropanoyl)amino | H | | | thiophen-2-yl | T73 | H | | | | CH₃ | 2.8[b] | 405[m3] |
| 402 | A16 | (phenylacetyl)amino | | | | thiophen-2-yl | T73 | H | | | | CH₃ | 2.82[b] | 439[m3] |
| 403 | A16 | (3-phenylpropanoyl)amino | | | | thiophen-2-yl | T73 | H | | | | CH₃ | 3.09[b] | 453[m3] |
| 404 | A16 | (3-methylbutanoyl)amino | | | | thiophen-2-yl | T73 | H | | | | CH₃ | 2.73[b] | 405[m3] |
| 405 | A8 | hexanoylamino | H | H | | thiophen-2-yl | T73 | H | | | | CH₃ | 3[b] | 414[m3] |
| 406 | A8 | [(pentyloxy)carbonyl]amino | H | H | | thiophen-2-yl | T73 | H | | | | CH₃ | 3.31[b] | 430[m3] |
| 407 | A8 | (2,2-dimethylpropanoyl)amino | H | H | | thiophen-2-yl | T73 | H | | | | CH₃ | 2.59[b] | 400[m3] |
| 408 | A8 | (phenylacetyl)amino | H | H | | thiophen-2-yl | T73 | H | | | | CH₃ | 2.64[b] | 434[m3] |
| 409 | A8 | (3-phenylpropanoyl)amino | H | H | | thiophen-2-yl | T73 | H | | | | CH₃ | 2.9[b] | 448[m3] |
| 410 | A8 | (3-methylbutanoyl)amino | H | H | | thiophen-2-yl | T73 | H | | | | CH₃ | 2.56[b] | 400[m3] |
| 411 | A8 | [(pentyloxy)carbonyl]amino | H | H | H | thiophen-2-yl | T14 | H | H | | | CH₃ | 2.71[b] | 428 |
| 412 | A2 | (3-methylbutanoyl)amino | H | H | H | thiophen-2-yl | T14 | H | H | | | CH₃ | 1.91[b] | 398 |
| 413 | A2 | (2,2-dimethylpropanoyl)amino | H | H | H | thiophen-2-yl | T14 | H | H | | | CH₃ | 1.78[b] | 398 |
| 414 | A2 | (phenylacetyl)amino | H | H | H | thiophen-2-yl | T73 | H | H | | | CH₃ | 2.05[b] | 432 |
| 415 | A2 | (2-methylpropanoyl)amino | H | H | H | thiophen-2-yl | T14 | H | H | | | CH₃ | 1.65[b] | 384 |
| 416 | A2 | 1,3-dioxo-1,3-dihydro-2H-isoindol-2-yl | H | H | | thiophen-2-yl | T73 | H | | | | CH₃ | 2.64[b] | 445[m3] |
| 417 | A2 | 1,3-dioxo-1,3-dihydro-2H-isoindol-2-yl | H | H | | thiophen-2-yl | T8 | H | H | | | CH₃ | 1.73[b] | 444 |
| 418 | A2 | amino | H | H | | thiophen-3-yl | T8 | H | H | | | CH₃ | 0.39[b] | 314 |
| 419 | A2 | amino | H | H | | thiophen-3-yl | T8 | H | H | | | CH₃ | 0.32[b] | 314 |
| 420 | A2 | 1,3-dioxo-1,3-dihydro-2H-isoindol-2-yl | H | H | | thiophen-3-yl | T8 | H | H | | | CH₃ | 1.66[b] | |
| 421 | A2 | amino | H | H | H | thiophen-3-yl | T8 | H | H | | | CH₃ | 0.22[b] | |
| 422 | A16 | amino | H | H | H | thiophen-3-yl | T8 | H | H | | | CH₃ | 0.45[b] | |
| 423 | A16 | amino | H | H | H | thiophen-3-yl | T8 | H | H | | | CH₃ | 0.08[b] | |
| 424 | A2 | [(pentyloxy)carbonyl]amino | H | H | H | thiophen-3-yl | T8 | H | (pentyloxy)carbonyl | | | CH₃ | 5.5[b] | |
| 425 | A2 | [(pentyloxy)carbonyl]amino | H | H | H | thiophen-3-yl | T8 | H | H | | | CH₃ | 2.82[b] | |
| 426 | A2 | hexanoylamino | H | H | H | thiophen-3-yl | T8 | H | H | | | CH₃ | 1.99[b] | |
| 427 | A2 | hexanoylamino | H | H | H | thiophen-3-yl | T8 | H | H | | | CH₃ | 1.99[b] | |
| 428 | A2 | hexanoylamino | H | H | H | thiophen-2-yl | T8 | H | H | | | CH₃ | 1.99[b] | |
| 429 | A16 | hexanoylamino | H | H | H | thiophen-3-yl | T8 | H | H | | | CH₃ | 1.93[b] | |
| 430 | A2 | (2-methylpropanoyl)amino | H | H | H | thiophen-2-yl | T8 | H | H | | | CH₃ | 1.67[b] | |
| 431 | A2 | (phenoxyacetyl)amino | H | H | H | thiophen-3-yl | T8 | H | H | | | CH₃ | 1.94[b] | |
| 432 | A2 | hexanoylamino | H | H | H | thiophen-3-yl | T8 | H | H | | | CH₃ | 1.99[b] | |
| 433 | A16 | (2-methylpropanoyl)amino | H | H | H | thiophen-2-yl | T8 | H | H | | | CH₃ | 1.53[b] | |
| 434 | A16 | (phenoxyacetyl)amino | H | H | H | thiophen-2-yl | T8 | H | H | | | CH₃ | 1.87[b] | |
| 435 | A2 | (phenoxyacetyl)amino | H | H | H | thiophen-2-yl | T8 | H | H | | | CH₃ | 1.96[b] | |
| 436 | A2 | (2,2-dimethylpropanoyl)amino | H | H | H | thiophen-3-yl | T8 | H | H | | | CH₃ | 1.7[b] | |
| 437 | A2 | butanoylamino | H | H | H | thiophen-3-yl | T8 | H | H | | | CH₃ | 1.52[b] | |
| 438 | A2 | heptanoylamino | H | H | H | thiophen-3-yl | T8 | H | H | | | CH₃ | 2.25[b] | |
| 439 | A2 | (2-methylpropanoyl)amino | H | H | H | thiophen-3-yl | T8 | H | H | | | CH₃ | 1.5[b] | |
| 440 | A2 | pentanoylamino | H | H | H | thiophen-3-yl | T8 | H | H | | | CH₃ | 1.75[b] | |
| 441 | A2 | decanoylamino | H | H | H | thiophen-3-yl | T8 | H | H | | | CH₃ | 3.02[b] | |
| 442 | A2 | (3-methylbutanoyl)amino | H | H | H | thiophen-3-yl | T8 | H | H | | | CH₃ | 1.7[b] | |

TABLE 1-continued

| Ex. | A | $Z^1$ | $Z^2$ | $Z^3$ | $Z^4$ | Q | T | $X^1$ | $X^2$ | $X^3$ | $X^4$ | $W^1$ | log p | MS_Measured |
|---|---|---|---|---|---|---|---|---|---|---|---|---|---|---|
| 443 | A2 | (2,2-dimethylpropanoyl)amino | H | H | H | thiophen-2-yl | T8 | H | H | | | $CH_3$ | $1.7^{[b]}$ | |
| 444 | A2 | (3-methylbutanoyl)amino | H | H | H | thiophen-2-yl | T8 | H | H | | | $CH_3$ | $1.69^{[b]}$ | |
| 445 | A2 | butanoylamino | H | H | H | thiophen-2-yl | T8 | H | H | | | $CH_3$ | $1.5^{[b]}$ | |
| 446 | A2 | heptanoylamino | H | H | H | thiophen-2-yl | T8 | H | H | | | $CH_3$ | $2.2^{[b]}$ | |
| 447 | A2 | pentanoylamino | H | H | H | thiophen-2-yl | T8 | H | H | | | $CH_3$ | $1.74^{[b]}$ | |
| 448 | A2 | decanoylamino | H | H | H | thiophen-2-yl | T8 | H | H | | | $CH_3$ | $2.98^{[b]}$ | |
| 449 | A16 | (2,2-dimethylpropanoyl)amino | H | H | H | thiophen-2-yl | T8 | H | H | | | $CH_3$ | $1.67^{[b]}$ | |
| 450 | A16 | (3-methylbutanoyl)amino | | | | thiophen-2-yl | T8 | H | H | | | $CH_3$ | $1.66^{[b]}$ | |
| 451 | A16 | butanoylamino | | | | thiophen-2-yl | T8 | H | H | | | $CH_3$ | $1.47^{[b]}$ | |
| 452 | A16 | heptanoylamino | | | | thiophen-2-yl | T8 | H | H | | | $CH_3$ | $2.14^{[b]}$ | |
| 453 | A16 | pentanoylamino | | | | thiophen-2-yl | T8 | H | H | | | $CH_3$ | $1.7^{[b]}$ | |
| 454 | A16 | decanoylamino | | | | thiophen-2-yl | T8 | H | H | | | $CH_3$ | $2.86^{[b]}$ | |
| 455 | A2 | (2-phenylbutanoyl)amino | H | H | H | thiophen-2-yl | T8 | H | H | | | $CH_3$ | $2.2^{[b]}$ | |
| 456 | A2 | (2-phenylbutanoyl)amino | H | H | H | thiophen-3-yl | T8 | H | H | | | $CH_3$ | $2.21^{[b]}$ | |
| 457 | A2 | [(pentyloxy)carbonyl]amino | H | H | H | thiophen-2-yl | T8 | H | H | | | $CH_3$ | $2.35^{[b]}$ | |
| 458 | A2 | amino | H | H | H | thiophen-2-yl | T8 | (pentyloxy)carbonyl | H | | | $CH_3$ | $2.05^{[b]}$ | |
| 459 | A16 | [(pentyloxy)carbonyl]amino | H | H | H | thiophen-2-yl | T8 | H | H | | | $CH_3$ | $2.16^{[b]}$ | |
| 460 | A16 | [(pentyloxy)carbonyl]amino | H | H | H | thiophen-2-yl | T8 | H | H | | | $CH_3$ | $2.25^{[b]}$ | |
| 461 | A16 | [(pentyloxy)carbonyl]amino | H | H | H | thiophen-3-yl | T8 | H | H | | | $CH_3$ | $2.22^{[b]}$ | |
| 462 | A16 | [(pentyloxy)carbonyl]amino | H | H | H | thiophen-3-yl | T8 | H | H | | | $CH_3$ | $2.23^{[b]}$ | |
| 463 | A2 | 1,3-dioxo-1,3-dihydro-2H-isoindol-2-yl | H | H | H | thiophen-2-yl | T2 | H | H | H | | $CH_3$ | $3.78^{[b]}$ | 472 |
| 464 | A2 | amino | H | H | H | 6-chloropyridin-3-yl | T2 | H | H | H | | $CH_3$ | $1.72^{[b]}$ | 342 |
| 465 | A2 | 1,3-dioxo-1,3-dihydro-2H-isoindol-2-yl | H | H | H | 3-chloro-5-(CF$_3$)pyridin-2-yl | T73 | H | H | | | $CH_3$ | $3.15^{[b]}$ | $542^{[m3]}$ |
| 466 | A2 | amino | H | H | H | 3-chloro-5-(CF$_3$)pyridin-2-yl | T73 | H | H | | | $CH_3$ | $1.3^{[b]}$ | $412^{[m3]}$ |
| 467 | A2 | (phenylacetyl)amino | H | H | H | 3-chloro-5-(CF$_3$)pyridin-2-yl | T73 | H | H | | | $CH_3$ | $3.46^{[b]}$ | $530^{[m3]}$ |
| 468 | A2 | hexanoylamino | H | H | H | 3-chloro-5-(CF$_3$)pyridin-2-yl | T73 | H | H | | | $CH_3$ | $3.85^{[b]}$ | $510^{[m3]}$ |
| 469 | A2 | [(pentyloxy)carbonyl]amino | H | H | H | 3-chloro-5-(CF$_3$)pyridin-2-yl | T73 | H | H | | | $CH_3$ | $4.41^{[b]}$ | $526^{[m3]}$ |
| 470 | A2 | (2,2-dimethylpropanoyl)amino | H | H | H | 3-chloro-5-(CF$_3$)pyridin-2-yl | T73 | H | H | | | $CH_3$ | $3.44^{[b]}$ | $496^{[m3]}$ |

TABLE 1-continued

| Ex. | A | $Z^1$ | $Z^2$ | $Z^3$ | $Z^4$ | Q | T | $X^1$ | $X^2$ | $X^3$ | $X^4$ | $W^1$ | log p | MS_Measured |
|---|---|---|---|---|---|---|---|---|---|---|---|---|---|---|
| 471 | A2 | (3-phenylpropanoyl)amino | H | H | H | 3-chloro-5-(CF$_3$)pyridin-2-yl | T73 | H | | | | $CH_3$ | 3.73[b] | 544[m3] |
| 472 | A8 | amino | H | H | | 3-chloro-5-(CF$_3$)pyridin-2-yl | T73 | H | | | | $CH_3$ | 1.2[b] | 413[m3] |
| 473 | A16 | amino | H | | | 3-chloro-5-(CF$_3$)pyridin-2-yl | T73 | H | | | | $CH_3$ | 1.56[b] | 418[m3] |
| 474 | A8 | hexanoylamino | H | H | | 3-chloro-5-(CF$_3$)pyridin-2-yl | T73 | H | | | | $CH_3$ | 3.51[b] | 511[m3] |
| 475 | A8 | [(pentyloxy)carbonyl]amino | H | H | | 3-chloro-5-(CF$_3$)pyridin-2-yl | T73 | H | | | | $CH_3$ | 3.8[b] | 527[m3] |
| 476 | A8 | (phenylacetyl)amino | H | H | | 3-chloro-5-(CF$_3$)pyridin-2-yl | T73 | H | | | | $CH_3$ | 3.13[b] | 531[m3] |
| 477 | A8 | (3-phenylpropanoyl)amino | H | H | | 3-chloro-5-(CF$_3$)pyridin-2-yl | T73 | H | | | | $CH_3$ | 3.39[b] | 545[m3] |
| 478 | A8 | (3-methylbutanoyl)amino | H | H | | 3-chloro-5-(CF$_3$)pyridin-2-yl | T73 | H | | | | $CH_3$ | 3.06[b] | 497[m3] |
| 479 | A16 | hexanoylamino | H | | | 3-chloro-5-(CF$_3$)pyridin-2-yl | T73 | H | | | | $CH_3$ | 3.6[b] | 516[m2] |
| 480 | A16 | [(pentyloxy)carbonyl]amino | H | | | 3-chloro-5-(CF$_3$)pyridin-2-yl | T73 | H | | | | $CH_3$ | 3.94[b] | 532[m2] |
| 481 | A16 | (2,2-dimethylpropanoyl)amino | H | | | 3-chloro-5-(CF$_3$)pyridin-2-yl | T73 | H | | | | $CH_3$ | 3.27[b] | 502[m2] |
| 482 | A16 | (phenylacetyl)amino | H | | | 3-chloro-5-(CF$_3$)pyridin-2-yl | T73 | H | | | | $CH_3$ | 3.27[b] | 536[m2] |
| 483 | A16 | (3-phenylpropanoyl)amino | H | | | 3-chloro-5-(CF$_3$)pyridin-2-yl | T73 | H | | | | $CH_3$ | 3.51[b] | 550[m2] |
| 484 | A16 | (3-methylbutanoyl)amino | H | | | 3-chloro-5-(CF$_3$)pyridin-2-yl | T73 | H | | | | $CH_3$ | 3.19[b] | 502[m2] |

TABLE 1-continued

| Ex. | A | $Z^1$ | $Z^2$ | $Z^3$ | $Z^4$ | Q | T | $X^1$ | $X^2$ | $X^3$ | $X^4$ | $W^1$ | log p | MS_Measured |
|---|---|---|---|---|---|---|---|---|---|---|---|---|---|---|
| 485 | A2 | $CF_3$ | H | H | methoxycarbonyl | pyridin-2-yl | T85 | H | H | H | H | | $2.48^{[a]}$ | |
| 486 | A16 | amino | H | | | 4-($CF_3$)pyridin-2-yl | T85 | H | H | H | $CH_3$ | | $1.57^{[b]}$ | 393 |
| 487 | A16 | (2,2-dimethylpropanoyl)amino | H | | | 4-($CF_3$)pyridin-2-yl | T85 | H | H | H | $CH_3$ | | $3.44^{[b]}$ | 478 |
| 488 | A16 | (3-methylbutanoyl)amino | H | | | 4-($CF_3$)pyridin-2-yl | T85 | H | H | H | $CH_3$ | | $3.31^{[b]}$ | 478 |
| 489 | A16 | [(pentyloxy)carbonyl]amino | H | | | 4-($CF_3$)pyridin-2-yl | T85 | H | H | H | $CH_3$ | | $4.13^{[b]}$ | 508 |
| 490 | A16 | hexanoylamino | H | | | 4-($CF_3$)pyridin-2-yl | T85 | H | H | H | $CH_3$ | | $3.76^{[b]}$ | 492 |
| 491 | A2 | cyclohexylethynyl | H | H | H | phenyl | T74 | H | | | | $CH_3$ | $3.67^{[b]}$ | |

Measurement of logP values was performed according EEC directive 79/831 Annex V.A8 by HPLC (High Performance Liquid Chromatography) on reversed phase columns with the following methods:

[a]Measurement was done at pH 2.3 with 0.1% phosphoric acid and acetonitrile as eluent.

[b]measurement of LC-MS was done at pH 2.7 with 0.1% formic acid in water and with acetonitrile (contains 0.1% formic acid) as eluent with a linear gradient from 10% acetonitrile to 95% acetonitrile.

[c]Measurement with LC-MS was done at pH 7.8 with 0.001 molar ammonium hydrogen carbonate solution in water as eluent with a linear gradient from 10% acetonitrile to 95% acetonitrile.

Calibration was done with not branched alkan2-ones (with 3 to 16 carbon atoms) with known logP-values (measurement of logP-values using retention times with linear interpolation between successive alkanones).. lambda-maX-values were determined using UV-spectra from 200 nm to 400 nm and the peak values of the chromatographic signals.

In table 1, M + H (or MH) means the molecular ion peak, plus or minus 1 a.m.u. (atomic mass unit) respectively, as observed in mass spectroscopy and M (ApcI+) means the molecular ion peak as it was found via positive atmospheric pressure chemical ionisation in mass spectroscopy Molecular Weight measurement, Method:

[m1]UPLC-LCT

[m2]LCT-premier

[m3]SQD-ESI

In the following list we describe the double bond geometry of the examples of table 1 as shown here:

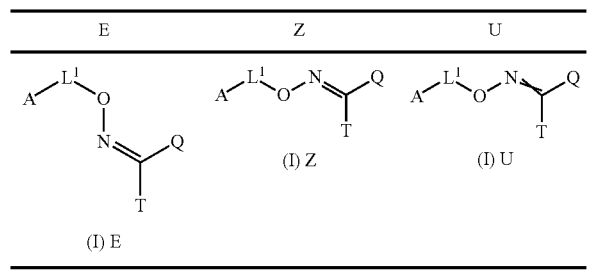

Example (Double bond geometry) of the examples of table 1:

1(Z), 2(U), 3(U), 4(U), 5(U), 6(U), 7(U), 8(U), 9(U), 10(U), 11(U), 12(U), 13(U), 14(U), 15(U), 16(U), 17(U), 18(U), 19(U), 20(U), 21(U), 22(U), 23(U), 24(U), 25(U), 26(U), 27(U), 28(U), 29(U), 30(U), 31(U), 32(U), 33(U), 34(U), 35(U), 36(U), 37(U), 38(U), 39(U), 40(U), 41(U), 42(U), 43(U), 44(U), 45(U), 46(U), 47(U), 48(Z), 49(Z), 50(U), 51(U), 52(U), 53(U), 54(U), 55(U), 56(U), 57(U), 58(U), 59(U), 60(U), 61(U), 62(U), 63(U), 64(U), 65(U), 66(U), 67(U), 68(U), 69(U), 70(U), 71(U), 72(U), 73(U), 74(U), 75(U), 76(U), 77(U), 78(U), 79(U), 80(U), 81(U), 82(U), 83(U), 84(U), 85(U), 86(U), 87(U), 88(U), 89(U), 90(U), 91(U), 92(U), 93(U), 94(U), 95(U), 96(U), 97(Z), 98(U), 99(U), 100(U), 101(U), 102(U), 103(U), 104(U), 105(U), 106(U), 107(U), 108(U), 109(U), 110(U), 111(U), 112(U), 113(U), 114(U), 115(Z), 116(Z), 117(Z), 118(Z), 119(Z), 120(U), 121(Z), 122(U), 123(Z), 124(U), 125(Z), 126(U), 127(U), 128(U), 129(U), 130(U), 131(U), 132(U), 133(U), 134(U), 135(U), 136(U), 137(U), 138(U), 139(U), 140(U), 141(U), 142(U), 143(U), 144(U), 145(U), 146(U), 147(U), 148(U), 149(U), 150(U), 151(U), 152(U), 153(U), 154(Z), 155(Z), 156(U), 157(U), 158(U), 159(U), 160(U), 161(U), 162(U), 163(Z), 164(Z), 165(U), 166(Z), 167(U), 168(Z), 169(Z), 170(E), 171(Z), 172(Z), 173(Z), 174(E), 175(U), 176(U), 177(U), 178(U), 179(U), 180(U), 181(U), 182(U), 183(U), 184(U), 185(U), 186(E), 187(Z), 188(Z), 189(E), 190(E), 191(E), 192(U), 193(U), 194(U), 195(E), 196(U), 197(U), 198(U), 199(U), 200(U), 201(U), 202(U), 203(U), 204(U), 205(U), 206(U), 207(U), 208(U), 209(U), 210(E), 211(U), 212(U), 213(U), 214(U), 215(U), 216(U), 217(U), 218(U), 219(U), 220(U), 221(U), 222(U), 223(U), 224(U), 225(U), 226(U), 227(U), 228(U), 229(U), 230(U), 231(U), 232(U), 233(U), 234(U), 235(U), 236(U), 237(U), 238(U), 239(U), 240(U), 241(U), 242(U), 243(U), 244(U), 245(U), 246(U), 247(U), 248(U), 249(U), 250(U), 251(U), 252(U), 253(U), 254(U), 255(U), 256(U), 257(U), 258(U), 259(U), 260(U), 261(U), 262(U), 263(U), 264(U), 265(U), 266(U), 267(U), 268(U), 269(U), 270(U), 271(U), 272(U), 273(U), 274(U), 275(U), 276(U), 277(U), 278(U), 279(U), 280(U), 281(U), 282(U), 283(U), 284(U), 285(U), 286(U), 287(U), 288(U), 289(U), 290(U), 291(U), 292(U), 293(U), 294(U), 295(U), 296(U), 297(U), 298(U), 299(U), 300(U), 301(U), 302(U), 303(U), 304(U), 305(U), 306(U), 307(U), 308(U), 309(U), 310(U), 311(U), 312(U), 313(U), 314(U), 315(U), 316(U), 317(U), 318(E), 319(Z), 320(Z), 321(Z), 322(E), 323(E), 324(U), 325(U), 326(U), 327(U), 328(U), 329(U), 330(U), 331(U), 332(U), 333(U), 334(U), 335(U), 336(U), 337(U), 338(U), 339(U), 340(U), 341(U), 342(U), 343(U), 344(U), 345(U), 346(U), 347(U), 348(U), 349(U), 350(E), 351(Z), 352(Z), 353(E), 354(U), 355(Z), 356(U), 357(U), 358(U), 359(U), 360(U), 361(U), 362(U), 363(U), 364(U), 365(U), 366(U), 367(U), 368(U), 369(U), 370(U), 371(U), 372(U), 373(U), 374(U), 375(U), 376(U), 377(U), 378(U), 379(U), 380(U), 381(U), 382(E), 383(E), 384(E), 385(U), 386(U), 387(U), 388(U), 389(U), 390(U), 391(U), 392(U), 393(U), 394(U), 395(U), 396(U), 397(U), 398(U), 399(U), 400(U), 401(U), 402(U), 403(U), 404(U), 405(U), 406(U), 407(U), 408(U), 409(U), 410(U), 411(U), 412(U), 413(U), 414(U), 415(U), 416(U), 417(U), 418(U), 419(E), 420(U), 421(U), 422(U), 423(U), 424(U), 425(E), 426(E), 427(U), 428(U), 429(U), 430(U), 431(U), 432(U), 433(U), 434(U), 435(U), 436(U), 437(U), 438(U), 439(U), 440(U), 441(U), 442(U), 443(U), 444(U), 445(U), 446(U), 447(U), 448(U), 449(U), 450(U), 451(U), 452(U), 453(U), 454(U), 455(U), 456(U), 457(U), 458(U), 459(U), 460(Z), 461(E), 462(U), 463(U), 464(U), 465(U), 466(U), 467(U), 468(U), 469(U), 470(U), 471(U), 472(U), 473(U), 474(U), 475(U), 476(U), 477(U), 478(U), 479(U), 480(U), 481(U), 482(U), 483(U), 484(U), 485(U), 486(U), 487(U), 488(U), 489(U), 490(U), 491(U),

Example A

*Phytophthora* Test (Tomato)/Preventive

Solvent: 49 parts by weight of N,N-Dimethylformamide
Emulsifier: 1 part by weight of Alkylarylpolyglycolether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Phytophthora infestans*. The plants remain for one day in an incubation cabinet at approximately 22° C. and a relative atmospheric humidity of 100%. Then the plants are placed in an incubation cabinet at approximately 20° C. and a relative atmospheric humidity of 96%.

The test is evaluated 7 days after the inoculation. 0% means an efficacy which corresponds to that of the control, while an efficacy of 100% means that no disease is observed.

In this test the following compounds of table 1 according to the invention showed efficacy of 70% or even higher at a concentration of 500ppm of active ingredient:

Example Nr. 35, 57, 65, 68, 69, 85, 87, 88, 91, 92, 94, 100, 101, 116, 117, 120, 121, 123, 125, 127, 157, 158, 159, 167, 216, 230, 231, 232, 234, 235, 236, 238, 239, 240, 242, 243, 244, 245, 246, 247, 248, 249, 250, 251, 252, 253, 254, 255, 256, 257, 258, 259, 261, 262, 263, 264, 265, 266, 267, 268, 269, 271, 273, 274, 275, 276, 278, 280, 281, 282, 283, 284, 285, 286, 287, 288, 289, 290, 291, 292, 293, 294, 296, 297, 298, 300, 301, 302, 303, 304, 306, 308, 309, 310, 313, 317, 320, 323, 324, 325, 326, 327, 328, 329, 331, 332, 333, 334, 335, 336, 340, 342, 344, 346, 347, 389, 411, 425, 427, 432, 433, 434, 435, 438, 440, 444, 446, 452, 455, 456 and 457.

Example B

*Plasmopara* Test (Grapevines)/Protective

Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. After the spray coating has dried on, the plants are inoculated with an aqueous spore suspension of *Plasmopara viticola* and then remain for 1 day in an incubation cabinet at approximately 20° C. and a relative atmospheric humidity of 100%. The plant is subsequently placed for 4 days in a greenhouse at approximately 21° C. and a relative atmospheric humidity of approximately 90%. The plants are then misted and placed for 1 day in an incubation cabinet.

The test is evaluated 6 days after the inoculation. 0% means an efficacy which corresponds to that of the control, while an efficacy of 100% means that no disease is observed.

In this test the following compounds of table 1 according to the invention showed efficacy of 70% or even higher at a concentration of 100 ppm of active ingredient:

Example Nr. 20, 21, 28, 29, 31, 33, 35, 36, 37, 45, 46, 65, 68, 69, 85, 88, 91, 92, 94, 100, 101, 120, 127, 157, 158, 159, 216, 234, 235, 236, 238, 240, 242, 245, 246, 247, 249, 250, 253, 255, 257, 259, 261, 262, 263, 264, 265, 266, 267, 268, 273, 274, 275, 278, 281, 282, 284, 285, 286, 288, 289, 290, 411, 425, 427, 432, 435, 446 and 456.

Example C

In Vitro-Test for the Calculation of the ED50-Value with *Pythium aphanidermatum*

Wells of 96-hole microtitre plates are filled with 10 µl of a solution of the test compound in methanol together with the emulsifier alkylaryl polyglycol ether. Thereafter, the solvent is evaporated in a hood. At the next step, into each well 200 µl of liquid potato dextrose medium is given that has been amended with an appropriate concentration of spores or mycelium suspension of the test fungus. The resulting concentrations of the test compounds in the microtitre well are 50, 5, 0.5 and 0.05 ppm. The resulting concentration of the emulsifier in all wells is constantly 300 ppm. With the aid of a photometer the extinction in all wells is measured at the wavelength of 620 nm.

The microtiter plates are then transferred for 3-5 days onto a shaker at 20° C. and 85% relative humidity.

At the end of the incubation time the growth of the test organisms is measured again photometrically at the wavelength of 620 nm The difference between the two extinction values (taken before and after incubation) is proportional to the growth of the test organism. Based on the Δ extinction data from the different test concentrations and that of the untreated test organism (control) a dose-response curve is calculated. The concentration that is necessary to give 50% growth inhibition is defined and reported as ED50-value (=Effective Dose that causes 50% growth inhibition) in ppm (=mg/l).

In this test the following compounds of table 1 according to the invention showed an ED50-value lower than 1 ppm:

Example Nr. 35, 51, 54, 55, 59, 60, 64, 65, 66, 67, 68, 69, 71, 81, 82, 83, 84, 85, 86, 87, 88, 89, 91, 92, 93, 94, 96, 100, 101, 107, 112, 113, 114, 115, 116, 117, 118, 119, 120, 121, 122, 123, 125, 126, 127, 130, 131, 132, 145, 146, 148, 149, 150, 153, 154, 155, 157, 158, 159, 160, 167, 173, 187, 188, 211, 212, 215, 216, 217, 218, 219, 220, 221, 222, 223, 224, 225, 229, 230, 231, 232, 234, 235, 236, 237, 238, 239, 240, 241, 242, 243, 244, 245, 246, 247, 248, 249, 250, 251, 252, 253, 318, 320, 324, 325, 326, 327, 328, 329, 331, 333, 334, 335, 336, 337, 339, 341, 342, 344, 345, 346, 347, 392, 393, 394, 396, 399, 400, 401, 402, 403, 404, 405, 406, 408, 411, 412, 413, 414, 415, 425, 427, 428, 429, 431, 432, 433, 434, 435, 436, 437, 438, 439, 440, 441, 442, 443, 444, 445, 446, 447, 448 and 461.

The following examples illustrate in a non-limiting manner the preparation and efficacy of the compounds of formula (I) according to the invention.

Preparation of 6-[({[(4-methyl-1,3-oxazol-5-yl)(phenyl)methylene]amino}oxy)methyl]pyridin-2-amine according to process P1

Step 1

Preparation of N-methoxy-N,4-dimethyl-1,3-oxazole-5-carboxamide

To a stirred solution of 4-methyl-1,3-oxazole-5-carboxylic acid (4.00 g, 31.5 mmol) in thionyl chloride (4 ml) were added 0.4 ml N,N-dimethylformamide and the mixture was refluxed for 2 hours. After cooling, the volatiles were removed in vacuo and the remaining material was suspended in tetrahydrofuran (10 ml). This suspension was added to a stirred suspension of N,O-dimethyl-hydroxylamine hydrochloride (3.38 g, 34.6 mmol) and triethylamine (9.55 g, 94.4 mmol) in tetrahydrofuran (10 ml). The reaction mixture was stirred at room temperature for 20 h. After evaporation of the solvent in vacuo dichloromethane and 1N HCl were added. The phases were separated, the organic layer was washed with brine, dried over $MgSO_4$, filtered and concentrated in vacuo. Purification of the crude material on silica gel afforded N-methoxy-N,4-dimethyl-1,3-oxazole-5-carboxamide (2.58 g, 45%) as an orange solid.

[M+1]=171

Step 2

Preparation of (4-methyl-1,3-oxazol-5-yl)(phenyl)methanone

To a mixture of lithium chloride (0.77 g, 18.2 mmol) and copper(I) iodide (0.087 g, 0.45 mmol) was added diethylether (30 ml). After stirring for 5 minutes a solution of N-methoxy-N,4-dimethyl-1,3-oxazole-5-carboxamide (2.58 g, 15.16 mmol) in diethylether (30 ml) was added followed by the slow addition of phenylmagnesium bromide (4.12 g, 22.74 mmol). After stirring for 20 hours at room temperature 1N HCl (20 mL) and water (30 mL) were added. The mixture was extracted with dichloromethane, the organic layer was washed with water, dried over $MgSO_4$, filtered and concentrated in vacuo. Purification of the crude material on silica gel afforded (4-methyl-1,3-oxazol-5-yl)(phenyl)methanone (1.08 g, 30%)

[M+1]=188

Step 3

Preparation of N-hydroxy-1-(4-methyl-1,3-oxazol-5-yl)-1-phenylmethanimine

To a stirred solution of (4-methyl-1,3-oxazol-5-yl)(phenyl)methanone (1.34 g, 7.15 mmol) in pyridine (40 mL), was added hydroxylamine hydrochloride (1.24 g, 17.9 mmol) and the reaction mixture was heated at 50° C. for 15 h. The reaction mixture was concentrated in vacuo. Water (60 mL) was added and the mixture was extracted with ethyl acetate (3×30 ml). The combined organic phases were dried over $MgSO_4$, filtered and concentrated in vacuo. Purification of the crude material on silica gel afforded N-hydroxy-1-(4-methyl-1,3-oxazol-5-yl)-1-phenylmethanimine (0.58 g, 39%).

[M+1]=203

Step 4

Preparation of 2-{6-[({[(4-methyl-1,3-oxazol-5-yl)(phenyl)methylene]amino}oxy)methyl]pyridin-2-yl}-1H-isoindole-1,3(2H)-dione (Compound 352)

To a solution of N-hydroxy-1-(4-methyl-1,3-oxazol-5-yl)-1-phenylmethanimine (0.15 g, 0.74 mmol) dissolved in acetonitrile (3 mL) were added 2-[6-(bromomethyl)pyridin-2-yl]-1H-isoindole-1,3(2H)-dione (259 mg, 0.82 mmol), cesium carbonate (507 mg, 1.56 mmol) and potassium iodide (12.3 mg, 0.074 mmol). After stirring for 8 hours at room temperature water was added and the mixture was extracted with ethyl acetate. The organic phase was dried over $MgSO_4$, filtered and concentrated in vacuo to afford 2-{6-[({[(4-methyl-1,3-oxazol-5-yl)(phenyl)methylene]amino}oxy)methyl]pyridin-2-yl}-1H-isoindole-1,3(2H)-dione (0.3 g, 88%).
[M+1]=439

Step 5

Preparation of 6-[({[(4-methyl-1,3-oxazol-5-yl)(phenyl)methylene]amino}oxy)methyl]pyridin-2-amine To a solution of 2-{6-[({[(4-methyl-1,3-oxazol-5-yl)(phenyl)methylene]amino}oxy)methyl]pyridin-2-yl}-1H-isoindole-1,3(2H)-dione (0.3 g, 0.69 mmol) dissolved in tetrahydrofuran (7 mL) was added hydrazine hydrate (171 mg, 3.4 mmol). After stirring for 24 hours at room temperature the precipitate formed was filtered. The filtrate was evaporated and purified on silica affording 6-[({[(4-methyl-1,3-oxazol-5-yl)(phenyl)methylene]amino}oxy)methyl]pyridin-2-amine (0.19 g, 85%).
[M+1]=309

Preparation of N-{6-[({[(4-methyl-1,3-oxazol-5-yl)(phenyl)methylene]amino}oxy)methyl]pyridin-2-yl}hexanamide (Compound 320) according to process P2

To a stirred solution of 6-[({[(4-methyl-1,3-oxazol-5-yl)(phenyl)methylene]amino}oxy)methyl]pyridin-2-amine (90 mg, 0.29 mmol) in dichloromethane (2 mL) were added pyridine (35 mg, 0.44 mmol) and after 15 min stirring n-hexanoyl chloride (43 mg, 0.32 mmol). After stirring at room temperature for 4 h the mixture was passed through a cartridge filled with basic alumina and 1 g silica. After rinsing with dichloromethane the final compound was eluted with heptane/ethylacetate (1/1) to afford after evaporation N-{6-[({[(4-methyl-1,3-oxazol-5-yl)(phenyl)methylene]amino}oxy)methyl]pyridin-2-yl}hexanamide (95 mg, 72%).
[M+1]=407

Preparation of 4-[({[(4-methyl-1,3-oxazol-5-yl)(phenyl)methylene]amino-}oxy)methyl]-1,3-thiazol-2-amine (Compound 351) according to process P1

To a solution of N-hydroxy-1-(4-methyl-1,3-oxazol-5-yl)-1-phenylmethanimine (0.18 g, 0.89 mmol prepared as described for example 320), dissolved in dioxane (17 mL) were added 4-(chloromethyl)-1,3-thiazol-2-amine hydrochloride (181 mg, 0.98 mmol), cesium carbonate (1.16 g, 3.56 mmol) and potassium iodide (15 mg, 0.9 mmol). After stirring for 48 hours at room temperature water was added and the mixture was extracted with ethyl acetate. The organic phase was dried over $MgSO_4$, filtered and concentrated in vacuo to afford after purification on silica 4-[({[(4-methyl-1,3-oxazol-5-yl)(phenyl)methylene]amino}oxy)methyl]-1,3-thiazol-2-amine (95 mg, 30%).
[M+1]=315

Preparation of pentyl{4-[({[(4-methyl-1,3-oxazol-5-yl)(phenyl)methylene]amino}oxy)methyl]-1,3-thiazol-2-yl}carbamate (Compound 321) according to process P2

To a stirred solution of 4-[({[(4-methyl-1,3-oxazol-5-yl)(phenyl)methylene]amino}oxy)methyl]-1,3-thiazol-2-amine (95 mg, 0.3 mmol) in dichloromethane (2 mL) were added pyridine (36 mg, 0.45 mmol) and after 15 min stirring pentyl carbonochloridoate (91 mg, 0.6 mmol). After stirring at room temperature for 4 h the mixture was passed through a cartridge filled with basic alumina and 1 g silica. After rinsing with dichloromethane the final compound was eluted with heptane/ethylacetate (1/1) to afford after purification on silica pentyl {4-[({[(4-methyl-1,3-oxazol-5-yl)(phenyl)methylene]amino}oxy) methyl]-1,3-thiazol-2-yl}carbamate (60 mg, 44%).
[M+1]=429

Preparation of 2-[({[(3,4-dichloro-1,2-thiazol-5-yl)(3-thienyl)methylene]amino}oxy)-methyl]pyrimidin-4-amine (compound 456) according to process P1

Step 1: Preparation of 3,4-dichloro-N-methoxy-N-methyl-1,2-thiazole-5-carboxamide To a solution of 3,4-dichloroisothiazole-5-carboxylic acid (4.00 g, 20.1 mmol) in dichloromethane (75 mL), cooled with an ice-brine bath, was added N,N-dimethylformamide (78 μL, 1 mmol) followed dropwise by oxalyl chloride (1.94 mL, 22.2 mmol). After stirring at room temperature for 2 h, meanwhile gas evolution had completely stopped, all volatiles were removed in vacuo to affor the crude acid chloride (4.30 g).

To a solution of this acid chloride (4.30 g, 19.8 mmol) in dichloromethane (75 mL) at 0° C. were sequentially added triethylamine (6.1 mL, 43.7 mmol) followed dropwise by a solution of N,O-dimethylhydroxylamine hydrochloride (2.33 g, 23.8 mmol) in dichloromethane (130 mL). After stirring at room temperature for 48 h, water was added to the reaction mixture, the layers were separated and the aqueous layer extracted with ethyl acetate. The combined organic layers were washed with sat. aq. Sodium bicarbonate, then water, then dried over $MgSO_4$ and concentrated in vacuo. The residue was purified on silica gel to afford 3,4-dichloro-N-methoxy-N-methyl-1,2-thiazole-5-carboxamide [4.00 g, yield 84%; HPLC/MS: m/z=241 (M+H); log $P_{(HCOOH)}$=1.66].

Step 2: Preparation of (3,4-dichloro-1,2-thiazol-5-yl)(3-thienyl)methanone

To a solution of 3,4-dichloro-N-methoxy-N-methyl-1,2-thiazole-5-carboxamide (3.80 g, 15.7 mmol) in tetrahydrofuran (130 mL) at −5° C. was added dropwise a solution of iodo(3-thienyl)magnesium in tetrahydrofuran (0.3 M, 158 mL, 47.4 mmol). After stirring at room temperature for 72 h, the reaction was worked-up by the addition of aq. HCl (1 M) until pH<7. After removal of the tetrahydrofuran in vacuo, the aqueous phase was extracted with ethyl acetate (3×50 mL). The organic layers were combined, dried over $MgSO_4$ and concentrated in vacuo. The residue was purified on silica gel to afford (3,4-dichloro-1,2-thiazol-5-yl)(3-thienyl)methanone [3.00 g, yield 65%; HPLC/MS: m/z=264 (M+H); log $P_{(HCOOH)}$=3.31].

Step 3: Preparation of 1-(3,4-dichloro-1,2-thiazol-5-yl)-N-hydroxy-1-(3-thienyl)methanimine A solution of (3,4-dichloro-1,2-thiazol-5-yl)(3-thienyl) methanone (3.00 g, 10.2 mmol) and hydroxylamine hydrochloride (844 mg, 25.5 mmol) in pyridine (30 mL) was stirred 4 h at 50° C. then overnight at room temperature. After removal of the solvent in vacuo, addition of water (50 mL) and extraction with ethyl acetate (3×40 mL), the combined organic layers were dried over MgSO₄ and concentrated in vacuo. The residue was purified on silica gel to afford 1-(3,4-dichloro-1,2-thiazol-5-yl)-N-hydroxy-1-(3-thienyl)methanimine [3.15 g, yield 99%; HPLC/MS: m/z=279 (M+H); log $P_{(HCOOH)}$=3.04].

Step 4: Preparation of 2-[({[(3,4-dichloro-1,2-thiazol-5-yl)(3-thienyl)methylene]amino}-oxy)methyl]pyrimidin-4-amine (example 456)

To a stirred suspension of 1-(3,4-dichloro-1,2-thiazol-5-yl)-N-hydroxy-1-(3-thienyl)methanimine (1.69 g, 6.06 mmol), 2-(chloromethyl)pyrimidin-4-amine (957 mg, 6.66 mmol) and potassium iodide (1.01 g, 6.06 mmol) in acetonitrile (15 mL) at 0° C. was added 1,5-diazabicyclo(4.3.0)non-5-ene (1.52 mL, 12.7 mmol). The mixture was stirred 10 min at 0° C., then overnight at room temperature. After dilution of the reaction mixture with water and extraction with ethyl acetate, the combined organic layers were dried over MgSO₄, concentrated in vacuo, and the residue purified on silica gel to afford 2-[({[(3,4-dichloro-1,2-thiazol-5-yl)(3-thienyl)methylene]amino}¬oxy)methyl]pyrimidin-4-amine [150 mg, yield 3%].

Preparation of 4-[({[(3,4-dichloro-1,2-thiazol-5-yl)(3-thienyl)methylene]amino}oxy)methyl]-1,3-thiazol-2-amine (example 457) according to process P1

To a stirred suspension of 1-(3,4-dichloro-1,2-thiazol-5-yl)-N-hydroxy-1-(3-thienyl)methanimine (1.60 g, 5.73 mmol), 4-(chloromethyl)-1,3-thiazol-2-amine hydrochloride (937 mg, 6.30 mmol) and potassium iodide (951 mg, 5.73 mmol) in acetonitrile (15 mL) at 0° C. was added 1,5-diazabicyclo(4.3.0)non-5-ene (1.44 mL, 12.0 mmol). The mixture was stirred 10 min at 0° C., then overnight at room temperature. After dilution of the reaction mixture with water and extraction with ethyl acetate, the combined organic layers were dried over MgSO₄, concentrated in vacuo, and the residue purified by reverse phase HPLC to afford 4-[({[(3,4-dichloro-1,2-thiazol-5-yl)(3-thienyl)methylene]amino}oxy)methyl]-1,3-thiazol-2-amine [16 mg, yield 0.7%].

Preparation of 6-{[({(3-bromo-4-methoxyphenyl)[3-chloro-5-(trifluoromethyl)pyridin-2-yl]methylene}amino)oxy]methyl}pyridin-2-amine (example 432) according to process P1

Step 1: Preparation of 1-(3-bromo-4-methoxyphenyl)-1-[3-chloro-5-(trifluoromethyl)pyridin-2-yl]-N-hydroxymethanimine A solution of (3-bromo-4-methoxyphenyl)[3-chloro-5-(trifluoromethyl)pyridin-2-yl]methanone (8.90 g, 22.5 mmol) and hydroxylamine hydrochloride (3.92 g, 56.3 mmol) in pyridine (60 mL) was stirred 2 h at 50° C. then overnight at room temperature. After removal of the solvent in vacuo, addition of water (50 mL) and extraction with ethyl acetate (3×40 mL), the combined organic layers were dried over MgSO₄ and concentrated in vacuo. The residue was purified on silica gel to afford 1-(3-bromo-4-methoxyphenyl)-1-[3-chloro-5-(trifluoromethyl)pyridin-2-yl]-N-hydroxymethanimine [9.00 g, yield 88%; HPLC/MS: m/z=410 (M+H); log $P_{(HCOOH)}$=3.37].

Step 2: Preparation of 2-(6-{[({(3-bromo-4-methoxyphenyl)[3-chloro-5-(trifluoromethyl)pyridin-2-yl]methylene}amino)oxy]methyl}pyridin-2-yl)-1H-isoindole-1,3(2H)-dione (example 430)

To a solution of 1-(3-bromo-4-methoxyphenyl)-1-[3-chloro-5-(trifluoromethyl)pyridin-2-yl]-N-hydroxymethanimine (4.30 g, 10.4 mmol) and 2-[6-(bromomethyl)pyridin-2-yl]-1H-isoindole-1,3(2H)-dione (3.66 g, 11.5 mmol) in acetonitrile (40 mL) were added cesium carbonate (7.18 g, 22.0 mmol) and potassium iodide (174 mg, 1.05 mmol). After stirring overnight at room temperature, the reaction mixture was diluter with water (100 mL) and ethyl acetate (50 mL). After phase separation and further extraction of the aqueous phase with ethyl acetate (2×30 mL), the combined organic layers were dried over MgSO₄ and concentrated in vacuo to afford 2-(6-{[({(3-bromo-4-methoxyphenyl)[3-chloro-5-(trifluoromethyl)pyridin-2-yl]methylene}amino)oxy]methyl}pyridin-2-yl)-1H-isoindole-1,3(2H)-dione as an oil [7.10 g, yield 94%; HPLC/MS: m/z=646 (M+H); log $P_{(HCOOH)}$=4.78].

Step 3: Preparation of 6-{[({(3-bromo-4-methoxyphenyl)[3-chloro-5-(trifluoromethyl)pyridin-2-yl]methylene}amino)oxy]methyl}pyridin-2-amine (example 432)

To a solution of 2-(6-{[({(3-bromo-4-methoxyphenyl)[3-chloro-5-(trifluoromethyl)pyridin-2-yl]methylene}amino)oxy]methyl}pyridin-2-yl)-1H-isoindole-1,3(2H)-dione (7.00 g, 9.75 mmol) in tetrahydrofuran (150 mL) was added hydrazine hydrate (2.37 mL, 48.7 mmol) dropwise. After stirring overnight at room temperature, the reaction mixture was filtered, and the filtrate concentrated in vacuo. Purification on silica gel afforded 6-{[({(3-bromo-4-methoxyphenyl)[3-chloro-5-(trifluoromethyl)pyridin-2-yl]methylene}amino)oxy]methyl}pyridin-2-amine as an oil [4.00 g, yield 75%; HPLC/MS: m/z=516 (M+H); log $P_{(HCOOH)}$=2.54].

Preparation of N-(6-{[({(3-bromo-4-methoxyphenyl)[3-chloro-5-(trifluoromethyl)pyridin-2-yl]methylene}amino)oxy]methyl}pyridin-2-yl)-3-methylbutanamide (example 444) according to process P2

A solution of 6-{[({(3-bromo-4-methoxyphenyl)[3-chloro-5-(trifluoromethyl)pyridin-2-yl]methylene}amino)oxy]methyl}pyridin-2-amine (300 mg, 0.58 mmol), triethylamine (0.16 mL, 1.16 mmol) isovaleryl chloride (0.284, 2.32 mmol) in 1,4-dioxane (5 mL) was shaken overnight. After concentration in vacuo, the residual oil was purified on silica gel to afford N-(6-{[({(3-bromo-4-methoxyphenyl)[3-chloro-5-(trifluoromethyl)pyridin-2-yl]methylene}amino)oxy]methyl}pyridin-2-yl)-3-methylbutanamide as an oil [178 mg, yield 48%; HPLC/MS: m/z=600 (M+H); log $P_{(HCOOH)}$=5.03].

Preparation of ({[(3-methyl-1,2-oxazol-4-yl)(2-thienyl)methylene]amino}oxy)(pyridin-2-yl)methanone according to process P1

Step 1: Preparation of (3-methyl-1,2-oxazol-4-yl)(2-thienyl)methanone

To a solution of 3-methylisoxazole-4-carboxylic acid (10.0 g, 78.6 mmol) in dichloromethane (310 mL), cooled with an ice-brine bath, was added N,N-dimethylformamide (0.30 mL, 3.9 mmol) followed dropwise by oxalyl chloride (7.55 mL, 86.5 mmol). After stirring at room temperature overnight (meanwhile gas evolution had completely stopped), all volatiles were removed in vacuo to affor the crude acid chloride (11.0 g).

To a solution of dried lithium chloride (1.85 g, 43.6 mmol) in diethylether (215 mL) was added copper iodide (208 mg, 1.1 mmol). The suspension was stirred until a clear homogenous solution was obtained. To this solution was added the crude acid chloride (5.3 g, 36.4 mmol), and the resulting solution was stirred for 5 min. Under ice-brine cooling, a solution of bromo(thiophen-2-yl)magnesium (1 M in THF, 36.6 mL, 36.6 mmol) was added dropwise. After stirring at room temperature overnight, the reaction was worked-up by the addition of aq. HCl (1 M) until pH<7. After removal of the tetrahydrofuran in vacuo, the aqueous phase was extracted with ethyl acetate (3×50 mL). The organic layers were combined, dried over $MgSO_4$ and concentrated in vacuo. The residue was purified on silica gel to afford (3-methyl-1,2-oxazol-4-yl)(2-thienyl)methanone [6.10 g, yield 87%; HPLC/MS: m/z=211 (M+H); log $P_{(HCOOH)}$=2.20].

Step 2: Preparation of N-hydroxy-1-(3-methyl-1,2-oxazol-4-yl)-1-(2-thienyl)methanimine A solution of (3-methyl-1,2-oxazol-4-yl)(2-thienyl)methanone (6.00 g, 31.0 mmol) and hydroxylamine hydrochloride (5.40 g, 77.6 mmol) in pyridine (80 mL) was stirred 5 h at 50° C. then overnight at room temperature. After removal of the solvent in vacuo, addition of water (50 mL) and extraction with ethyl acetate (3×40 mL), the combined organic layers were dried over $MgSO_4$ and concentrated in vacuo. The residue was purified on silica gel to afford N-hydroxy-1-(3-methyl-1,2-oxazol-4-yl)-1-(2-thienyl)methanimine [6.45 g, yield 99%; HPLC/MS: m/z=219 (M+H); log $P_{(HCOOH)}$=1.75].

Step 3: Preparation of ({[(3-methyl-1,2-oxazol-4-yl)(2-thienyl)methylene]amino}oxy)(pyridin-2-yl)methanone To a solution of N-hydroxy-1-(3-methyl-1,2-oxazol-4-yl)-1-(2-thienyl)methanimine (200 mg, 0.96 mmol) and pyridine-2-carbonyl chloride hydrochloride (684 mg, 3.84 mmol) in 1,4-dioxane (5 mL) was added triethylamine (0.47 mL, 3.36 mmol). After shaking overnight at room temperature, water and ethyl acetate were added, the layers were separated, the organic layer were dried over $MgSO_4$ and concentrated in vacuo. Purification of the residue on silica gel afforded ({[(3-methyl-1,2-oxazol-4-yl)(2-thienyl)methylene]amino}oxy)¬pyridin-2-yl)methanone [266 mg, yield 84%; HPLC/MS: m/z=314 (M+H); log $P_{(HCOOH)}$=2.25].

Preparation of 2-[({[(1-methyl-1H-imidazol-2-yl)(phenyl)methylene]amino}oxy)methyl]pyrimidin-4-amine (Example 7) according to process P1

Step 1: Preparation of (1-methyl-1H-imidazol-2-yl)(phenyl)methanone

To a solution of N-methylimidazole (10.0 g, 122 mmol) in acetonitrile (120 mL) was added benzoyl chloride (14.1 mL, 122 mmol) followed by triethylamine (17.0 mL, 122 mmol), while keeping the internal temperature at 5° C. The mixture was stirred 18 h at room temperature. After filtration, the filtrate was concentrated in vacuo, diluted with ethyl acetate (200 mL) and sequentially washed with sat. aq. sodium bicarbonate (150 mL), water (100 mL) and brine (100 mL). The organic layer was dried over $MgSO_4$ and concentrated in vacuo.to afford (1-methyl-1H-imidazol-2-yl)(phenyl)methanone [21.0 g, yield 83%; HPLC/MS: m/z=187 (M+H); log $P_{(HCOOH)}$=1.38].

Step 2: Preparation of N-hydroxy-1-(1-methyl-1H-imidazol-2-yl)-1-phenylmethanimine A solution of (1-methyl-1H-imidazol-2-yl)(phenyl)methanone (20.8 g, 112 mmol) and hydroxylamine hydrochloride (19.4 g, 279 mmol) in pyridine (120 mL) was stirred 8 h at 50° C. then overnight at room temperature. After removal of the solvent in vacuo, addition of water (500 mL) induced precipitation of a white solid that was filtered off, washed with water (2×50 mL) and dried. A second filtration of the liquor yielded a second crop of solid. The combined crops afforded N-hydroxy-1-(1-methyl-1H-imidazol-2-yl)-1-phenylmethanimine [18.5 g, yield 80%; HPLC/MS: m/z=202 (M+H); log $P_{(HCOOH)}$=0.24].

Step 3: Preparation of 2-[({[(1-methyl-1H-imidazol-2-yl)(phenyl)methylene]amino}oxy)-methyl]pyrimidin-4-amine (Example 7)

To a solution of N-hydroxy-1-(1-methyl-1H-imidazol-2-yl)-1-phenylmethanimine (3.50 g, 17.4 mmol) and 2-(chloromethyl)pyrimidin-4-amine (2.62 g, 18.3 mmol) in acetonitrile (120 mL) were added cesium carbonate (5.67 g, 17.4 mmol) and potassium iodide (289 mg, 1.74 mmol). After stirring 6 h at 60° C., overnight at room temperature, then again 8 h at 60° C., the reaction mixture was diluted with water (150 mL), sat. aq. sodium bicarbonate (50 mL) and extracted with dichloromethane (2×100 mL). The combined organic layers were dried over $MgSO_4$ and concentrated in vacuo to afford 2-[({[(1-methyl-1H-imidazol-2-yl)(phenyl)methylene]amino}oxy)methyl]pyrimidin-4-amine as a foamy solid [4.80 g, yield 76%; HPLC/MS: m/z=309 (M+H); log $P_{(Neutral)}$=1.42].

Preparation of N-{2-[({[(1-methyl-1H-imidazol-2-yl)(phenyl)methylene]amino}-oxy)methyl]pyrimidin-4-yl}cyclopropanecarboxamide (Example 193) according to process P2

A solution of 2-[({[(1-methyl-1H-imidazol-2-yl)methylene]amino}oxy)methyl]pyrimidin-4-amine (200 mg, 0.64 mmol), triethylamine (0.18 mL, 1.29 mmol), cyclopropanecarboxylic acid chloride (136 mg, 1.29 mmol) in dichloromethane (10 mL) was stirred 6 h30 at room temperature. After dilution with water (50 mL), the layers were separated and the aqueous layer further extracted with dichloromethane (30 mL). The combined organic layers were dried over $MgSO_4$ and the solvents removed in vacuo. Purification on silica gel afforded N-{2-[({[(1-methyl-1 H-imidazol-2-yl)(phenyl)methylene]amino}oxy)methyl]pyrimidin-4-yl}cyclopropanecarboxamide as an oil [19 mg, yield 7%; HPLC/MS: m/z=377 (M+H); log $P_{(HCOOH)}$=1.50].

Preparation of pentyl{2-[({[(1-methyl-1H-imidazol-2-yl)(phenyl)methylene]amino}oxy)-methyl]pyrimidin-4-yl}carbamate (example 61) according to process P2

A solution of 2-[({[(1-methyl-1H-imidazol-2-yl)(phenyl)methylene]amino}oxy)methyl]pyrimidin-4-amine (200 mg, 0.64 mmol), triethylamine (0.18 mL, 1.29 mmol), chloroformic acid n-amyl ester (0.19 mL, 1.29 mmol) in dichloromethane (10 mL) was stirred 4 h20 at room temperature. After dilution with water (50 mL), the layers were separated and the aqueous layer further extracted with dichloromethane (30 mL). The combined organic layers were dried over $MgSO_4$ and the solvents removed in vacuo. Purification on silica gel afforded pentyl {2-[({[(1-methyl-1H-imidazol-2-yl)(phenyl)methylene]amino}oxy)methyl]pyrimidin-4-yl}carbamate as an oil [34 mg, yield 12%; HPLC/MS: m/z=423 (M+H); log $P_{(HCOOH)}$=2.28].

Preparation of 4-[({[(1-methyl-1H-imidazol-5-yl)(phenyl)methylene]amino}oxy)methyl]-1,3-thiazol-2-amine (example 122) according to process P1

Step 1: Preparation of (1-methyl-1H-imidazol-5-yl)(phenyl)methanone

To a solution of 5-bromo-1-methyl-1H-imidazole (10 g, 62 mmol) in dichloromethane (50 mL) was added dropwise ethylmagnesium bromide (3 M in $Et_2O$, 20.7 mL, 62 mmol). After stirring at room temperature for 15 min, the reaction mixture was cooled down to 0° C. with an ice-brine bath and N-methoxy-N-methylbenzamide (9.46 mL, 62 mmol) was added dropwise. The mixture was stirred for 2 h at room temperature. After standing for one night at room temperature, the mixture is worked-up by addition of water (150 mL), then acidified with aq. HCl (1 M) until pH=7. After extraction with dichloromethane (2×100 mL), the organic layers were washed with water (100 mL) then dried over $MgSO_4$ and concentrated in vacuo. The resulting orange solid was washed with pentane to afford (1-methyl-1H-imidazol-5-yl)(phenyl)methanone [8.50 g, yield 66%; HPLC/MS: m/z=187 (M+H); log $P_{(HCOOH)}$=0.79].

Step 2: Preparation of N-hydroxy-1-(1-methyl-1H-imidazol-5-yl)-1-phenylmethanimine A solution of (1-methyl-1H-imidazol-5-yl)(phenyl)methanone (14.0 g, 75 mmol) and hydroxylamine hydrochloride (13.1 g, 188 mmol) in pyridine (60 mL) was stirred for 72 h at room temperature, and for 3 h at 50° C. After removal of the solvent in vacuo, addition of water (600 mL) and extraction with ethyl acetate (4×150 mL), the combined organic layers were washed with water (150 mL), dried over $MgSO_4$ and concentrated in vacuo. The resulting yellow solid was washed with pentane to afford N-hydroxy-1-(1-methyl-1H-imidazol-5-yl)-1-phenylmethanimine [7.12 g, yield 42%; HPLC/MS: m/z=202 (M+H); log $P_{(HCOOH)}$=0.41]. Further extraction of the neutralised combined aqueous layers afforded a second crop of N-hydroxy-1-(1-methyl-1H-imidazol-5-yl)-1-phenylmethanimine [5.75 g, yield 34%; HPLC/MS: m/z=202 (M+H); log $P_{(HCOOH)}$=0.41], combined yield 76%.

Step 3: Preparation of 4-[({[(1-methyl-1H-imidazol-5-yl)(phenyl)methylene]amino}oxy)methyl]-1,3-thiazol-2-amine (example 122)

To a solution of N-hydroxy-1-(1-methyl-1H-imidazol-5-yl)-1-phenylmethanimine (3.90 g, 19.4 mmol) and 4-(chloromethyl)-1,3-thiazol-2-amine hydrochloride (3.95 g, 21.3 mmol) in acetonitrile (50 mL) were added cesium carbonate (13.3 g, 40.7 mmol) and potassium iodide (322 mg, 1.93 mmol). After stirring at room temperature for 29 h, N-N-dimethylformamide (5 mL) was added and the mixture was further at room temperature for 72 h. The reaction mixture was filtered, the insolubles washed with acetone, and the filtrate concentrated in vacuo. Purification on silica gel afforded 4-[({[(1-methyl-1H-imidazol-5-yl)(phenyl)methylene]amino}oxy)methyl]-1,3-thiazol-2-amine [1.09 g, yield 16%; HPLC/MS: m/z=314 (M+H); log $P_{(HCOOH)}$=0.69].

Preparation of 2-[({[1-methyl-1H-imidazol-5-yl)(phenyl)methylene]amino}oxy)methyl]pyrimidin-4-amine (example 105) according to process P1

To a solution of N-hydroxy-1-(1-methyl-1H-imidazol-5-yl)-1-phenylmethanimine (3.90 g, 19.4 mmol) and 2-(chloromethyl)pyrimidin-4-amine (3.06 g, 21.3 mmol) in acetonitrile (50 mL) were added cesium carbonate (13.3 g, 40.7 mmol) and potassium iodide (322 mg, 1.93 mmol). After stirring at room temperature for 29 h, N-N-dimethylformamide (5 mL) was added and the mixture was further at room temperature for 72 h. The reaction mixture was filtered, the insolubles washed with acetone, and the filtrate concentrated in vacuo. Purification on silica gel afforded 2-[({[(1-methyl-1H-imidazol-5-yl)(phenyl)methylene]amino}oxy)methyl]pyrimidin-4-amine [3.61 g, yield 16%; HPLC/MS: m/z=309 (M+H); log $P_{(HCOOH)}$<0.23].

Preparation of 6-[({[(1-methyl-1H-imidazol-5-yl)(phenyl)methylene]amino}oxy)methyl]pyridin-2-amine (example 108) according to process P1

Step 1

Preparation of 2-{6-[({[(1-methyl-1H-imidazol-5-yl)(phenyl)methylene]amino}oxy)methyl]pyridin-2-yl}-1H-isoindole-1,3(2H)-dione (example 100)

To a solution of N-hydroxy-1-(1-methyl-1H-imidazol-5-yl)-1-phenylmethanimine (3.90 g, 19.4 mmol) and 2-[6-(bromomethyl)pyridin-2-yl]-1H-isoindole-1,3(2H)-dione (6.79 g, 21.4 mmol) in acetonitrile (50 mL) were added cesium carbonate (13.3 g, 40.7 mmol) and potassium iodide (322 mg, 1.93 mmol). After stirring at room temperature for 29 h, the reaction mixture was filtered, the insolubles washed with acetone and diisopropylether, and the filtrate concentrated in vacuo. Purification on silica gel afforded 2-{6-[({[(1-methyl-1H-imidazol-5-yl)(phenyl)methylene]amino}oxy)methyl]pyridin-2-yl}-1H-isoindole-1,3(2H)-dione [1.88 g, yield 21%; HPLC/MS: m/z=438 (M+H); log $P_{(HCOOH)}$=1.81].

Step 2

Preparation of 6-[({[(1-methyl-1H-imidazol-5-yl)(phenyl)methylene]amino}oxy)methyl]pyridin-2-amine (example 108)

To a solution of 2-{6-[({[(1-methyl-1H-imidazol-5-yl)(phenyl)methylene]amino}oxy)methyl]-pyridin-2-yl}-1H-isoindole-1,3(2H)-dione (1.87 g, 4.27 mmol) in tetrahydrofuran (20 mL) was added dropwise hydrazine hydrate (1.04 mL, 21.4 mmol). After stirring at room temperature for 29 h, the reaction mixture was filtered, the insolubles washed with ethyl acetate, and the filtrate concentrated in vacuo. Purification on silica gel afforded 6-[({[(1-methyl-1H-imidazol-5-yl)(phenyl)methylene]amino}oxy)methyl]pyridin-2-amine [1.07 g, yield 77%; HPLC/MS: m/z=308 (M+H); log $P_{(HCOOH)}$=0.29].

Preparation of 3-methyl-N-{6-[({[(1-methyl-1H-imidazol-5-yl)(phenyl)methylene]amino}oxy)-methyl]pyridin-2-yl}butanamide (example 145) according to process P2

To a solution of 6-[({[(1-methyl-1H-imidazol-5-yl)(phenyl)methylene]amino}oxy)methyl]pyridin-2-amine (149 mg, 0.53 mmol) in 1,4-dioxane (10 mL) were sequentially added triethylamine (0.17 mL, 1.21 mmol), isovaleric anhydride (0.48 mL, 2.42 mmol) and N,N-dimethylformamide (3 drops). After refluxing for 7.5 h, the mixture was concentrated in vacuo, diluted in ethyl acetate (50 mL), washed with water (2×30 mL), dried over MgSO$_4$ and concentrated to dryness in vacuo. Purification on silica gel afforded 3-methyl-N-{6-[({[(1-methyl-1H-imidazol-5-yl)(phenyl)methylene]amino}¬oxy)¬methyl]pyridin-2-yl}butanamide [124 mg, yield 62%; HPLC/MS: m/z=392 (M+H); log P$_{(HCOOH)}$=1.84].

Preparation of pentyl{2-[({[(1-methyl-1H-imidazol-5-yl)(phenyl)methylene]amino}oxy)-methyl]pyrimidin-4-yl}carbamate (example 139) according to process P2

To a solution of 2-[({[(1-methyl-1H-imidazol-5-yl)(phenyl)methylene]amino}oxy)methyl]pyrimidin-4-amine (200 mg, 0.65 mmol) in 1,4-dioxane (10 mL) were sequentially added triethylamine (0.18 mL, 1.30 mmol) and chloroformic acid pentyl ester (0.38 mL, 2.60 mmol). After stirring at room temperature for 19 h, the mixture was concentrated in vacuo, diluted in ethyl acetate (50 mL), washed with water (20 mL), dried over MgSO$_4$ and concentrated to dryness in vacuo. Purification on silica gel afforded pentyl{2-[({[(1-methyl-1H-imidazol-5-yl)(phenyl)methylene]amino}oxy)methyl]pyrimidin-4-yl}carbamate [26 mg, yield 9%; HPLC/MS: m/z=423 (M+H); log P$_{(HCOOH)}$=2.66].

Preparation of N-(cyclopropylcarbonyl)-N-(2-{[({[2-(cyclopropylcarbonyl)-1-methyl-1H-imidazol-5-yl](phenyl)methylene}amino)oxy]methyl}pyrimidin-4-yl)cyclopropanecarboxamide (example 312) according to process P2

To a solution of 2-[({[(1-methyl-1H-imidazol-5-yl)(phenyl)methylene]amino}oxy)methyl]-pyrimidin-4-amine (200 mg, 0.65 mmol) in 1,4-dioxane (10 mL) were sequentially added triethylamine (0.18 mL, 1.30 mmol) and cyclopropanecarboxylic acid (0.24 mL, 2.60 mmol). After stirring at room temperature for 24 h, the mixture was concentrated in vacuo, diluted in ethyl acetate (50 mL), washed with water (20 mL), dried over MgSO$_4$ and concentrated to dryness in vacuo. Purification on silica gel afforded N-(cyclopropylcarbonyl)-N-(2-{[({[2-(cyclopropylcarbonyl)-1-methyl-1H-imidazol-5-yl](phenyl)methylene}amino)oxy]methyl}pyrimidin-4-yl)cyclopropanecarboxamide [69 mg, yield 20%; HPLC/MS: m/z=513 (M+H); log P$_{(HCOOH)}$=3.73].

Preparation of N-(cyclopropylcarbonyl)-N-{2-[({[(1-methyl-1H-imidazol-5-yl)(phenyl)methylene]-amino}oxy)methyl]pyrimidin-4-yl}cyclopropanecarboxamide (example 114) according to process P2

To a solution of 2-[({[(1-methyl-1H-imidazol-5-yl)(phenyl)methylene]amino}oxy)methyl]-pyrimidin-4-amine (200 mg, 0.65 mmol) in 1,4-dioxane (10 mL) were sequentially added triethylamine (0.18 mL, 1.30 mmol) and cyclopropanecarboxylic acid (0.24 mL, 2.60 mmol). After stirring at room temperature for 24 h, the mixture was concentrated in vacuo, diluted in ethyl acetate (50 mL), washed with water (20 mL), dried over MgSO$_4$ and concentrated to dryness in vacuo. Purification on silica gel afforded N-(cyclopropylcarbonyl)-N-{2-[({[(1-methyl-1H-imidazol-5-yl)(phenyl)¬methylene]¬amino}oxy)methyl]pyrimidin-4-yl}cyclopropanecarboxamide [23 mg, yield 8%; HPLC/MS: m/z=445 (M+H); log P$_{(HCOOH)}$>=1.75].

Preparation of 2-methyl-N-{4-[({[(1-methyl-1H-imidazol-5-yl)(phenyl)methylene]amino}-oxy)methyl]-1,3-thiazol-2-yl}propanamide (example 143) according to process P2

To a solution of 4-[({[(1-methyl-1H-imidazol-5-yl)(phenyl)methylene]amino}oxy)methyl]-1,3-thiazol-2-amine (165 mg, 0.53 mmol) in 1,4-dioxane (15 mL) were sequentially added triethylamine (0.18 mL, 1.30 mmol), isobutyric anhydride (0.44 mL, 2.60 mmol) and N,N-dimethylformamide (3 drops). After refluxing for 6.5 h, the mixture was concentrated in vacuo, diluted in ethyl acetate (50 mL), washed with water (2×30 mL), dried over MgSO$_4$ and concentrated to dryness in vacuo. Purification on silica gel afforded 2-methyl-N-{4-[({[(1-methyl-1H-imidazol-5-yl)(phenyl)methylene]amino}¬oxy)methyl]-1,3-thiazol-2-yl}propanamide [178 mg, yield 84%; HPLC/MS: m/z=384 (M+H); log P$_{(HCOOH)}$=1.63].

Preparation of 6-[({[(1,2-dimethyl-1H-imidazol-5-yl)(phenyl)methylene]amino}oxy)methyl]pyridin-2-amine (example 257) according to process P1

Step 1: Preparation of (1,2-dimethyl-1H-imidazol-5-yl)(phenyl)methanone

To a solution of 5-bromo-1,2-dimethyl-1H-imidazole (10.0 g, 57.1 mmol) in dichloromethane (50 mL) was added dropwise ethylmagnesium bromide (3 M in Et$_2$O, 19.0 mL, 57.0 mmol). After stirring at room temperature for 30 min, the reaction mixture was cooled down to 0° C. with an ice-brine bath and N-Methoxy-N-methyl-benzamide (8.70 mL, 57.1 mmol) was added dropwise. The mixture was stirred for 7.5 h at room temperature. The mixture was worked-up by addition of water (100 mL), then acidified with aq. HCl (1 M) until pH=7. After extraction with dichloromethane (2×75 mL), the organic layers were washed with water (2×100 mL) then dried over MgSO$_4$ and concentrated in vacuo. Purification of the residue on silica gel afforded (1,2-dimethyl-1H-imidazol-5-yl)(phenyl)methanone [8.41 g, yield 44%; HPLC/MS: m/z=201 (M+H); log P$_{(HCOOH)}$=0.56].

Step 2: Preparation of 1-(1,2-dimethyl-1H-imidazol-5-yl)-N-hydroxy-1-phenylmethanimine A solution of (1,2-dimethyl-1H-imidazol-5-yl)(phenyl)methanone (8.41 g, 42 mmol) and hydroxylamine hydrochloride (7.30 g, 105 mmol) in pyridine (60 mL) was stirred for 5 h at room temperature, and for 3 h at 50° C. Hydroxylamine hydrochloride (3.00 g, 43 mmol) was added again and the reaction mixture was stirred for 9.5 h at 50° C. After removal of the solvent in vacuo and addition of water (600 mL), the pH of the aqueous solution was adjusted to pH>7 by addition of aq. NaOH (1 M). After extraction with ethyl acetate (4×150 mL), the combined organic layers were washed with water (150 mL), dried over MgSO$_4$ and concentrated in vacuo. Purification on silica gel afforded 1-(1,2-dimethyl-1H-imidazol-5-yl)-N-hydroxy-1-phenylmethanimine [2.31 g, yield 24%; HPLC/MS: m/z=216 (M+H); log $P_{(HCOOH)}$=0.43].

Step 3: Preparation of 2-{6-[({[(1,2-dimethyl-1H-imidazol-5-yl)(phenyl)methylene]amino}oxy)-methyl]pyridin-2-yl}-1H-isoindole-1,3(2H)-dione (example 236)

To a solution of 1-(1,2-dimethyl-1H-imidazol-5-yl)-N-hydroxy-1-phenylmethanimine (2.29 g, 10.6 mmol) and 2-[6-(bromomethyl)pyridin-2-yl]-1H-isoindole-1,3(2H)-dione (3.71 g, 11.7 mmol) in acetonitrile (100 mL) were added cesium carbonate (7.27 g, 22.3 mmol) and potassium iodide (176 mg, 1.06 mmol). After stirring at room temperature for 31.5 h, the reaction mixture was filtered, the insolubles washed with dichloromethane, and the filtrate concentrated in vacuo. Purification on silica gel afforded 2-{6-[({[(1,2-dimethyl-1H-imidazol-5-yl)(phenyl)methylene]amino}oxy)¬methyl]pyridin-2-yl}-1H-isoindole-1,3(2H)-dione [848 mg, yield 16%; HPLC/MS: m/z=452 (M+H); log $P_{(HCOOH)}$=1.84].

Step 4: Preparation of 6-[({[(1,2-dimethyl-1H-imidazol-5-yl)(phenyl)methylene]amino}oxy)-methyl]pyridin-2-amine (example 257)

To a solution of 2-{6-[({[(1,2-dimethyl-1H-imidazol-5-yl)(phenyl)methylene]amino}-oxy)methyl]pyridin-2-yl}-1H-isoindole-1,3(2H)-dione (1.02 g, 2.26 mmol) in tetrahydrofuran (30 mL) was added dropwise hydrazine hydrate (0.55 mL, 11.3 mmol). After stirring at room temperature for 28 h, the reaction mixture was filtered, the insolubles washed with ethyl acetate, and the filtrate concentrated in vacuo. Purification on silica gel afforded 6-[({[(1,2-dimethyl-1H-imidazol-5-yl)(phenyl)methylene]amino}oxy)methyl]pyridin-2-amine [370 mg, yield 43%; HPLC/MS: m/z=322 (M+H); log $P_{(HCOOH)}$=0.39].

Preparation of 4-[({[(1-methyl-1H-imidazol-5-yl)(2-thienyl)methylene]amino}oxy)methyl]-1,3-thiazol-2-amine (example 495) according to process P1

Step 1: Preparation of N-methoxy-N-methylthiophene-2-carboxamide

To a solution of thiophene-2-carbonyl chloride (100.6 mL, 940 mmol) and N,O-dimethylhydroxylamine hydrochloride (100.9 g, 1.03 mol) in dichloromethane (1 L) at 0° C. was added dropwise triethylamine (262 mL, 1.88 mol). After stirring at room temperature for 3 h, the reaction mixture was poured into a mixture of water (2 L) and concentrated aq. HCl (36%, 80 mL), the layers were separated and the aqueous layer extracted with dichloromethane (2×200 mL). The combined organic layers were washed with water (200 mL), then dried over MgSO$_4$ and concentrated in vacuo to afford N-methoxy-N-methylthiophene-2-carboxamide [153.4 g, yield 95%; HPLC/MS: m/z=172 (M+H); log $P_{(HCOOH)}$=1.44].

Step 2: Preparation of (1-methyl-1H-imidazol-5-yl)(2-thienyl)methanone

To a solution of 5-bromo-1-methyl-imidazole (18.8 g, 117 mmol) in dichloromethane (50 mL) was added dropwise ethylmagnesium bromide (3 M in Et$_2$O, 38.9 mL, 117 mmol). After stirring at room temperature for 30 min, the reaction mixture was cooled down to 0° C. with an ice-brine bath and N-methoxy-N-methylthiophene-3-carboxamide (20.0 g, 117 mmol) was added dropwise. The mixture was stirred for 5.5 h at room temperature. The mixture was worked-up by addition of water (400 mL), then acidified with aq. HCl (1 M) until pH=7. After extraction with dichloromethane (3×100 mL), the organic layers were washed with water (2×100 mL) then dried over MgSO$_4$ and concentrated in vacuo. Purification of the residue on silica gel afforded (1-methyl-1H-imidazol-5-yl)(2-thienyl)methanone [10.2 g, yield 36%; HPLC/MS: m/z=193 (M+H); log $P_{(HCOOH)}$=0.52].

Step 3: Preparation of N-hydroxy-1-(1-methyl-1H-imidazol-5-yl)-1-(2-thienyl)methanimine A solution of (1-methyl-1H-imidazol-5-yl)(2-thienyl)methanone (10.14 g, 52.7 mmol) and hydroxylamine hydrochloride (12.8 g, 185 mmol) in pyridine (60 mL) was stirred for 9 h at 50° C., then for 8 h at 60° C. Hydroxylamine hydrochloride (6.40 g, 92 mmol) was added again and the reaction mixture was stirred for 6 h at 110° C. After removal of the solvent in vacuo and addition of water (200 mL), the pH of the aqueous solution was adjusted to pH>7 by addition of aq. NaOH (1 M), which resulted in precipitation of a yellow solid. After filtration, the solid was washed with water and pentane, and dried in vacuo to afford a first crop of N-hydroxy-1-(1-methyl-1H-imidazol-5-yl)-1-(2-thienyl)methanimine. The combined aqueous phases were extracted with dichloromethane, the combined organic layers were dried over MgSO$_4$ and concentrated in vacuo. The residue was purified recrystallized from diisopropylether to afford a second crop of N-hydroxy-1-(1-methyl-1H-imidazol-5-yl)-1-(3-thienyl)methanimine. The crops were combined and recrystallized from diisopropylether to afford final N-hydroxy-1-(1-methyl-1H-imidazol-5-yl)-1-(2-thienyl)methanimine [8.22 g, yield 71%; HPLC/MS: m/z=208 (M+H); log $P_{(HCOOH)}$=0.45].

Step 4: Preparation of 2-{6-[({[(1-methyl-1H-imidazol-5-yl)(2-thienyl)methylene]amino}-oxy)methyl]pyridin-2-yl}-1H-isoindole-1,3(2H)-dione (example 494)

To a solution of N-hydroxy-1-(1-methyl-1H-imidazol-5-yl)-1-(2-thienyl)methanimine (4.10 g, 19.8 mmol) and 2-[6-(bromomethyl)pyridin-2-yl]-1H-isoindole-1,3(2H)-dione (6.89 g, 21.7 mmol) in acetonitrile (100 mL) were added cesium carbonate (13.5 g, 41.4 mmol) and potassium iodide (328 mg, 1.98 mmol). After stirring at room temperature for 24 h, the reaction mixture was filtered, the insolubles washed with ethyl acetate, and the combined filtrates concentrated in vacuo. Purification on silica gel afforded 2-{6-[({[(1-methyl-1H-imidazol-5-yl)(2-thienyl)methylene]amino}oxy)methyl]pyridin-2-yl}-1H-isoindole-1,3(2H)-dione [7.91 g, yield 86%; HPLC/MS: m/z=444 (M+H); log $P_{(HCOOH)}$=1.66].

Step 5: Preparation of 4-[({[(1-methyl-1H-imidazol-5-yl)(2-thienyl)methylene]amino}oxy)methyl]-1,3-thiazol-2-amine (example 495)

To a solution of N-hydroxy-1-(1-methyl-1H-imidazol-5-yl)-1-(2-thienyl)methanimine (4.08 g, 19.7 mmol) and 4-(chloromethyl)-1,3-thiazol-2-amine hydrochloride (4.01 g, 21.7 mmol) in acetonitrile (50 mL) were added cesium carbonate (13.5 g, 41.4 mmol) and potassium iodide (327 mg, 1.97 mmol). After stirring at room temperature for 51 h, potassium iodide (5.90 g, 35.5 mmol) was added and the mixture was stirred for 72 h at room temperature then at 70°

C. for 3.5 h. The reaction mixture was filtered, the insolubles washed with acetone and methanol, and the filtrate concentrated in vacuo, diluted in ethyl acetate (50 mL), washed with water (2×30 mL), dried over MgSO$_4$ and concentrated to dryness in vacuo. Purification of the residue on silica gel afforded 4-[({[(1-methyl-1H-imidazol-5-yl)(2-thienyl)methylene]amino}oxy)methyl]-1,3-thiazol-2-amine [1.54 g, yield 23%; HPLC/MS: m/z=320 (M+H); log P$_{(HCOOH)}$=0.22].

Preparation of 6-[({[(1-methyl-1H-imidazol-5-yl)(3-thienyl)methylene]amino}oxy)methyl]pyridin-2-amine (example 493) according to process P1

Step 1: Preparation of N-methoxy-N-methylthiophene-3-carboxamide

To a solution of thiophene-3-carboxylic acid (85.0 g, 663 mmol) in dichloromethane (1 L), cooled with an ice-brine bath, was added thionyl chloride (250 mL, 3.43 mol). After stirring at room temperature until gas evolution had become less vigorous, the reaction mixture was further stirred at reflux for 3 h. After cooling down to room temperature, all volatiles were removed in vacuo, the residue was dissolved in toluene and concentrated again in vacuo twice, to afford the crude acid chloride (97.7 g).

To a solution of this crude thiophene-3-carbonyl chloride (97.7 g, 666 mmol) and N,O-dimethylhydroxylamine hydrochloride (71.5 g, 733 mmol) in dichloromethane (600 mL) at 0° C. was added dropwise triethylamine (186 mL, 1.33 mol). After stirring at room temperature for 3 h, the reaction mixture was poured into water (2 L), the layers were separated and the aqueous layer extracted with dichloromethane (2×200 mL). The combined organic layers were washed with water (200 mL), then dried over MgSO$_4$ and concentrated in vacuo to afford N-methoxy-N-methylthiophene-3-carboxamide [102.2 g, yield 90%; HPLC/MS: m/z=172 (M+H); log P$_{(HCOOH)}$=1.30].

Step 2: Preparation of (1-methyl-1H-imidazol-5-yl)(3-thienyl)methanone

To a solution of 5-Bromo-1-methyl-imidazole (18.8 g, 117 mmol) in dichloromethane (50 mL) was added dropwise ethylmagnesium bromide (3 M in Et$_2$O, 38.9 mL, 117 mmol). After stirring at room temperature for 30 min, the reaction mixture was cooled down to 0° C. with an ice-brine bath and N-methoxy-N-methylthiophene-3-carboxamide (20.0 g, 117 mmol) was added dropwise. The mixture was stirred for 3.5 h at room temperature. The mixture was worked-up by addition of water (400 mL), then acidified with aq. HCl (1 M) until pH=7. After extraction with dichloromethane (3×100 mL), the organic layers were washed with water (100 mL) then dried over MgSO$_4$ and concentrated in vacuo. Purification of the residue on silica gel afforded (1-methyl-1H-imidazol-5-yl)(3-thienyl)methanone [11.6 g, yield 41%; HPLC/MS: m/z=193 (M+H); log P$_{(HCOOH)}$=0.43].

Step 3: Preparation of N-hydroxy-1-(1-methyl-1H-imidazol-5-yl)-1-(3-thienyl)methanimine A solution of (1-methyl-1H-imidazol-5-yl)(3-thienyl)methanone (11.6 g, 60.0 mmol) and hydroxylamine hydrochloride (14.6 g, 210 mmol) in pyridine (60 mL) was stirred 9 h at 60° C. then left to stand for 72 h at room temperature. After removal of the solvent in vacuo, addition of water (200 mL), pH adjustment to approx 7 with aq. NaOH (1 M) induced precipitation of a solid. Filtration, sequential washings of the precipitate with water and heptane, and drying of the solid afforded a first crop of N-hydroxy-1-(1-methyl-1H-imidazol-5-yl)-1-(3-thienyl)methanimine. The combined aqueous phases were extracted with dichloromethane, the combined organic layers were dried over MgSO$_4$ and concentrated in vacuo. The residue was purified recrystallized from heptane to afford a second crop of N-hydroxy-1-(1-methyl-1H-imidazol-5-yl)-1-(3-thienyl)methanimine. The crops were combined and recrystallized from diisopropylether to afford final N-hydroxy-1-(1-methyl-1H-imidazol-5-yl)-1-(3-thienyl)methanimine [9.95 g, yield 76%; HPLC/MS m/z=208 (M+H); log P$_{(HCOOH)}$=0.21].

Step 4: Preparation of 2-{6-[({[(1-methyl-1H-imidazol-5-yl)(3-thienyl)methylene]amino}oxy)-methyl]pyridin-2-yl}-1H-isoindole-1,3(2H)-dione (example 491)

To a solution of N-hydroxy-1-(1-methyl-1H-imidazol-5-yl)-1-(3-thienyl)methanimine (4.96 g, 23.9 mmol) and 2-[6-(bromomethyl)pyridin-2-yl]-1H-isoindole-1,3(2H)-dione (8.35 g, 26.3 mmol) in acetonitrile (100 mL) were added cesium carbonate (16.4 g, 50.3 mmol) and potassium iodide (397 mg, 2.39 mmol). After stirring at room temperature for 28 h, the reaction mixture was filtered, the insolubles washed with ethyl acetate, and the combined filtrates concentrated in vacuo. Purification on silica gel afforded 2-{6-[({[(1-methyl-1H-imidazol-5-yl)(3-thienyl)methylene]amino}oxy)¬methyl]pyridin-2-yl}-1H-isoindole-1,3(2H)-dione [6.91 g, yield 62%; HPLC/MS: m/z=444 (M+H); log P$_{(HCOOH)}$=1.73].

Step 5: Preparation of 6-[({[(1-methyl-1H-imidazol-5-yl)(3-thienyl)methylene]amino}oxy)-methyl]pyridin-2-amine (example 493)

To a solution of 2-{6-[({[(1-methyl-1H-imidazol-5-yl)(3-thienyl)methylene]amino}oxy)-methyl]pyridin-2-yl}-1H-isoindole-1,3(2H)-dione (6.80 g, 15.3 mmol) in tetrahydrofuran (30 mL) was added dropwise hydrazine hydrate (3.72 mL, 76.7 mmol). After stirring at room temperature for 30 h, the reaction mixture was filtered, the insolubles washed with ethyl acetate, and the filtrate concentrated in vacuo. Purification on silica gel afforded 6-[({[(1-methyl-1H-imidazol-5-yl)(3-thienyl)methylene]amino}oxy)¬methyl]pyridin-2-amine [3.02 g, yield 60%; HPLC/MS: m/z=314 (M+H); log P$_{(HCOOH)}$=0.39].

Preparation of 4-[({[(1-methyl-1H-imidazol-5-yl)(3-thienyl)methylene]amino}oxy)methyl]-1,3-thiazol-2-amine (example 496) according to process P1

To a solution of N-hydroxy-1-(1-methyl-1H-imidazol-5-yl)-1-(3-thienyl)methanimine (4.96 g, 23.9 mmol) and 4-(chloromethyl)-1,3-thiazol-2-amine hydrochloride (4.88 g, 26.3 mmol) in acetonitrile (50 mL) were added cesium carbonate (13.5 g, 41.4 mmol) and potassium iodide (327 mg, 1.97 mmol). After stirring at room temperature for 51 h, 1,4-dioxane (25 mL) and potassium iodide (5.90 g, 35.5 mmol) were added and the mixture was stirred for 72 h at room temperature then at 70° C. for 3.5 h. The reaction mixture was filtered, the insolubles washed with acetone and methanol, and the filtrate concentrated in vacuo, diluted in ethyl acetate (50 mL), washed with water (2×30 mL), dried over MgSO$_4$ and concentrated to dryness in vacuo. Purification of the residue on silica gel afforded 4-[({[(1-methyl-1H- imidazol-5-yl)(3-thienyl)methylene]amino}oxy)-methyl]-1,3-thiazol-2-amine [850 mg, yield 11%; HPLC/MS: m/z=320 (M+H); log P$_{(HCOOH)}$=0.45].

Preparation of 6-[({[(3,6-dimethylpyrazin-2-yl)(phenyl)methylene]amino}oxy)methyl]pyridin-2-amine (example 447) according to process P1

Step 1: Preparation of (3,6-dimethylpyrazin-2-yl)(phenyl)acetonitrile

To a solution of benzyl cyanide (2.00 g, 17.1 mmol) and 3-Chloro-2,5-dimethyl-pyrazine (2.03 g, 14.2 mmol) in tetrahydrofuran (100 mL) was added dropwise sodium bis-(trimethylsilyl)amide (1 M in THF, 35.6 mL, 35.6 mmol). After stirring at room temperature for 18 h, the reaction mixture was poured into sat. aq. NH$_4$Cl (150 mL). After extraction with ethyl acetate (150 mL), the organic layer was washed with water (100 mL), dried over MgSO$_4$ and concentrated in vacuo to afford (3,6-dimethylpyrazin-2-yl)(phenyl)acetonitrile [4.07 g, yield 96%; HPLC/MS: m/z=223 (M+H); log P$_{(HCOOH)}$=2.28].

Step 2: Preparation of (3,6-dimethylpyrazin-2-yl)(phenyl)methanone

To a solution of (3,6-dimethylpyrazin-2-yl)(phenyl)acetonitrile (3.81 g, 17.1 mmol) in methanol (50 mL) was added aq. NaOH (30 wt-%, 30 mL). After stirring for 29 h at room temperature, methanol (30 mL) and aq. NaOH (30 wt-%, 20 mL) were added and the solution was further stirred for 5 h.

After removal of the methanol in vacuo, water (100 mL) was added. After extraction with ethyl acetate (3×90 mL), the combined organic layers were washed with water (2×100 mL), dried over MgSO$_4$ and concentrated in vacuo to afford (3,6-dimethylpyrazin-2-yl)(phenyl)methanone [3.02 g, yield 75%; HPLC/MS: m/z=213 (M+H); log P$_{(HCOOH)}$=2.18].

Step 3: Preparation of 1-(3,6-dimethylpyrazin-2-yl)-N-hydroxy-1-phenylmethanimine A solution of (3,6-dimethylpyrazin-2-yl)(phenyl)methanone (3.02 g, 14.2 mmol) and hydroxylamine hydrochloride (2.47 g, 35.5 mmol) in pyridine (50 mL) was stirred 7 h at 70° C. After removal of the solvent in vacuo, addition of water (100 mL) and extraction with ethyl acetate (2×100 mL), the combined organic layers were washed with water (100 mL), dried over MgSO$_4$ and concentrated in vacuo to afford 1-(3,6-dimethylpyrazin-2-yl)-N-hydroxy-1-phenylmethanimine as an orange honey [3.39 g, yield 99%; HPLC/MS: m/z=228 (M+H); log P$_{(HCOOH)}$=1.70].

Step 4: Preparation of 2-{6-[({[(3,6-dimethylpyrazin-2-yl)(phenyl)methylene]amino}oxy)-methyl]pyridin-2-yl}-1H-isoindole-1,3(2H)-dione (example 446)

To a solution of 1-(3,6-dimethylpyrazin-2-yl)-N-hydroxy-1-phenylmethanimine (3.38 g, 14.9 mmol) and 2-[6-(bromomethyl)pyridin-2-yl]-1H-isoindole-1,3(2H)-dione (5.19 g, 16.4 mmol) in acetonitrile (50 mL) were added cesium carbonate (10.2 g, 31.2 mmol) and potassium iodide (3.70 mg, 22.3 mmol). After stirring at room temperature for 7 h, the reaction mixture was filtered, the insolubles washed with ethyl acetate, and the combined filtrates concentrated in vacuo, diluted in ethyl acetate (150 mL), washed with water (2×150 mL), dried over MgSO$_4$ and concentrated to dryness in vacuo. Purification on silica gel afforded 2-{6-[({[(3,6-dimethylpyrazin-2-yl)(phenyl)methylene]amino}oxy)methyl]pyridin-2-yl}-1H-isoindole-1,3(2H)-dione [2.79 g, yield 41%; HPLC/MS: m/z=464 (M+H); log P$_{(HCOOH)}$=3.35].

Step 5: Preparation of 6-[({[(3,6-dimethylpyrazin-2-yl)(phenyl)methylene]amino}oxy)methyl]-pyridin-2-amine (example 447)

To a solution of 2-{6-[({[(3,6-dimethylpyrazin-2-yl)(phenyl)methylene]amino}oxy)methyl]pyridin-2-yl}-1H-isoindole-1,3(2H)-dione (4.08 g, 8.80 mmol) in tetrahydrofuran (60 mL) was added dropwise hydrazine hydrate (2.14 mL, 44.0 mmol). After stirring at room temperature for 6 h, the reaction mixture was filtered, the insolubles washed with ethyl acetate, and the combined filtrates concentrated in vacuo, diluted in ethyl acetate (100 mL), washed with water (70 mL), dried over MgSO$_4$ and concentrated to dryness in vacuo. Purification on silica gel afforded 6-[({[(3,6-dimethylpyrazin-2-yl)(phenyl)methylene]amino}oxy)methyl]pyridin-2-amine [1.97 g, yield 64%; HPLC/MS: m/z=334 (M+H); log P$_{(HCOOH)}$=1.31].

Preparation of 6-[({[(1-methyl-1H-1,2,4-triazol-5-yl)(phenyl)methylene]amino}oxy)methyl]pyridin-2-amine (example 4), according to process P1

Step 1: Preparation of (1-methyl-1H-1,2,4-triazol-5-yl)(phenyl)methanone

To a solution of 1-methyl-1H-1,2,4-triazole (5.0 g, 60.17 mmol, 1 eq.) in 250 ml of MeCN cooled to −5° C. were added Benzoyl chloride (8.45 g, 60.17 mmol, 1 eq.) and TEA (6.39 g, 8.8 ml, 63.18 mmol, 1.05 eq.) dropwise. Upon complete addition the temperature was raised to r.t. and the reaction stirred overnight. The white solid was removed by filtration and the solvent evaporated. The yellow residue was triturated in EtOAc and the white solid removed by filtration. The solvent was evaporated and the resulting brown solid was recrystalised in EtOAc/IPE to give (1-methyl-1H-1,2,4-triazol-5-yl)(phenyl)methanone (6.5 g, 58% yield) as a white solid.

HPLC/MS: m/z=188 (M+H)

Step 2: Preparation of ((Z)-N-hydroxy-1-(1-methyl-1H-1,2,4-triazol-5-yl)-1-phenylmethanimine To a solution of (1-methyl-1H-1,2,4-triazol-5-yl)(phenyl)methanone (5.5 g, 29.38 mmol, 1 eq.) in 100 ml of pyridine was added hydroxylamine hydrochloride (5.1 g, 73.45 mmol, 2.5 eq.). The temperature was raised to 50° C. and the reaction stirred overnight. The solvent was then evaporated and the residue dissolved in DCM and washed with H$_2$O. The organic layer was washed with 0.1N HCl and dried over MgSO$_4$. The solvent was evaporated to give ((Z)-N-hydroxy-1-(1-methyl-1H-1,2,4-triazol-5-yl)-1-phenylmethanimine (5.28 g, 89% yield) as a white solid.

HPLC/MS: m/z=203 (M+H)

Step 3: Preparation of 2-{6-[({[(1-methyl-1H-1,2,4-triazol-5-yl)(phenyl)methylene]amino}oxy)methyl]pyridin-2-yl}-1H-isoindole-1,3(2H)-dione (example 13)

To a stirred solution of ((Z)-N-hydroxy-1-(1-methyl-1H-1,2,4-triazol-5-yl)-1-phenylmethanimine (7 g, 34.61 mmol, 1.0 eq.) in 500 ml of MeCN was added Cs$_2$CO$_3$ (12.40 g, 38.07 mmol, 1.1 eq.) followed by KI (0.575 g, 3.46 mmol, 0.1 eq.) in one portion. The resulting suspension was stirred for 5 mins before addition of 2-[6-(bromomethyl)pyridin-2-yl]-1H-isoindole-1,3(2H)-dione (10.97 g, 34.61 mmol, 1.0 eq.) in one portion. The reaction was stirred for 4 h at room temperature. The solid was removed by filtration and washed with 250 ml of fresh MeCN. The filtrate was evaporated, and 500 ml of EtOAc were added. The organic layer was washed with H$_2$O and dried over MgSO4 then concentrated. Chromatography of the crude on silica gel gave 2-{6-[({[(1-methyl-1H-1,2,4-triazol-5-yl)(phenyl)methylene]amino}oxy)methyl]pyridin-2-yl}-1H-isoindole-1,3(2H)-dione (11.27 g, 74% yield) as a white solid.

HPLC/MS: m/z=439 (M+H)

Step 4: Preparation of 6-[({[(1-methyl-1H-1,2,4-triazol-5-yl)(phenyl)methylene]amino}oxy)methyl]pyridin-2-amine To a solution of 2-{6-[({[(1-methyl-1H-1,2,4-triazol-5-yl)(phenyl)methylene]amino}oxy)methyl]pyridin-2-yl}-1H-isoindole-1,3(2H)-dione (11.27 g, 25.70 mmol, 1 eq.) in 500 ml of THF was added hydrazine hydrate (6.43 g, 128.52 mmol, 5 eq.). The reaction was stirred overnight at room temperature. The solvent was evaporated and the residue dissolved in EtOAc. Water was added and the layers separated. The aqueous layer was extracted with EtOAc and the organics were combined, dried over MgSO$_4$ and concentrated to give 6-[({[(1-methyl-1H-1,2,4-triazol-5-yl)(phenyl)methylene]amino}oxy)methyl]pyridin-2-amine (7.85 g, 99%) as a clear viscous oil.

HPLC/MS: m/z=309 (M+H)

Preparation of N-{6-[({[(1-methyl-1H-1,2,4-triazol-5-yl)(phenyl)methylene]amino}oxy)methyl]pyridin-2-yl}hexanamide (example 28), according to process P2

To a solution of 6-[({[(1-methyl-1H-1,2,4-triazol-5-yl)(phenyl)methylene]amino}oxy)methyl]pyridin-2-amine (0.151 g, 0.486 mmol, 1 eq.) in 2 ml of DCM was added TEA (0.098 g, 0.973 mmol, 2 eq.) followed by hexanoyl chloride (0.072 g, 0.053mmol, 1.1 eq.). The reaction was stirred 4 h at room temperature and the solvent was evaporated. The crude was purified by chromatography on silica gel to give N-{6-[({[(1-methyl-1H-1,2,4-triazol-5-yl)(phenyl)methylene]amino}oxy)methyl]pyridin-2-yl}hexanamide (0.156 g, 79% yield) as a clear viscous oil.

HPLC/MS: m/z=407 (M+H)

Preparation of N-[(6-bromopyridin-2-yl)methoxy]-1-(4-methyl-4H-1,2,4-triazol-3-yl)-1-phenylmethanimine (example 228), according to process P1

Step 1: Preparation of 4-methyl-3-(methylsulfanyl)-4H-1,2,4-triazole

To a solution of 4-methyl-4H-1,2,4-triazole-3-thiol (25 g, 217.08 mmol, 1 eq.) in 150 ml of DMF was added K$_2$CO$_3$ (33 g, 238.19 mmol, 1.1 eq.) followed by iodomethane (30.81 g, 217.08 mmol, 1.0 eq.). The reaction was stirred overnight at room temperature and the solvent was evaporated. The crude was triturated in DCM and the solid removed by filtration. The solvent was evaporated to give 4-methyl-3-(methylsulfanyl)-4H-1,2,4-triazole (30.20 g, 96% yield) as a brown viscous oil.

Step 2: Preparation of 4-methyl-3-(methylsulfonyl)-4H-1,2,4-triazole

To a solution of 4-methyl-3-(methylsulfanyl)-4H-1,2,4-triazole (31 g, 239.96 mmol, 1 eq.) in 1000 ml of DCM cooled to 0° C. was added NaHCO$_3$ (42.33 g, 503.92 mmol, 2.1 eq.) followed by m-CPBA (70%, 118.31 g, 479.92 mmol, 2.0 eq.) portion wise. The reaction was warmed to r.t. and stirred. A sat. aqueous 1/1 Na$_2$S$_2$O$_3$/Na$_2$CO$_3$ solution was added slowly and the mixture stirred 15 min. The layers were separated and the organics were washed with H$_2$O, dried over MgSO$_4$ and concentrated. The crude was triturated in IPE and filtered to give 4-methyl-3-(methylsulfonyl)-4H-1,2,4-triazole (9.35 g, 59% yield) as yellow solid.

Step 3: Preparation of 4-methyl-4H-1,2,4-triazole-3-carbonitrile

To a solution of 4-methyl-3-(methylsulfonyl)-4H-1,2,4-triazole (8.5 g, 52.76 mmol, 1 eq.) in 16 ml of DMSO was added KCN (8.58 g, 131.83 mmol, 2.5 eq.). The reaction was heated to 150° C. for 8 h. The solvent was evaporated, then the residue was triturated in EtOAc and the solid removed by filtration. The solvent was evaporated to give 4-methyl-4H-1,2,4-triazole-3-carbonitrile (4.27 g, 75% yield, 70% purity) as a brown viscous oil.

Step 4: Preparation of (4-methyl-4H-1,2,4-triazol-3-yl)(phenyl)methanone

To a solution of 4-methyl-4H-1,2,4-triazole-3-carbonitrile (70%, 4.27 g, 27.64 mmol, 1 eq.) in 200 ml of THF cooled to −40° C. was added TMSCl (6.0 g, 55.29 mmol, 2.0 eq.) followed by phenylmagnesium bromide (2.8 M, 14.81 ml, 41.47 mmol, 1.4 eq.). The reaction was stirred at −40° C. for 1 h and quenched with 1N HCl. EtOAc was added and the layers separated. The aqueous layer was extracted with EtOAc and the organics combined, dried over MgSO$_4$ and concentrated. The residue was triturated in EtOAc and the solid removed by filtration. The crude was purified by chromatography on silica gel to give (4-methyl-4H-1,2,4-triazol-3-yl)(phenyl)methanone (2.45 g, 48% yield) as a yellow solid.

HPLC/MS: m/z=188 (M+H)

Step 5: Preparation of N-hydroxy-1-(4-methyl-4H-1,2,4-triazol-3-yl)-1-phenylmethanimine To a solution of (4-methyl-4H-1,2,4-triazol-3-yl)(phenyl)methanone (2.4 g, 12.82 mmol, 1 eq.) in 100 ml of pyridine was added hydroxylamine hydrochloride (3.56 g, 51.28 mmol, 4.0 eq.). The temperature was raised to 50° C. and the reaction stirred overnight. The solvent was then evaporated and the residue dissolved in DCM and washed with H$_2$O. The organic layer was washed with 0.1N HCl and dried over MgSO$_4$. The solvent was evaporated to give N-hydroxy-1-(4-methyl-4H-1,2,4-triazol-3-yl)-1-phenylmethanimine (2.51 g, 89% yield) as a white solid.

HPLC/MS: m/z=203 (M+H)

Step 6: Preparation of N-[(6-bromopyridin-2-yl)methoxy]-1-(4-methyl-4H-1,2,4-triazol-3-yl)-1-phenylmethanimine To a stirred solution of N-hydroxy-1-(4-methyl-4H-1,2,4-triazol-3-yl)-1-phenylmethanimine (0.45 g, 2.22 mmol, 1.0 eq.) in 20 ml of MeCN was added Cs$_2$CO$_3$ (0.795 g, 2.44 mmol, 1.1 eq.) followed by KI (0.0365 g, 0.22 mmol, 0.1 eq.) in one portion. The resulting suspension was stirred for 5 mins before addition of 2-bromo-6-(bromomethyl)pyridine (0.586 g, 2.33 mmol, 1.05 eq.) in one portion. The reaction was stirred for 4 h at room temperature. The solid was removed by filtration and washed with 250 ml of fresh MeCN. The filtrate was evaporated, and 500 ml of EtOAc were added. The organic layer was washed with H$_2$O and dried over MgSO4 then concentrated. Chromatography of the crude on silica gel gave N-[(6-bromopyridin-2-yl)methoxy]-1-(4-methyl-4H-1,2,4-triazol-3-yl)-1-phenylmethanimine (0.748 g, 90% yield) as a yellow oil.

HPLC/MS: m/z=373 (M+H)

Preparation of N-{[6-(cyclopropylethynyl)pyridin-2-yl]methoxy}-1-(4-methyl-4H-1,2,4-triazol-3-yl)-1-phenylmethanimine, (example 229), according to process P4

To a stirred solution of N-[(6-bromopyridin-2-yl)methoxy]-1-(4-methyl-4H-1,2,4-triazol-3-yl)-1-phenylmethanimine (0.125 g, 0.33 mmol, 1 eq.) in 3 ml dry THF "degassed" with N$_2$, was added Cyclopropylacetylene (0.95 g, 0.1 mmol, 3 eq.) followed by N-ethyldiisopropylamine (0.216 g, 1.67 mmol, 5 eq.), Copper Iodide (0.012 g, 0.06 mmol, 0.2 eq.) and Tetrakis(triphenylphosphine)palladium (0.077 g, 0.06 mmol, 0.2 eq.). The reaction was microwaved 120° C./normal/fixed hold/pre stir 100 s for 180 s. The reaction was diluted with EtOAc and filtered through a "celite" plug. The solvent was evaporated and the residue purified by chromatography on silica gel to give N-{[6-(cyclopropylethynyl)pyridin-2-yl]methoxy}-1-(4-methyl-4H-1,2,4-triazol-3-yl)-1-phenylmethanimine (0.068 g, 56% yield) as a yellow viscous oil.

HPLC/MS: m/z=358 (M+H)

The invention claimed is:
1. A compound of formula (I)

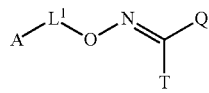

(I)

wherein

T is a substituted or non-substituted heterocyclyl group selected from the group consisting of $T^{73}$ to $T^{84}$:

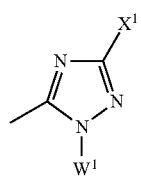

$T^{73}$

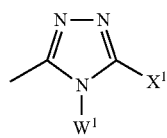

$T^{74}$

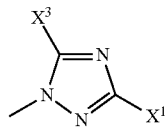

$T^{75}$

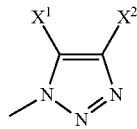

$T^{76}$

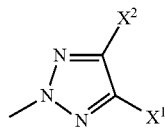

$T^{77}$

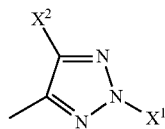

$T^{78}$

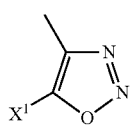

$T^{79}$

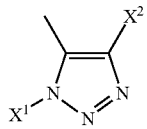

$T^{80}$

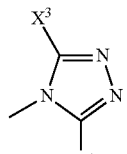

$T^{81}$

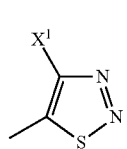

$T^{82}$

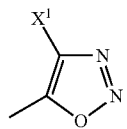

$T^{83}$

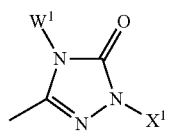

$T^{84}$ wherein $X^1$ to $X^3$ independently selected from the group consisting of a hydrogen atom, a halogen atom, a nitro group, a hydroxy group, a cyano group, an amino group, a sulphenyl group, a formyl group, a substituted or non-substituted carbaldehyde O—($C_1$-$C_8$-alkyl)oxime, a formyloxy group, a formylamino group, a carbamoyl group, a N-hydroxycarbamoyl group, a pentafluoro-$\lambda^6$-sulphenyl group, a formylamino group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$-alkyl-($C_1$-$C_8$-alkylamino)-amino group, a substituted or non-substituted (hydroxyimino)-$C_1$-$C_6$-alkyl group, substituted or non-substituted $C_1$-$C_8$-alkyl, substituted or non-substituted tri($C_1$-$C_8$-alkyl)silyl-$C_1$-$C_8$-alkyl, substituted or non-substituted $C_3$-$C_8$-cycloalkyl, substituted or non-substituted tri($C_1$-$C_8$-alkyl)silyl-$C_3$-$C_8$-cycloalkyl, substituted or non-substituted $C_1$-$C_8$-halogenoalkyl having 1 to 5 halogen atoms, a substituted or non-substituted $C_3$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_2$-$C_8$-alkenyloxy, substituted or non substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-$C_1$-$C_8$-alkylcarbamoylamino, substituted or non-substituted di-$C_1$-$C_8$-halogenoalkylcarbamoylamino having 1 to 5 halogen atoms, substituted or non-substituted N—$C_1$-$C_8$-alkyl-($C_1$-$C_8$-alkylcarbamoyl)amino, substituted or non-substituted N—$C_1$-$C_8$-alkyl-($C_1$-$C_8$-halogenoalkylcarbamoyl)amino having 1 to 5 halogen atoms, substituted or non-substituted N—$C_1$-$C_8$-alkyl-(di-$C_1$-$C_8$-alkylcarbamoyl)amino, substituted or non-substituted N—$C_1$-$C_8$-alkyl-(di-$C_1$-$C_8$-halogenoalkylcarbamoyl)amino having 1 to 5 halogen atoms, substituted or non-substituted $C_1$-$C_8$-alkylaminocarbonyloxy, substituted or non-substituted di-$C_1$-$C_8$-alkylaminocarbonyloxy, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyl, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylthioylamino, substituted or non-substituted $C_1$-$C_8$-halogenoalkylthioylamino having 1 to 5 halogen atoms, substituted or non-substituted ($C_1$-$C_8$-alkyl-carbamothioyl)-oxy, substituted or non-substituted (di-$C_1$-$C_8$-alkyl-carbamothioyl)-oxy, substituted or non-substituted $C_1$-$C_8$-alkylsulfinyl, substituted or non-substituted $C_1$-$C_8$-halogenoalkylsulfinyl having 1 to 5 halogen atoms, substituted or non-substituted $C_1$-$C_8$-alkylsulfonyl, substituted or non substituted $C_1$-$C_8$-halogenoalkylsulfoyl having 1 to 5 halogen atoms, substituted or non-substituted $C_1$-$C_8$-alkylaminosulfamony, substituted or non-substituted di-$C_1$-$C_8$-alkylaminosulfamoyl, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$alkynyloxyimino)-$C_1$-$C_6$-alkyl, substituted or non-substituted (benzyloxyimino)-$C_1$-$C_6$-alkyl, substituted or non-substituted benzyloxy, substituted or non-substituted benzylsulfenyl, substituted or non-substituted benzylamino, substituted or non-substituted phenoxy, substituted or non-substituted phenylsulfenyl, substituted or non-substituted phenylamino, substituted or non-substituted aryl, substituted or non-substituted aryl-[$C_1$-$C_8$]-alkyl, substituted or non-substituted tri($C_1$-$C_8$-alkyl)-silyloxy, substituted or non-substituted $C_1$-$C_8$-alkylsulfenylamino, substituted or non-substituted $C_1$-$C_8$-halogenoalkylsulfinylamino having 1 to 5 halogen atoms, substituted or non-substituted $C_1$-$C_8$-alkylsulfonylamino, substituted or non-substituted $C_1$-$C_8$-halogenoalkylsulfonylamino having 1 to 5 halogen atoms, substituted or non-substituted $C_1$-$C_8$-alkoxysulfonylamino, substituted or non-substituted $C_1$-$C_8$-halogenoxysulphonylamino having 1 to 5 halogen atoms, substituted or non-substituted tri($C_1$-$C_8$-alkyl)-silyl, substituted or non-substituted ($C_1$-$C_6$-alkylideneamino)oxy, substituted or non-substituted ($C_1$-$C_6$-alkenylideneamino)oxy, substituted or non-substituted ($C_1$-$C_6$-alkynylideneamino)oxy, substituted or non-substituted (benzylideneamino)oxy;

$W^1$ is selected from the group consisting of a hydrogen atom, a formyl group, a substituted or non-substituted carbaldehyde O—($C_1$-$C_8$-alkyl)oxime, a carbamoyl group, a N-hydroxycarbamoyl group, a formylamino group, substituted or non-substituted $C_1$-$C_8$-alkyl, substituted or non-substituted tri($C_1$-$C_8$-alkyl)silyl-$C_1$-$C_8$-alkyl, substituted or non-substituted $C_3$-$C_8$-cycloalkyl, substituted or non-substituted tri($C_1$-$C_8$-alkyl)silyl-$C_3$-$C_8$-cycloalkyl, substituted or non-substituted $C_1$-$C_8$-halogenoalkyl having 1 to 5 halogen atoms, substituted or non-substituted $C_3$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_2$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyll, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylsulfinyl, substituted or non-substituted $C_1$-$C_8$-halogenoalkylsulfinyl having 1 to 5 halogen atoms, substituted or non-substituted $C_1$-$C_8$-alkylsulfonyl, substituted or non-substituted $C_1$-$C_8$-halogenoalkylsulfonyl having 1 to 5 halogen atoms, substituted or non-substituted $C_1$-$C_8$-alkylaminosulfamoyl, substituted or non-substituted di-$C_1$-$C_8$-alkylaminosulfamoyl, substituted or non-substituted aryl, substituted or non-substituted aryl-[$C_1$-$C_8$]-alkyl;

$L^1$ represents a direct bond or a divalent group selected in the list consisting of —$(CR^1R^2)_n$— —$(CR^1R^2)_m$—C(=O)—$(CR^1R^2)_p$— —$(CR^1R^2)_m$—$(CR^1=CR^2)$—$(CR^1R^2)_p$— —$(CR^1R^2)_m$—C(=O)—O—$(CR^1R^2)_p$— —$(CR^1R^2)_m$—C≡C—$(CR^1R^2)_p$— —$(CR^1R^2)_m$—O—C(=O)—$(CR^1R^2)_p$— —$(CR^1R^2)_m$—O—$(CR^1R^2)_p$— —$(CR^1R^2)_m$—C(=O)—NH—$(CR^1R^2)_p$— —$(CR^1R^2)_m$—NH—$(CR^1R^2)_p$— —$(CR^1R^2)_m$—NH—C(=O)—$(CR^1R^2)_p$— wherein n represents 1, 2, 3 or 4;

m and p independently represent 0, 1, 2 or 3;

$R^1$ and $R^2$ are independently selected from the group consisting of a hydrogen atom, a halogen atom, a cyano group, substituted or non-substituted $C_1$-$C_8$-alkyl, substituted or non-substituted $C_3$-$C_8$-cycloalkyl, substituted or non-substituted $C_1$-$C_8$-halogenoalkyl having 1 to 5 halogen atoms, substituted or non-substituted $C_3$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms;

A is selected from the group consisting of $A^1$ to $A^{58}$:

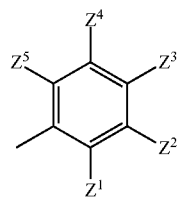

$A^1$

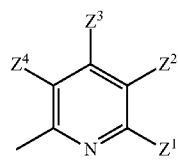

$A^2$

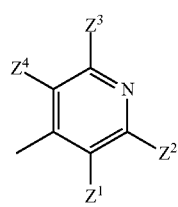

$A^3$

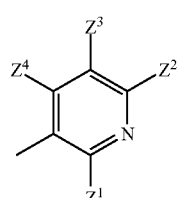

$A^4$

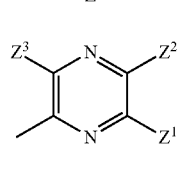

$A^5$

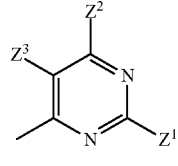

$A^6$

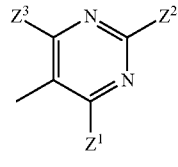

$A^7$

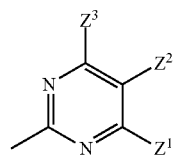

$A^8$

-continued
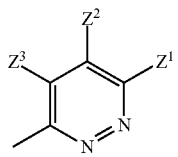 A⁹
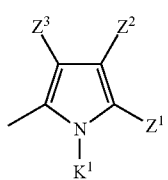 A¹⁰
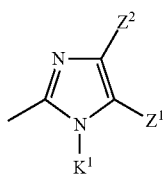 A¹¹
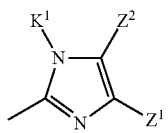 A¹²
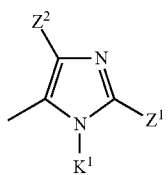 A¹³
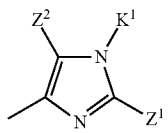 A¹⁴
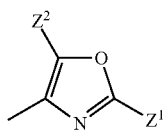 A¹⁵
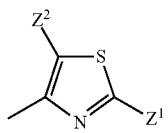 A¹⁶
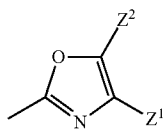 A¹⁷
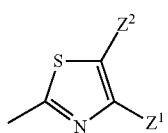 A¹⁸
-continued
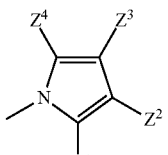 A¹⁹
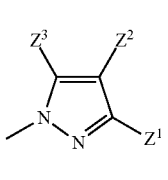 A²⁰
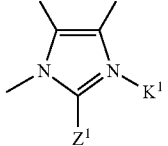 A²¹
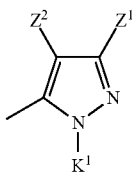 A²²
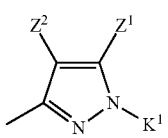 A²³
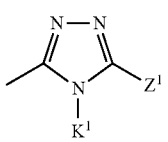 A²⁴
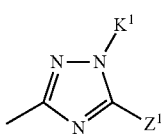 A²⁵
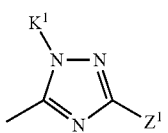 A²⁶
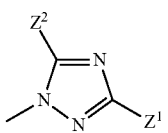 A²⁷
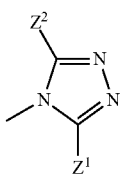 A²⁸

-continued
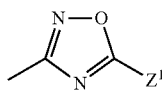
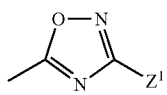
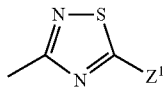
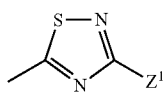
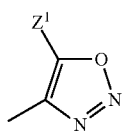
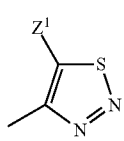
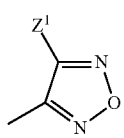
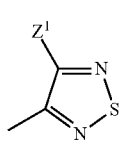
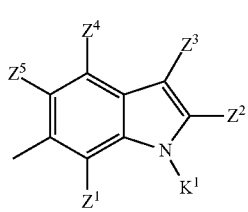
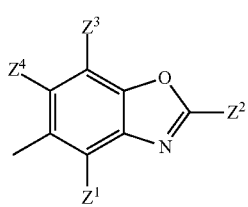
-continued
A$^{29}$
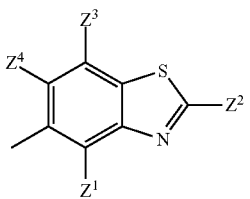
A$^{30}$
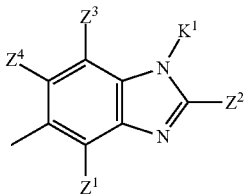
A$^{31}$
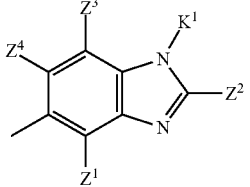
A$^{32}$
A$^{33}$
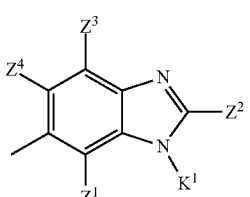
A$^{34}$
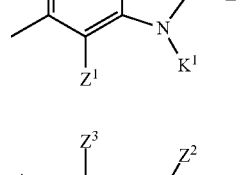
A$^{35}$
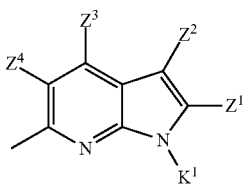
A$^{36}$
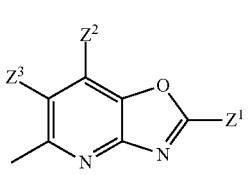
A$^{37}$
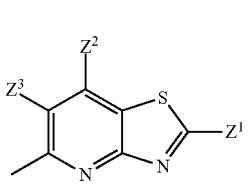
A$^{38}$
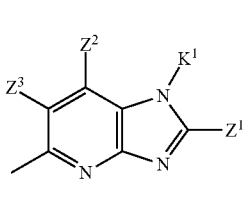
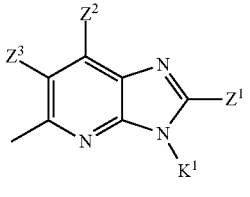
A$^{39}$
A$^{40}$
A$^{41}$
A$^{42}$
A$^{43}$
A$^{44}$
A$^{45}$
A$^{46}$ -continued

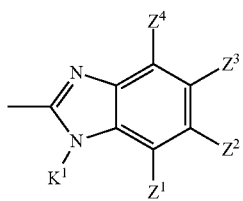
A⁴⁷

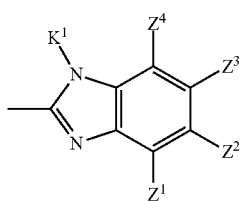
A⁴⁸

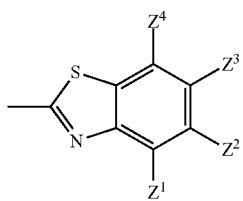
A⁴⁹

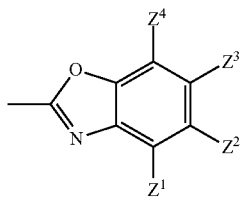
A⁵⁰

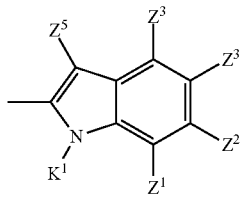
A⁵¹

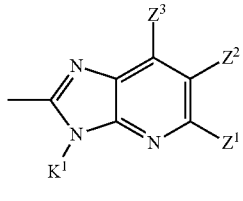
A⁵²

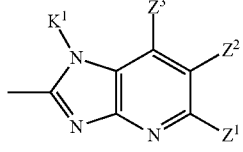
A⁵³

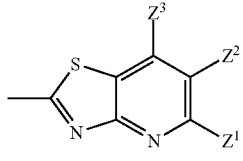
A⁵⁴

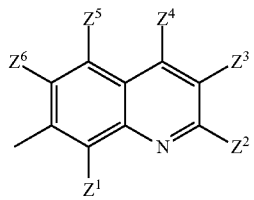
A⁵⁵

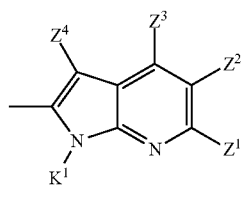
A⁵⁶

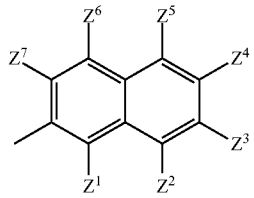
A⁵⁷

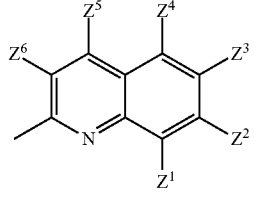
A⁵⁸ wherein $Z^1, Z^2, Z^3, Z^4, Z^5, Z^6$, and $Z^7$ are independently selected from the group consisting of a hydrogen atom, a halogen atom, a nitro group, a hydroxy group, a cyano group, an amino group, a sulphenyl group, a formyl group, a substituted or non-substituted carbaldehyde O—($C_1$-$C_8$-alkyl)oxime, a formyloxy group, a formylamino group, a carbamoyl group, a N-hydroxycarbamoyl group, a pentafluoro-$\lambda^6$-sulfenyl group, a formylamino group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$-alkyl-($C_1$-$C_8$-alkylamino)-amino group, a substituted or non-substituted (hydroxyimino)-$C_1$-$C_6$-alkyl group, substituted or non-substituted $C_1$-$C_8$-alkyl, substituted or non-substituted tri ($C_1$-$C_8$-alkyl)silyl-$C_1$-$C_8$-alkyl, substituted or non-substituted $C_3$-$C_8$-cycloalkyl, substituted or non-substituted tri($C_1$-$C_8$-alkyl)silyl-$C_3$-$C_8$-cycloalkyl, substituted or non-substituted $C_1$-$C_8$-halogenoalkyl having 1 to 5 halogen atoms, substituted or non-substituted $C_3$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted ($C_1$-$C_8$-alkoxycarbonyl)amino, substituted or non-substituted ($C_3$-$C_8$-cycloalkoxycarbonyl)amino, substituted or non-substituted $C_1$-$C_8$-halogenoalkoxy having 1 to 5 halogen atoms, substituted or non-substituted $C_1$-$C_8$alkylsulfenyl, substituted or non-substituted $C_1$-$C_8$-halogenoalkylsulfenyl having 1 to 5 halogen atoms, substituted or non-substituted $C_2$-$C_8$-alkenyloxy, substituted or non-substituted ($C_2$-$C_8$-alkenyloxycarbonyl)amino, substituted or non-substituted $C_2$-$C_8$-halogenoalkenyloxy having 1 to 5 halogen atoms, substituted or non-substituted $C_3$-$C_8$-alkynyloxy, substituted or non-substituted ($C_3$-$C_8$-alkynyloxycarbonyl)amino, substituted or non-substituted $C_3$-$C_8$-halogenoalkynyloxy having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$alkoxycarbamoyl, substituted or non-substituted N—$C_1$-$C_8$-alkyl-$C_1$-$C_8$-alkoxycarbamoyl, substituted or non-substituted $C_1$-$C_8$alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted aryloxycarbonylamino, substituted or non-substituted hetercyclyloxycarbonylamino, substituted or non-substituted arylcarbonylamino, substituted or non-substituted hetercyclylcarbonylamino, substituted or non-substituted $C_1$-$C_8$-alkylcarbamoylamino, substituted or non-substituted $C_1$-$C_8$halogenoalkylcarbamoylamino having 1 to 5 halogen atoms, substituted or non-substituted di-$C_1$-$C_8$-alkylcarbamoylamino, substituted or non-substituted di-$C_1$-$C_8$-halogenoalkylcarbamoylamino having 1 to 5 halogen atoms, substituted or non-substituted N—$C_1$-$C_8$-alkyl-($C_1$-$C_8$-alkylcarbamoyl)amino, substituted or non-substituted N—$C_1$-$C_8$-alkyl-($C_1$-$C_8$-halogenoalkylcarbamoyl)amino having 1 to 5 halogen atoms, substituted or non-substituted N—$C_1$-$C_8$-alkyl-(di-$C_1$-$C_8$-alkylcarbamoyl)amino, substituted or non-substituted N—$C_1$-$C_8$-alkyl-(di-$C_1$-$C_8$halogenoalkylcarbamoyl)amino having 1 to 5 halogen atoms, substituted or non-substituted $C_1$-$C_8$-alkylaminocarbonyloxy, substituted or non-substituted di-$C_1$-$C_8$-alkylaminocarbonyloxy, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyl, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylthioylamino, substituted or non-substituted ($C_1$-$C_8$-alkoxythiocarbonyl)amino, substituted or non-substituted $C_1$-$C_8$-halogenoalkylthioylamino having 1 to 5 halogen atoms, substituted or non-substituted ($C_1$-$C_8$-alkyl-carbamothioyl)-oxy, substituted or non-substituted (di-$C_1$-$C_8$-alkyl-carbamothioyl)-oxy, substituted or non-substituted $C_1$-$C_8$-alkylsulfinyl, substituted or non-substituted $C_1$-$C_8$-halogenoalkylsulfinyl having 1 to 5 halogen atoms, substituted or non-substituted $C_1$-$C_8$-alkylsulfonyl, substituted or non-substituted $C_1$-$C_8$-halogenoalkylsulfonyl having 1 to 5 halogen atoms, substituted or non-substituted $C_1$-$C_8$-alkylaminosulfamoyl, substituted or non-substituted di-$C_1$-$C_8$-alkylaminosulfamoyl, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$-alkynyloxyimino)-$C_1$-$C_6$-alkyl, substituted or non-substituted (benzyloxyimino)-$C_1$-$C_6$-alkyl, substituted or non-substituted benzyloxy, substituted or non-substituted benzylsulfenyl, substituted or non-substituted benzylamino, substituted or non-substituted phenoxy, substituted or non-substituted phenylsulfenyl, substituted or non-substituted phenylamino, substituted or non-substituted aryl, substituted or non-substituted (arylcarbonyl)amino, substituted or non-substituted (heterocyclylcarbonyl)amino substituted or non-substituted aryl-[$C_1$-$C_8$]-alkyl, substituted or non-substituted tri($C_1$-$C_8$alkyl)-silyloxy, substituted or non-substituted $C_1$-$C_8$-alkylsulfenylamino, substituted or non-substituted $C_1$-$C_8$-halogenoalkylsulfinylamino having 1 to 5 halogen atoms, substituted or non-substituted $C_1$-$C_8$-alkylsulfonylamino, substituted or non-substituted $C_1$-$C_8$-halogenoalkylsulfonylamino having 1 to 5 halogen atoms, substituted or non-substituted $C_1$-$C_8$-alkoxysulfonylamino, substituted or non-substituted $C_1$-$C_8$-halogenoxysulfonylamino having 1 to 5 halogen atoms, substituted or non-substituted tri($C_1$-$C_8$-alkyl)-silyl, substituted or non-substituted ($C_1$-$C_6$-alkylideneamino)oxy, substituted or non-substituted ($C_1$-$C_6$-alkenylideneamino)oxy, substituted or non-substituted ($C_1$-$C_6$-alkynylideneamino)oxy, substituted or non-substituted (benzylideneamino)oxy;

$K^1$ and $K^2$ is selected from the group consisting of a hydrogen atom, a formyl group, a substituted or non-substituted carbaldehyde O—($C_1$-$C_8$-alkyl)oxime, a carbamoyl group, a N-hydroxycarbamoyl group, a formylamino group, substituted or non-substituted $C_1$-$C_8$-alkyl, substituted or non-substituted tri($C_1$-$C_8$-alkyl)silyl-$C_1$-$C_8$-alkyl, substituted or non-substituted C3-$C_8$-cycloalkyl, substituted or non-substituted tri($C_1$-$C_8$-alkyl)silyl-$C_1$-$C_8$-cycloalkyl, substituted or non-substituted $C_1$-$C_8$-halogenoalkyl having 1 to 5 halogen atoms, substituted or non-substituted $C_3$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_2$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyl, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylsulfinyl, substituted or non-substituted $C_1$-$C_8$-halogenoalkylsulfinyl having 1 to 5 halogen atoms, substituted or non-substituted $C_1$-$C_8$-alkylsulfonyl, substituted or non-substituted $C_1$-$C_8$-halogenoalkylsulfonyl having 1 to 5 halogen atoms, substituted or non-substituted $C_1$-$C_8$-alkylaminosulfamoyl, substituted or non-substituted di-$C_1$-$C_8$-alkylaminosulfamoyl, substituted or non-substituted aryl, substituted or non-substituted aryl-[$C_1$-$C_8$]-alkyl;

Q is selected in the list consisting of $Q^1$ to $Q^{112}$:

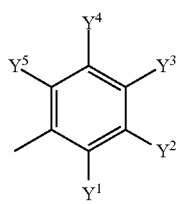

$Q^1$

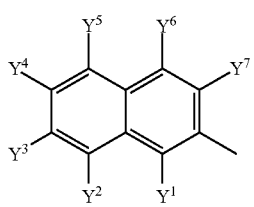

$Q^2$

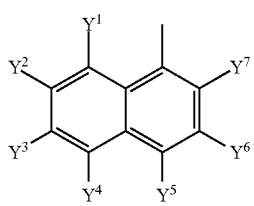

$Q^3$

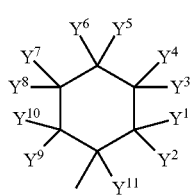

$Q^4$

-continued

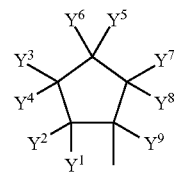

$Q^5$

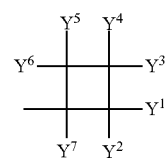

$Q^6$

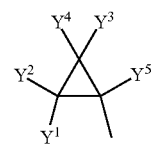

$Q^7$

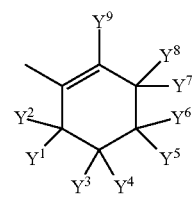

$Q^8$

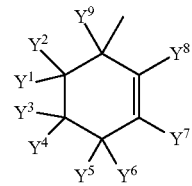

$Q^9$

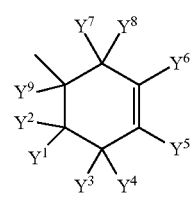

$Q^{10}$

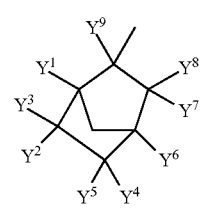

$Q^{11}$

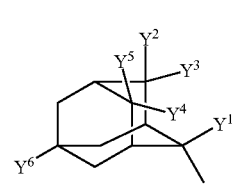

$Q^{12}$

-continued
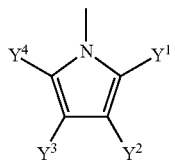  Q13
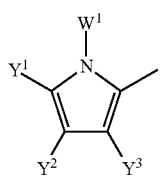  Q14
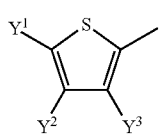  Q15
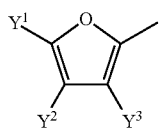  Q16
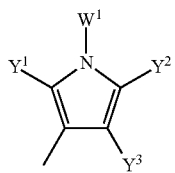  Q17
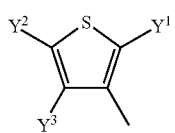  Q18
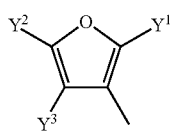  Q19
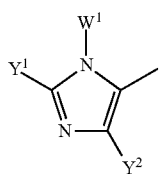  Q20
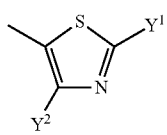  Q21
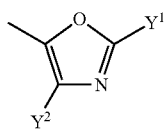 Q22
-continued
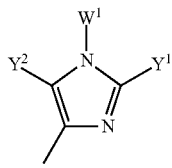 Q23
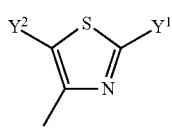 Q24
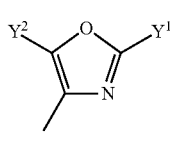 Q25
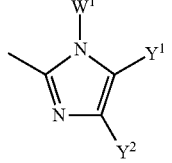 Q26
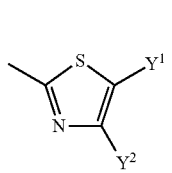 Q27
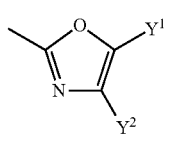 Q28
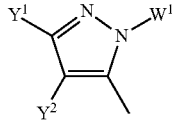 Q29
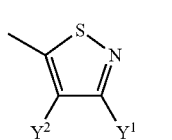 Q30
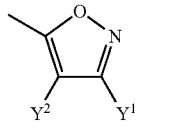 Q31
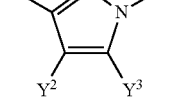 Q32

-continued
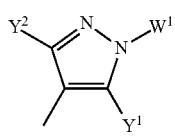
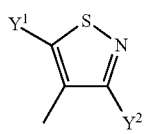
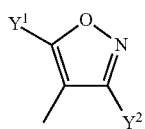
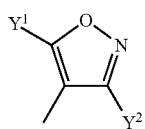
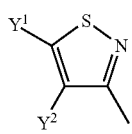
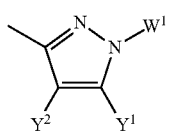
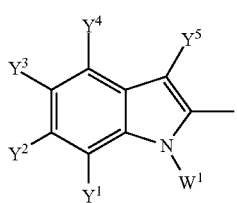
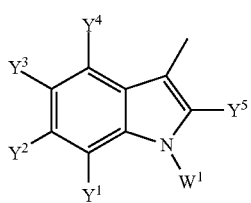
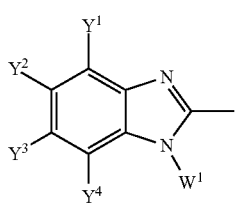
-continued
  Q33
  Q34
  Q35
  Q36
  Q37
  Q38
  Q39
  Q40
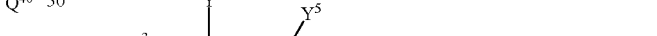  Q41
Q42
Q43
Q44
Q45
Q46
Q47
Q48

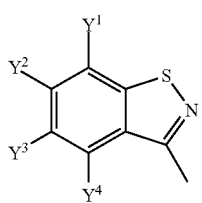 Q⁴⁹
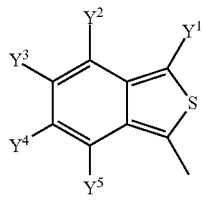 Q⁵⁶
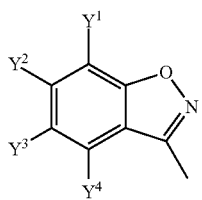 Q⁵⁰
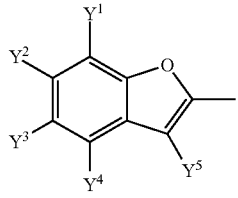 Q⁵⁷
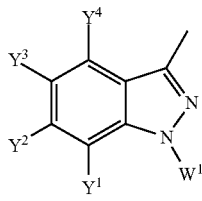 Q⁵¹
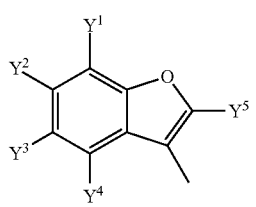 Q⁵⁸
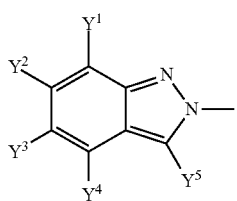 Q⁵²
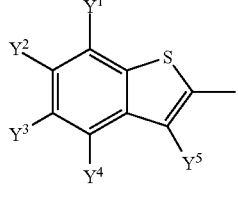 Q⁵⁹
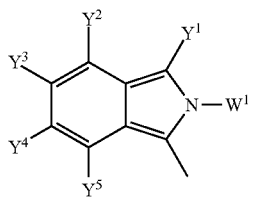 Q⁵³
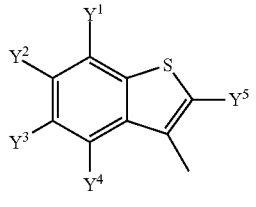 Q⁶⁰
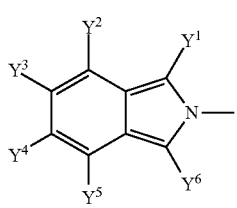 Q⁵⁴
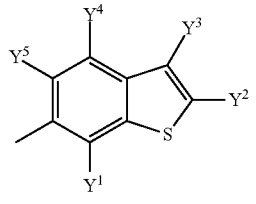 Q⁶¹
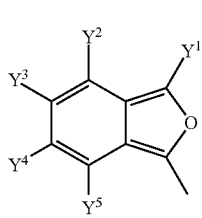 Q⁵⁵
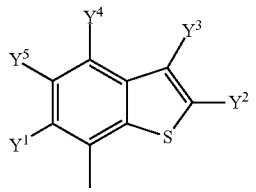 Q⁶²

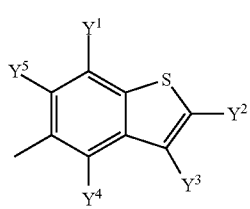 Q63
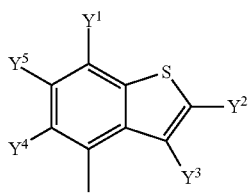 Q64
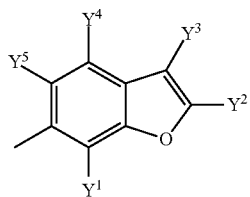 Q65
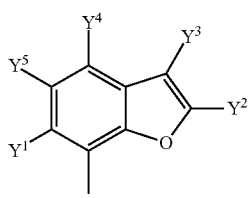 Q66
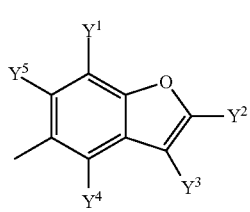 Q67
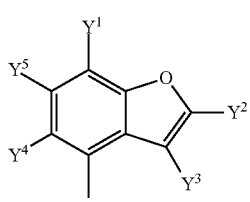 Q68
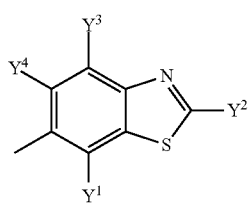 Q69
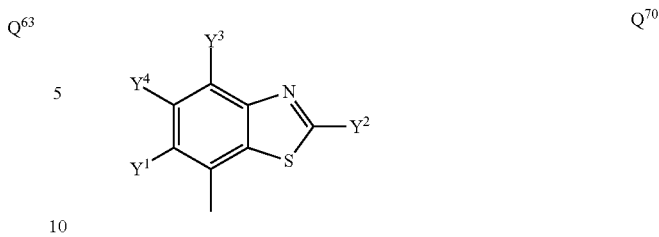 Q70
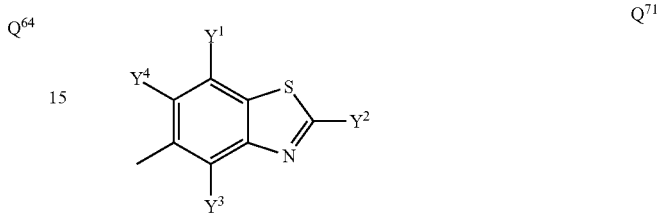 Q71
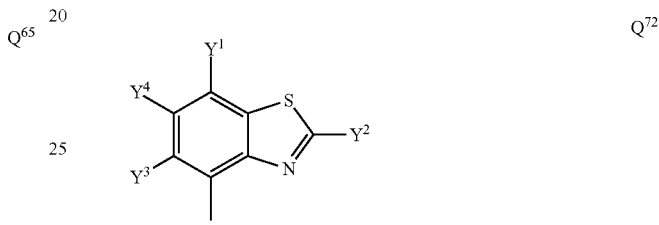 Q72
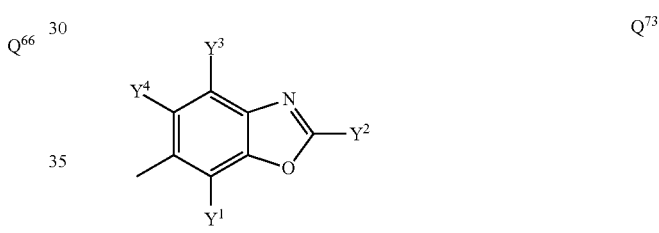 Q73
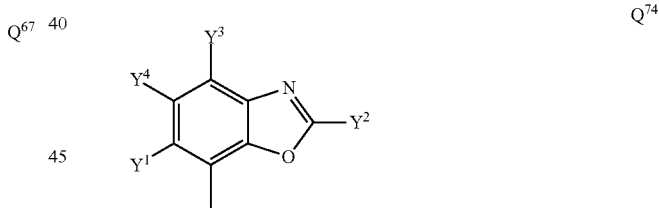 Q74
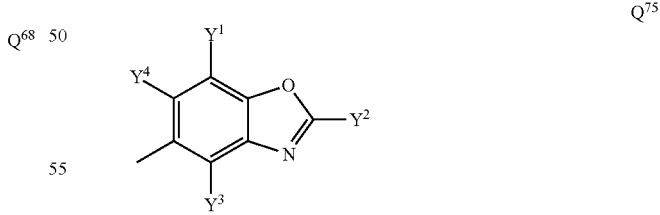 Q75
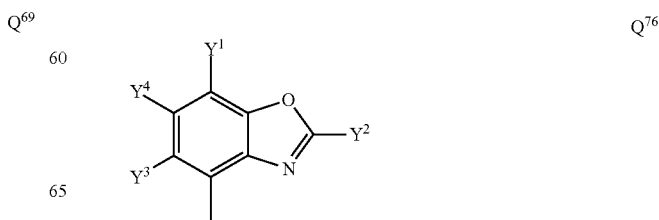 Q76

| | |
|---|---|
| 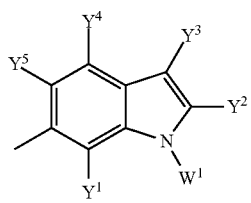 | Q77 |
| 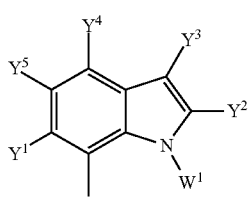 | Q78 |
| 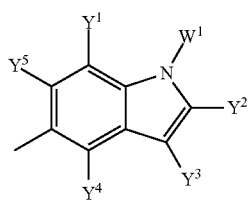 | Q79 |
| 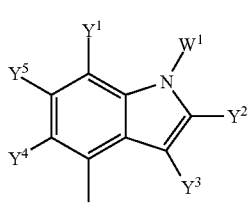 | Q80 |
| 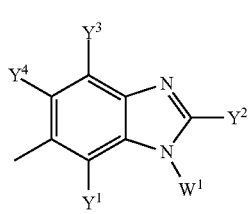 | Q81 |
| 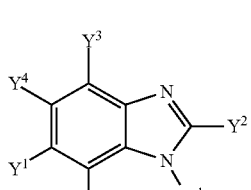 | Q82 |
| 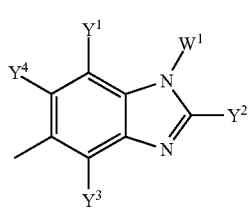 | Q83 |
| 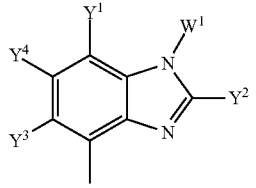 | Q84 |
| 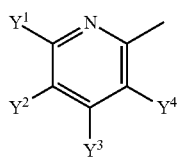 | Q85 |
| 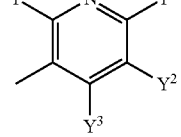 | Q86 |
| 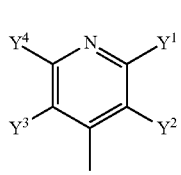 | Q87 |
| 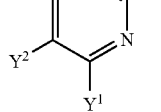 | Q88 |
| 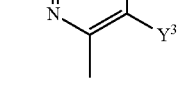 | Q89 |
| 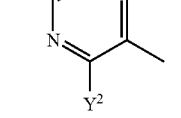 | Q90 |
| 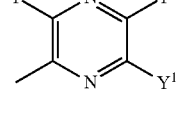 | Q91 |
| 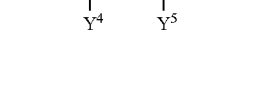 | Q92 |

163
-continued
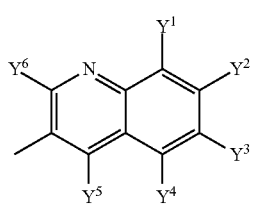
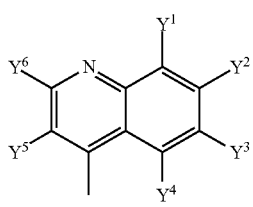
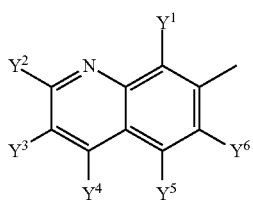
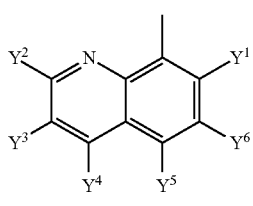
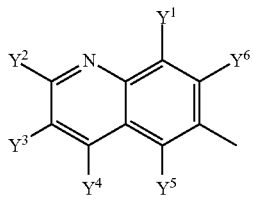
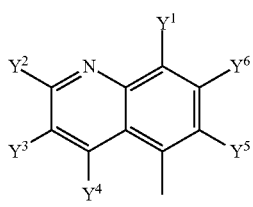
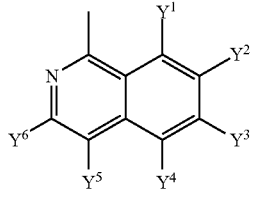
164
-continued
Q93
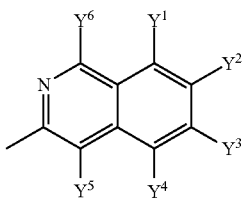
Q94
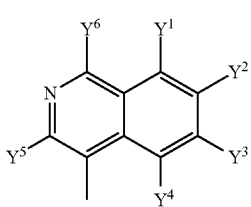
Q95
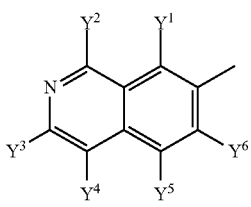
Q96
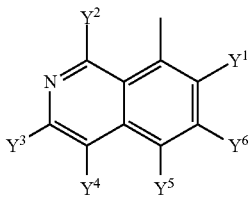
Q97
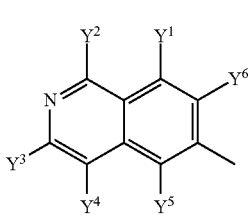
Q98
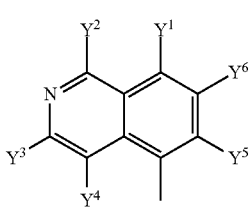
Q99
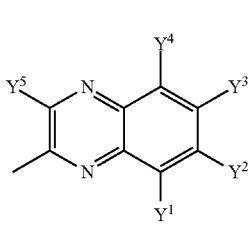
Q100
Q101
Q102
Q103
Q104
Q105
Q106

-continued

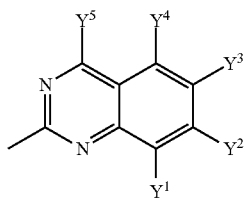
Q107

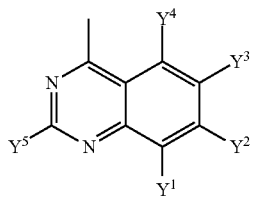
Q108

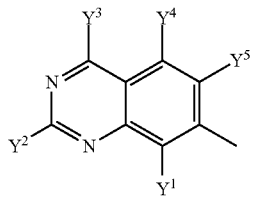
Q109

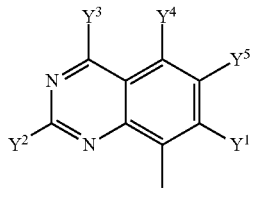
Q110

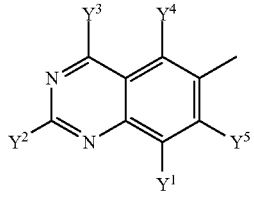
Q111

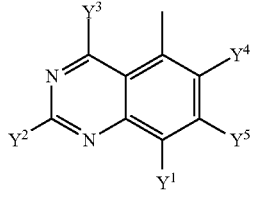
Q112 wherein
$Y^1$ to $Y^{11}$ are independently selected from the group consisting of a hydrogen atom, a nitro group, a hydroxyl group, a cyano group, an amino group, a sulfenyl group, a formyl group, a substituted or non-substituted carbaldehyde O—($C_1$-$C_8$-alkyl)oxime, a formyloxy group, a formylamino group, a carbamoyl group, a N-hydroxycarbamoyl group, a pentafluoro-$\lambda^6$-sulphenyl group, a formylamino group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$-alkyl -($C_1$-$C_8$-alkylamino)-amino group, a substituted or non-substituted (hydroxyimino)-$C_1$-$C_6$-alkyl group, substituted or non-substituted $C_1$-$C_8$-alkyl, substituted or non-substituted tri($C_1$-$C_8$-alkyl)silyl-$C_1$-$C_8$-alkyl, substituted or non-substituted $C_3$-$C_8$-cycloalkyl, substituted or non-substituted tri($C_1$-$C_8$-alkyl)silyl-$C_3$-$C_8$-cycloalkyl, substituted or non-substituted $C_1$-$C_8$-halogenoalkyl having 1 to 5 halogen atoms, substituted or non-substituted $C_3$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$alkylamino, substituted or non-substituted di-$C_1$-$C_8$-alkylamino, substituted or non-substituted $C_1$-$C_8$alkoxy, substituted or non-substituted $C_1$-$C_8$-halogenoalkoxy having 1 to 5 halogen atoms, substituted or non-substituted $C_1$-$C_8$-alkylsulfenyl, substituted or non-substituted $C_1$-$C_8$-halogenoalkylsulfenyl having 1 to 5 halogen atoms, substituted or non-substituted $C_2$-$C_8$-alkenyloxy, substituted or non substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-$C_1$-$C_8$-alkylcarbamoylamino, substituted or non-substituted di-$C_1$-$C_8$-halogenoalkylcarbamoylamino having 1 to 5 halogen atoms, substituted or non-substituted N—$C_1$-$C_8$-alkyl-($C_1$-$C_8$alkylcarbamoyl)amino, substituted or non-substituted N—$C_1$-$C_8$-alkyl-($C_1$-$C_8$-halogenoalkylcarbamoyl)amino having 1 to 5 halogen atoms, substituted or non-substituted N—$C_1$-$C_8$-alkyl-(di-$C_1$-$C_8$-alkylcarbamoyl)amino, substituted or non-substituted N—$C_1$-$C_8$-alkyl-(di-$C_1$-$C_8$-halogenoalkylcarbamoyl)amino having 1 to 5 halogen atoms, substituted or non-substituted $C_1$-$C_8$-alkylaminocarbonyloxy, substituted or non-substituted di-$C_1$-$C_8$-alkylaminocarbonyloxy, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyl, substituted or non-substituted $C_1$-$C_8$-alkoxycarbamothioyl, substituted or non-substituted N—$C_1$-$C_8$alkyl-$C_1$-$C_8$-alkoxycarbamothioyl, substituted or non-substituted $C_1$-$C_8$-alkylthioylamino, substituted or non-substituted $C_1$-$C_8$-halogenoalkylthioylamino having 1 to 5 halogen atoms, substituted or non-substituted ($C_1$-$C_8$-alkyl-carbamothioyl)-oxy, substituted or non-substituted (di-$C_1$-$C_8$-alkyl-carbamothioyl)-oxy, substituted or non-substituted $C_1$-$C_8$-alkylsulfinyl, substituted or non-substituted $C_1$-$C_8$-halogenoalkylsulfinyl having 1 to 5 halogen atoms, substituted or non-substituted $C_1$-$C_8$-alkylsulfonyl, substituted or non substituted $C_1$-$C_8$-halogenoalkylsulfonyl having 1 to 5 halogen atoms, substituted or non-substituted $C_1$-$C_8$alkylaminosulfamoyl, substituted or non-substituted di-$C_1$-$C_8$-alkylaminosulfamoyl, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$alkynyloxyimino)-$C_1$-$C_6$-alkyl, substituted or non-substituted (benzyloxyimino)-$C_1$-$C_6$-alkyl, substituted or non-substituted benzyloxy, substituted or non-substituted benzylsulfenyl, substituted or non-substituted benzylamino, substituted or non-substituted phenoxy, substituted or non-substituted phenylsulfenyl, substituted or non-substituted phenylamino, substituted or non-substituted aryl, substituted or non-substituted aryl-[$C_1$-$C_8$]-alkyl, substituted or non-substituted tri($C_1$-$C_8$-alkyl)-silyloxy, substituted or non-substituted $C_1$-$C_8$-alkylsulfenylamino, substituted or non substituted silyloxy, substituted or non-substituted $C_1$-$C_8$-alkylsulfenylamino, substituted or non-substituted $C_1$-$C_8$-halogenoalkylsulfinylamino having 1 to 5 halogen atoms, substituted or non-substituted $C_1$-$C_8$-alkylsulfonylamino, substituted or non-substituted $C_1$-$C_8$-halogenoalkylsulfonylamino having 1 to 5 halogen atoms, substituted or non-substituted $C_1$-$C_8$-alkoxysulfonylamino, substituted or non-substituted $C_1$-$C_8$-halogenoxysulfonylamino having 1 to 5 halogen atoms, substituted or non-substituted tri($C_1$-$C_8$-alkyl)-silyl, substituted or non-substituted ($C_1$-$C_6$-alkylideneamino)oxy, substituted or non-substituted ($C_1$-$C_6$-alkenylideneamino)oxy, substituted or non-substituted ($C_1$-$C_6$-alkynylideneamino)oxy, and substituted or non-substituted (benzylideneamino)oxy; and $W^1$ is as defined above;

as well as salts, N-oxides, or (E) and (Z) isomers and mixtures thereof.

2. The compound of claim 1 wherein $L^1$ represents a direct bond or a divalent group selected in the list consisting of
—$(CR^1R^2)$—
—$C(=O)$—$(CR^1R^2)_p$—
—$(CR^1R^2)_m$—O—
—$(CR^1R^2)_m$—$C(=O)$—O—
—$(CR^1R^2)_m$—NH—
—$(CR^1R^2)_m$—$C(=O)$—NH—
—$(CR^1R^2)_m$—$C(=O)$— and
—$(CR^1R^2)_m$—NH—$C(=O)$—
wherein
n represents 1 or 2;
m and p independently represent 0 or 1;
$R^1$ and $R^2$ independently represent a hydrogen atom, a halogen atom, a cyano group, substituted or non-substituted $C_1$-$C_8$-alkyl, substituted or non-substituted $C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms.

3. The compound according to claim 2 wherein $L^1$ is a direct bond or a divalent group selected from the list consisting of
—$(CR^1R^2)$—,
—$C(=O)$—$(CR^1R^2)$— and
—$C(=O)$—;
wherein $R^1$ and $R^2$ are independently selected in the list consisting of hydrogen, halogen, methyl, ethyl, isopropyl, trifluoromethyl, difluoromethyl, allyl, ethynyl, propargyl, cyclopropyl, methoxy, trifluoromethoxy and cyano.

4. A compound according to claim 1 wherein $X^1$ to $X^3$ are independently selected from the group consisting of a hydrogen atom, a halogen atom, a cyano group, an amino group, a sulphenyl group, a pentafluoro-$\lambda^6$-sulphenyl group, substituted or non-substituted $C_1$-$C_8$-alkyl, substituted or non-substituted tri($C_1$-$C_8$-alkyl)silyl-$C_1$-$C_8$-alkyl, substituted or non-substituted $C_1$-$C_8$-cycloalkyl, substituted or non-substituted tri($C_1$-$C_8$-alkyl)silyl-$C_3$-$C_8$-cycloalkyl, substituted or non-substituted $C_1$-$C_8$-halogenoalkyl having 1 to 5 halogen atoms, substituted or non substituted $C_3$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyll, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non substituted $C_1$-$C_8$alkylsulfonyl, substituted or non-substituted $C_1$-$C_8$-halogenoalkylsulphenyl having 1 to 5 halogen atoms, substituted or non-substituted ($C_1$-$C_6$-alkenyloxyimino)-$C_1$-$C_6$-alkyl, substituted or non-substituted ($C_1$-$C_6$-alkynyloxyimino)-$C_1$-$C_6$-alkyl, substituted or non-substituted ($C_1$-$C_6$-alkynyloxyimino)-$C_1$-$C_6$-alkyl, substituted or non-substituted (benzyloxyimino)-$C_1$-$C_6$-alkyl, substituted or non-substituted benzyloxy, substituted or non-substituted benzylsulphenyl, substituted or non-substituted phenoxy, substituted or non-substituted phenylsulphenyl, substituted or non-substituted aryl, substituted or non-substituted aryl-[$C_1$-$C_8$]-alkyl, substituted or non-substituted tri($C_1$-$C_8$-alkyl)-silyloxy, substituted or non-substituted tri($C_1$-$C_8$-alkyl)-silyl.

5. A compound according to claim 4 wherein $X^1$ to $X^3$ are independently selected from the group consisting of a hydrogen atom, a halogen atom, methyl, isopropyl, isobutyl, tert-butyl, trifluoromethyl, difluoromethyl, allyl, ethynyl, propargyl, cyclopropyl, benzyl, phenethyl, methoxy, trifluoromethoxy, acetyl, trifluoroacetyl and cyano.

6. A compound according to claim 1 wherein $W^1$ is selected from the group consisting of a hydrogen atom, a halogen atom, a cyano group, substituted or non-substituted $C_1$-$C_8$-alkyl, substituted or non-substituted $C_1$-$C_8$-cycloalkyl, substituted or non-substituted $C_1$-$C_8$-halogenoalkyl having 1 to 5 halogen atoms, a $C_2$-$C_8$-alkenyl, substituted or non-substituted $C_2$-$C_8$-alkynyl, substituted or non-substituted $C_1$-$C_8$alkoxy, substituted or non-substituted $C_1$-$C_8$-halogenoalkoxy having 1 to 5 halogen atoms, substituted or non-substituted phenoxy, substituted or non-substituted aryl, substituted or non-substituted aryl-[$C_1$-$C_8$]-alkyl.

7. A compound according to claim 6 wherein $W^1$ is selected from the gropu consisting of a hydrogen atom, a halogen atom, methyl, ethyl, isopropyl, isobutyl, terbutyl, trifluoromethyl, difluoromethyl, allyl, ethynyl, propargyl, cyclopropyl, methoxy, trifluoromethoxy and cyano.

8. A compound according to claim 1 wherein A is selected from the group consisting of $A^2$, $A^6$, $A^8$, and $A^{11}$ through $A^{18}$.

9. A compound according to claim 1 wherein $Z^1$ is selected from the group consisting of a hydrogen atom, a halogen atom, a hydroxy group, a cyano group, an amino group, a formyloxy group, a formylamino group, a carbamoyl group, a N-hydroxycarbamoyl group, a pentafluoro-$\lambda^6$-sulphenyl group, a formylamino group, substituted or non-substituted $C_1$-$C_8$-alkoxyamino group, substituted or non-substituted N—$C_1$-$C_8$-alkyl-($C_1$-$C_8$-alkoxy)-amino group, a substituted or non-substituted (hydroxyimino)-C.sub.1-C.sub 6-alkyl group, substituted or non-substituted $C_1$-$C_8$-alkyl, substituted or non-substituted tri($C_1$-$C_8$-alkyl)silyl-$C_1$-$C_8$-alkyl, substituted or non-substituted $C_3$-$C_8$-cycloalkyl, substituted or non-substituted tri($C_1$-$C_8$-alkyl)silyl-$C_3$-$C_8$-cycloalkyl, substituted or non-substituted $C_1$-$C_8$-halogenoalkyl having 1 to 5 halogen atoms, substituted or non-substituted $C_3$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted ($C_1$-$C_8$-alkoxycarbonyl) amino, substituted or non-substituted $C_1$-$C_8$-alkylcarbamoylamino, substituted or non-substituted $C_1$-$C_8$halogenoalkylcarbamoylamino having 1 to 5 halogen atoms, substituted or non-substituted di-$C_1$-$C_8$-alkylcarbamoylamino, substituted or non-substituted di-$C_1$-$C_8$-halogenoalkylcarbamoylamino having 1 to 5 halogen atoms, substituted or non-substituted N—$C_1$-$C_8$-alkyl-($C_1$-$C_8$-alkylcarbamoyl)amino, substituted or non-substituted N—$C_1$-$C_8$-alkyl-($C_1$-$C_8$-halogenoalkylcarbamoyl)amino having 1 to 5 halogen atoms, substituted or non-substituted N—$C_1$-$C_8$-alkyl-(di-$C_1$-$C_8$-alkylcarbamoyl)amino, substituted or non-substituted N—$C_1$-$C_8$-alkyl-(di-$C_1$-$C_8$-halogenoalkylcarbamoyl)amino having 1 to 5 halogen atoms, substituted or non-substituted $C_1$-$C_8$-alkylaminocarbonyloxy, substituted or non-substituted di-$C_1$-$C_8$-alkylaminocarbonyloxy, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyl, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non substituted $C_1$-$C_8$-alkylthioylamino, substituted or non-substituted $C_1$-$C_8$-halogenoalkylthioylamino having 1 to 5 halogen atoms, substituted or non-substituted ($C_1$-$C_8$-alkyl-carbamothioyl)-oxy, substituted or non-substituted substituted or non-substituted (di-$C_1$-$C_8$-alkyl-carbamothioyl)-oxy, substituted or non-substituted $C_1$-$C_8$-alkylaminosulfamonyl, substituted or non-substituted di-$C_1$-$C_8$-alkylaminosulfamoyl, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$-alkynyloxyimino)-$C_1$-$C_6$-alkyl, substituted or non-substituted (benzyloxyimino)-$C_1$-$C_6$-alkyl, substituted or non-substituted benzyloxy, substituted or non-substituted benzylsulfenyl, substituted or non-substituted benzylamino, substituted or non-substituted phenoxy, substituted or non-substituted phenylsulfenyl, substituted or non-substituted phenylamino, substituted or non-substituted aryl, substituted or non-substituted aryl-[$C_1$-$C_8$]-alkyl, substituted or non-substituted tri($C_1$-$C_8$-alkyl)-silyloxy, substituted or non-substituted $C_1$-$C_8$-halogenoalkylsulfinylamino having 1 to 5 halogen atoms, substituted or non-substituted $C_1$-$C_8$-alkylsulfinylamino, substituted or non-substituted $C_1$-$C_8$-halogenoalkylsulfonylamino having 1 to 5 halogen atoms, substituted or non-substituted $C_1$-$C_8$-alkoxysulfonylamino, substituted or non-substituted $C_1$-$C_8$-halogenoxysulphonylamino having 1 to 5 halogen atoms, substituted or non-substituted tri($C_1$-$C_8$-alkyl)-silyl, substituted or non-substituted ($C_1$-$C_6$-alkylideneamino)oxy, substituted or non-substituted ($C_1$-$C_6$-alkenylideneamino)oxy, substituted or non-substituted ($C_1$-$C_6$alkynylideneamino)oxy, and substituted or non-substituted (benzylideneamino)oxy.

10. A compound according to claim 9 wherein $Z^1$ is selected from the group consisting of a hydrogen atom, a halogen atom, a cyano group, an amino group, a formyloxy group, a formylamino group, a carbamoyl group, a N-hydroxycarbamoyl group, a formylamino group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted $C_1$-$C_8$-alkyl, substituted or non-substituted tri($C_1$-$C_8$-alkyl)silyl-$C_1$-$C_8$-alkyl, substituted or non-substituted $C_3$-$C_8$-cycloalkyl, substituted or non-substituted $C_1$-$C_8$-halogenoalkyl having 1 to 5 halogen atoms, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulfenyl, substituted or non-substituted $C_1$-$C_8$-alkylcarbonyl, substituted or non-substituted N—($C_1$-$C_8$-alkoxy)-$C_1$-$C_8$-alkanimidoyl, substituted or non substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkylcarbonylamino, substituted or non-substituted ($C_1$-$C_8$-alkoxycarbonyl)amino, substituted or non-substituted $C_1$-$C_8$-halogenoalkylcarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-$C_1$-$C_8$-alkylcarbamoylamino, substituted or non-substituted di-$C_1$-$C_8$-halogenoalkylcarbamoylamino having 1 to 5 halogen atoms, substituted or non-substituted N—$C_1$-$C_8$-alkyl-($C_1$-$C_8$-alkylcarbamoyl)amino, substituted or non-substituted N—$C_1$-$C_8$-alkyl-($C_1$-$C_8$-halogenoalkylcarbamoyl)amino having 1 to 5 halogen atoms, substituted or non-substituted N—$C_1$-$C_8$-alkyl-(di-$C_1$-$C_8$-alkylcarbamoyl)amino, substituted or non-substituted N—$C_1$-$C_8$-alkyl-(di-$C_1$-$C_8$-halogenoalkylcarbamoyl)amino having 1 to 5 halogen atoms, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyl, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylthioylamino, substituted or non-substituted $C_1$-$C_8$-halogenoalkylthioylamino having 1 to 5 halogen atoms, substituted or non-substituted benzylamino, substituted or non-substituted phenoxy, substituted or non-substituted phenylamino, substituted or non-substituted aryl, substituted or non-substituted aryl-[$C_1$-$C_8$]-alkyl, substituted or non-substituted $C_1$-$C_8$-halogenoalkylsulfinylamino having 1 to 5 halogen atoms, substituted or non-substituted $C_1$-$C_8$-alkylsulfonylamino, and substituted or non-substituted $C_1$-$C_8$-halogenoalkylsulfonylamino having 1 to 5 halogen atoms.

11. A compound according to claim 1 wherein $Z^2$ to $Z^7$ are independently selected from the group consisting of a hydrogen atom, a halogen atom, a cyano group, substituted or non-substituted $C_1$-$C_8$-alkyl, substituted or non-substituted $C_3$-$C_8$-cycloalkyl, substituted or non-substituted $C_1$-$C_8$-halogenoalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted phenoxy, substituted or non-substituted aryl, and substituted or non-substituted aryl-[$C_1$-$C_8$]-alkyl.

12. A compound according to claim 11 wherein $Z^2$ to $Z^7$ are independently selected from the group consisting of hydrogen, halogen, methyl, ethyl, isopropyl, isobutyl, terbutyl, trifluoromethyl, difluoromethyl, allyl, ethynyl, propargyl, cyclopropyl, methoxy, trifluoromethoxy, acetyl, and cyano.

13. A compound according to claim 1 $K^1$ is selected from the group consisting of hydrogen, methyl, ethyl, isopropyl, isobutyl, terbutyl, allyl, propargyl, cyclopropyl, acetyl, trifluoroacetyl and mesyl.

14. A compound according to claim 1 wherein Q is selected from the group consisting of $Q^1$, $Q^{15}$, $Q^{16}$, $Q^{18}$, $Q^{19}$, $Q^{21}$, $Q^{24}$, $Q^{27}$, $Q^{85}$, $Q^{86}$, $Q^{87}$, $Q^{88}$, $Q^{89}$, $Q^{90}$, and $Q^{91}$.

15. A compound according to claim 1 wherein $Y^1$ through $Y^{11}$ are independently selected from the group consisting of a hydrogen atom, a halogen atom, a cyano group, an amino group, a sulphenyl group, a pentafluoro-$\lambda^6$-sulphenyl group, substituted or non-substituted $C_1$-$C_8$-alkyl, substituted or non-substituted tri($C_1$-$C_8$-alkyl)silyl-$C_1$-$C_8$-alkyl, substituted or non-substituted $C_3$-$C_8$-cycloalkyl, substituted or non-substituted tri($C_1$-$C_8$-alkyl)silyl-$C_3$-$C_8$-cycloalkyl, substituted or non-substituted $C_1$-$C_8$-halogenoalkyl having 1 to 5 halogen atoms, substituted or non-substituted $C_3$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulfenyl, substituted or non-substituted $C_1$-$C_8$-halogenoalkylsulfenyl having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyll, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non substituted $C_1$-$C_8$-alkylsulfonyl, substituted or non-substituted $C_1$-$C_8$-halogenoalkylsulfenyl having 1 to 5 halogen atoms, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$-alkynyloxyimino)-$C_1$-$C_6$-alkyl, substituted or non-substituted (benzyloxyimino)-$C_1$-$C_6$-alkyl, substituted or non-substituted benzyloxy, substituted or non-substituted benzylsulfenyl, substituted or non-substituted phenoxy, substituted or non-substituted phenylsulfenyl, substituted or non-substituted aryl, substituted or non-substituted aryl-[$C_1$-$C_8$]-alkyl, substituted or non-substituted tri($C_1$-$C_8$-alkyl)-silyloxy, substituted or non-substituted tri($C_1$-$C_8$-alkyl)-silyl.

16. A compound according to claim 15 wherein $Y^1$ through $Y^{11}$ are independently selected from the group consisting of a hydrogen atom, a halogen atom, methyl, isopropyl, isobutyl, tertbutyl, trifluoromethyl, difluoromethyl, allyl, ethynyl, propargyl, cyclopropyl, methoxy, trifluoromethoxy and cyano.

17. A compound of formula (I)

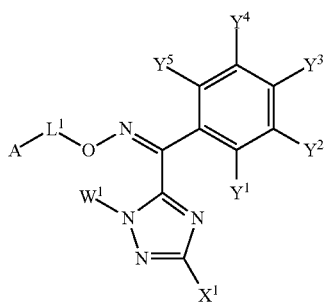

wherein

X¹ is selected from the group consisting of a hydrogen atom, a halogen atom, a nitro group, a hydroxy group, a cyano group, an amino group, a sulfenyl group, a formyl group, a substituted or non-substituted carbaldehyde O—($C_1$-$C_8$alkyl)oxime, a formyloxy group, a formylamino group, a carbamoyl group, a N-hydroxycarbamoyl group, a pentafluoro-$\lambda^6$-sulfenyl group, a formylamino group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$alkyl-($C_1$-$C_8$-alkylamino)-amino group, a substituted or non-substituted (hydroxyimino)-$C_1$-$C_6$-alkyl group, substituted or non-substituted $C_1$-$C_8$-alkyl, substituted or non-substituted tri($C_1$-$C_8$-alkyl)silyl-$C_1$-$C_8$-alkyl, substituted or non-substituted $C_3$-$C_8$-cycloalkyl, substituted or non-substituted tri($C_1$-$C_8$alkyl)silyl-$C_3$-$C_8$-cycloalkyl, substituted or non-substituted $C_1$-$C_8$-halogenoalkyl having 1 to 5 halogen atoms, substituted or non-substituted $C_3$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulfenyl, substituted or non-substituted $C_1$-$C_8$-halogenoalkylsulfenyl having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$alkylcarbarmoyl, substituted or non-substituted N—$C_1$-$C_8$alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$halogenoalkylcarbonyloxy having 1 to 5 halogen atoms, substituted or non-substituted $C_1$-$C_8$-alkylearbonylamino, substituted or non-substituted $C_1C_8$-halogenoalkylcarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-$C_1$-$C_8$-alkylcarbamoylamino, substituted or non-substituted di-$C_1$-$C_8$-halogenoalkylcarbamoylamino having 1 to 5 halogen atoms, substituted or non-substituted N—$C_1$-$C_8$alkyl-($C_1$-$C_8$-alkylcarbamoyl)amino, substituted or non-substituted N—$C_1$-$C_8$alkyl -($C_1$-$C_8$-halogenoalkylcarbamoyl)amino having 1 to 5 halogen atoms, substituted or non-substituted N—$C_1$-$C_8$-alkyl-(di-$C_1$-$C_8$-alkylcarbamoyl)amino, substituted or non-substituted N—$C_1$-$C_8$-alkyl-(di-$C_1$-$C_8$-halogenoalkylcarbarnoyl)amino having 1 to 5 halogen atoms, substituted or non-substituted $C_1$-$C_8$-alkylaminocarbonyloxy, substituted or non-substituted di-$C_1$-$C_8$-alkylaminocarbonyloxy, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyl, substituted or non-substituted $C_1$-$C_8$-alkoxycarbamothioyl, substituted or non-substituted N—$C_1$-$C_8$alkyl-$C_1$-$C_8$-alkoxycarbamothioyl, substituted or non-substituted $C_1$-$C_8$-alkylthioylamino, substituted or non-substituted $C_1$-$C_8$-halogenoalkylthioylamino having 1 to 5 halogen atoms, substituted or non-substituted ($C_1$-$C_8$-alkyl-carbamothioyl)-oxy, substituted or non-substituted (di-$C_1$-$C_8$-alkyl-carbamothioyl)-oxy, substituted or non-substituted $C_1$-$C_8$-alkylsulfinyl, substituted or non-substituted $C_1$-$C_8$-halogenoalkylsulfinyl having 1 to 5 halogen atoms, substituted or non-substituted $C_1$-$C_8$-alkylsulfonyl, substituted or non-substituted $C_1$-$C_8$-halogenoalkylsulfonyl having 1 to 5 halogen atoms, substituted or non-substituted $C_1$-$C_8$-alkylaminosulfamoyl, substituted or non-substituted di-$C_1$-$C_8$alkylaminosulfamoyl, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$-alkynyloxyimino)-$C_1$-$C_6$-alkyl, substituted or non-substituted (benzyloxyimino)-$C_1$-$C_6$-alkyl, substituted or non-substituted benzyloxy, substituted or non-substituted benzylsulfenyl, substituted or non-substituted benzylamino, substituted or non-substituted phenoxy, substituted or non-substituted phenylsulfenyl, substituted or non-substituted phenylamino, substituted or non-substituted aryl, substituted or non-substituted aryl-[$C_1$-$C_8$-]alkyl, substituted or non-substituted tri($C_1$-$C_8$alkyl)-silyloxy, substituted or non-substituted $C_1$-$C_8$-alkylsulfenylamino, substituted or non-substituted $C_1$-$C_8$-halogenoalkylsulfinylamino having 1 to 5 halogen atoms, substituted or non-substituted $C_1$-$C_8$-alkylsulfonylamino, substituted or non-substituted $C_1$-$C_8$-halogertoalkylsulfonylamino having 1 to 5 halogen atoms, substituted or non-substituted $C_1$-$C_8$-alkoxysulfonylamino, substituted or non-substituted $C_1$-$C_8$halogenoxysulphonylamino having 1 to 5 halogen atoms, substituted or non-substituted tri($C_1$-$C_8$alkyl)-silyl, substituted or non-substituted ($C_1$-$C_6$-alkylideneamino)oxy, substituted or non-substituted ($C_1$-$C_6$-alkenylideneamino)oxy, substituted or non-substituted ($C_1$-$C_6$-alkynylideneamino)oxy, and substituted or non-substituted (benzylideneamino)oxy;

W¹ is selected from the group consisting of a hydrogen atom, a formy l group, a substituted or non-substituted carbaldehyde O—($C_1$-$C_8$-alky)oxime, a carbamoyl group, a N-hydroxyearbamoyl group, a fomylamino group, substituted or non-substituted $C_1$-$C_8$alkyl, substituted or non-substituted tri($C_1$-$C_8$alkyl)silyl-$C_1$-$C_8$-alkyl, substituted or non-substituted $C_3$-$C_8$cycloalkyl, substituted or non-substituted tri($C_1$-$C_8$alkyl)silyl-$C_3$-$C_8$cycloalkyl, substituted or non-substituted $C_1C_8$halogenoalkyl having 1 to 5 halogen atoms, substituted or non-substituted $C_3$-$C_8$halogenocycloalkyl having 1 to 5 halogen atoms, a $C_2$-$C_8$-alkenyl, substituted or non-substituted $C_2$-$C_8$alkynyl, substituted or non-substituted $C_1$-$C_8$alkylamino, substituted or non-substituted di-$C_1$-$C_8$alkylamino, substituted or non-substituted $C_1C_8$alkoxy, substituted or non-substituted $C_1$-$C_8$-halogenoalkoxy having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_2$-$C_8$alkynyloxy, substituted or non-substituted $C_3$-$C_8$halogenoalkynyloxy having 1 to 5 halogen atoms, substituted or non-substituted $C_1$-$C_8$alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylearbonyl having 1 to 5 halogen atoms, substituted or non-substituted $C_1$-$C_8$-alkylcarbamoyl, substituted or non-substituted di-$C_1$-$C_8$-alkylearbamoyl, substituted or non-substituted N—$C_1$-$C_8$-alkyloxycarbamoyl substituted or non-substituted $C_1$-$C_8$-alkoxyearbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylearbamothioyl, substituted or non-substituted di-$C_1$-$C_8$-alkylcarbamothioyl, substituted or non-substituted N—$C_1$-$C_8$-alkyloxycarbarnothioyl, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylsulfinyl, substituted or non-substituted $C_1$-$C_8$halogenoalkylsulfinyl having 1 to 5 halogen atoms, substituted or non-substituted $C_1$-$C_8$-alkylsulfonyl, substituted or non-substituted $C_1$-$C_8$-halogenoalkylsulfonyl having 1 to 5 halogen atoms, substituted or non-substituted $C_1$-$C_8$ -alkylaminosulfamoyl, substituted or non-substituted di-$C_1$-$C_8$alkylaminosulfamoyl, substituted or non-substituted aryl, and substituted or non-substituted aryl-[$C_1$-$C_8$]-alkyl;

$L^1$ represents a direct bond or a divalent group selected from the group consisting of —$(CR^1R^2)_n$— —$(CR^1R^2)_m$—C(=O)—$(CR^1R^2)_p$— —$(CR^1R^2)_m$—$(CR^1=CR^2)$—$(CR^1R^2)_p$— —$(CR^1R^2)_m$—C(=O)—O—$(CR^1R^2)_p$— —$(CR^1R^2)_m$—C≡C—$(CR^1R^2)_p$— —$(CR^1R^2)_m$—O—C(=O)—$(CR^1R^2)_p$— —$(CR^1R^2)_m$—O—$(CR^1R^2)_p$— —$(CR^1R^2)_m$—C(=O)—NH—$(CR^1R^2)_p$— —$(CR^1R^2)_m$—NH—$(CR^1R^2)_p$— —$(CR^1R^2)_m$—NH—C(=O)—$(CR^1R^2)_p$— wherein
n is 1, 2, 3 or 4;
m and p are independently 0, 1, 2 or 3;
$R^1$ and $R^2$ are independently selected from the group consisting of a hydrogen atom, a halogen atom, a cyano group, substituted or non-substituted $C_1$-$C_8$-alkyl, substituted or non-substituted $C_3$-$C_8$-cycloalkyl, substituted or non-substituted $C_1$-$C_8$-halogenoalkyl having 1 to 5 halogen atoms, substituted or non-substituted $C_3$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms;

A is selected from the group consisting of $A^1$ to $A^{58}$:

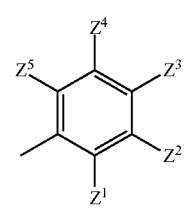

$A^1$

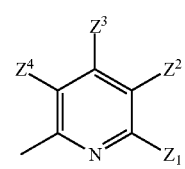

$A^2$

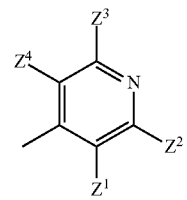

$A^3$

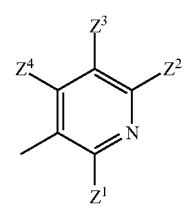

$A^4$

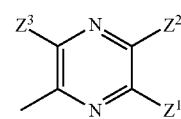

$A^5$

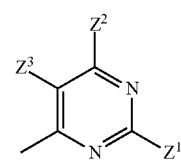

$A^6$

-continued
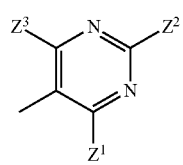 A⁷
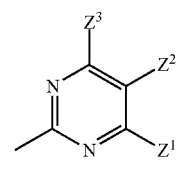 A⁸
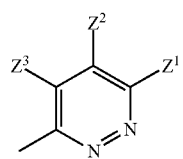 A⁹
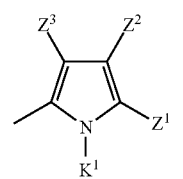 A¹⁰
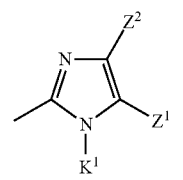 A¹¹
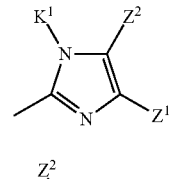 A¹²
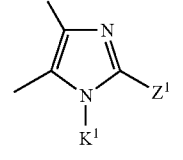 A¹³
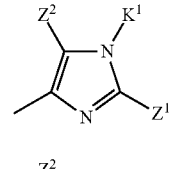 A¹⁴
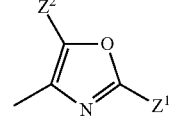 A¹⁵
-continued
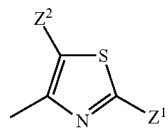 A¹⁶
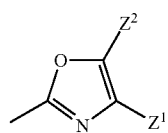 A¹⁷
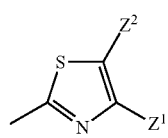 A¹⁸
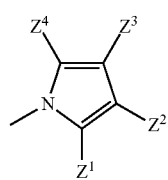 A¹⁹
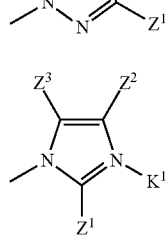 A²⁰
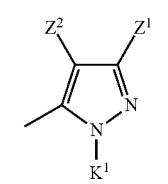 A²¹
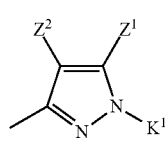 A²²
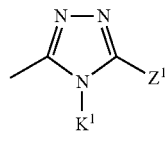 A²³
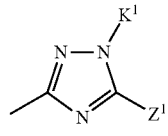 A²⁴
A²⁵

179
-continued
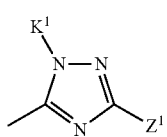
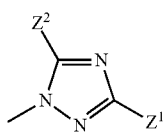
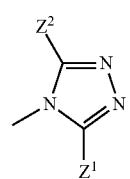
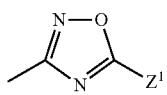
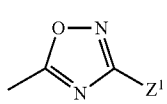
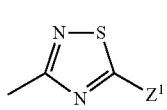
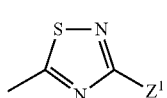
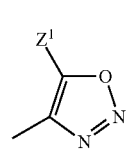
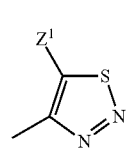
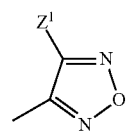
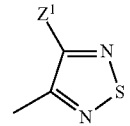
$A^{26}$
$A^{27}$
$A^{28}$
$A^{29}$
$A^{30}$
$A^{31}$
$A^{32}$
$A^{33}$
$A^{34}$
$A^{35}$
$A^{36}$
180
-continued
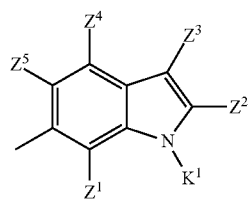
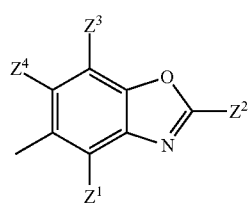
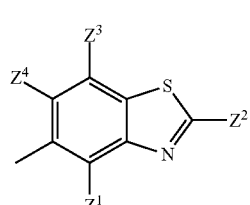
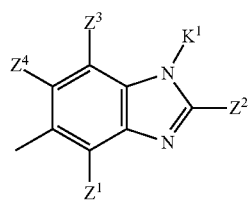
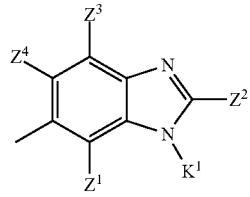
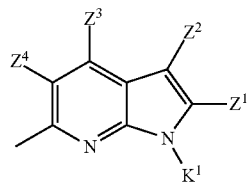
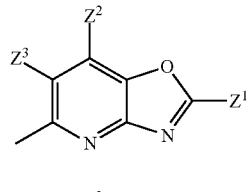
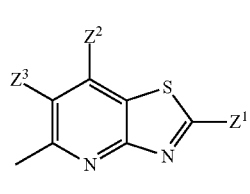
$A^{37}$
$A^{38}$
$A^{39}$
$A^{40}$
$A^{41}$
$A^{42}$
$A^{43}$
$A^{44}$ $A^{45}$ 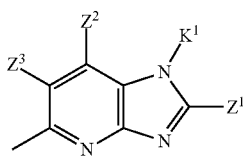

$A^{46}$ 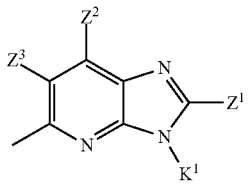

$A^{47}$ 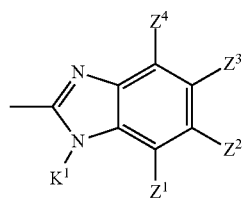

$A^{48}$ 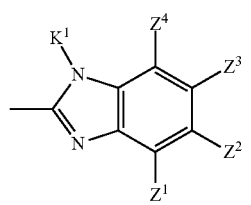

$A^{49}$ 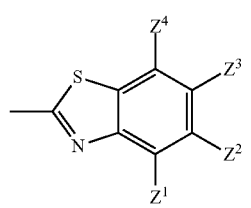

$A^{50}$ 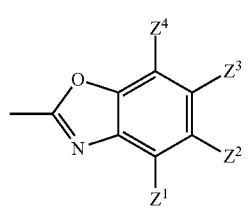

$A^{51}$ 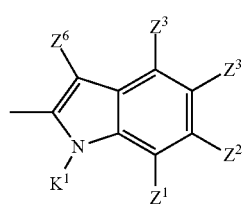

$A^{52}$ 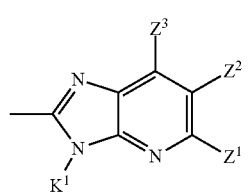

$A^{53}$ 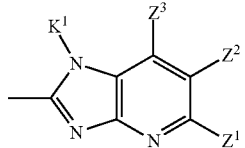

$A^{54}$ 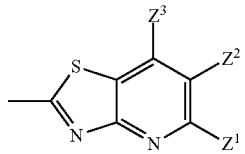

$A^{55}$ 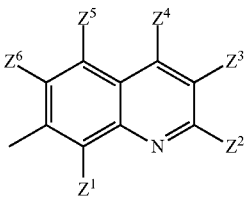

$A^{56}$ 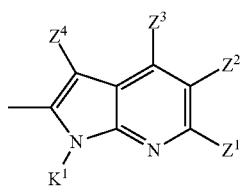

$A^{57}$ 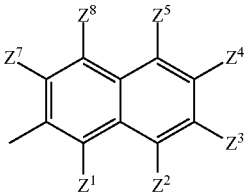

$A^{58}$ 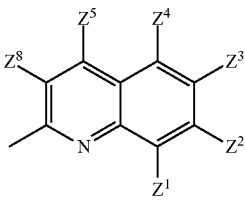

wherein
$Z^1$, $Z^2$, $Z^3$, $Z^4$, $Z^5$, $Z^6$, and $Z^7$ are independently selected from the group consisting of a hydrogen atom, a halogen atom, a nitro group, a hydroxy group, a cyano group, an amino group, a sulphenyl group, a formyl group, a substituted or non-substituted carbaldehyde O—($C_1$-$C_8$-alkyl)oxime, a formyloxy group, a formylamino group, a carbamoyl group, a N-hydroxycarbamoyl group, a pentafluoro-$\lambda^6$-sulfenyl group, a formylamino group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$-alkyl-($C_1$-$C_8$-alkylamino) amino group, a substituted or non-substituted (hydroxyimino)-$C_1$-$C_6$-alkyl group, substituted or non-substituted $C_1$-$C_8$-alkyl, substituted or non-substituted tri ($C_1$-$C_8$-alkyl)silyl-$C_1$-$C_8$-alkyl, substituted or non-substituted $C_3$-$C_8$-cycloalkyl, substituted or non-substituted tri($C_1$-$C_8$-alkyl)silyl-$C_3$-$C_8$-cycloalkyl, substituted or non-substituted $C_1$-$C_8$-halogenoalkyl having 1 to 5 halogen atoms, substituted or non-substituted $C_3$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted ($C_1$-$C_8$-alkoxycarbonyl)amino, substituted or non-substituted ($C_3$-$C_8$-cycloalkoxycarbonyl)amino, substituted or non-substituted $C_1$-$C_8$-halogenoalkoxy having 1 to 5 halogen atoms, substituted or non-substituted $C_1$-$C_8$alkylsulfenyl, substituted or non-substituted $C_1$-$C_8$-halogenoalkylsulfenyl having 1 to 5 halogen atoms, substituted or non-substituted $C_2$-$C_8$-alkenyloxy, substituted or non-substituted ($C_2$-$C_8$-alkenyloxycarbonyl)amino, substituted or non-substituted $C_2$-$C_8$-halogenoalkenyloxy having 1 to 5 halogen atoms, substituted or non-substituted $C_3$-$C_8$-alkynyloxy, substituted or non-substituted ($C_3$-$C_8$-alkynyloxycarbonyl)amino, substituted or non-substituted $C_3$-$C_8$-halogenoalkynyloxy having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted aryloxycarbonylamino, substituted or non-substituted hetercyclyloxycarbonylamino, substituted or non-substituted arylcarbonylamino, substituted or non-substituted hetercyclylcarbonylamino, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-$C_1$-$C_8$-alkylcarbamoylamino, substituted or non-substituted di-$C_1$-$C_8$-halogenoalkylcarbamoylamino, having 1 to 5 halogen atoms, substituted or non-substituted N—$C_1$-$C_8$-alkyl-($C_1$-$C_8$-alkylcarbamoyl)amino, substituted or non-substituted N—$C_1$-$C_8$-alkyl-($C_1$-$C_8$-halogenoalkylcarbamoyl)amino having 1 to 5 halogen atoms, substituted or non-substituted N—$C_1$-$C_8$-alkyl-(di-$C_1$-$C_8$-alkylcarbamoyl)amino, substituted or non-substituted N—$C_1$-$C_8$-alkyl-(di-$C_1$-$C_8$halogenoalkylcarbamoyl)amino having 1 to 5 halogen atoms, substituted or non-substituted $C_1$-$C_8$-alkylaminocarbonyloxy, substituted or non-substituted di-$C_1$-$C_8$-alkylaminocarbonyloxy, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyl, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylthioylamino, substituted or non-substituted ($C_1$-$C_8$-alkoxythiocarbonyl)amino, substituted or non-substituted $C_1$-$C_8$-halogenoalkylthioylamino having 1 to 5 halogen atoms, substituted or non-substituted ($C_1$-$C_8$-alkyl-carbamothioyl)-oxy, substituted or non-substituted (di-$C_1$-$C_8$-alkyl-carbamothioyl)-oxy, substituted or non-substituted $C_1$-$C_8$-alkylsulfinyl, substituted or non-substituted $C_1$-$C_8$-halogenoalkylsulfinyl having 1 to 5 halogen atoms, substituted or non-substituted $C_1$-$C_8$-alkylsulfonyl, substituted or non-substituted $C_1$-$C_8$-halogenoalkylsulfonyl having 1 to 5 halogen atoms, substituted or non-substituted $C_1$-$C_8$-alkylaminosulfamoyl, substituted or non-substituted di-$C_1$-$C_8$-alkylaminosulfamoyl, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$-alkynyloxyimino)-$C_1$-$C_6$-alkyl, substituted or non-substituted (benzyloxyimino)-$C_1$-$C_6$-alkyl, substituted or non-substituted benzyloxy, substituted or non-substituted benzylsulfenyl, substituted or non-substituted benzylamino, substituted or non-substituted phenoxy, substituted or non-substituted phenylsulfenyl, substituted or non-substituted phenylamino, substituted or non-substituted aryl, substituted or non-substituted (arylcarbonyl)amino, substituted or non-substituted (heterocyclylcarbonyl)amino substituted or non-substituted aryl-[$C_1$-$C_8$]-alkyl, substituted or non-substituted tri($C_1$-$C_8$alkyl)-silyloxy, substituted or non-substituted $C_1$-$C_8$-alkylsulfenylamino, substituted or non-substituted $C_1$-$C_8$-halogenoalkylsulfinylamino having 1 to 5 halogen atoms, substituted or non-substituted $C_1$-$C_8$-alkylsulfonylamino, substituted or non-substituted $C_1$-$C_8$-halogenoalkylsulfonylamino having 1 to 5 halogen atoms, substituted or non-substituted $C_1$-$C_8$-alkoxysulfonylamino, substituted or non-substituted $C_1$-$C_8$-halogenoxysulfonylamino having 1 to 5 halogen atoms, substituted or non-substituted tri($C_1$-$C_8$-alkyl)-silyl, substituted or non-substituted ($C_1$-$C_6$-alkylideneamino)oxy, substituted or non-substituted ($C_1$-$C_6$-alkenylideneamino)oxy, substituted or non-substituted ($C_1$-$C_6$-alkynylideneamino)oxy, substituted or non-substituted (benzylideneamino)oxy;

$K^1$ is selected from the group consisting of a hydrogen atom, a formyl group, a substituted or non-substituted carbaldehyde O—($C_1$-$C_8$-alkyl)oxime, a carbamoyl group, a N-hydroxycarbamoyl group, a formylamino group, substituted or non-substituted $C_1$-$C_8$-alkyl, substituted or non-substituted tri($C_1$-$C_8$-alkyl)silyl-$C_1$-$C_8$-alkyl, substituted or non-substituted $C_3$-$C_8$-cycloalkyl, substituted or non-substituted tri($C_1$-$C_8$-alkyl)silyl-$C_3$-$C_8$-cycloalkyl, substituted or non-substituted $C_1$-$C_8$-halogenoalkyl having 1 to 5 halogen atoms, substituted or non-substituted $C_3$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_2$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyll, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylsulfinyl, substituted or non-substituted $C_1$-$C_8$-halogenoalkylsulfinyl having 1 to 5 halogen atoms, substituted or non-substituted $C_1$-$C_8$-alkylsulfonyl, substituted or non-substituted $C_1$-$C_8$-halogenoalkylsulfonyl having 1 to 5 halogen atoms, substituted or non-substituted $C_1$-$C_8$-alkylaminosulfamoyl, substituted or non-substituted di-$C_1$-$C_8$-alkylaminosulfamoyl, substituted or non-substituted aryl, substituted or non-substituted aryl-[$C_1$-$C_8$]-alkyl;

$Y^1$ to $Y^5$ are independently selected from the group consisting of a hydrogen atom, a nitro group, a hydroxyl group, a cyano group, an amino group, a sulfenyl group, a formyl group, a substituted or non-substituted carbaldehyde O—($C_1$-$C_8$-alkyl)oxime, a formyloxy group, a formylamino group, a carbamoyl group, a N-hydroxycarbamoyl group, a pentafluoro-$\lambda^6$sulphenyl group, a formylamino group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$-alkyl -($C_1$-$C_8$-alkylamino)-amino group, a substituted or non-substituted (hydroxyimino)-$C_1$-$C_6$-alkyl group, substituted or non-substituted $C_1$-$C_8$-alkyl, substituted or non-substituted tri($C_1$-$C_8$-alkyl)silyl-$C_1$-$C_8$-alkyl, substituted or non-substituted $C_3$-$C_8$-cycloalkyl, substituted or non-substituted tri($C_1$-$C_8$-alkyl)silyl-$C_3$-$C_8$-cycloalkyl, substituted or non-substituted $C_1$-$C_8$-halogenoalkyl having 1 to 5 halogen atoms, substituted or non-substituted $C_3$-$C_8$-halogenocycloalkyl having 1 to 5 halogen atoms, a $C_2$-$C_8$-alkenyl, substituted or non-substituted $C_2$-$C_8$-alkenyl, substituted or non-substituted $C_2$-$C_8$-alkynyl, substituted or non-substituted di-$C_1$-$C_8$alkylamino, substituted or non-substituted $C_1$-$C_8$alkoxy, substituted or non-substituted $C_1$-$C_8$-halogenoalkoxy having 1 to 5 halogen atoms, substituted or non-substituted $C_1$-$C_8$-alkylsulfenyl, substituted or non-substituted $C_1$-$C_8$-halogenoalkylsulfenyl having 1 to 5 halogen atoms, substituted or non-substituted $C_2$-$C_8$-alkenyloxy, substituted or non substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-$C_1$-$C_8$-alkylcarbamoylamino, substituted or non-substituted di-$C_1$-$C_8$-halogenoalkylcarbamoylamino having 1 to 5 halogen atoms, substituted or non-substituted N—$C_1$-$C_8$-alkyl-($C_1$-$C_8$alkylcarbamoyl)amino, substituted or non-substituted N—$C_1$-$C_8$-alkyl -($C_1$-$C_8$-halogenoalkylcarbamoyl)amino having 1 to 5 halogen atoms, substituted or non-substituted N—$C_1$-$C_8$-alkyl-(di-$C_1$-$C_8$-alkylcarbamoyl)amino, substituted or non-substituted N—$C_1$-$C_8$-alkyl-(di-$C_1$-$C_8$-halogenoalkylcarbamoyl)amino having 1 to 5 halogen atoms, substituted or non-substituted $C_1$-$C_8$-alkylaminocarbonyloxy, substituted or non-substituted di-$C_1$-$C_8$-alkylaminocarbonyloxy, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyl, substituted or non-substituted $C_1$-$C_8$-alkoxycarbamothioyl, substituted or non-substituted N—$C_1$-$C_8$alkyl-$C_1$-$C_8$-alkoxycarbamothioyl, substituted or non-substituted $C_1$-$C_8$-alkylthioylamino, substituted or non-substituted $C_1$-$C_8$-halogenoalkylthioylamino having 1 to 5 halogen atoms, substituted or non-substituted ($C_1$-$C_8$-alkyl-carbamothioyl)-oxy, substituted or non-substituted (di-$C_1$-$C_8$-alkyl-carbamothioyl)-oxy, substituted or non-substituted $C_1$-$C_8$-alkylsulfinyl, substituted or non-substituted $C_1$-$C_8$-halogenoalkylsulfinyl having 1 to 5 halogen atoms, substituted or non-substituted $C_1$-$C_8$-alkylsulfonyl, substituted or non substituted $C_1$-$C_8$-halogenoalkylsulfonyl having 1 to 5 halogen atoms, substituted or non-substituted $C_1$-$C_8$alkylaminosulfamoyl, substituted or non-substituted di-$C_1$-$C_8$-alkylaminosulfamoyl, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$alkynyloxyimino)-$C_1$-$C_6$-alkyl, substituted or non-substituted (benzyloxyimino)-$C_1$-

$C_6$-alkyl, substituted or non-substituted benzyloxy, substituted or non-substituted benzylsulfenyl, substituted or non-substituted benzylamino, substituted or non-substituted phenoxy, substituted or non-substituted phenylsulfenyl, substituted or non-substituted phenylamino, substituted or non-substituted aryl, substituted or non-substituted aryl-[$C_1$-$C_8$]-alkyl, substituted or non-substituted tri($C_1$-$C_8$-alkyl)-silyloxy, substituted or non-substituted $C_1$-$C_8$-alkylsulfenylamino, substituted or non substituted $C_1$-$C_8$-halogenoalkylsulfinylamino having 1 to 5 halogen atoms, substituted or non-substituted $C_1$-$C_8$-alkylsulfonylamino, substituted or non-substituted $C_1$-$C_8$-halogenoalkylsulfonylamino having 1 to 5 halogen atoms, substituted or non-substituted $C_1$-$C_8$-alkoxysulfonylamino, substituted or non-substituted $C_1$-$C_8$-halogenoxysulfonylamino having 1 to 5 halogen atoms, substituted or non-substituted tri($C_1$-$C_8$-alkyl)-silyl, substituted or non-substituted ($C_1$-$C_6$-alkylideneamino)oxy, substituted or non-substituted ($C_1$-$C_6$-alkenylideneamino)oxy, substituted or non-substituted ($C_1$-$C_6$-alkynylideneamino)oxy, substituted or non-substituted (benzylideneamino)oxy; and as well as salts, N-oxides, or (E) and (Z) isomers and mixtures thereof.

18. The compound of the structural formula:

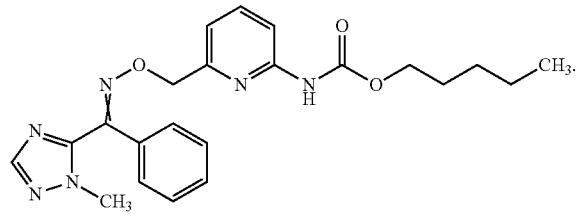 [SMILES: CCCCCOC(=O)Nc1cccc(CON=C(c2ccccc2)c2ncnn2C)n1]

19. The compound of claim 17 wherein $X^1$ is methyl and and $Y^1$ through $Y^5$ are all hydrogen.

* * * * *